United States Patent
Larsen et al.

(10) Patent No.: US 10,799,507 B2
(45) Date of Patent: Oct. 13, 2020

(54) 5-(7H-PYRROLO[2,3-D]PYRIMIDIN-4-YL)-5-AZASPIRO[2.5]OCTANE-8-CARBOXYLIC ACID DERIVATIVES AS NOVEL JAK KINASE INHIBITORS

(71) Applicant: LEO Pharma A/S, Ballerup (DK)

(72) Inventors: Mogens Larsen, Ballerup (DK);
Andreas Ritzen, Ballerup (DK);
Bjarne Nørremark, Ballerup (DK);
Daniel Rodriguez Greve, Ballerup (DK)

(73) Assignee: Leo Pharma A/S, Ballerup (DK)

( * ) Notice: Subject to any disclaimer, the term of this patent is extended or adjusted under 35 U.S.C. 154(b) by 0 days.

(21) Appl. No.: 16/483,079

(22) PCT Filed: Feb. 1, 2018

(86) PCT No.: PCT/EP2018/052507
§ 371 (c)(1),
(2) Date: Aug. 2, 2019

(87) PCT Pub. No.: WO2018/141842
PCT Pub. Date: Aug. 9, 2018

(65) Prior Publication Data
US 2020/0009147 A1    Jan. 9, 2020

(30) Foreign Application Priority Data
Feb. 3, 2017 (EP) ..................... 17154630

(51) Int. Cl.
*C07D 487/04* (2006.01)
*A61K 31/519* (2006.01)

(52) U.S. Cl.
CPC .......... *A61K 31/519* (2013.01); *C07D 487/04* (2013.01)

(58) Field of Classification Search
CPC .................................................. C07D 487/04
See application file for complete search history.

(56) References Cited

FOREIGN PATENT DOCUMENTS

| WO | WO 99/65909 | 12/1999 |
|----|----|----|
| WO | WO 2011/003418 A1 | 1/2011 |
| WO | WO 2012/093169 A1 | 7/2012 |

OTHER PUBLICATIONS

Vippagunta et al. (2001).*
Wolff et al. (1997).*
Banker et al. (1997).*
Harrison, Bryce A., et al., "Novel Class of LIM-Kinase 2 Inhibitors for the Treatment of Ocular Hypertension and Associated Glaucoma," J. Med. Chem., vol. 52, pp. 6515-6518 (2009).
O'Shea, John J. et al., "Cytokine Signaling in 2002: New Surprises in the Jak/Stat Pathway," Cell., vol. 109, pp. S121-S131 (2002).
O'Shea, J.J., "Targeting the Jak/STAT pathway for immunosuppression," Ann. Rheum. Dis., vol. 63 (Suppl. 2: pp. ii67-ii71), (2004).
O'Shea, John J., M.D., "JAKs and STATs in Immunity, Immunodeficiency, and Cancer," The New England Journal of Medicine, vol. 368, No. 2, pp. 161-170 (2013).
Schindler, Christian W., "Series Introduction: JAK-STAT signaling in human disease," J. Clin. Invest., vol. 109, No. 9, pp. 1133-1137 (2002).
Schindler, Christian et al., "JAK-STAT Signaling: From Interferons to Cytokines," Journal of Biological Chemistry, vol. 282, No. 28, pp. 20059-20063 (2007).
Schartz, Daniella M. et al., "Type I/II cytokines, JAKs, and new strategies for treating autoimmune diseases," Nat. Rev. Rheumatol., vol. 12, No. 1, pp. 25-36 (2016).
International Search Report for International Application No. PCT/EP2018/052507, dated May 16, 2018. (4 pages).
Written Opinion of the International Searching Authority for International Application No. PCT/EP2018/05207. (5 pages).

* cited by examiner

*Primary Examiner* — Paul V Ward
(74) *Attorney, Agent, or Firm* — Finnegan, Henderson, Farabow, Garrett & Dunner, LLP

(57) ABSTRACT

The present invention relates to a compound according to formula (I)

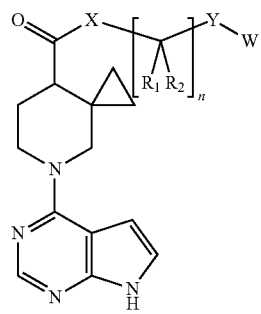

wherein X represents NH or O; n is an integer selected from 1-3; Y represents a bond, —C(O)O—*, —C(O)OR$_3$—* or —C(O)NHR$_3$—*; W is selected from the group consisting of phenyl, pyridyl, (C$_3$-C$_7$)cycloalkyl and 4-6 membered heterocycloalkyl; or pharmaceutically acceptable salts, hydrates, or solvates thereof. The invention relates further to said compounds for use in therapy, to pharmaceutical compositions comprising said compounds, to methods of treating diseases, with said compounds, and to the use of said compounds in the manufacture of medicaments.

20 Claims, No Drawings

5-(7H-PYRROLO[2,3-D]PYRIMIDIN-4-YL)-5-AZASPIRO[2.5]OCTANE-8-CARBOXYLIC ACID DERIVATIVES AS NOVEL JAK KINASE INHIBITORS

This application is a national stage filing under 35 U.S.C. § 371 of International Application No. PCT/EP2018/052507, filed on Feb. 1, 2018, which claims priority of European Patent Application No. 17154630.2, filed on Feb. 3, 2017. The contents of these applications are each incorporated herein by reference.

FIELD OF THE INVENTION

This invention relates to compounds which are inhibitors of protein tyrosine kinases, such as the Janus kinases, to said compounds for use in therapy, to pharmaceutical compositions comprising said compounds and to methods of treating diseases with said compounds.

BACKGROUND OF THE INVENTION

This invention relates to novel compounds which are inhibitors of protein tyrosine kinases such as the Janus kinases, JAK1, JAK2, JAK3 and TYK2.

Protein tyrosine kinases are a family of enzymes catalyzing the transfer of the terminal phosphate of adenosine triphosphate to tyrosine residues in protein substrates. Phosphorylation of tyrosine residues on protein substrates leads to transduction of intracellular signals which regulate a wide variety of processes such as cell growth differentiation and activation, metabolism, hematopoiesis, host defense and immuno-regulation. As the elucidation of the molecular mechanisms in a number of inflammatory conditions and other disorders of the immune system (e.g. autoimmune diseases), highlighted the critical role of these intracellular signal pathways modulation of the activity of protein tyrosine kinases appears to be an attractive route to the management of inflammatory diseases. A large number of protein tyrosine kinases have been identified which may be receptor protein tyrosine kinases, e.g. the insulin receptor, or non-receptor protein tyrosine kinases.

The protein tyrosine kinases JAK1, JAK2, JAK3 and TYK2 selectively associate with the cytoplasmic domains of various cytokine receptor chains and have essential roles in cytokine-dependent regulation of tissue homeostasis, initiation of innate immunity, shaping adaptive immune responses and inflammatory processes. They are critical in signal transduction in response to their activation via tyrosine phosphorylation by stimulation of cytokine receptors. (1) Schindler C. et al. JAK-STAT signaling: from interferons to cytokines. J. Biol. Chem 2007; 282(28):20059; (2) O'Shea J. J. Targeting the Jak/STAT pathway for immunosuppression; Ann. Rheum. Dis. 2004; 63 Suppl 2:ii67; (3) Schindler C. Series introduction. JAK-STAT signaling in human disease; J. Clin. Invest. 2002; 109(9):1133); (4) O'Shea et. Al. Cell, Vol. 109, S121-S131, 2002; (5) Schwartz D.M. et al. Nat. Rev. Rheumatol., 2016; 12(1): 25-36; (6) O'Shea et al. New. Eng. J. Med. 2013; 368(2): 161-170.

While JAK1, JAK2 and TYK2 are ubiquitously expressed JAK3 is predominantly expressed in hematopoietic cells.

JAK1 plays a critical role in mediation of biological responses and JAK1 is widely expressed and associated with several major cytokine receptor families. It is involved in signaling by members of the IL-2 receptor γ subunit family (IL-2, IL-4, IL-7R, IL-9R, IL-15R and IL-21R), the IL-4 receptor family (IL-4R, IL-13R), the gp130 receptor family and class II cytokine receptors comprising of IL-10 receptor family and both type I and type II IFN receptor family.

JAK2 is implicated in signaling by several single chain receptors (including Epo-R, GHR, PRL-R), the IL-3 receptor family, the gp130 receptor family, the IL-12 receptor family (IL-12 and IL-23) and some Class II receptor cytokine family. Thus, JAK2 plays a critical role in transducing signals for Epo, IL-3, GM-CSF, IL-5 and IFNγ. JAK2 knockout mice exhibit an embryonic lethal phenotype.

JAK3 is involved in signal transduction by receptors that employ the common gamma chain of the type I cytokine receptor family also known as IL-2 receptor family (e.g. IL-2, IL-4, IL-7, IL-9, IL-15 and IL-21). XSCID patient populations have been identified with reduced levels of JAK3 protein or with genetic defects to the common gamma chain, suggesting that immune suppression should result from blocking signaling through the JAK3 pathway. Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as immune system diseases, in particular autoimmune diseases.

TYK2 is implicated in type I interferons, IL-6, IL-10, IL-12 and IL-23 signaling. A human patient with a TYK2 deficiency has been described and this patient had a primary immunodeficiency disorder characterized as a hyper-IgE-like syndrome with many opportunistic infections by virus, bacteria and fungi. Because IL-23 has been found to play an important role in many chronic inflammatory conditions, a TYK2 inhibitor could conceivably be very effective in treating diseased influenced by IL-23.

Inhibitors of the Janus kinases are expected to show utility in the treatment of inflammatory and non-infectious autoimmune diseases wherein these kinases are involved. Recently the pan-JAK inhibitors Tofacitinib and Ruxolitinib have been launched for the treatment of rheumatoid arthritis and myelofibrosis, respectively.

Hence, JAK inhibitors may furthermore be useful in the treatment of diseases related to activity of Janus kinases, including, for example skin diseases like proliferative and inflammatory skin disorders, psoriasis, atopic dermatitis, scleroderma, rosacea, skin cancers, dermatis, dermatitis herpetiformis, dermatomyositis, vitiligo, alopecia areata, contact dermatitis, eczema, xerosis, urticaria and chronic idiophatic pruritus; respiratory diseases like asthma, chronic obstructive pulmonary disease, pulmonary fibrosis, cystic fibrosis, rhinitis, bronchiolitis, byssinosis, pneumoconiosis, bronchiectasis, hypersensitivity pneumonitis, lung cancers, mesothelioma and sarcoidosis; gastrointestinal diseases like inflammatory bowel disease, ulcerative colitis, Crohn's disease, retroperitoneal fibrosis, celiac disease and cancers; eye diseases like myasthenia gravis, Sjögren's syndrome, conjunctivitis, scleritis, uveitis, dry eye syndrome, keratitis, iritis; systemic indications like lupus, multiple sclerosis, rheumatoid arthritis, type I diabetes and complications from diabetes, cancers, ankylosing spondylitis and psoriatic arthritis; as well as other autoimmune diseases and indications where immunosuppression would be desirable for example in organ transplantation.

WO 2011/003418 discloses Heterocyclic Compounds as JAK Receptor and protein Tyrosine Kinase Inhibitors.

WO 2012/093169 discloses Novel Sulfamide Piperazine Derivatives as Protein Kinase Inhibitors and Pharmaceutical Use thereof.

SUMMARY OF THE INVENTION

Characterisation in our laboratories of JAK kinase inhibitors of the 4-(4,7-Diaza-spiro[2.5]oct-7-yl)-7H-pyrrolo[2,3-d]pyrimidine scaffold which were disclosed in the prior art documents cited above; showed that several of these compounds to variable extend degrade to a major metabolite 4-(4,7-diaza-spiro[2.5]oct-7-yl)-7H-pyrrolo[2,3-d]pyrimidine (A) upon in vivo and in vitro administration. Further characterisation of the metabolite (A); lead to the discovery that this metabolite exhibits genotoxic properties. The discovery prevented further clinical development of said compounds.

It is thus an object of this invention to provide novel compounds which exhibit a high inhibitory activity on one or more of the Janus kinase receptors JAK1, JAK2, JAK3 and TYK2 and which can not form the genotoxic metabolite 4-(4,7-Diaza-spiro[2.5]oct-7-yl)-7H-pyrrolo[2,3-d]pyrimidine (A) upon in vivo or in vitro administration.

Compounds of the present invention exhibit a high inhibitory activity on one or more of the Janus kinase receptors JAK1, JAK2, JAK3 and TYK2 and furthermore the compounds possess a 5-(7H-pyrrolo[2,3-d]pyrimidin-4-yl)-5-azaspiro[2.5]octane-8-carboxylic acid-scaffold (B) which can not form metabolite (A) due to the replacement of nitrogen with carbon at the 8-position and due to the presence of a carbon-carbon bond at the 8-position.

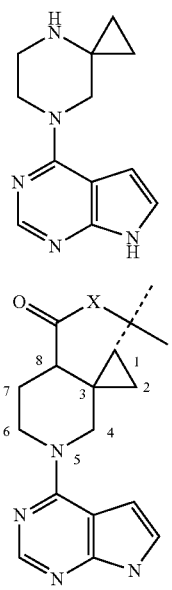

(A)

(B)

Compounds of the present invention may furthermore have advantageous properties such as improved metabolic stability properties and metabolic elimination properties, dermal stability and delivery properties, systemic exposure characteristics after local delivery, all of which may make them especially suitable to be used as active pharmaceutical ingredients in topical drug formulations.

A particular advantage of some compounds of the present invention is that they display stability in keratinocytes, while displaying high clearance in human liver microsomes and/or human hepatocytes, thus indicating both stability of the compounds in skin and high systemic clearance of the compounds, thereby indicating reduced risk of adverse side effects upon topical administration while retaining efficacy in skin.

Compounds of the present invention may furthermore have favorable solubility properties.

Compounds of the present invention may furthermore have advantageous safety properties, such as highly selective JAK inhibitory activity compared to other kinases and/or advantageous cytotoxic, phototoxic and genotoxic properties.

Accordingly, the invention relates to compounds of general formula I:

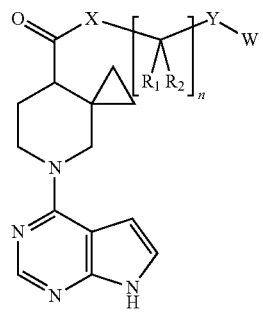

I wherein X represents NH or O;

wherein $R_1$ and $R_2$ each independently are selected from the group consisting of hydrogen, deuterium, hydroxyl, cyano, halogen, $(C_1-C_3)$alkyl and hydroxyl$(C_1-C_3)$alkyl;

n is an integer selected from 1-3;

Y represents a bond, —C(O)O—*, —C(O)O$R_3$—* or —C(O)NH$R_3$—* wherein * denotes the point of attachment to W, and wherein $R_3$ represents $(C_1-C_4)$alkylene;

W is selected from the group consisting of phenyl, pyridyl, $(C_3-C_7)$cycloalkyl and 4-6 membered heterocycloalkyl comprising one or two heteroatoms selected from O, S or N, wherein said phenyl, pyridyl, $(C_3-C_7)$cycloalkyl and 4-6 membered heterocycloalkyl comprising one or two heteroatoms selected from O, S or N, are optionally substituted with one or more substitutents independently selected from hydroxyl, cyano, halogen, oxo, $(C_1-C_4)$alkyl, hydroxyl $(C_1-C_4)$alkyl, halo$(C_1-C_4)$alkyl, cyano$(C_1-C_4)$alkyl, $(C_1-C_4)$alkoxy, halo$(C_1-C_4)$alkoxy and —SO$_2$NH$_2$;

or pharmaceutically acceptable salts, hydrates or solvates thereof.

In a further aspect the invention relates to a compound according to general formula I above for use as a medicament.

In another aspect the invention relates to a compound according to general formula I above for use in the prophylaxis and/or treatment of diseases of the immune system such as autoimmune diseases, or of diseases related to deregulation of the immune system.

In yet another aspect the invention relates to a pharmaceutical composition comprising a compound according to general formula I above together with a pharmaceutically acceptable vehicle or excipient or pharmaceutically acceptable carrier(s).

DETAILED DESCRIPTION OF THE INVENTION

Definitions

The term "$(C_a\text{-}C_b)$alkyl" is intended to indicate a radical obtained when one hydrogen atom is removed from a branched or linear hydrocarbon. Said $(C_a\text{-}C_b)$alkyl comprises 1-6, preferably 1-4, such as 1-3, such as 2-3 or such as 1-2 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, n-pentyl, isopentyl, neopentyl, n-hexyl and isohexyl. The number of carbon atoms in "$(C_a\text{-}C_b)$alkyl" is indicated by the prefix "$(C_a\text{-}C_b)$", wherein a is the minimum number and b is the maximum number of carbons in the hydrocarbon radical. Thus, for example $(C_1\text{-}C_4)$alkyl is intended to indicate an alkyl radical comprising from 1 to 4 carbon atoms.

The term "$(C_1\text{-}C_4)$alkylene" is intended to indicate a divalent saturated aliphatic hydrocarbyl group preferably having from 1 to 4 and more preferably 1 to 3 carbon atoms, such as 1 to 2 carbon atoms or such as 1 carbon atom that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$—) or (—$CH(CH_3)CH_2$—), and the like.

The terms "$(C_a\text{-}C_b)$alkyloxy" and "$(C_a\text{-}C_b)$alkoxy" are intended to indicate a radical of the formula —OR', wherein R' is $(C_a\text{-}C_b)$alkyl as indicated herein, wherein the $(C_a\text{-}C_b)$ alkyl group is appended to the parent molecular moiety through an oxygen atom, e.g. methoxy (—$OCH_3$), ethoxy (—$OCH_2CH_3$), n-propoxy, isopropoxy, butoxy, tert-butoxy, and the like.

The term "cyano" is intended to indicate a —CN group attached to the parent molecular moiety through the carbon atom.

The term "cyano$(C_a\text{-}C_b)$alkyl" is intended to indicate a $(C_a\text{-}C_b)$alkyl group as defined herein substituted with one or more cyano atoms as defined herein, such as cyanomethyl or cyanoethyl.

The term "$(C_a\text{-}C_b)$cycloalkyl" is intended to indicate a saturated cycloalkane hydrocarbon radical, comprising $(C_a\text{-}C_b)$ carbon atoms, such as 3-7 carbon atoms, preferably 3-6 carbon atoms, such as 3-5 carbon atoms or such as 3-4 carbon atoms, e.g. cyclopropyl, cyclobutyl, cyclopentyl, cyclohexyl, or cycloheptyl.

The term "halo$(C_a\text{-}C_b)$alkyl" is intended to indicate a $(C_a\text{-}C_b)$alkyl group as defined herein substituted with one or more halogen atoms as defined herein, e.g. fluoro or chloro, such as difluoromethyl or trifluoromethyl.

The terms "halo$(C_a\text{-}C_b)$alkyloxy" and "halo$(C_a\text{-}C_b)$alkoxy" are intended to indicate an halo$(C_a\text{-}C_b)$alkyl group as defined herein which is appended to the parent molecular moiety through an oxygen atom, such as difluoromethoxy or trifluoromethoxy.

The term "halogen" is intended to indicate a substituent from the $7^{th}$ main group of the periodic table, such as fluoro, chloro and bromo.

The term "4-6 membered heterocycloalkyl comprising one or two heteroatoms selected from O, S or N" is intended to indicate a $(C_4\text{-}C_6)$cycloalkane radical as described herein, wherein one or two carbon atoms are replaced by one or two heteroatoms, thus comprising 2-, 3-, 4 or 5 carbon atoms and further comprising one or two heteroatoms selected from O, N, or S, such as comprising 3-, 4 or 5 carbon atoms and further comprising one heteroatom selected from O, N, or S. The heterocycloalkyl radical may be connected to the parent molecular moiety through a carbon atom or a nitrogen atom contained anywhere within the heterocycloalkyl group. Representative examples of heterocycloalkyl groups include, but are not limited to piperazinyl, morpholinyl, oxetanyl, thietanyl, tetrahydropyranyl, tetrahydrofuranyl or piperidinyl.

The number of carbon atoms in a hydrocarbon radical (e.g. alkyl, cycloalkyl) is indicated by the prefix "$(C_a\text{-}C_b)$", wherein a is the minimum number and b is the maximum number of carbons in the hydrocarbon radical. Thus, for example $(C_1\text{-}C_4)$alkyl is intended to indicate an alkyl radical comprising from 1 to 4 carbon atoms, and $(C_3\text{-}C_5)$cycloalkyl is intended to indicate a cycloalkyl radical comprising from 3 to 5 carbon ring atoms.

The term "hydroxy" or "hydroxyl" is intended to indicate an —OH radical.

The term "hydroxy$(C_a\text{-}C_b)$alkyl" or "hydroxyl$(C_a\text{-}C_b)$alkyl" is intended to indicate a $(C_a\text{-}C_b)$alkyl group as defined above substituted with one or more hydroxy, e.g. hydroxymethyl, hydroxyethyl, hydroxypropyl.

The term "oxo" is intended to indicate an oxygen atom which is connected to the parent molecular moiety via a double bond (=O).

The group C(O) is intended to represent a carbonyl group (C=O).

The group S(O) is intended to represent a sulfoxide group (S=O).

The group $S(O)_2$ or $SO_2$ is intended to represent a sulfone group (O=S=O).

If substituents are described as being independently selected from a group, each substituent is selected independent of the other. Each substituent may therefore be identical of different from the other substituent(s).

The term "optionally substituted" means "unsubstituted or substituted", and therefore the general formulas described herein encompasses compounds containing the specified optional substituent(s) as well as compounds that do not contain the optional substituent(s).

The term "pharmaceutically acceptable salt" is intended to indicate salts prepared by reacting a compound of formula I, which comprise a basic moiety, with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I comprising an acidic moiety may also be prepared by reaction with a suitable base such as sodium hydroxide, potassium hydroxide, magnesium hydroxide, calcium hydroxide, silver hydroxide, ammonia or the like, or suitable non-toxic amines, such as lower alkylamines, hydroxy-lower alkylamines, cycloalkylamines, or benzylamines, or L-arginine or L-lysine. Further examples of pharmaceutical acceptable salts are listed in Berge, S.M.; J. Pharm. Sci.; (1977), 66(1), 1-19, which is incorporated herein by reference.

The term "solvate" is intended to indicate a species formed by interaction between a compound, e.g. a compound of formula I, and a solvent, e.g. alcohol, glycerol or water, wherein said species are in a crystalline form. When water is the solvent, said species is referred to as a hydrate.

The term "treatment" as used herein means the management and care of a patient for the purpose of combating a disease, disorder or condition. The term is intended to include the delaying of the progression of the disease, disorder or condition, the amelioration, alleviation or relief of symptoms and complications, and/or the cure or elimination of the disease, disorder or condition. The term includes prevention of the condition, wherein prevention is to be understood as the management and care of a patient for the purpose of combating the disease, condition or disorder and includes the administration of the active compounds to prevent the onset of the symptoms or complications. Nonetheless, prophylactic (preventive) and therapeutic (curative) treatments are two separate aspects.

All references, including publications, patent applications and patents, cited herein are hereby incorporated by reference in their entirety and to the same extent as if each reference were individually and specifically indicated to be incorporated by reference, regardless of any separately provided incorporation of particular documents made elsewhere herein.

EMBODIMENTS OF THE INVENTION

In an embodiment the invention provides a compound according to general formula I, wherein X represents NH.

In an embodiment the invention provides a compound according to general formula I, wherein X represents O.

In an embodiment the invention provides a compound according to general formula I, wherein n is 1.

In an embodiment the invention provides a compound according to general formula I, wherein n is 2.

In an embodiment the invention provides a compound according to general formula I, wherein Y represents a bond.

In an embodiment the invention provides a compound according to general formula I, wherein Y represents a —C(O)O—*, —C(O)OR$_3$—* or —C(O)NHR$_3$—* wherein * denotes the point of attachment to W, and wherein R$_3$ represents methylene.

In an embodiment the invention provides a compound according to general formula I, wherein R$_1$ and R$_2$ each independently are selected from the group consisting of hydrogen, hydroxyl, methyl and hydroxymethyl.

In an embodiment the invention provides a compound according to general formula I, wherein W is selected from the group consisting of (C$_3$-C$_6$)cycloalkyl, phenyl, pyridyl, tetrahydropyranyl and thiethanyl, wherein said (C$_3$-C$_6$)cycloalkyl, phenyl, pyridyl, tetrahydropyranyl and thiethanyl are optionally substituted with one or more substitutents independently selected from fluoro, cyano, —SO$_2$NH$_2$, hydroxyl, oxo, methyl, ethyl, hydroxymethyl, cyanomethy and methoxy.

In an embodiment the invention provides a compound according to general formula I, wherein the compound is selected from the list consisting of (8S)—N-[(2S)-2-cyclopentyl-2-hydroxy-ethyl]-5-(7H-pyrrolo[2,3-d]pyrimidin-4-yl)-5-azaspiro[2.5]octane-8-carboxamide, (8S)—N-(2-cyclohexyl-2-hydroxy-ethyl)-5-(7H-pyrrolo[2,3-d]pyrimidin-4-yl)-5-azaspiro[2.5]octane-8-carboxamide, (8S)—N-[(1S,2S)-2-cyclohexyl-2-hydroxy-1-methyl-ethyl]-5-(7H-pyrrolo[2,3-d]pyrimidin-4-yl)-5-azaspiro[2.5]octane-8-carboxamide, (8S)—N-[(2S)-2-cyclohexyl-2-hydroxy-ethyl]-5-(7H-pyrrolo[2,3-d]pyrimidin-4-yl)-5-azaspiro[2.5]octane-8-carboxamide, (8S)—N-[(1S,2S)-2-cyclopentyl-2-hydroxy-1-methyl-ethyl]-5-(7H-pyrrolo[2,3-d]pyrimidin-4-yl)-5-azaspiro[2.5]octane-8-carboxamide, (8S)—N-[(1S,2S)-2-(4-fluorophenyl)-2-hydroxy-1-methyl-ethyl]-5-(7H-pyrrolo[2,3-d]pyrimidin-4-yl)-5-azaspiro[2.5]octane-8-carboxamide, (8S)—N-[(2S)-2-(4-fluorophenyl)-2-hydroxy-ethyl]-5-(7H-pyrrolo[2,3-d]pyrimidin-4-yl)-5-azaspiro[2.5]octane-8-carboxamide, (8S)—N-[(2S)-2-(4-cyanophenyl)-2-hydroxy-ethyl]-5-(7H-pyrrolo[2,3-d]pyrimidin-4-yl)-5-azaspiro[2.5]octane-8-carboxamide, (8S)—N-[(1S,2S)-2-(4-fluorophenyl)-2-hydroxy-1-(hydroxymethyl)ethyl]-5-(7H-pyrrolo[2,3-d]pyrimidin-4-yl)-5-azaspiro[2.5]octane-8-carboxamide, (8S)—N-[(2R)-2-hydroxy-2-tetrahydropyran-4-yl-ethyl]-5-(7H-pyrrolo[2,3-d]pyrimidin-4-yl)-5-azaspiro[2.5]octane-8-carboxamide, (8S)—N-[(2R)-2-cyclopentyl-2-hydroxy-ethyl]-5-(7H-pyrrolo[2,3-d]pyrimidin-4-yl)-5-azaspiro[2.5]octane-8-carboxamide, (8S)—N-[(2R)-2-(5-fluoro-2-pyridyl)-2-hydroxy-ethyl]-5-(7H-pyrrolo[2,3-d]pyrimidin-4-yl)-5-azaspiro[2.5]octane-8-carboxamide (8S)—N-[(4-cyanophenyl)methyl]-5-(7H-pyrrolo[2,3-d]pyrimidin-4-yl)-5-azaspiro[2.5]octane-8-carboxamide, (8S)—N-[(1S)-1-(4-cyano-3-fluoro-phenyl)ethyl]-5-(7H-pyrrolo[2,3-d]pyrimidin-4-yl)-5-azaspiro[2.5]octane-8-carboxamide, (8S)—N-[(2R)-2-cyclohexyl-2-hydroxy-ethyl]-5-(7H-pyrrolo[2,3-d]pyrimidin-4-yl)-5-azaspiro[2.5]octane-8-carboxamide, (8S)—N-[(4-cyano-3-fluoro-phenyl)methyl]-5-(7H-pyrrolo[2,3-d]pyrimidin-4-yl)-5-azaspiro[2.5]octane-8-carboxamide, (8S)—N-[(1R)-1-(4-fluorophenyl)-2-hydroxy-ethyl]-5-(7H-pyrrolo[2,3-d]pyrimidin-4-yl)-5-azaspiro[2.5]octane-8-carboxamide, (8S)—N-[(1R)-1-(4-cyanophenyl)-2-hydroxy-ethyl]-5-(7H-pyrrolo[2,3-d]pyrimidin-4-yl)-5-azaspiro[2.5]octane-8-carboxamide, N-[(1R)-1-(4-cyanophenyl)-2-hydroxy-ethyl]-5-(7H-pyrrolo[2,3-d]pyrimidin-4-yl)-5-azaspiro[2.5]octane-8-carboxamide, (8S)—N-[(1S)-1-(4-cyano-2-fluoro-phenyl)ethyl]-5-(7H-pyrrolo[2,3-d]pyrimidin-4-yl)-5-azaspiro[2.5]octane-8-carboxamide, N-[(1S)-1-(4-cyanophenyl)ethyl]-5-(7H-pyrrolo[2,3-d]pyrimidin-4-yl)-5-azaspiro[2.5]octane-8-carboxamide, (8S)—N-[(1S)-1-(4-cyanophenyl)ethyl]-5-(7H-pyrrolo[2,3-d]pyrimidin-4-yl)-5-azaspiro[2.5]octane-8-carboxamide, (8S)—N-[[3,3-difluoro-1-(hydroxymethyl)cyclobutyl]methyl]-5-(7H-pyrrolo[2,3-d]pyrimidin-4-yl)-5-azaspiro[2.5]octane-8-carboxamide, (8S)—N-[(1R)-1-cyclohexyl-2-hydroxy-ethyl]-5-(7H-pyrrolo[2,3-d]pyrimidin-4-yl)-5-azaspiro[2.5]octane-8-carboxamide, (8S)—N-[(2R)-2-cyclobutyl-2-hydroxy-ethyl]-5-(7H-pyrrolo[2,3-d]pyrimidin-4-yl)-5-azaspiro[2.5]octane-8-carboxamide, N-[(4-cyanophenyl)methyl]-5-(7H-pyrrolo[2,3-d]pyrimidin-4-yl)-5-azaspiro[2.5]octane-8-carboxamide, (8S)—N-[(1S)-1-(4-cyanophenyl)-2-hydroxy-1-methyl-ethyl]-5-(7H-pyrrolo[2,3-d]pyrimidin-4-yl)-5-azaspiro[2.5]octane-8-carboxamide, (8S)—N-[(1R)-1-(4-cyanophenyl)-2-hydroxy-1-methyl-ethyl]-5-(7H-pyrrolo[2,3-d]pyrimidin-4-yl)-5-azaspiro[2.5]octane-8-carboxamide, (8S)—N-[(2R)-2-(4-cyanophenyl)-2-hydroxy-ethyl]-5-(7H-pyrrolo[2,3-d]pyrimidin-4-yl)-5-azaspiro[2.5]octane-8-carboxamide, (8S)—N-[(1S,2S)-2-(5-fluoro-2-pyridyl)-2-hydroxy-1-(hydroxymethyl)ethyl]-5-(7H-pyrrolo[2,3-d]pyrimidin-4-yl)-5-azaspiro[2.5]octane-8-carboxamide, (8S)—N-[(4-cyano-2-fluoro-phenyl)methyl]-5-(7H-pyrrolo[2,3-d]pyrimidin-4-yl)-5-azaspiro[2.5]octane-8-carboxamide, (8S)—N-[(2S)-2-cyclopentyl-2-hydroxy-ethyl]-5-(7H-pyrrolo[2,3-d]pyrimidin-4-yl)-5-azaspiro[2.5]octane-8-carboxamide, 5-(7H-pyrrolo[2,3-d]pyrimidin-4-yl)-N-[(4-sulfamoyl-phenyl)methyl]-5-azaspiro[2.5]octane-8-carboxamide, (8S)—N-[(1R)-1-(2,4-difluorophenyl)-2-hydroxy-ethyl]-5-(7H-pyrrolo[2,3-d]pyrimidin-4-yl)-5-azaspiro[2.5]octane-8-carboxamide, N-[[3,3-difluoro-1-(hydroxymethyl)cyclobutyl]methyl]-5-(7H-pyrrolo[2,3-d]pyrimidin-4-yl)-5-azaspiro[2.5]octane-8-carboxamide, (8S)—N-[(2S)-2-(5-cyano-2-pyridyl)-2-hydroxy-ethyl]-5-(7H-pyrrolo[2,3-d]pyrimidin-4-yl)-5-azaspiro[2.5]octane-8-carboxamide, (8S)—N-[(1R)-1-(4-cyano-2-methyl-phenyl)-2-hydroxy-ethyl]-5-(7H-pyrrolo[2,3-d]pyrimidin-4-yl)-5-azaspiro[2.5]octane-8-carboxamide, (8S)—N-[2-(5-fluoro-2-pyridyl)-2-hydroxy-ethyl]-5-(7H-pyrrolo[2,3-d]pyrimidin-4-yl)-5-azaspiro[2.5]octane-8-carboxamide, N-[2-(4-cyanophenyl)-2-hydroxy-ethyl]-5-(7H-pyrrolo[2,3-d]pyrimidin-4-yl)-5-azaspiro[2.5]octane-8-carboxamide, (8S)—N-[(1S,2S)-2-(4-fluoro-3-methyl-phenyl)-2-hydroxy-1-methyl-ethyl]-5-(7H-pyrrolo[2,3-d]pyrimidin-4-yl)-5-azaspiro[2.5]octane-8-carboxamide, (8S)—N-[(1S,2R)-2-(5-fluoro-2-pyridyl)-2-hydroxy-1-methyl-ethyl]-5-(7H-pyrrolo[2,3-d]pyrimidin-4-yl)-5-azaspiro[2.5]octane-8-carboxamide, (3,3-difluorocyclobutyl)methyl (2R)-3-hydroxy-2-[[(8S)-5-(7H-pyrrolo[2,3-d]pyrimidin-4-yl)-5-azaspiro[2.5]octane-8-carbonyl]amino]propanoate, (8S)—N-[(1S,2S)-2-(4-cyanophenyl)-2-hydroxy-1-methyl-ethyl]-5-(7H-pyrrolo[2,3-d]pyrimidin-4-yl)-5-azaspiro[2.5]octane-8-carboxamide, (8S)—N-[(2R)-2-(5-fluoro-4-methyl-2-pyridyl)-2-hydroxy-ethyl]-5-(7H-pyrrolo[2,3-d]pyrimidin-4-yl)-5-azaspiro[2.5]octane-8-carboxamide, (8S)—N-[(1S,2R)-2-(4-fluorophenyl)-2-hydroxy-1-methyl-ethyl]-5-(7H-pyrrolo[2,3-d]pyrimidin-4-yl)-5-azaspiro[2.5]octane-8-carboxamide, (8S)—N-[(2S)-2-(5-fluoro-2-pyridyl)-2-hydroxy-ethyl]-5-(7H-pyrrolo[2,3-d]pyrimidin-4-yl)-5-azaspiro[2.5]octane-8-carboxamide, (8S)—N-[(1R)-1-(5-cyano-2-pyridyl)-2-hydroxy-ethyl]-5-(7H-pyrrolo[2,3-d]pyrimidin-4-yl)-5-azaspiro[2.5]octane-8-carboxamide, (8S)—N-[(1S)-1-(5-cyano-2-pyridyl)ethyl]-5-(7H-pyrrolo[2,3-d]pyrimidin-4-yl)-5-azaspiro[2.5]octane-8-carboxamide, (8S)—N-[(1-hydroxycyclopentyl)methyl]-5-(7H-pyrrolo[2,3-d]pyrimidin-4-yl)-5-azaspiro[2.5]octane-8-carboxamide, (8S)—N-[(1S,2R)-2-(4-fluorophenyl)-2-hydroxy-1-(hydroxymethyl)ethyl]-5-(7H-pyrrolo[2,3-d]pyrimidin-4-yl)-5-azaspiro[2.5]octane-8-carboxamide, (8S)—N-[(2S)-2-hydroxy-2-phenyl-ethyl]-5-(7H-pyrrolo[2,3-d]pyrimidin-4-yl)-5-azaspiro[2.5]octane-8-carboxamide, (8S)—N-[[1-(hydroxymethyl)cyclopentyl]methyl]-5-(7H-pyrrolo[2,3-d]pyrimidin-4-yl)-5-azaspiro[2.5]octane-8-carboxamide, N-[(4-fluorophenyl)methyl]-5-(7H-pyrrolo[2,3-d]pyrimidin-4-yl)-5-azaspiro[2.5]octane-8-carboxamide, (8S)—N-[(1R)-1-(4-cyano-3-methyl-phenyl)-2-hydroxy-ethyl]-5-(7H-pyrrolo[2,3-d]pyrimidin-4-yl)-5-azaspiro[2.5]octane-8-carboxamide, 5-(7H-pyrrolo[2,3-d]pyrimidin-4-yl)-N-[(3-sulfamoyl-phenyl)methyl]-5-azaspiro[2.5]octane-8-carboxamide, N-[(3,3-difluorocyclobutyl)methyl]-5-(7H-pyrrolo[2,3-d]pyrimidin-4-yl)-5-azaspiro[2.5]octane-8-carboxamide, (8S)—N-[(1R)-1-(5-cyano-2-pyridyl)-2-hydroxy-1-methyl-ethyl]-5-(7H-pyrrolo[2,3-d]pyrimidin-4-yl)-5-azaspiro[2.5]octane-8-carboxamide, N-[[1-(hydroxymethyl)cyclopentyl]methyl]-5-(7H-pyrrolo[2,3-d]pyrimidin-4-yl)-5-azaspiro[2.5]octane-8-carboxamide, N-[(3-cyanocyclobutyl)methyl]-5-(7H-pyrrolo[2,3-d]pyrimidin-4-yl)-5-azaspiro[2.5]octane-8-carboxamide, N-[1-(4-fluorophenyl)ethyl]-5-(7H-pyrrolo[2,3-d]pyrimidin-4-yl)-5-azaspiro[2.5]octane-8-carboxamide, (8S)—N-[(3,3-difluorocyclobutyl)methyl]-5-(7H-pyrrolo[2,3-d]pyrimidin-4-yl)-5-azaspiro[2.5]octane-8-carboxamide, N-[(2S)-2-hydroxy-2-phenyl-ethyl]-5-(7H-pyrrolo[2,3-d]pyrimidin-4-yl)-5-azaspiro[2.5]octane-8-carboxamide, (8S)—N-[(2S)-2-hydroxy-2-(p-tolyl)ethyl]-5-(7H-pyrrolo[2,3-d]pyrimidin-4-yl)-5-azaspiro[2.5]octane-8-carboxamide, N-[(1S)-1-(4-methoxyphenyl)ethyl]-5-(7H-pyrrolo[2,3-d]pyrimidin-4-yl)-5-azaspiro[2.5]octane-8-carboxamide, (8S)—N-[(1R)-1-(3-cyanophenyl)-2-hydroxy-ethyl]-5-(7H-pyrrolo[2,3-d]pyrimidin-4-yl)-5-azaspiro[2.5]octane-8-carboxamide, (8S)—N-[(1-hydroxycyclobutyl)methyl]-5-(7H-pyrrolo[2,3-d]pyrimidin-4-yl)-5-azaspiro[2.5]octane-8-carboxamide, N-[(1R)-2-hydroxy-1-phenyl-ethyl]-5-(7H-pyrrolo[2,3-d]pyrimidin-4-yl)-5-azaspiro[2.5]octane-8-carboxamide, N-[(3-cyanophenyl)methyl]-5-(7H-pyrrolo[2,3-d]pyrimidin-4-yl)-5-azaspiro[2.5]octane-8-carboxamide, (8S)—N-[(4-cyano-2-methoxy-phenyl)methyl]-5-(7H-pyrrolo[2,3-d]pyrimidin-4-yl)-5-azaspiro[2.5]octane-8-carboxamide, (8S)—N-[(1S,2S)-2-hydroxy-1-methyl-2-(p-tolypethyl]-5-(7H-pyrrolo[2,3-d]pyrimidin-4-yl)-5-azaspiro[2.5]octane-8-carboxamide, (8S)—N-[(1-hydroxycyclohexyl)methyl]-5-(7H-pyrrolo[2,3-d]pyrimidin-4-yl)-5-azaspiro[2.5]octane-8-carboxamide, (8S)—N-[(1S,2R)-2-(5-fluoro-4-methyl-2-pyridyl)-2-hydroxy-1-methyl-ethyl]-5-(7H-pyrrolo[2,3-d]pyrimidin-4-yl)-5-azaspiro[2.5]octane-8-carboxamide, N-[(5-cyano-2-pyridyl)methyl]-5-(7H-pyrrolo[2,3-d]pyrimidin-4-yl)-5-azaspiro[2.5]octane-8-carboxamide, (8S)—N-[(1R)-1-(4-fluoro-2-methyl-phenyl)-2-hydroxy-ethyl]-5-(7H-pyrrolo[2,3-d]pyrimidin-4-yl)-5-azaspiro[2.5]octane-8-carboxamide, (8S)—N-[(1S)-1-(5-cyano-2-pyridyl)-2-hydroxy-1-methyl-ethyl]-5-(7H-pyrrolo[2,3-d]pyrimidin-4-yl)-5-azaspiro[2.5]octane-8-carboxamide, benzyl (2R)-3-hydroxy-2-[[(8S)-5-(7H-pyrrolo[2,3-d]pyrimidin-4-yl)-5-azaspiro[2.5]octane-8-carbonyl]amino]propanoate, N-[(3-fluorophenyl)methyl]-5-(7H-pyrrolo[2,3-d]pyrimidin-4-yl)-5-azaspiro[2.5]octane-8-carboxamide, N-(cyclopentylmethyl)-5-(7H-pyrrolo[2,3-d]pyrimidin-4-yl)-5-azaspiro[2.5]octane-8-carboxamide, N-[[(1S,3S)-3-cyanocyclopentyl]methyl]-5-(7H-pyrrolo[2,3-d]pyrimidin-4-yl)-5-azaspiro[2.5]octane-8-carboxamide, (8S)—N-[(1R)-1-(4-cyano-3-fluoro-phenyl)ethyl]-5-(7H-pyrrolo[2,3-d]pyrimidin-4-yl)-5-azaspiro[2.5]octane-8-carboxamide, N-(4-pyridylmethyl)-5-(7H-pyrrolo[2,3-d]pyrimidin-4-yl)-5-azaspiro[2.5]octane-8-carboxamide, N-[(1S)-1-(3-cyanophenyl)ethyl]-5-(7H-pyrrolo[2,3-d]pyrimidin-4-yl)-5-azaspiro[2.5]octane-8-carboxamide, cyclopentylmethyl (2R)-3-hydroxy-2-[[(8S)-5-(7H-pyrrolo[2,3-d]pyrimidin-4-yl)-5-azaspiro[2.5]octane-8-carbonyl]amino]propanoate, N-[(1-hydroxycyclopentyl)methyl]-5-(7H-pyrrolo[2,3-d]pyrimidin-4-yl)-5-azaspiro[2.5]octane-8-carboxamide, (8S)—N-[(1R)-1-(4-cyano-2-ethyl-phenyl)-2-hydroxy-ethyl]-5-(7H-pyrrolo[2,3-d]pyrimidin-4-yl)-5-azaspiro[2.5]octane-8-carboxamide, N-[(4-methoxyphenyl)methyl]-5-(7H-pyrrolo[2,3-d]pyrimidin-4-yl)-5-azaspiro[2.5]octane-8-carboxamide, cyclopropylmethyl (2R)-3-hydroxy-2-[[(8S)-5-(7H-pyrrolo[2,3-d]pyrimidin-4-yl)-5-azaspiro[2.5]octane-8-carbonyl]amino]propanoate, (8S)—N-[(4-cyano-3-methoxy-phenyl)methyl]-5-(7H-pyrrolo[2,3-d]pyrimidin-4-yl)-5-azaspiro[2.5]octane-8-carboxamide, N-[(1S)-1-(4-cyanophenyl)-2-hydroxy-ethyl]-5-(7H-pyrrolo[2,3-d]pyrimidin-4-yl)-5-azaspiro[2.5]octane-8-carboxamide, N-benzyl-5-(7H-pyrrolo[2,3-d]pyrimidin-4-yl)-5-azaspiro[2.5]octane-8-carboxamide cyclopentyl (2R)-3-hydroxy-2-[[(8S)-5-(7H-pyrrolo[2,3-d]pyrimidin-4-yl)-5-azaspiro[2.5]octane-8-carbonyl]amino]propanoate, (8S)—N-[(1S)-1-(4-cyano-2-methoxy-phenyl)ethyl]-5-(7H-pyrrolo[2,3-d]pyrimidin-4-yl)-5-azaspiro[2.5]octane-8-carboxamide,

[1-(hydroxymethyl)cyclobutyl]methyl (2R)-3-hydroxy-2-[[(8S)-5-(7H-pyrrolo[2,3-d]pyrimidin-4-yl)-5-azaspiro[2.5]octane-8-carbonyl]amino]propanoate, N-[(1S)-1-phenylethyl]-5-(7H-pyrrolo[2,3-d]pyrimidin-4-yl)-5-azaspiro[2.5]octane-8-carboxamide, (8S)—N-[(1R)-1-[4-fluoro-2-(hydroxymethyl)phenyl]-2-hydroxy-ethyl]-5-(7H-pyrrolo[2,3-d]pyrimidin-4-yl)-5-azaspiro[2.5]octane-8-carboxamide, (8S)—N-[(1R)-1-(4-cyano-2-fluoro-phenyl)ethyl]-5-(7H-pyrrolo[2,3-d]pyrimidin-4-yl)-5-azaspiro[2.5]octane-8-carboxamide, N-[[(1R,2R)-2-cyanocyclopropyl]methyl]-5-(7H-pyrrolo[2,3-d]pyrimidin-4-yl)-5-azaspiro[2.5]octane-8-carboxamide, N-[(2R)-2-hydroxy-2-phenyl-ethyl]-5-(7H-pyrrolo[2,3-d]pyrimidin-4-yl)-5-azaspiro[2.5]octane-8-carboxamide, (8S)—N-[(1S,2S)-2-hydroxy-1-methyl-2-(2-pyridyl)ethyl]-5-(7H-pyrrolo[2,3-d]pyrimidin-4-yl)-5-azaspiro[2.5]octane-8-carboxamide, (8S)—N-[(1S,2R)-2-(5-fluoro-2-pyridyl)-2-hydroxy-1-(hydroxymethyl)ethyl]-5-(7H-pyrrolo[2,3-d]pyrimidin-4-yl)-5-azaspiro[2.5]octane-8-carboxamide, (8S)—N-[(2S)-2-(3-cyanophenyl)-2-hydroxy-ethyl]-5-(7H-pyrrolo[2,3-d]pyrimidin-4-yl)-5-azaspiro[2.5]octane-8-carboxamide, (8S)—N-[(1S,2S)-2-(5-fluoro-2-pyridyl)-2-hydroxy-1-methyl-ethyl]-5-(7H-pyrrolo[2,3-d]pyrimidin-4-yl)-5-azaspiro[2.5]octane-8-carboxamide, (8S)—N-[(1S)-1-(5-cyano-2-pyridyl)-2-hydroxy-ethyl]-5-(7H-pyrrolo[2,3-d]pyrimidin-4-yl)-5-azaspiro[2.5]octane-8-carboxamide, (8S)—N-[(1R)-1-(4-fluoro-2-methoxy-phenyl)-2-hydroxy-ethyl]-5-(7H-pyrrolo[2,3-d]pyrimidin-4-yl)-5-azaspiro[2.5]octane-8-carboxamide, (8S)—N-[(2S)-2-(5-fluoro-4-methyl-2-pyridyl)-2-hydroxy-ethyl]-5-(7H-pyrrolo[2,3-d]pyrimidin-4-yl)-5-azaspiro[2.5]octane-8-carboxamide, N-[(1R)-1-(4-cyanophenyl)ethyl]-5-(7H-pyrrolo[2,3-d]pyrimidin-4-yl)-5-azaspiro[2.5]octane-8-carboxamide, N-[[1-(cyanomethyl)cyclopropyl]methyl]-5-(7H-pyrrolo[2,3-d]pyrimidin-4-yl)-5-azaspiro[2.5]octane-8-carboxamide, N-[(1R)-1-(3,4-difluorophenyl)ethyl]-5-(7H-pyrrolo[2,3-d]pyrimidin-4-yl)-5-azaspiro[2.5]octane-8-carboxamide, N-phenethyl-5-(7H-pyrrolo[2,3-d]pyrimidin-4-yl)-5-azaspiro[2.5]octane-8-carboxamide N-(cyclobutylmethyl)-5-(7H-pyrrolo[2,3-d]pyrimidin-4-yl)-5-azaspiro[2.5]octane-8-carboxamide,

[1-(hydroxymethyl)cyclopropyl]methyl (2R)-3-hydroxy-2-[[(8S)-5-(7H-pyrrolo[2,3-d]pyrimidin-4-yl)-5-azaspiro[2.5]octane-8-carbonyl]amino]propanoate, N-[(1R)-1-(3-cyanophenyl)ethyl]-5-(7H-pyrrolo[2,3-d]pyrimidin-4-yl)-5-azaspiro[2.5]octane-8-carboxamide, N-(2-hydroxy-1-methyl-1-phenyl-ethyl)-5-(7H-pyrrolo[2,3-d]pyrimidin-4-yl)-5-azaspiro[2.5]octane-8-carboxamide, N-[(3-methoxhenyl)methyl]-5-(7H-pyrrolo[2,3-d]pyrimidin-4-yl)-5-azaspiro[2.5]octane-8-carboxamide, (8S)—N-[(1R)-1-(4-cyano-2-methoxy-phenyl)-2-hydroxy-ethyl]-5-(7H-pyrrolo[2,3-d]pyrimidin-4-yl)-5-azaspiro[2.5]octane-8-carboxamide, (8S)—N-[(1R)-1-(4-cyano-2-ethyl-phenyl)ethyl]-5-(7H-pyrrolo[2,3-d]pyrimidin-4-yl)-5-azaspiro[2.5]octane-8-carboxamide, (8S)—N-[(1R)-2-hydroxy-1-(2-pyridyl)ethyl]-5-(7H-pyrrolo[2,3-d]pyrimidin-4-yl)-5-azaspiro[2.5]octane-8-carboxamide, N-[(1R)-1-(3-cyano-4-fluoro-phenyl)ethyl]-5-(7H-pyrrolo[2,3-d]pyrimidin-4-yl)-5-azaspiro[2.5]octane-8-carboxamide, N-[(1R)-1-(3-fluoro-4-methoxy-phenyl)ethyl]-5-(7H-pyrrolo[2,3-d]pyrimidin-4-yl)-5-azaspiro[2.5]octane-8-carboxamide, (8S)—N-[(1S,2R)-2-(4-cyanophenyl)-2-hydroxy-1-methyl-ethyl]-5-(7H-pyrrolo[2,3-d]pyrimidin-4-yl)-5-azaspiro[2.5]octane-8-carboxamide, N-[(1S)-2-hydroxy-1-phenyl-ethyl]-5-(7H-pyrrolo[2,3-d]pyrimidin-4-yl)-5-azaspiro[2.5]octane-8-carboxamide, N-(3-pyridylmethyl)-5-(7H-pyrrolo[2,3-d]pyrimidin-4-yl)-5-azaspiro[2.5]octane-8-carboxamide, (8S)—N-[(2R)-3-[[3,3-difluoro-1-(hydroxymethyl)cyclobutyl]methylamino]-2-hydroxy-3-oxo-propyl]-5-(7H-pyrrolo[2,3-d]pyrimidin-4-yl)-5-azaspiro[2.5]octane-8-carboxamide, (8S)—N-[(2R)-3-[(3,3-difluorocyclobutyl)methylamino]-2-hydroxy-3-oxo-propyl]-5-(7H-pyrrolo[2,3-d]pyrimidin-4-yl)-5-azaspiro[2.5]octane-8-carboxamide, N-[(1R)-1-(4-fluoro-2-methoxy-phenyl)ethyl]-5-(7H-pyrrolo[2,3-d]pyrimidin-4-yl)-5-azaspiro[2.5]octane-8-carboxamide, (8S)—N-[(1S)-1-cyclohexyl-2-hydroxy-ethyl]-5-(7H-pyrrolo[2,3-d]pyrimidin-4-yl)-5-azaspiro[2.5]octane-8-carboxamide, (8S)—N-[(1S,2S)-2-(5-fluoro-4-methyl-2-pyridyl)-2-hydroxy-1-methyl-ethyl]-5-(7H-pyrrolo[2,3-d]pyrimidin-4-yl)-5-azaspiro[2.5]octane-8-carboxamide, N-[(1R)-1-(3-fluorophenyl)ethyl]-5-(7H-pyrrolo[2,3-d]pyrimidin-4-yl)-5-azaspiro[2.5]octane-8-carboxamide, (8S)—N-[(1S)-2-hydroxy-1-(2-pyridyl)ethyl]-5-(7H-pyrrolo[2,3-d]pyrimidin-4-yl)-5-azaspiro[2.5]octane-8-carboxamide, N-[(1R)-1-phenylethyl]-5-(7H-pyrrolo[2,3-d]pyrimidin-4-yl)-5-azaspiro[2.5]octane-8-carboxamide, N-[(1R)-1-benzyl-2-hydroxy-ethyl]-5-(7H-pyrrolo[2,3-d]pyrimidin-4-yl)-5-azaspiro[2.5]octane-8-carboxamide, Benzyl (2S)-3-hydroxy-2-[[(8S)-5-(7H-pyrrolo[2,3-d]pyrimidin-4-yl)-5-azaspiro[2.5]octane-8-carbonyl]amino]propanoate, N-[(1R)-1-(3-methoxhenyl)ethyl]-5-(7H-pyrrolo[2,3-d]pyrimidin-4-yl)-5-azaspiro[2.5]octane-8-carboxamide, N-[(1S)-1-benzyl-2-hydroxy-ethyl]-5-(7H-pyrrolo[2,3-d]pyrimidin-4-yl)-5-azaspiro[2.5]octane-8-carboxamide, (8R)—N-[(2S)-2-(4-cyanophenyl)-2-hydroxy-ethyl]-5-(7H-pyrrolo[2,3-d]pyrimidin-4-yl)-5-azaspiro[2.5]octane-8-carboxamide, N-[(1R)-1-(4-fluoro-3-methoxy-phenyl)ethyl]-5-(7H-pyrrolo[2,3-d]pyrimidin-4-yl)-5-azaspiro[2.5]octane-8-carboxamide, N-[(1R)-1-(5-methoxy-3-pyridyl)ethyl]-5-(7H-pyrrolo[2,3-d]pyrimidin-4-yl)-5-azaspiro[2.5]octane-8-carboxamide, (8R)—N-[(4-cyanophenyl)methyl]-5-(7H-pyrrolo[2,3-d]pyrimidin-4-yl)-5-azaspiro[2.5]octane-8-carboxamide, (8S)—N-[(1R,2S)-2-(4-cyanophenyl)-2-hydroxy-1-methyl-ethyl]-5-(7H-pyrrolo[2,3-d]pyrimidin-4-yl)-5-azaspiro[2.5]octane-8-carboxamide, (8S)—N-[(1S)-1-cyclobutyl-2-hydroxy-ethyl]-5-(7H-pyrrolo[2,3-d]pyrimidin-4-yl)-5-azaspiro[2.5]octane-8-carboxamide, (8S)—N-[(1R)-1-cyclobutyl-2-hydroxy-ethyl]-5-(7H-pyrrolo[2,3-d]pyrimidin-4-yl)-5-azaspiro[2.5]octane-8-carboxamide, (8S)—N-[(1S,2S)-2-(3,4-difluorophenyl)-2-hydroxy-1-methyl-ethyl]-5-(7H-pyrrolo[2,3-d]pyrimidin-4-yl)-5-azaspiro[2.5]octane-8-carboxamide, (8S)—N-[(1S,2S)-2-(3-fluorophenyl)-2-hydroxy-1-methyl-ethyl]-5-(7H-pyrrolo[2,3-d]pyrimidin-4-yl)-5-azaspiro[2.5]octane-8-carboxamide, (8S)—N-[(1S,2S)-2-hydroxy-1-methyl-2-(3-pyridyl)ethyl]-5-(7H-pyrrolo[2,3-d]pyrimidin-4-yl)-5-azaspiro[2.5]octane-8-carboxamide, (8S)—N-[(1S,2S)-2-hydroxy-1-methyl-2-phenyl-ethyl]-5-(7H-pyrrolo[2,3-d]pyrimidin-4-yl)-5-azaspiro[2.5]octane-8-carboxamide, (3,3-difluorocyclobutyl)methyl 5-(7H-pyrrolo[2,3-d]pyrimidin-4-yl)-5-azaspiro[2.5]octane-8-carboxylate, (3,3-difluorocyclobutyl)methyl (8S)-5-(7H-pyrrolo[2,3-d]pyrimidin-4-yl)-5-azaspiro[2.5]octane-8-carboxylate, (3,3-difluorocyclobutyl)methyl (8R)-5-(7H-pyrrolo[2,3-d]pyrimidin-4-yl)-5-azaspiro[2.5]octane-8-carboxylate,

[1-(hydroxymethyl)cyclopropyl]methyl (8S)-5-(7H-pyrrolo[2,3-d]pyrimidin-4-yl)-5-azaspiro[2.5]octane-8-carboxylate,

[1-(hydroxymethyl)cyclobutyl]methyl (8S)-5-(7H-pyrrolo[2,3-d]pyrimidin-4-yl)-5-azaspiro[2.5]octane-8-carboxylate,

[1-(hydroxymethyl)cyclopentyl]methyl (8S)-5-(7H-pyrrolo[2,3-d]pyrimidin-4-yl)-5-azaspiro[2.5]octane-8-carboxylate,

[3,3-difluoro-1-(hydroxymethyl)cyclobutyl]methyl (8S)-5-(7H-pyrrolo[2,3-d]pyrimidin-4-yl)-5-azaspiro[2.5]octane-8-carboxylate,

[1-(hydroxymethyl)cyclohexyl]methyl (8S)-5-(7H-pyrrolo[2,3-d]pyrimidin-4-yl)-5-azaspiro[2.5]octane-8-carboxylate,

[3-(hydroxymethyl)-1,1-dioxo-thietan-3-yl]methyl (8S)-5-(7H-pyrrolo[2,3-d]pyrimidin-4-yl)-5-azaspiro[2.5]octane-8-carboxylate,

[1-(cyanomethyl)cyclopropyl]methyl (8S)-5-(7H-pyrrolo[2,3-d]pyrimidin-4-yl)-5-azaspiro[2.5]octane-8-carboxylate and

[1-(cyanomethyl)cyclopropyl]methyl 5-(7H-pyrrolo[2,3-d]pyrimidin-4-yl)-5-azaspiro[2.5]octane-8-carboxylate, or pharmaceutically acceptable salts, hydrates or solvates thereof.

In an embodiment the invention provides a compound according to general formula I, wherein said compound is selected from (8S)—N-[(1S,2S)-2-cyclopentyl-2-hydroxy-1-methyl-ethyl]-5-(7H-pyrrolo[2,3-d]pyrimidin-4-yl)-5-azaspiro[2.5]octane-8-carboxamide or pharmaceutically acceptable salts, hydrates or solvates thereof.

In an embodiment the invention provides a compound according to general formula I, wherein said compound is selected from (8S)—N-[(1S,2R)-2-(5-fluoro-2-pyridyl)-2-hydroxy-1-methyl-ethyl]-5-(7H-pyrrolo[2,3-d]pyrimidin-4-yl)-5-azaspiro[2.5]octane-8-carboxamide or pharmaceutically acceptable salts, hydrates or solvates thereof.

In an embodiment the invention provides a compound according to general formula I, wherein said compound is selected from [3,3-difluoro-1-(hydroxymethyl)cyclobutyl]methyl (8S)-5-(7H-pyrrolo[2,3-d]pyrimidin-4-yl)-5-azaspiro[2.5]octane-8-carboxylate or pharmaceutically acceptable salts, hydrates or solvates thereof.

In an embodiment the invention provides a compound according to general formula I, wherein said compound is selected from (8S)—N-[(1S,2S)-2-cyclopentyl-2-hydroxy-1-methyl-ethyl]-5-(7H-pyrrolo[2,3-d]pyrimidin-4-yl)-5-azaspiro[2.5]octane-8-carboxamide or pharmaceutically acceptable salts thereof.

In an embodiment the invention provides a compound according to general formula I, wherein said compound is selected from (8S)—N-[(1S,2R)-2-(5-fluoro-2-pyridyl)-2-hydroxy-1-methyl-ethyl]-5-(7H-pyrrolo[2,3-d]pyrimidin-4-yl)-5-azaspiro[2.5]octane-8-carboxamide or pharmaceutically acceptable salts thereof.

In an embodiment the invention provides a compound according to general formula I, wherein said compound is selected from [3,3-difluoro-1-(hydroxymethyl)cyclobutyl]methyl (8S)-5-(7H-pyrrolo[2,3-d]pyrimidin-4-yl)-5-azaspiro[2.5]octane-8-carboxylate or pharmaceutically acceptable salts thereof.

In an embodiment the invention provides a compound according to general formula I, wherein said compound is selected from (8S)—N-[(1S,2S)-2-cyclopentyl-2-hydroxy-1-methyl-ethyl]-5-(7H-pyrrolo[2,3-d]pyrimidin-4-yl)-5-azaspiro[2.5]octane-8-carboxamide or hydrates thereof.

In an embodiment the invention provides a compound according to general formula I, wherein said compound is selected from (8S)—N-[(1S,2R)-2-(5-fluoro-2-pyridyl)-2- hydroxy-1-methyl-ethyl]-5-(7H-pyrrolo[2,3-d]pyrimidin-4-yl)-5-azaspiro[2.5]octane-8-carboxamide or hydrates thereof.

In an embodiment the invention provides a compound according to general formula I, wherein said compound is selected from [3,3-difluoro-1-(hydroxymethyl)cyclobutyl] methyl (8S)-5-(7H-pyrrolo[2,3-d]pyrimidin-4-yl)-5-azaspiro[2.5]octane-8-carboxylate or hydrates thereof.

In an embodiment the invention provides a compound according to general formula I, wherein said compound is selected from (8S)—N-[(1S,2S)-2-cyclopentyl-2-hydroxy-1-methyl-ethyl]-5-(7H-pyrrolo[2,3-d]pyrimidin-4-yl)-5-azaspiro[2.5]octane-8-carboxamide or solvates thereof.

In an embodiment the invention provides a compound according to general formula I, wherein said compound is selected from (8S)—N-[(1S,2R)-2-(5-fluoro-2-pyridyl)-2-hydroxy-1-methyl-ethyl]-5-(7H-pyrrolo[2,3-d]pyrimidin-4-yl)-5-azaspiro[2.5]octane-8-carboxamide or solvates thereof.

In an embodiment the invention provides a compound according to general formula I, wherein said compound is selected from [3,3-difluoro-1-(hydroxymethyl)cyclobutyl] methyl (8S)-5-(7H-pyrrolo[2,3-d]pyrimidin-4-yl)-5-azaspiro[2.5]octane-8-carboxylate or solvates thereof.

In an embodiment the invention provides a compound according to general formula I, wherein n is 2 and at least one of $R_1$ or $R_2$ independently is selected from the group consisting of hydroxyl, methyl and hydroxymethyl.

In an embodiment the invention provides a compound according to general formula I, wherein n is 1 and at least one of $R_1$ or $R_2$ independently is selected from the group consisting of hydroxyl, methyl and hydroxymethyl.

In an embodiment the invention provides a compound according to general formula I and Ia,

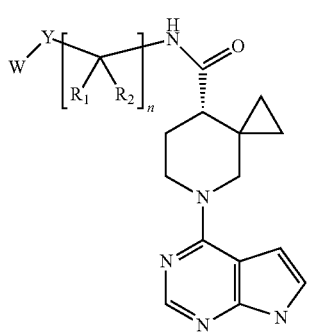

wherein $R_1$ and $R_2$ each independently are selected from the group consisting of hydrogen, deuterium, hydroxyl, cyano, halogen, $(C_1-C_3)$alkyl and hydroxyl$(C_1-C_3)$alkyl;
n is an integer selected from 1-3;
Y represents a bond, —C(O)O—*, —C(O)O$R_3$—* or —C(O)NH$R_3$—* wherein * denotes the point of attachment to W, and wherein $R_3$ represents $(C_1-C_4)$alkylene;
W is selected from the group consisting of phenyl, pyridyl, $(C_3-C_7)$cycloalkyl and 4-6 membered heterocycloalkyl comprising one or two heteroatoms selected from O, S or N, wherein said phenyl, pyridyl, $(C_3-C_7)$cycloalkyl and 4-6 membered heterocycloalkyl comprising one or two heteroatoms selected from O, S or N, are optionally substituted with one or more substitutents independently selected from hydroxyl, cyano, halogen, oxo, $(C_1-C_4)$alkyl, hydroxyl $(C_1-C_4)$alkyl, halo$(C_1-C_4)$alkyl, cyano$(C_1-C_4)$alkyl, $(C_1-C_4)$alkoxy, halo$(C_1-C_4)$alkoxy and —SO$_2$NH$_2$;

or pharmaceutically acceptable salts, hydrates or solvates thereof.

In an embodiment the invention provides a compound according to general formula I and Ib

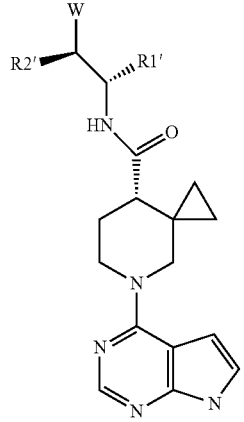

wherein $R_1'$ and $R_2'$ each independently are selected from the group consisting of hydroxyl, cyano, halogen, $(C_1-C_3)$ alkyl and hydroxyl$(C_1-C_3)$alkyl;
W is selected from the group consisting of phenyl, pyridyl, $(C_3-C_7)$cycloalkyl and 4-6 membered heterocycloalkyl comprising one or two heteroatoms selected from O, S or N, wherein said phenyl, pyridyl, $(C_3-C_7)$cycloalkyl and 4-6 membered heterocycloalkyl comprising one or two heteroatoms selected from O, S or N, are optionally substituted with one or more substitutents independently selected from hydroxyl, cyano, halogen, oxo, $(C_1-C_4)$alkyl, hydroxyl $(C_1-C_4)$alkyl, halo$(C_1-C_4)$alkyl, cyano$(C_1-C_4)$alkyl, $(C_1-C_4)$ alkoxy, halo$(C_1-C_4)$alkoxy and —SO$_2$NH$_2$;

or pharmaceutically acceptable salts, hydrates or solvates thereof.

In an embodiment the invention provides a compound according to general formula I wherein X represents O;
wherein $R_1$ and $R_2$ each independently are selected from the group consisting of hydrogen, deuterium, hydroxyl, cyano, halogen, $(C_1-C_3)$alkyl and hydroxyl$(C_1-C_3)$alkyl;
n is 1;
Y represents a bond;
W is selected from the group consisting of $(C_3-C_7)$ cycloalkyl and 4-6 membered heterocycloalkyl comprising one or two heteroatoms selected from O, S or N, wherein said $(C_3-C_7)$cycloalkyl and 4-6 membered heterocycloalkyl comprising one or two heteroatoms selected from O, S or N, are optionally substituted with one or more substitutents independently selected from hydroxyl, cyano, halogen, oxo, $(C_1-C_4)$alkyl, hydroxyl$(C_1-C_4)$alkyl, halo$(C_1-C_4)$alkyl, cyano$(C_1-C_4)$alkyl, $(C_1-C_4)$alkoxy, halo$(C_1-C_4)$alkoxy and —SO$_2$NH$_2$;

or pharmaceutically acceptable salts, hydrates or solvates thereof.

In an embodiment the invention provides a compound according to general formula I wherein X represents O;
wherein $R_1$ and $R_2$ represent hydrogen;
n is 1;
Y represents a bond;

W is selected from the group consisting of ($C_3$-$C_7$) cycloalkyl and 4-6 membered heterocycloalkyl comprising one or two heteroatoms selected from O, S or N, wherein said ($C_3$-$C_7$)cycloalkyl and 4-6 membered heterocycloalkyl comprising one or two heteroatoms selected from O, S or N, are optionally substituted with one or more substitutents independently selected from hydroxyl, cyano, halogen, oxo, ($C_1$-$C_4$)alkyl, hydroxyl($C_1$-$C_4$)alkyl, cyano($C_1$-$C_4$)alkyl;

or pharmaceutically acceptable salts, hydrates or solvates thereof.

Any combination of two or more embodiments described herein is considered within the scope of the present invention.

The present invention includes all embodiments wherein n, $R_1$, $R_2$, $R_3$, $R_a$, $R_b$ and $R_c$ are combined in any combination as anywhere described herein.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline forms, such as polymorphs and pseudopolymorphs, and also mixtures thereof.

Compounds of formula I comprise asymmetrically substituted (chiral) carbon atoms which give rise to the existence of isomeric forms, e.g. enantiomers and possibly diastereomers. The present invention relates to all such isomers, either in optically pure form or as mixtures thereof (e.g. racemates and racemic mixtures or partially purified optical mixtures). Pure stereoisomeric forms of the compounds and the intermediates of this invention may be obtained by the application of procedures known in the art. The various isomeric forms may be separated by physical separation methods such as selective crystallization and chromatographic techniques, e.g. high pressure liquid chromatography using chiral stationary phases. Enantiomers may be separated from each other by selective crystallization of their diastereomeric salts which may be formed with optically active amines, or with optically active acids. Optically purified compounds may subsequently be liberated from said purified diastereomeric salts. Enantiomers may also be resolved by the formation of diastereomeric derivatives. Alternatively, enantiomers may be separated by chromatographic techniques using chiral stationary phases. Pure stereoisomeric forms may also be derived from the corresponding pure stereoisomeric forms of the appropriate starting materials, provided that the reaction occur stereoselectively or stereospecifically. Preferably, if a specific stereoisomer is desired, said compound will be synthesized by stereoselective or stereospecific methods of preparation. These methods will advantageously employ chiral pure starting materials.

Furthermore, when a double bond or a fully or partially saturated ring system is present in the molecule geometric isomers may be formed. It is intended that any geometric isomer, as separated, pure or partially purified geometric isomers or mixtures thereof are included within the scope of the invention. The relative stereochemistry of a racemic mixture is indicated by a * in the naming of the relevant compounds of the present invention.

In the compounds of general Formula I, the atoms may exhibit their natural isotopic abundances, or one or more of the atoms may be artificially enriched in a particular isotope having the same atomic number, but an atomic mass or mass number different from the atomic mass or mass number found in nature. The present invention is meant to include all suitable isotopic variations of the compounds of general Formula I. For example, different isotopic forms of hydrogen include $^1H$, $^2H$ and $^3H$ and different isotopic forms of carbon include $^{12}C$, $^{13}C$ and $^{14}C$. Isotopically enriched compounds within general formula I can be prepared by conventional techniques well known to a person skilled in the art or by processes analogous to those described in the General Methods and Examples herein using appropriate isotopically enriched reagents and/or intermediates.

In one or more embodiments of the present invention, the compounds of formula I as defined above are useful in therapy and in particular useful for treatment of for example skin diseases like proliferative and inflammatory skin disorders, psoriasis, atopic dermatitis, scleroderma, rosacea, skin cancers, dermatis, dermatitis herpetiformis, dermatomyositis, vitiligo, alopecia areata, contact dermatitis, eczema, xerosis, ichthyosis, urticaria and chronic idiopathic pruritus; respiratory diseases like asthma, chronic obstructive pulmonary disease, pulmonary fibrosis, cystic fibrosis, rhinitis, bronchiolitis, byssinosis, pneumoconiosis, bronchiectasis, hypersensitivity pneumonitis, lung cancers, mesothelioma and sarcoidosis; gastrointestinal diseases like inflammatory bowel disease, ulcerative colitis, Crohn's disease, retroperitoneal fibrosis, celiac disease and cancers; eye diseases like myasthenia gravis, Sjögren's syndrome, conjunctivitis, scleritis, uveitis, dry eye syndrome, keratitis, iritis; systemic indications like lupus, multiple sclerosis, rheumatoid arthritis, type I diabetes and complications from diabetes, cancers, ankylosing spondylitis and psoriatic arthritis; as well as other autoimmune diseases and indications where immunosuppression would be desirable for example in organ transplantation.

In an embodiment the invention provides compounds of formula I as defined above for use in the prophylaxis and/or treatment of psoriasis or atopic dermatitis.

In an embodiment the invention provides a method of preventing, treating or ameliorating diseases of the immune system, such as autoimmune diseases, the method comprising administering to a person suffering from at least one of said diseases an effective amount of one or more compounds according to general formula I above optionally together with a pharmaceutically acceptable carrier or one or more excipients, optionally in combination with other therapeutically active compounds.

In an embodiment the invention provides a method of preventing, treating or ameliorating psoriasis or atopic dermatitis the method comprising administering to a person suffering from at least one of said diseases an effective amount of one or more compounds according to general formula I above optionally together with a pharmaceutically acceptable carrier or one or more excipients, optionally in combination with other therapeutically active compounds.

In an embodiment the invention provides a compound according to formula I for use in the manufacture of a medicament for the prophylaxis and/or treatment of diseases of the immune system, such as autoimmune disease, such as psoriasis or atopic dermatitis.

In one or more embodiments of the present invention, the compounds of formula I as defined above are useful as an anti-inflammatory agent capable of modulating the activity of a protein tyrosine kinase of the JAK family of protein tyrosine kinases, such as JAK1, JAK2, JAK3 or TYK2 protein tyrosine kinases.

Besides being useful for human treatment, the compounds of the present invention may also be useful for veterinary treatment of animals including mammals such as horses, cattle, sheep, pigs, dogs, and cats.

Pharmaceutical Compositions of the Invention

For use in therapy, compounds of the present invention are typically in the form of a pharmaceutical composition. The invention therefore relates to a pharmaceutical composition comprising a compound of formula I, optionally together with one or more other therapeutically active compound(s), together with pharmaceutically acceptable excipients, vehicles or carrier(s). The excipient must be "acceptable" in the sense of being compatible with the other ingredients of the composition and not deleterious to the recipient thereof.

Conveniently, the active ingredient comprises from 0.0001-99.9% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.001 mg and 1000 mg, preferably between 0.1 mg and 300 mg, such as 50-200 mg of a compound of formula I.

A suitable dosage of the compound of the invention will depend, inter alia, on the age and condition of the patient, the severity of the disease to be treated and other factors well known to the practising physician. The compound may be administered either orally, parenterally, topically, transdermally or interdermally or other routes according to different dosing schedules, e.g. daily, weekly or with monthly intervals. In general a single dose will be in the range from 0.001 to 400 mg/kg body weight. The compound may be administered as a bolus (i.e. the entire daily dosis is administered at once) or in divided doses two or more times a day.

In the context of topical treatment it may be more appropriate to refer to a "usage unit", which denotes a single dose which is capable of being administered to a patient, and which may be readily handled and packed, remaining as a physically and chemically stable unit dose comprising either the active material as such or a mixture of it with solid, semisolid or liquid pharmaceutical diluents or carriers.

The term "usage unit" in connection with topical use means a unitary, i.e. a single dose, capable of being administered topically to a patient in an application per square centimetre of the treatment area of from 0.001 microgram to 1 mg and preferably from 0.05 microgram to 0.5 mg of the active ingredient in question.

It is also envisaged that in certain treatment regimes, administration with longer intervals, e.g. every other day, every week, or even with longer intervals may be beneficial.

If the treatment involves administration of another therapeutically active compound it is recommended to consult Goodman & Gilman's The Pharmacological Basis of Therapeutics, 9$^{th}$ Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral (including sustained or controlled release), rectal, parenteral (including subcutaneous, intraperitoneal, intramuscular, intraarticular and intravenous), transdermal, intradermal, ophthalmic, topical, nasal, sublingual or buccal administration.

The formulations may conveniently be presented in dosage unit form and may be prepared by but not restricted to any of the methods well known in the art of pharmacy, e.g. as disclosed in Remington, *The Science and Practice of Pharmacy*, 21ed ed., 2005. All methods include the step of bringing the active ingredient into association with the carrier, which constitutes one or more accessory ingredients. In general, the formulations are prepared by uniformly and intimately bringing the active ingredient into association with a liquid carrier, semisolid carrier or a finely divided solid carrier or combinations of these, and then, if necessary, shaping the product into the desired formulation.

Formulations of the present invention suitable for oral and buccal administration may be in the form of discrete units as capsules, sachets, tablets, chewing gum or lozenges, each containing a predetermined amount of the active ingredient; in the form of a powder, granules or pellets; in the form of a solution or a suspension in an aqueous liquid or non-aqueous liquid, such as ethanol or glycerol; or in the form of a gel, a nano- or microemulsion, an oil-in-water emulsion, a water-in-oil emulsion or other dispensing systems. The oils may be edible oils, such as but not restricted to e.g. cottonseed oil, sesame oil, coconut oil or peanut oil. Suitable dispersing or suspending agents for aqueous suspensions include synthetic or natural surfactants and viscosifyring agents. The active ingredients may also be administered in the form of a bolus, electuary or paste.

A tablet may be made by compressing, moulding or freeze drying the active ingredient optionally with one or more accessory ingredients. Compressed tablets may be prepared by compressing, in a suitable machine, the active ingredient(s) in a free-flowing form such as a powder or granules, optionally mixed by a binder and/or filler; a lubricant; a disintegrating agent or a dispersing agent. Moulded tablets may be made by moulding, in a suitable machine, a mixture of the powdered active ingredient and suitable carrier moistened with an inert liquid diluent. Freeze dried tablets may be formed in a freeze-dryer from a solution of the drug substance. A suitable filler can be included.

Formulations for rectal administration may be in the form of suppositories in which the compound of the present invention is admixed with low melting point, water soluble or insoluble solids, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. Furthermore, the formulation may contain cosolvent, solubilising agent and/or complexation agents. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol.9, 1994, are also suitable for parenteral administration.

Alternatively, the compounds of formula I may be presented as a sterile, solid preparation, e.g. a freeze-dried powder, which is readily dissolved in a sterile solvent immediately prior to use.

Transdermal formulations may be in the form of a plaster, patch, microneedles, liposomal or nanoparticulate delivery systems or other cutaneous formulations applied to the skin.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol.2, 1989, may also be used to present the active ingredient for ophthalmic administration.

Formulations suitable for topical, such as dermal, intradermal or ophthalmic administration include liquid or semi-solid preparations such as liniments, lotions, gels, applicants, sprays, foams, filmforming systems, microneedles, micro- or nano-emulsions, oil-in-water or water-in-oil emulsions such as creams, ointments or pastes; or solutions or suspensions such as drops.

For topical administration, the compound of formula I may typically be present in an amount of from 0.001 to 20% by weight of the composition, such as 0.01% to about 10%, such as 0.1-5% but may also be present in an amount of up to about 100% of the composition.

Formulations suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T. Rhodes (Eds.), page 427-432, Marcel Dekker, New York; Modern Pharmaceutics, $3^{th}$ ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of formula I may include one or more additional ingredients such as diluents, buffers, flavouring agents, colourant, surface active agents, thickeners, penetration enhancing agents, solubility enhancing agents preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

Methods of Preparation

The compounds of the present invention can be prepared in a number of ways well known to those skilled in the art of synthesis. The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art of organic synthesis. Not all compounds falling into a given class may be compatible with some of the reaction conditions required in some of the methods described. Such restrictions to the substituents which are compatible with the reaction conditions will be readily apparent to one skilled in the art and alternative methods can be used.

Starting materials are either known or commercially available compounds or can be prepared by routine synthetic methods well known to a person skilled in the art.

General Procedures, Preparations and Examples $^1$H nuclear magnetic resonance (NMR) spectra were recorded at 300 MHz or 600 MHz. Chemical shift values ($\delta$, in ppm) are quoted in the specified solvent relative to internal tetramethylsilane ($\delta$=0.00) or chloroform ($\delta$=7.26). The value of a multiplet, either defined (doublet (d), double doublet (dd), triplet (t), quartet (q)) or not (m) at the approximate mid point is given unless a range is quoted. (br) indicates a broad peak. The organic solvents used were usually anhydrous. Chromatography was performed on Merck silica gel 60 (0.040-0-063 mm). The solvent ratios indicated refer to v:v unless otherwise noted.

The following abbreviations have been used throughout:
AcOH acetic acid
BINAP 2,2'-bis(diphenylphosphino)-1,1'-binaphthyl
BOC tert-butoxycarbonyl
Bz benzyl
Cbz carboxybenzyl
DABCO 1,4-diazabicyclo[2.2.2]octane
DCM dichloromethane
DIPEA N-ethyl-N-(propan-2-yl)propan-2-amine
DMAP N,N-Dimethylpyridin-4-amine
DMF N,N'-Dimethylformamide
DMSO dimethyl sulfoxide
EDCl 1-ethyl-3-(3-dimethylaminopropyl)carbodiimide
Et ethyl
EtOAc ethylacetate
EtOH ethanol
HATU 1-[bis(dimethylamino)methylene]-1H-1,2,3-triazolo[4,5-b]pyridinium 3-oxide hexafluorophosphate
HOBt N-hydroxybenzotriazole
L litre
LG leaving group
m milli
MBTE methyl tert-butyl ether
Me methyl
MeCN acetonitrile
NMR nuclear magnetic resonance
Ms mesylate
PG protecting group
Ph phenyl
Pr n-propyl
rt room temperature
SEM 2-(trimethylsilyl)ethoxymethyl
SNAr nucleophilic aromatic substitution
TBDMS tert-butyldimethylsilyl
TFA trifluoroacetic acid
THF tetrahydrofuran
TLC thin layer chromatography
Ts tosyl
v volume Preparative HPLC-MS Preparative HPLC-MS was performed on a Dionex APS-system with two Shimadzu PP150 prep. pumps and a Thermo MSQ Plus mass spectrometer. Column: Waters XTerra C-18, 150 mm×19 mm, 5 µm; solventsystem: A=water (0.1% formic acid) and B=acetonitrile (0.1% formic acid); flow rate=18 mL/min; method (10 min): Linear gradient method going from 10% B to 100% B in 6 minutes and staying at 100% B for another 2 minutes. The fractions were collected based on ion traces of relevant ions and PDA signal (240-400 nm).

UPLC-MS

Column: Waters Aquity UPLC HSS T3 1.8 µm, 2.1×50 mm.

Column temperature: 60 degrees Celcius.

UV: PDA 210-400 nm.

Injection volume: 2 μl.
Eluents: A: 10 mM Ammoniaacetate with 0.1% HCOOH added.
B: 100% Acetonitrile with 0.1% HCOOH added.

|  | Time | % A | % B | Flow |
|---|---|---|---|---|
| Gradient: | 0.0 | 95 | 5 | 1.2 |
|  | 0.9 | 5 | 95 | 1.2 |
|  | 0.91 | 5 | 95 | 1.3 |
|  | 1.2 | 5 | 95 | 1.3 |
|  | 1.21 | 5 | 95 | 1.2 |
|  | 1.4 | 95 | 5 | 1.2 |

MS: Electrospray switching between positive and negative ionisation.
Instrument: Waters Aquity UPLC
Waters SQD
UPLC-MS Method 7
Column: Acquity UPLC HSS T3 1.8 μm; 2.1×50 mm
Flow: 0.7 ml/min
Column temp.: 30° C.
Mobile phases: A: 10 mM Amm.acetate+0.1% HCOOH
B: CH3CN+0.1% HCOOH
UV: 240-400 nm
Injection volume: 2 μl

| Gradient: | 0.0 min. | 99% A | 1% B |
|---|---|---|---|
|  | 0.5 min. | 94% A | 6% B |
|  | 1.0 min. | 94% A | 6% B |
|  | 2.6 min. | 5% A | 95% B |
|  | 3.8 min. | 5% A | 95% B |
|  | 3.81 min. | 99% A | 1% B |
|  | 4.8 min. | 99% A | 1% B |

UPLC (inlet method): XE Metode 7 CM
MS—method: PosNeg_50_1000
Instruments: Waters Acquity UPLC
Waters LCT Premier XE
Chiral SFC Separation Column/dimensions: Chiral pak AD-H(250×30)mm
% CO2: 75.0%
% Co-solvent: 15.0% (MeOH)
Total Flow: 90.0 g/min
Back Pressure: 100 bar
UV: 285 nm
Stack time: 5.8 min
Load/inj: 26 mg
Solvent: Ethanol
Loadability/Inj: 80.0 mg/Inj Total No of injections 900
Instrument details: Make/Model: Thar SFC 200 new
Absolute Configuration Final test compounds, see Table 1, derived from either Intermediate (S)-SEM-acid or Intermediate (S)-acid gave more potent JAK inhibitors than similar compounds derived from either Intermediate rac-acid, Intermediate (R)-SEM-acid or Intermediate (R)-acid, see example 154 (racemic) vs example 155 (derived from Intermediate (S)-SEM-acid) vs. example 156 (derived from (R)-SEM-acid).

The absolute configuration was determined for Example 41 and Example 163 using X-ray crystallography, showing to be (S) at the C4 position of the piperidine ring. These two examples were prepared using Intermediate (S)-SEM-acid and hence all examples derived from Intermediate (S)-SEM-acid will have the same absolute configuration. Likewise, examples derived from the opposite enantiomer, namely Intermediate (R)-SEM-acid will be of the opposite absolute configuration, namely (R).

Example 41 and Example 163 were both co-crystallized with the JAK2 catalytic domain, and the X-ray structures of these ligand-protein complexes were solved. The absolute configurations of the ligands were assigned based on these crystal structures, and the absolute configuration of the Intermediate SEM-acid and the Intermediate acid used to prepare Examples 41 and 163 could thus be assigned as well.

General Procedure of Preparation

The compounds of the invention (I) can for example be prepared by the general methods outlined in Scheme 1 wherein R, R1, R2, Y, W, X and n are defined as described herein.

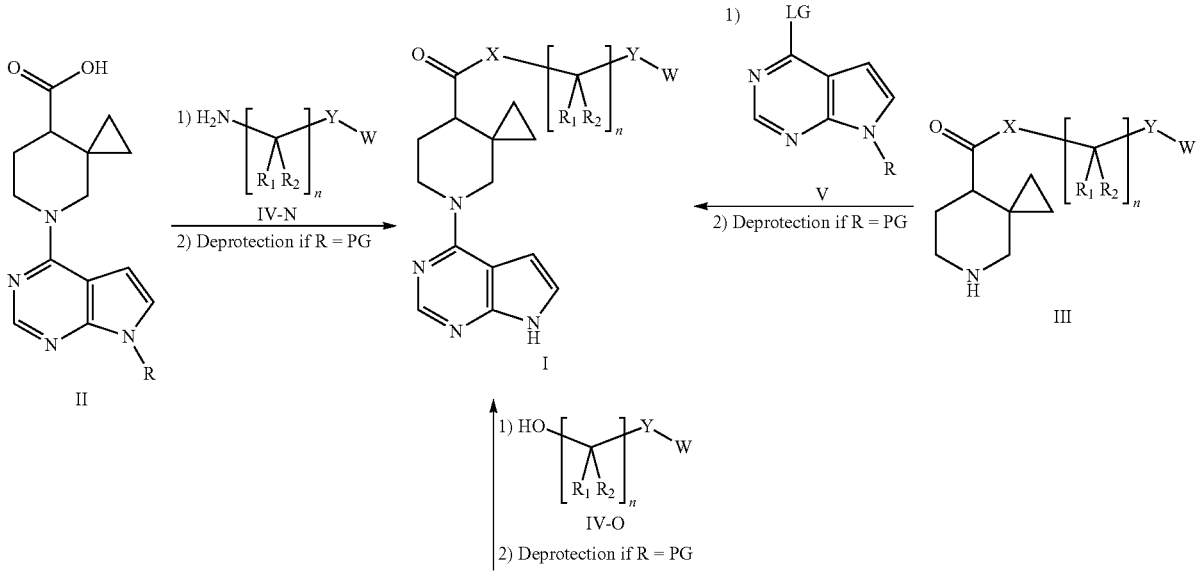

Scheme 1

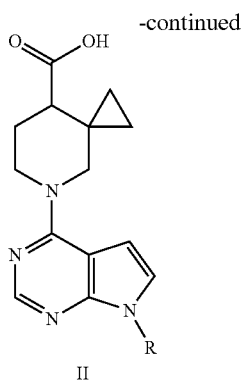

II

R is either —H or PG, where PG represents a suitable protecting group (see eg "Greene's Protective Groups in Organic Synthesis", 5$^{th}$ ed., Wuts P. G. M., John Wiley & Sons Inc.), such as, but not restricted to Bz, BOC, SEM and Ts.

LG represents a suitable leaving group, such as, but not restricted to: fluorine, chlorine, bromide, iodide, methoxy, N-imidazolyl-, —OMs or —OTs.

Compounds of general formula I (where X is NH) can be prepared by coupling of compounds of general formula II with amines of general formula IV-N under amide bond formation conditions, using for instance HATU or EDCI as coupling reagent in solvents like DMF or DCM using an alkyl amine base like DIPEA. In cases where II is protected (R=PG) the protection group is selectively removed to yield I.

Compounds of general formula I (where X is O) can be prepared by coupling of compounds of general formula II with alcohols of general formula IV-O under ester forming conditions, using for instance EDCI as coupling reagent in solvents like DMF or DCM with the use of DMAP. In cases where II is protected (R=PG) the protection group is selectively removed to yield I.

Alternatively, compounds of general formula I can be prepared by coupling of compounds of general formula III with compounds of general formula V under SnAr conditions, for instance using a solvent like DMF, MeCN or water and a base like DIPEA or $K_2CO_3$ at a suitable temperature such as from room temperature to 200° C. by conventional heating or microwave induced heating. In cases where V is protected (R=PG) the protection group is selectively removed to yield I.

Alternatively, the reaction between III and V to form I can be performed in the presence of a transition metal based catalyst with a suitable ligand and a suitable base and in a suitable solvent, at a suitable temperature such as from room temperature to 200° C. by conventional heating or microwave induced heating. Typical transition metals includes Pd and Cu, suitable ligands includes P-based ligands like 2,2'-bis(diphenylphosphino)1,1'-binaphthyl and 4,5-bis-diphenylphosphanyl-9,9-dimethyl-9H-xanthene, and N-based ligands like N,N'-dimethylcyclohexane-1,2-diamine, suitable bases includes $Cs_2CO_3$, sodium tert-butoxide and $K_3PO_4$, and suitable solvents include dioxane and toluene.

In cases where V is protected (R=PG) the protection group is selectively removed to yield I.

Some compounds of the general formula IV-N and IV-O are either commercially available or are prepared from commercially available molecules by synthetic transformations according to standard procedures known to a chemist skilled in the art of organic synthesis.

Other compounds of the general formula IV-N and IV-O are not commercially available and require special synthetic transformations as described in the experimental section under Intermediates.

Compounds of the general formula V are either commercially available or are prepared from commercially available molecules by synthetic transformations according to standard procedures known to a chemist skilled in the art of organic synthesis.

Compounds of general formula II can for example be prepared as outlined in Scheme 2.

Scheme 2

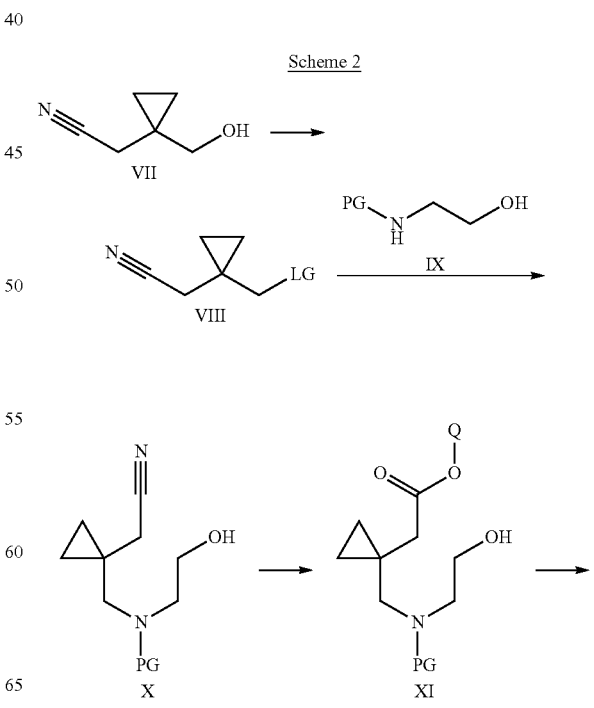

-continued

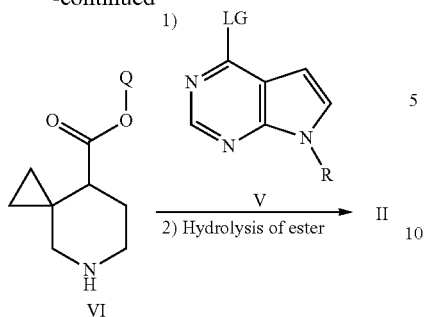

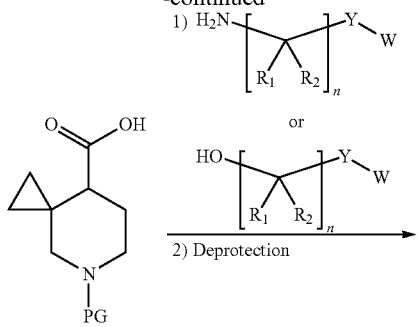

Commercially available VII can be activated by transforming the hydroxy group into a leaving group like halogen or Ts, which can then be further reacted with commercially available IX to give X. The cyano group in compound X can then be hydrolysed to the corresponding carboxylic acid followed by esterification to give compound XI, where Q is a simple alkyl like Et. Transformation of the hydroxy group in XI in to halogen or Ts, followed by intramolecular ring closure under basic conditions and deprotection yields racemic VI.

Compound VI can be coupled with compounds of general formula V under SnAr conditions, for instance using a solvent like DMF, MeCN or water and a base like DIPEA or $K_2CO_3$ at a suitable temperature such as from room temperature to 200° C. by conventional heating or microwave induced heating. Hydrolysis of the carboxylic acid ester yields II.

Alternatively, the reaction between VI and V can be performed in the presence of a transition metal based catalyst with a suitable ligand and a suitable base and in a suitable solvent, at a suitable temperature such as from room temperature to 200° C. by conventional heating or microwave induced heating. Typical transition metals includes Pd and Cu, suitable ligands includes P-based ligands like 2,2'-bis(diphenylphosphino)1,1'-binaphthyl and 4,5-bis-diphenylphosphanyl-9,9-dimethyl-9H-xanthene, and N-based ligands like N,N'-dimethylcyclohexane-1,2-diamine, suitable bases includes $Cs_2CO_3$, sodium tert-butoxide and $K_3PO_4$, and suitable solvents include dioxane and toluene.

Hydrolysis of the carboxyilic acid ester yields II.

Compound VI can also be modified by synthetic transformations according to standard procedures known to a chemist skilled in the art of organic synthesis to give compounds of general formula III which can then be coupled with compounds of general formula V as outlined in Scheme 3.

Scheme 3

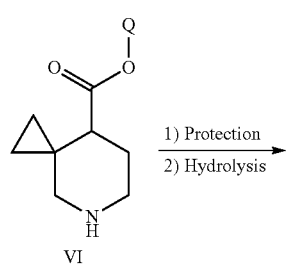

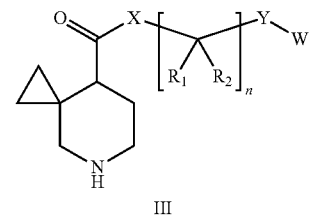

Alternatively, compounds of general formula VI can be prepared as outlined in Scheme 4.

Scheme 4

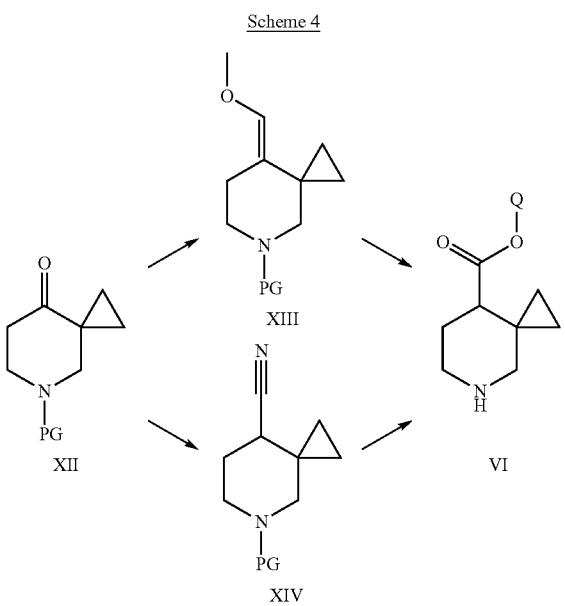

Commercially available XII (PG=BOC or Bz) can be transformed in to XIII under Horner-Wadsworth-Emmons type conditions by reaction with e.g. (methoxymethyl)phosphonic acid diethylester, follow by ether cleavage, oxidation and esterification to yield VI.

Alternatively, commercially available XII (PG=BOC or Bz) can be transformed in to XIV in a Van Leusen reaction using tosylmethyl isocyanide (Tosmic). Hydrolysis of the nitril group and esterification yields VI.

Alternatively, compounds of general formula VI can be prepared as outlined in Scheme 5

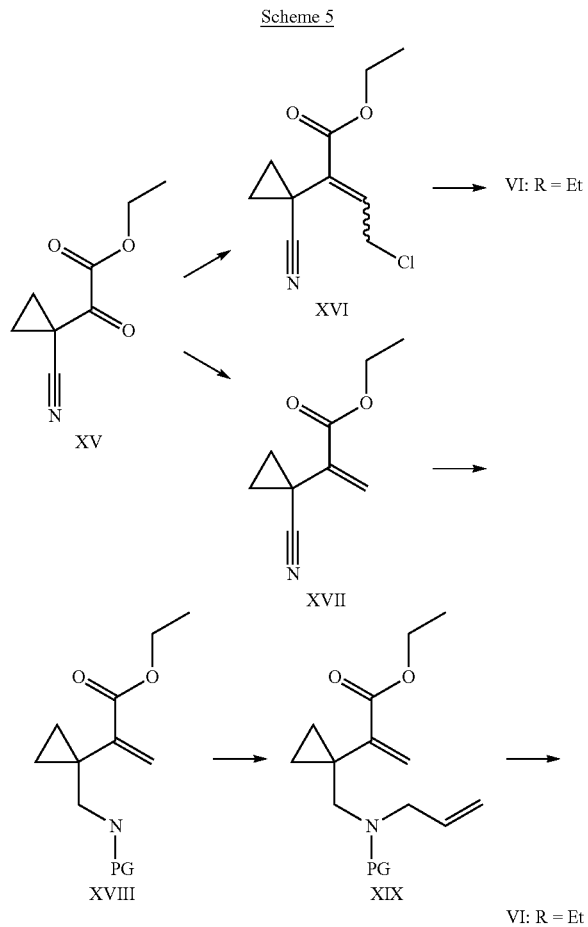

Commercially available XV can be transformed in to XVI under Horner-Wadsworth-Emmons type conditions by reaction with e.g. commercially available chloroethylphosphonic acid diethylester, follow by reduction of the nitrile, intramolecular cyclization and alkene reduction to yield VI (Q=Et).

Alternatively, commercially available XV can be transformed in to XVII under for instance Tebbe or Wittig methylenation conditions, followed by reduction of the nitrile, appropriate N protection and N-allylation to give compounds of general formula XIX. Under ring-closing methathesis conditions, followed by hydrogenation of the alkenen, compounds of general formula XIX can be converted in to compounds of general formula VI (Q=Et).

INTERMEDIATES

Intermediate 1

[1-(Cyanomethyl)Cyclopropyl]Methyl 4-Methylbenzenesulfonate

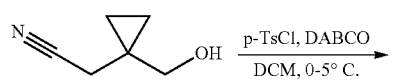

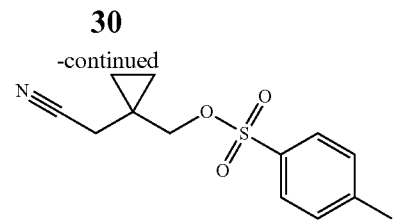

A solution of p-TsCl (165.0 mmol, 31.46 g) in DCM (60 mL) was added slowly to a solution of 2-[1-(hydroxymethyl)cyclopropyl]acetonitrile (150.0 mmol, 16.67 g) and DABCO (187.5 mmol, 21.03 g) in DCM (200 mL) at 5° C. A white precipitate was formed after few minutes. Stirred at rt for 30 minutes and diluted with Et$_2$O (150 mL). The white solid (DABCO—HCl) was filtered off and washed with ether. The combined organic layers were washed with 0.5% HCl (100 mL), dried (Na$_2$SO$_4$) and evaporated. Chromatographed on silica using EtOAc:heptane as eluent. Intermediate 1 (36.67 g) was isolated as a thick clear oil in 92% yield.

$^1$HNMR (300 MHz, Chloroform-d): δ 7.88-7.71 (m, 2H), 7.45-7.29 (m, 2H), 3.93 (s, 2H), 2.48 (d, J=10.0 Hz, 5H), 0.78-0.63 (m, 4H).

Intermediate 2

2-[1-[[Benzyl(2-hydroxyethypamino]methyl]cyclopropyl]acetonitrile

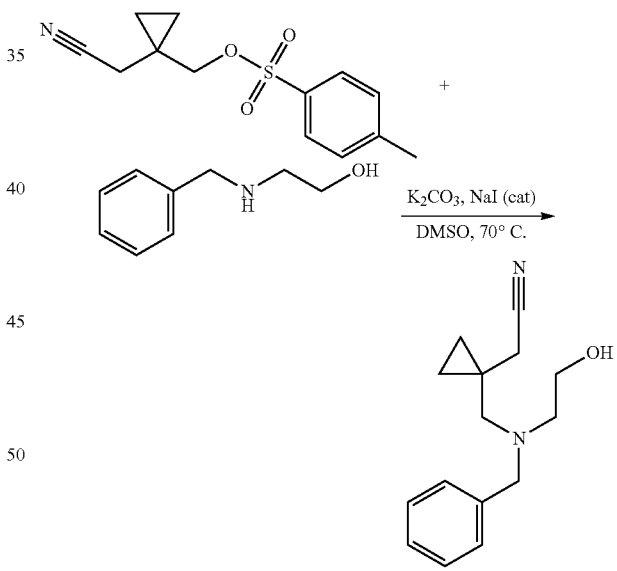

A solution of Intermediate 1 (106 mmol, 28.0 g) in dry THF (20 mL) was added dropwise (over ~45 min) to a mixture of N-benzyl-ethanolamine (211 mmol, 31.9 g), anhydrous potassium carbonate (106 mmol, 14.6 g) and NaI (10.6 mmol, 1.58 g) in dry DMSO (100 mL) at 70° C. The mixture was stirred overnight at 74° C. under argon. Cooled and poured into water (400 mL) and extracted with Et$_2$O (4×150 mL), dried (Na$_2$SO$_4$) and evaporated. The crude product was chromatographed on silica using heptane:EtOAc as eluent. Intermediate 2 (12.65 g) was isolated as a pale yellow oil in 49% yield.

$^1$HNMR (300 MHz, Chloroform-d): δ 7.40-7.19 (m, 5H), 3.72-3.64 (m, 4H), 2.67 (t, J=5.5 Hz, 2H), 2.52 (s, 2H), 2.48 (s, 2H), 2.18 (t, J=5.4 Hz, 1H), 0.66-0.56 (m, 2H), 0.56-0.47 (m, 2H).

Intermediate 3

Ethyl 2-[1-[[benzyl(2-hydroxyethyl)amino]methyl]cyclopropyl]acetate

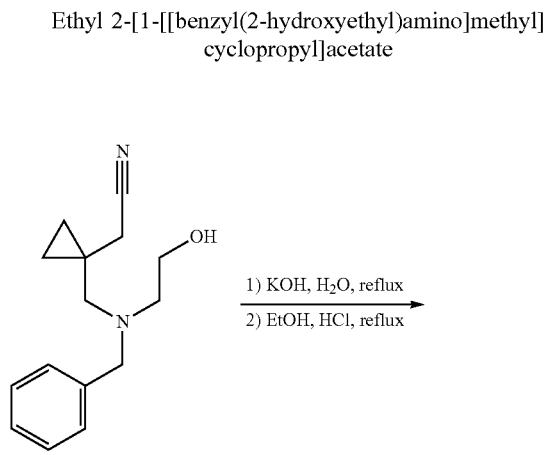

A mixture of Intermediate 2 (26.5 mmol, 6.48 g) and KOH (424 mmol, 23.8 g) in water (100 mL) was refluxed for 2 days giving a clear pale yellow solution of the potassium carboxylate. Concentrated HCl was added until pH~3-4 and the resulting mixture were evaporated to dryness. The solid consists of carboxylic acid and KCl. While drying on the freeze dryer, a solution of acetyl chloride (13 mL, 183 mmol) in abs. EtOH (400 mL) was prepared. This HCl solution was transferred to the solid and the mixture was refluxed for 3 hours. All the volatiles were evaporated and the residue was treated with 0.5 M NaOH until pH~9-10. Extraction with EtOAc (3×100 mL), followed by drying (Na$_2$SO$_4$), filtration and concentration in vacuum gave Intermediate 3 (7.65 g) as an orange oil in 99% yield which was used directly in the next step without further purification.

UPLC-MS: $t_R$=0.45 (M+H$^+$)=292.3

$^1$HNMR (300 MHz, Chloroform-d): δ 7.37-7.18 (m, 5H), 4.12 (q, J=7.1 Hz, 2H), 3.66 (s, 2H), 3.60-3.52 (m, 2H), 2.61-2.53 (m, 2H), 2.47 (s, 2H), 2.40 (s, 2H), 1.24 (t, J=7.1 Hz, 3H), 0.59-0.38 (m, 4H).

Intermediate 4

Ethyl 5-Benzyl-5-Azaspiro[2.5]Octane-8-Carboxylate

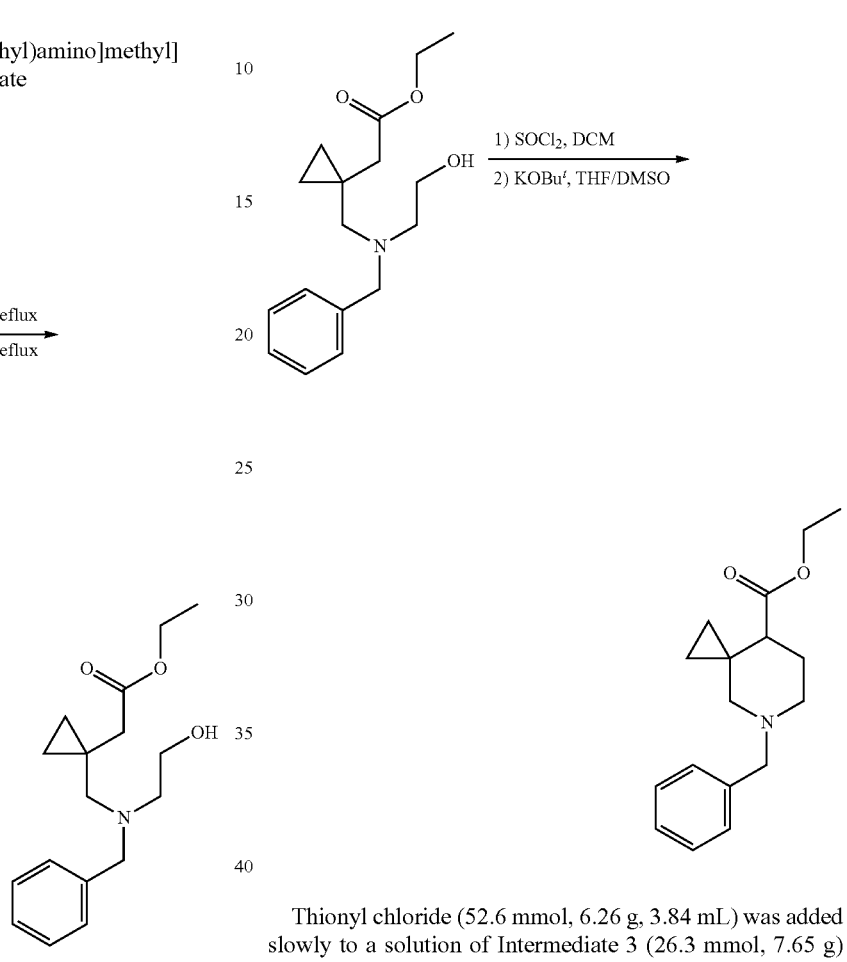

Thionyl chloride (52.6 mmol, 6.26 g, 3.84 mL) was added slowly to a solution of Intermediate 3 (26.3 mmol, 7.65 g) in DCM (80 mL) and stirred at rt for 2 hours. All the volatiles were evaporated and ethyl 2-[1-[[benzyl(2-chloroethyl)amino]methyl]-cyclopropyl]acetate hydrochloride (9.11 g) was isolated as a pale yellow solid 100% yield, and used directly in the next step without further purification.
UPLC-MS: $t_R$=0.99 (M+H$^+$)=310.2

Ethyl 2-[1-[[benzyl(2-chloroethyl)amino]methyl]cyclopropyl]acetate hydrochloride (26.3 mmol, 9.11 g) was dissolved in dry DMSO (50 mL) and added quickly to a solution of potassium tert-butoxide (65.8 mmol, 7.38 g) in dry THF (250 mL) at rt under argon. The dark brown solution was stirred at rt for 1 hour, poured into water (300 mL) and extracted with Et$_2$O (3×100 mL). The ether layer was washed with brine (2×50 mL), dried (Na$_2$SO$_4$) filtered through a short silica plug and evaporation gave Intermediate 4 (5.87 g) as an orange oil in 81% yield.

UPLC-MS: $t_R$=0.53 (M+H$^+$)=274.2

$^1$HNMR (300 MHz, Chloroform-d): δ 7.39-7.16 (m, 5H), 4.11 (qd, J=7.1, 1.5 Hz, 2H), 3.56-3.41 (m, 2H), 2.64-2.47 (m, 2H), 2.35 (d, J=11.6 Hz, 1H), 2.16 (t, J=5.4 Hz, 1H), 2.00 (dtt, J=17.1, 13.1, 6.4 Hz, 3H), 1.24 (t, J=7.1 Hz, 3H), 0.65-0.54 (m, 1H), 0.47-0.30 (m, 3H).

Intermediate 5

Ethyl 5-Azaspiro[2.5]Octane-8-Carboxylate

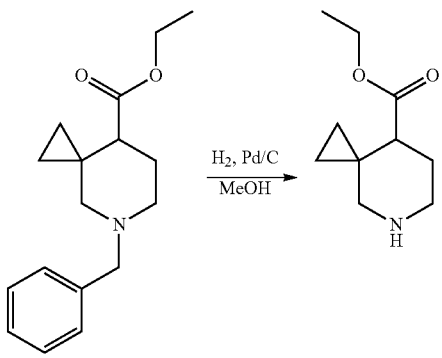 [SMILES: "MeOH" ; CCOC(=O)C1CCN(Cc2ccccc2)CC12CC2 ; CCOC(=O)C1CCNCC12CC2]

Intermediate 4 (6.80 mmol, 1.86 g) was dissolved in MeOH (60 mL) and hydroge-nated over 10% Pd/C (0.50 g) at 4 bar H$_2$(g) on the Parr shaker for 3 hours. Filtration and evaporation gave Intermediate 5 (1.10 g) as a pale yellow oil in 88% yield which was used without further purification.

$^1$HNMR (300 MHz, Chloroform-d): δ 4.13 (qd, J=7.1, 1.8 Hz, 2H), 2.36 (d, J=13.1 Hz, 1H), 2.25 (t, J=5.3 Hz, 1H), 1.94 (dtd, J=13.5, 5.9, 3.5 Hz, 1H), 1.80 (dddd, J=13.5, 8.8, 4.8, 4.0 Hz, 1H), 1.26 (t, J=7.1 Hz, 3H), 0.66-0.56 (m, 1H), 0.46-0.34 (m, 3H).

Intermediate Rac-SEM-Acid

5-[7-(2-Trimethylsilylethoxymethyl)Pyrrolo[2,3-d]Pyrimidin-4-Yl]-5-Azaspiro[2.5]Octane-8-Carboxylic Acid (Rac-SEM-Acid)

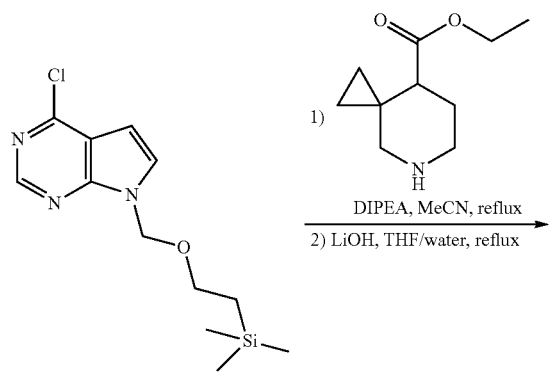

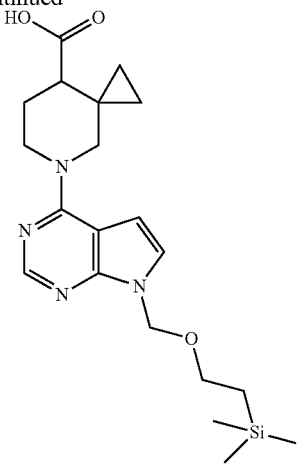

S$_N$Ar Reaction:

A mixture of Intermediate 5 (60 g, 330.5 mmol), 2-[(4-chloropyrrolo[2,3-d]pyrimidin-7-yl)methoxy]ethyl-trimethyl-silane (85 g, 330.5 mmol) and DIPEA (108 mL, 625 mmol) in dry MeCN (500 mL) was refluxed for 16 hours. All the volatiles were evaporated and the resulting residue was treated with water and extracted with ethyl acetate (2×500 mL). The combined organic layers were washed with brine (500 mL), dried over Na$_2$SO$_4$, concentrated and chromatographed on silica using EtOAc:heptane as eluent. Ethyl 5-[7-(2-trimethylsilylethoxymethyl)pyrrolo[2,3-d]pyrimidin-4-yl]-5-azaspiro[2.5]octane-8-carboxylate (rac-SEM ethyl ester) was isolated as a light brown oil (63 g) in 49% yield and used directly in the next step.

Ester Hydrolysis:

To a solution of rac-SEM ethyl ester from above (63 g, 146.5 mmol) in THF (630 mL), LiOH·H$_2$O (61.4 g, 1465 mmol) and H$_2$O (190 mL) were added and refluxed for 72 hours. On completion volatiles were evaporated under vacuum and the resulting reaction mixture was washed with EtOAc. Separated aqueous layer was acidified with 6M HCl (pH~4), and the obtained solid was filtered and dried in vacuum to afford 5-[7-(2-trimethylsilyl-ethoxymethyl)pyrrolo[2,3-d]pyrimidin-4-yl]-5-azaspiro[2.5]octane-8-carboxylic acid (Intermediate rac-SEM-acid) as a white solid (33 g) in 56% yield.

UPLC-MS: t$_R$=0.76 (M+H$^+$)=403.4

$^1$HNMR (600 MHz, DMSO-d$_6$) δ 12.27 (s br, 1H), 8.16 (s, 1H), 7.34 (d, J=3.7 Hz, 1H), 6.65 (d, J=3.8 Hz, 1H), 5.50 (s, 2H), 4.19 (dt, J=13.4, 4.9 Hz, 1H), 3.82-3.67 (m, 3H), 3.49 (dd, J=8.5, 7.5 Hz, 2H), 2.29 (t, J=5.2 Hz, 1H), 1.95 (m, 2H), 0.80 (dd, J=8.5, 7.4 Hz, 2H), 0.55 (ddd, J=18.1, 9.6, 4.7 Hz, 2H), 0.41 (ddd, J=23.2, 9.4, 4.8 Hz, 2H), −0.10 (s, 9H).

Separation of the enantiomers of Intermediate rac-SEM-acid was achieved using chiral SCF chromatography and gave the pure enantiomers.

Intermediate (S)-SEM-Acid

The first eluting enantiomer, t$_R$=2.74 min, chemical purity 99% and ee=99%. $^1$H NMR identical to Intermediate rac-SEM-acid

Intermediate (R)-SEM-Acid

The first eluting enantiomer, t$_R$=3.37 min, chemical purity 99% and ee=99%. $^1$H NMR identical to Intermediate rac-SEM-acid Intermediate (S)-Acid (8S)-5-(7H-pyrrolo[2,3-d]pyrimidin-4-yl)-5-azaspiro[2.5]octane-8-carboxylic acid

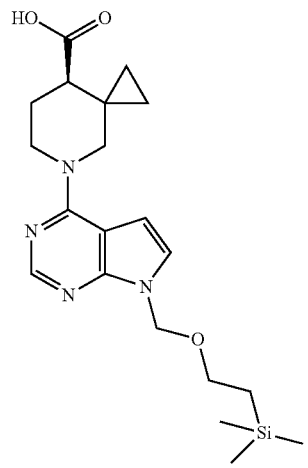

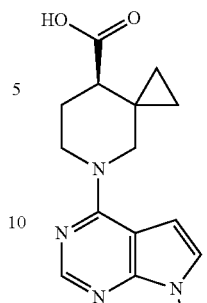

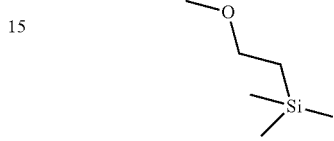

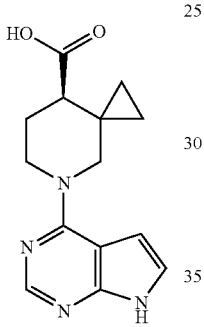

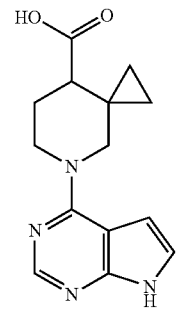

TFA (35.89 mmol, 2.75 mL) was added to a solution of Intermediate (S)-SEM-acid (3.0 mmol, 1.20 g) in MeCN (5 mL) and stirred at rt for 18 hours. LCMS showed full conversion to the formaldehyde adduct (N—CH$_2$OH). All the volatiles were evaporated and the residue was dissolved in MeCN (4 mL) and 1,2-diaminoethane (30 mmol, 2.00 mL) was added. The mixture was stirred at rt for 2 hours and 50° C. for 20 min giving a slurry. All the volatiles were evaporated and the residue was stirred in water (10 mL) and acidified to pH=3 with 1M KHSO$_4$.

Intermediate (S)-acid (2.39 mmol, 80% Yield, 652 mg) was isolated as a white solid.

UPLC-MS: t$_R$=0.37 (M+H$^+$)=273.3

$^1$HNMR (300 MHz, DMSO-d$_6$) δ 11.65 (s, 1H), 8.10 (s, 1H), 7.21-7.08 (m, 1H), 6.54 (d, J=3.6 Hz, 1H), 4.19 (dt, J=13.4, 5.0 Hz, 1H), 3.85-3.64 (m, 3H), 2.29 (t, J=5.2 Hz, 1H), 2.07-1.85 (m, 2H), 0.62-0.34 (m, 4H, cyclopropane).

Intermediate (R)-Acid (8R)-5-(7H-pyrrolo[2,3-d]pyrimidin-4-yl)-5-azaspiro[2.5]octane-8-carboxylic acid The compound was prepared in a similar manner as described for Intermediate (S)-acid, but starting from Intermediate (R)-SEM-acid.

$^1$H NMR identical to Intermediate (S)-Acid

UPLC-MS method 7: t$_R$=1.63 (M+H$^+$)=273.13

Intermediate Rac-Acid 5-(7H-pyrrolo[2,3-d]pyrimidin-4-yl)-5-azaspiro[2.5]octane-8-carboxylic acid

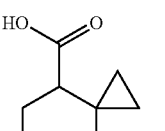

-continued

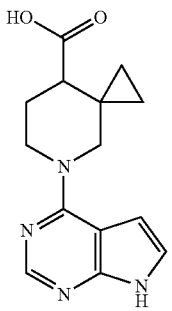

The compound was prepared in a similar manner as described for Intermediate (S)-acid, but starting from Intermediate rac-SEM-acid.

¹H NMR identical to Intermediate (S)-acid
UPLC-MS method 7: $t_R$=1.63 (M+H⁺)=273.13

Intermediate 6 tert-butyl N-[(1S)-2-cyclopentyl-1-methyl-2-oxo-ethyl]carbamate

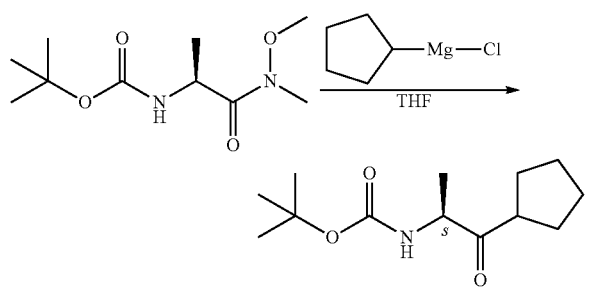

Cyclopentylmagnesium chloride (2 M in Et₂O, 61.6 mmol, 30.8 mL) was added to a solution of tert-butyl N-[(1S)-2-[methoxy(methyl)amino]-1-methyl-2-oxo-ethyl]-carbamate (20.5 mmol, 4.77 g) in dry THF (100 mL) under argon at −50° C. The mixture was stirred for 20 min at −50° C., the cooling bath was removed and the mixture was allowed to warm to rt. Stirred for another 2 hours at rt. TLC showed no more starting material. Quenched with 10% NH₄Cl (50 mL), extracted with EtOAc (2×50 mL), dried (Na₂SO₄) and evaporated. Vacuum-Flash Chromatographed on silica using EtOAc:heptane as eluent.

Intermediate 6 (15.4 mmol, 3.71 g) was isolated as a white solid in 75% yield.

¹HNMR (300 MHz, Chloroform-d): δ 5.31 (s br, 1H), 4.42 (t br, J=7.3 Hz, 1H), 3.11-2.94 (m, 1H), 2.06-1.52 (m, 8H), 1.44 (s, 9H), 1.33 (d, J=7.2 Hz, 3H).

Intermediate 7 tert-butyl N-[(1S,2S)-2-cyclopentyl-2-hydroxy-1-methyl-ethyl]carbamate

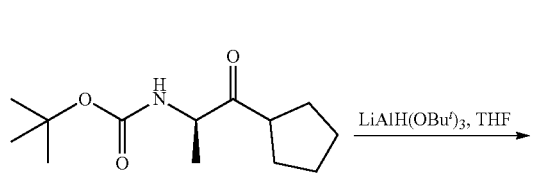

-continued

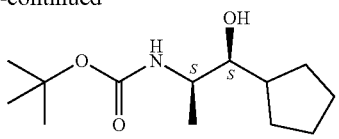

Lithium tri-tert-butoxyaluminum hydride in THF (14.4 mmol, 14.4 mL) was added to a solution of Intermediate 6 (14.4 mmol, 3.47 g) in dry THF (100 mL) at −60° C. under argon. Stirred for 30 minutes at this temp, cooling bath removed and warmed to rt. Quenched with 3% citric acid (50 mL), extracted with EtOAc (2×50 mL), dried (Na₂SO₄) and evaporated. A clear oil was isolated which contained 78% (S,S) and 22% (R,S). Chromatographed twice on silica using EtOAc:heptane (0→40%) as eluent. TLC (EtOAc:heptane, 1:1 v/v): $R_f$ (S,S) 0.70 and $R_f$ (R,S)≈0.63

Intermediate 7 (2.28 g) was isolates as a clear oil in 64% yield.

¹HNMR (300 MHz, Chloroform-d): δ 4.75 (s br, 1H), 3.74 (t, br, 1H), 3.22 (s, br, 1H), 1.95 (m, 2H), 1.79 (m, 2H), 1.70-1.50 (m, 2H), 1.44 (s, 9H), 1.39-1.22 (m, 3H), 1.19 (dd, J=6.9, 0.9 Hz, 3H), 0.99-0.80 (m, 1H).

Intermediate 8

[(1S,2S)-2-Cyclopentyl-2-Hydroxy-1-Methyl-Ethyl] Ammonium Chloride

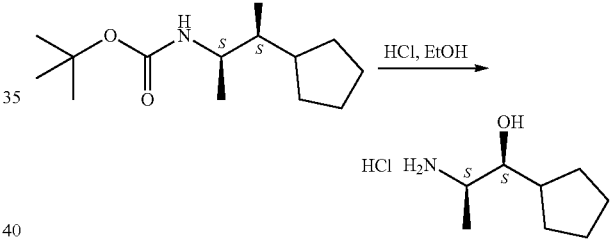

Intermediate 7 (13.2 mmol, 3.21 g) was dissolved in 1 M HCl in EtOH (40 mL) and stirred at 50° C. for 2 hours (until TLC showed no more starting material). Evaporated to dryness, and Intermediate 8 (13.2 mmol, 100% Yield, 2.37 g) was isolated as a white crystalline solid. Used directly as is.

¹HNMR (300 MHz, DMSO-d₆): δ 7.90 (s, 3H, —NH₃⁺), 3.31 (t, J=6.0 Hz, 1H), 3.00 (m, J=6.0 Hz, 1H), 1.97 (dt, J=13.5, 7.9 Hz, 1H), 1.73-1.26 (m, 8H), 1.19 (d, J=6.7 Hz, 3H).

Intermediate 9 tert-butyl N-[(1S)-2-(5-fluoro-2-pyridyl)-1-methyl-2-oxo-ethyl]carbamate

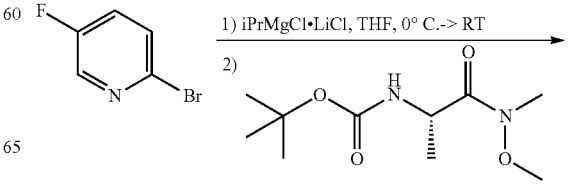

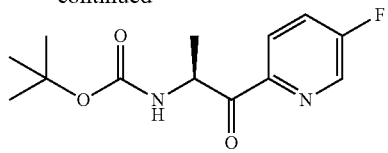

Isopropylmagnesiumchloride-lithium chloride complex (1.3 M in THF, 65 mmol, 50.0 mL) was added to a solution of 2-bromo-5-fluoropyridine (60.0 mmol, 10.6 g) in dry THF (50 mL) under argon at 0° C. The mixture was stirred for 20 min on ice bath and then 2 hours at rt giving a coffee colored solution.

Meanwhile, 3 M MeMgBr in Et$_2$O (16 mL, 48 mmol) was added slowly to a suspension of tert-butyl N-[(1S)-2-[methoxy(methyl)amino]-1-methyl-2-oxo-ethyl]carbamate (50.0 mmol, 11.6 g) in dry THF (250 mL) under argon at −20° C., resulting in a clear solution of the mono-Mg salt (pre-protonation protocol).

The Grignard solution was cannulated into the NH deprotonated Weinreb solution. Stirred at 0° C. for 30 min and rt for 1 hour. LCMS showed full conversion to product. Quenched with 10% NH$_4$Cl (100 mL). The THF layer was dried (Na$_2$SO$_4$) and evaporated. Intermediate 9 (13.45 g) was isolated as a brown oil in quantitative yield, and used directly in the following step without further purification.

UPLC-MS: $t_R$=0.72 (M+H$^+$)=213.1 (loss of isobutene)

$^1$HNMR (300 MHz, Chloroform-d) δ 8.53 (d, J=2.8 Hz, 1H), 8.13 (dd, J=8.7, 4.6 Hz, 1H), 7.53 (td, J=8.3, 2.8 Hz, 1H), 5.65 (d broad, J=8.1 Hz, 1H), 5.38 (s, 1H), 1.45 (s, 9H), 1.43 (d, J=6.5 Hz, 3H).

Intermediate 10

(1R,2S)-2-amino-1-(5-fluoro-2-pyridyl)propan-1-ol

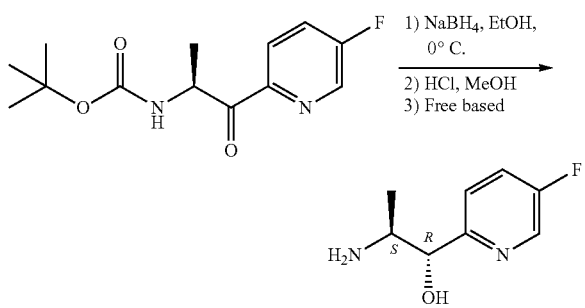

Reduction:

NaBH$_4$ (20.0 mmol, 0.76 g) was added to a solution of Intermediate 9 (50.1 mmol, 13.45 g) in 96% EtOH (200 mL) at 0-5° C. and stirred overnight at rt. LCMS showed a diastereomeric mixture where the (S,S) isomer is the major component: ca. 80% and the desired (R,S) is ca. 20%. Reaction mixture quenched with 10% NH$_4$Cl (100 mL). Most of the EtOH was evaporated and the aq. layer was extracted with Et$_2$O (2×100 mL), dried (Na$_2$SO$_4$) and evaporated to a brown syrup. Chromatographed on silica using EtOAc:heptane as eluent. tert-butyl N-[(1S,2R)-2-(5-fluoro-2-pyridyl)-2-hydroxy-1-methyl-ethyl]carbamate was isolated as an orange oil (2.15 g) in 15% yield.

TLC (EtOAc:heptane, 1:1 v/v): R$_f$ (S,S)≈0.53 and Rf (R,S)≈0.48

UPLC-MS: $t_R$=0.60 (M+H$^+$)=215.2 (loss of isobutene)

BOC-Deprotection and Free Based:

tert-butyl N-[(1S,2R)-2-(5-fluoro-2-pyridyl)-2-hydroxy-1-methyl-ethyl]carbamate (2.15 g) was dissolved in 2 M HCl in MeOH (25 mL) and stirred at rt for 2 hours. All the volatiles were evaporated and the 4 M NaOH (10 mL) was added. Extracted with DCM (4×40 mL), dried (Na$_2$SO$_4$) and evaporated. Intermediate 10 was isolated as an orange oil (1.16 g) in 86% yield.

$^1$HNMR (300 MHz, Chloroform-d) δ 8.41 (dd, J=2.1, 1.0 Hz, 1H), 7.45-7.35 (m, 2H), 4.42 (d, J=4.6 Hz, 1H), 3.20 (qd, J=6.6, 4.5 Hz, 1H), 1.15 (d, J=6.6 Hz, 3H).

The aminoalcohol (1R,2S)-2-amino-1-(5-fluoro-4-methyl-2-pyridyl)propan-1-ol was synthesised accordingly starting from 2-bromo-5-fluoro-4-methylpyridine Intermediate 11 tert-butyl (4S)-4-(4-fluorobenzoyl)-2,2-dimethyl-oxazolidine-3-carboxylate

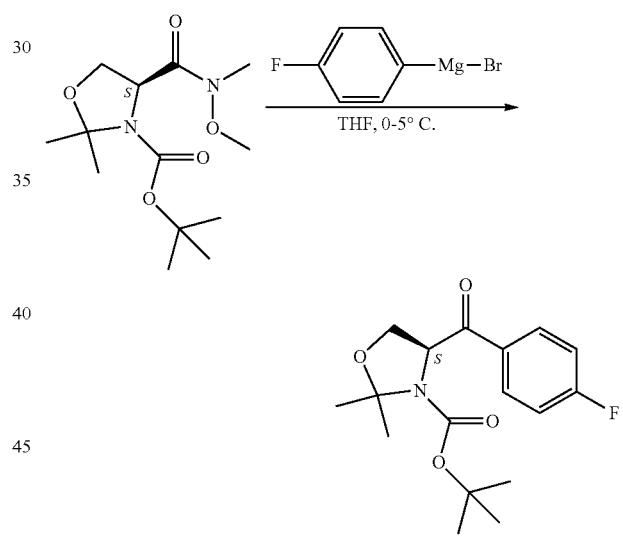

2 M 4-fluorophenylmagnesium bromide (26.1 mmol, 13.1 mL) in Et$_2$O was added slowly to a solution of tert-butyl (4S)-4-[methoxy(methyl)carbamoyl]-2,2-dimethyl-oxazolidine-3-carboxylate (23.8 mmol, 6.85 g, Tetrahedron Letters (2014), 6903-6906) in dry THF (80 mL) at 0-5° C. under argon. The ice-bath was removed and the mixture was warmed to rt and stirred for 2 hours. LCMS showed full conversion. Quenched with 10% NH$_4$Cl (50 mL), extracted with Et$_2$O (2×50 mL), dried (Na$_2$SO$_4$) and evaporated to an orange oil. Chromatographed on silica using EtOAc:heptane as eluent. Intermediate 11 (3.10 g) was isolated as a white crystals in 40% yield. $^1$HNMR showed BOC rotamers in a 4:5 ratio.

UPLC-MS: $t_R$=0.84 (M+H$^+$)=224.2 (loss of BOC)

$^1$HNMR (300 MHz, Chloroform-d) δ 8.00-7.92 (m, 2H), 7.22-7.10 (m, 2H), 5.42 (dd, J=7.4, 3.0 Hz, 0.44H, α-H), 5.36-5.30 (m, 0.56H, α-H), 4.30 (td, J=8.5, 3.9 Hz, 1H), 3.93

(ddd, J=8.9, 5.4, 3.3 Hz, 1H), 1.74 (d, J=10.8 Hz, 2H), 1.59 (d, J=11.1 Hz, 2H), 1.50 (s, 4H, BOC), 1.28 (s, 5H, BOC).

Intermediate 12

(1S,2S)-2-amino-1-(4-fluorophenyl)propane-1,3-diol hydrochloride and (1R,2S)-2-amino-1-(4-fluorophenyl)propane-1,3-diol hydrochloride

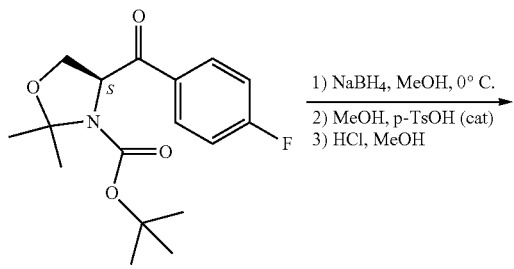

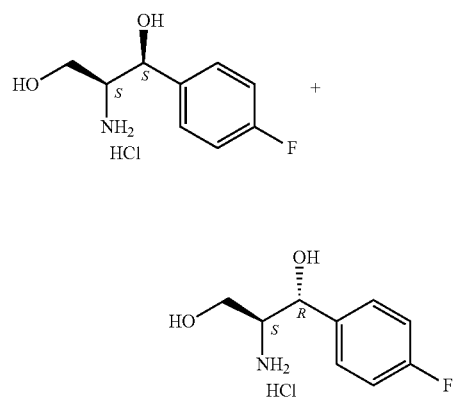

Reduction:

NaBH$_4$ (14.1 mmol, 532 mg) was added to a solution of Intermediate 11 (9.37 mmol, 3030 mg) in 96% EtOH (120 mL) at 0-5° C. Stirred at rt for 2 hours. All the volatiles were evaporated and 10% NH$_4$Cl (40 mL) was added. Extracted with EtOAc (2×50 mL), dried (Na$_2$SO$_4$) and evaporated. The mixture (2.68 g, 87% combined yield) was isolated as a clear oil and used directly in the next step.

Acetonide Deprotection:

The alcohol mixture was dissolved in MeOH (15 mL) and p-TsOH (130 mg) was added and stirred until LCMS showed full deprotection (~2 hour at rt). K$_2$CO$_3$ (100 mg) was added in order to neutralise the acid, and the mixture was filtered. Evaporated and chromatographed on silica. The two diastereomers of Intermediate 12 could not be separated on TLC (in several eluent systems, R$_f$=0.15 in EtOAc:heptane 1:1). Mixture isolated as a clear oil (ca. 1.20 g).

UPLC-MS: t$_R$=0.56 (R,S)-isomer and t$_R$=0.57 (S,S)-isomer

BOC-Deprotection:

The diastereomeric mixture was dissolved in 2 M HCl in MeOH (10 mL) and stirred at rt for 2 hours. Evaporated to dryness (0.90 g). Used directly as obtained.

Intermediate 13 tert-butyl N-[(1S)-2-(4-cyanophenyl)-1-methyl-2-oxo-ethyl]carbamate

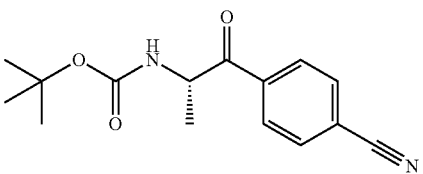 [SMILES: C[C@H](NC(=O)OC(C)(C)C)C(=O)c1ccc(C#N)cc1]

Solution 1: Isopropylmagnesium chloride lithium chloride complex (1.3 M in THF, 20.0 mmol, 15 mL) was added to a solution of 4-bromobenzonitrile (20.0 mmol, 3.64 g) in dry THF (25 mL) at −20° C. under argon. The resulting yellow-orange solution was stirred at −20° C. for 3 hours.

Meanwhile, a solution of de-protonated Weinreb amide was prepared:

Solution 2: Cyclopentylmagnesium chloride (2M in Ether, 15.0 mmol, 7.50 mL) was added slowly to a suspension of tert-butyl N-[(1S)-2-[methoxy(methyl)amino]-1-methyl-2-oxo-ethyl]carbamate (15.00 mmol, 3.48 g) in dry THF (50 mL) at −15° C. under argon and stirred for 5 minutes. Resulting in a clear solution.

The Grignard solution Solution 1 was cannulated into solution 2 and stirred at −10° C. for 2 hours, cooling bath removed and slowly warmed to rt and left here for another 2 hours. The reaction mixture was diluted with Et$_2$O (50 mL) and quenched by adding 5% citric acid (50 mL). The organic layer was separated, dried (Na$_2$SO$_4$) and evaporated. An orange oil was isolated which solidified on standing. Triturated with heptane and filtration gave Intermediate 13

(12.4 mmol, 62.0% Yield, 3.40 g) as an off-white solid.

$^1$HNMR (300 MHz, Chloroform-d) δ 8.08 (d, J=8.3 Hz, 2H), 7.80 (d, J=8.4 Hz, 2H), 5.40 (d, J=7.9 Hz, 1H), 5.26 (p, J=7.3 Hz, 1H), 1.45 (s, 9H), 1.39 (d, J=7.2 Hz, 3H).

Intermediate 14 tert-butyl N-[(1S,2S)-2-(4-cyanophenyl)-2-hydroxy-1-methyl-ethyl]-carbamate and

Intermediate 15 tert-butyl N-[(1S,2R)-2-(4-cyanophenyl)-2-hydroxy-1-methyl-ethyl]-carbamate

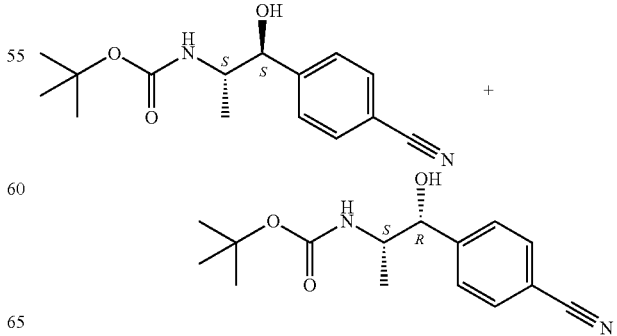

NaBH₄ (1.90 mmol, 72.0 mg) was added to a solution of Intermediate 13 (1.27 mmol, 348 mg) in dry THF (20 mL) at rt. Stirred overnight at rt. AcOH (0.25 mL) was added in order to quench excess NaBH₄. Evaporation and redissolved in EtOAc (20 mL) and washed with brine (10 mL), dried (Na₂SO₄) and evaporated. Chromatographed on silica using EtOAc:heptane as eluent.

Intermediate 14 (0.160 mmol, 12.6% Yield, 44.1 mg) isolated as a clear oil.

¹HNMR (300 MHz, Chloroform-d) δ 7.67-7.55 (m, 2H), 7.49-7.43 (m, 2H), 4.76 (d, J=8.6 Hz, 1H), 4.66 (t, J=4.4 Hz, 1H), 3.90-3.79 (m, 1H), 1.36 (s, 9H, Boc), 1.13 (d, J=6.7 Hz, 3H).

Intermediate 15 (0.637 mmol, 50.2% yield, 176.1 mg) isolated as a white solid.

¹HNMR (300 MHz, Chloroform-d) δ 7.69-7.59 (m, 2H), 7.51-7.40 (m, 2H), 4.97-4.86 (m, 1H), 4.59-4.52 (m, 1H), 4.01 (br s, 1H), 3.65 (s, 1H), 1.46 (s, 9H), 0.99 (d, J=7.0 Hz, 3H).

Intermediate 16 tert-butyl N-[(1S,2R)-2-(5-fluoro-2-pyridyl)-2-hydroxy-1-(hydroxymethyl)-ethyl]carbamate and Intermediate 17 tert-butyl N-[(1S,2S)-2-(5-fluoro-2-pyridyl)-2-hydroxy-1-(hydroxymethyl)-ethyl]carbamate

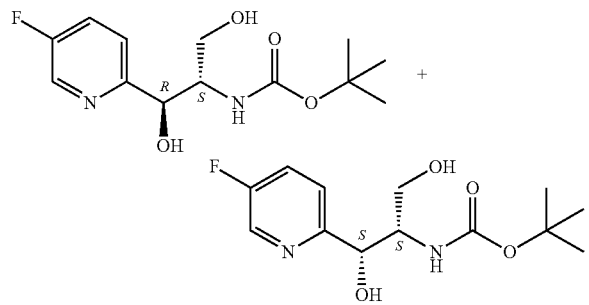

Isopropylmagnesiumchloride-lithium chloride complex (1.3 M in THF, 1.20 mmol, 0.92 mL) was added to a solution of 2-bromo-5-fluoropyridine (1.20 mmol, 210 mg) in dry THF (3 mL) under argon at 0° C. The mixture was stirred for 20 min on ice and ~2 hours at rt (coffee colored solution).

The Grignard solution was added to a solution of (S)-Garner aldehyde (1.00 mmol, 230 mg) in dry toluene (4 mL) at 0° C. under argon. Stirred overnight at rt. Quenched with sat. NH₄Cl (4 mL). The organic layer was dried (Na₂SO₄) and evaporated. Mixture of diastereomers (110 mg, 34%) were isolated.

Acetonide deprotection: The crude mixture was dissolved in MeOH (2 mL) and p-TsOH (20 mg) was added. Stirred at rt for 18 hours. Sat. NaHCO₃ (5 mL) was added and extracted with EtOAc (2×5 mL). Org. layer was dried (Na₂SO₄) and evaporated. Chromatographed on silica using EtOAc:heptane as eluent.

Intermediate 16 (43% yield, 42 mg) isolated as a clear oil.

¹HNMR (600 MHz, Chloroform-d) δ 8.39 (d, J=2.9 Hz, 1H), 7.57 (dd, J=8.8, 4.4 Hz, 1H), 7.47 (td, J=8.4, 2.8 Hz, 1H), 5.39 (d, J=7.6 Hz, 1H), 5.15-5.09 (m, 1H), 4.99 (s, 1H), 4.05-4.00 (m, 1H), 3.92 (dd, J=11.6, 2.9 Hz, 1H), 3.64 (dd, J=11.6, 4.5 Hz, 1H), 1.39 (s, 9H).

Intermediate 17 (6% Yield, 6 mg) isolated as a clear oil.

¹HNMR (600 MHz, Chloroform-d) δ 8.38 (s br, 1H), 7.48-7.45 (m, 2H), 5.17 (d, J=9.0 Hz, 1H), 5.05 (d, J=3.4 Hz, 1H), 4.81 (s br, 1H), 4.01 (dq, J=8.8, 4.2 Hz, 1H), 3.91 (dd, J=11.3, 4.0 Hz, 1H), 3.81 (dd, J=11.3, 5.0 Hz, 1H), 1.30 (s, 9H).

Intermediate 18

(1R,2S)-2-amino-1-(5-fluoro-2-pyridyl)propane-1,3-diol

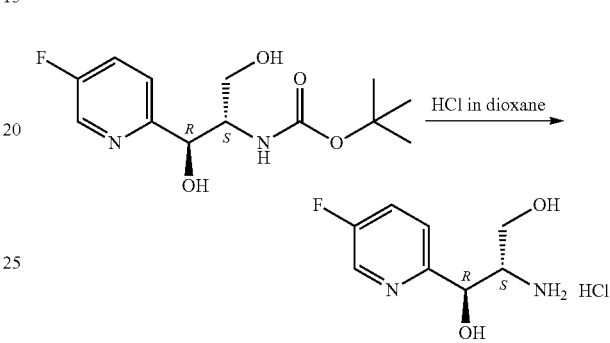

Intermediate 16 (42 mg, 0.146 mmol) was dissolved in 4 M HCl in dioxane (1 mL) and stirred for 2 hours at rt. Solvent evaporated off to afford the product in quantitative yield.

Intermediate 18 (27 mg, 82%) was used without further purification.

¹HNMR (300 MHz, CD₃OD) δ 8.51 (s br, 1H), 7.81-7.56 (m, 2H), 5.04 (d, J=3.8 Hz, 1H), 3.74-3.67 (m, 2H), 3.60-3.52 (m, 1H).

Intermediate 19

(1S,2S)-2-amino-1-(5-fluoro-2-pyridyl)propane-1,3-diol

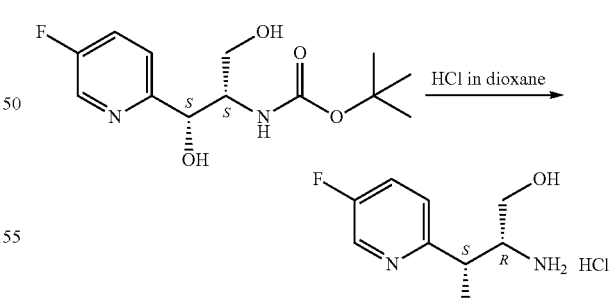

Intermediate 17 (6 mg, 0.146 mmol) was dissolved in 4 M HCl in dioxane (1 mL) and stirred for 2 hours at rt. Solvent evaporated off to afford the product in quantitative yield.

Intermediate 19 (4 mg, quantitative) was used without further purification.

¹HNMR (300 MHz, CD₃OD) δ 8.70 (s br, 1H), 8.05 (td, J=8.4, 2.8 Hz, 1H), 7.92 (dd, J=8.9, 4.6 Hz, 1H), 5.10 (d, J=5.6 Hz, 1H), 3.81-3.72 (m, 1H).

Intermediate 20

Racemic 6-(2-amino-1-hydroxy-ethyl)pyridine-3-carbonitrile

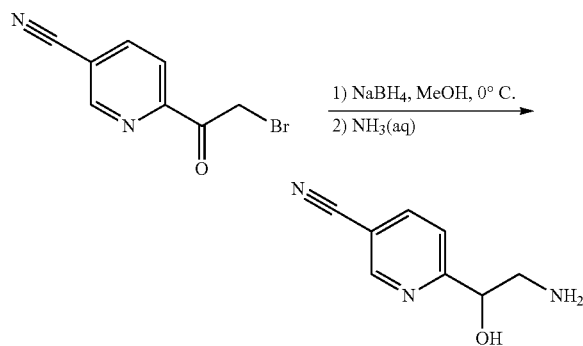

NaBH₄ (0.227 g, 7.33 mmol) was added to a solution of 6-(2-bromoacetyl)pyridine-3-carbonitrile in MeOH (20 mL) at 0° C. under argon. Stirred for another 30 minutes.

Evaporated and conc. NH₃ (27%, 20 mL) was added. The mixture was stirred overnight at rt. All the volatiles were evaporated. Used without further purification.

Intermediate 21 tert-butyl N-[2-(5-fluoro-4-methyl-2-pyridyl)-2-oxo-ethyl]carbamate

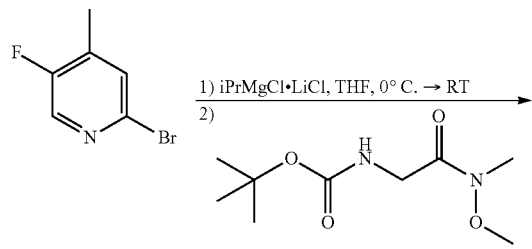

Isopropylmagnesiumchloride-lithium chloride complex (1.3 M in THF, 16.4 mmol, 13.0 mL) was added to a solution of 2-bromo-5-fluoro-4-methylpyridine (3.12 g, 16.4 mmol) in dry THF (16 mL) under argon at 0° C. The mixture was stirred for 20 min on ice and ~2 hours at rt (coffee colored solution).

The Grignard solution was cannulated into a solution of tert-butyl N-[2-[methoxy(methyl)amino]-2-oxo-ethyl]carbamate (1.75 g, 8.0 mmol) in dry THF (20 mL) at rt and stirred 1 hour. Quenched with 10% NH₄Cl (20 mL). The THF layer was dried (Na₂SO₄) and evaporated. Recrystallised from heptane gave Intermediate 21 (1.42 g, 66%) as a white solid.

UPLC-MS: $t_R$=0.74 (M+H⁺)=213.1 (loss of isobutene)
¹HNMR (300 MHz, Chloroform-d) δ 8.38 (s, 1H), 7.95 (d, J=6.3 Hz, 1H), 5.33 (s br, 1H), 4.82 (d, J=5.1 Hz, 2H), 2.37 (d, J=1.8 Hz, 3H), 1.48 (s, 9H).

Intermediate 22

2-Amino-1-(5-Fluoro-4-Methyl-2-Pyridyl)Ethanol Hydrochloride

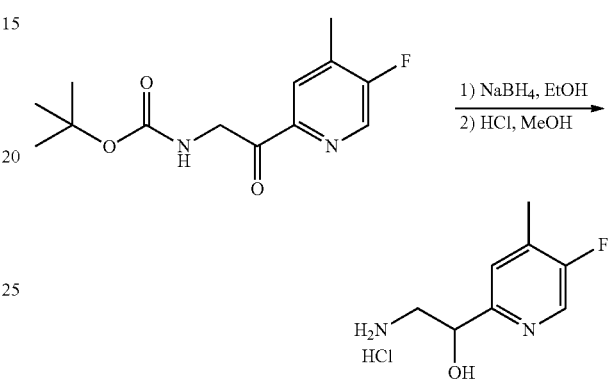

NaBH₄ (99 mg, 2.63 mmol) was added to a solution of Intermediate 21 (1.42 g, 5.26 mmol) in 96% EtOH (40 mL) at 0-5° C. The pale yellow solution was stirred for 30 minutes. AcOH (0.25 mL) was added in order to destroy excess NaBH₄. All the volatiles were evaporated and the residue was partioned between EtOAc (50 mL):sat NaHCO₃ (40 mL). The EtOAc layer was dried (Na₂SO₄) and evaporated. The The BOC-protected aminoalcohol (1.40 g, 98.6%) was redissolved in 1 M HCl in MeOH (30 mL) and stirred at 50° C. for 1 hour. All the volatiles were evaporated yielding Intermediate 22 (1.10 g, 92%) as a pale yellow soild. Used directly in the next step without further purification.

UPLC-MS: $t_R$=0.28 (M+H⁺)=171.2
¹HNMR (300 MHz, DMSO-d₆) δ 8.46 (d, J=1.6 Hz, 1H), 8.22 (s, 3H), 7.59 (d, J=6.4 Hz, 1H), 4.91 (dd, J=8.9, 3.5 Hz, 1H), 3.28-3.15 (m, 1H), 3.01-2.87 (m, 1H), 2.33 (d, J=1.7 Hz, 3H).

Intermediate 23

(2R)-2-Hydroxy-3-[[[(8S)-5-(7H-Pyrrolo[2,3-d]Pyrimidin-4-Yl)-5-Azaspiro[2.5]Octane-8-Carbonyl]Amino]Propanoic Acid

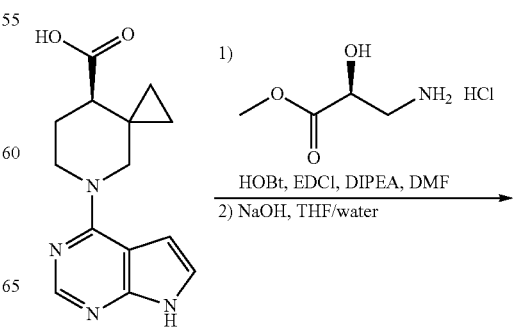

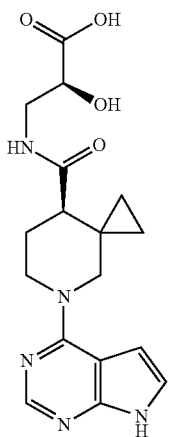

A mixture of Intermediate (S)-acid (0.367 mmol, 100 mg), methyl (2R)-3-amino-2-hydroxypropanoate hydrochloride (76 mg, 0.44 mmol), HOBt (50 mg, 0.367 mmol) and DIPEA (0.367 mmol, 65 µL) in DMF (1 mL) was stirred for 5 minutes. EDCI (78 mg, 0.404 mmol) was added, the mixture was stirred at rt for 18 hour. HPLC purified. Pure fractions were evaporated and redissolved in THF (5 mL) and 1 M NaOH (1 mL) was added. Stirred at rt for 3 hours, evaporated and acidified with 1 M HCl until pH≈3-4. The precipitate was filtered off and dried in vacuo. Intermediate 23 was isolated as a white solid.

UPLC-MS: $t_R$=0.29 (M+H$^+$)=360.3

$^1$HNMR (600 MHz, DMSO-d$_6$) δ 12.53 (s, 1H), 11.63 (s, 1H), 8.08 (s, 1H), 7.82 (s, 1H), 7.14 (s, 1H), 6.52 (s, 1H), 4.23-3.79 (m, 4H), 3.58 (d, J=13.2 Hz, 1H), 2.34 (s, 1H), 1.92 (s, 1H), 1.81 (s, 1H), 0.71-0.30 (m, 4H).

Intermediate 24

[1-(Hydroxymethyl)Cyclopropyl]Methyl (2R)-2-Amino-3-[Tert-Butyl(Dimethyl)Silyl]Oxy-Propanoate

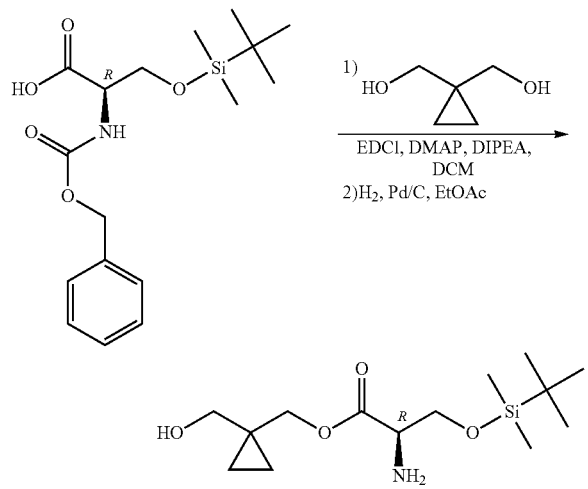

Step 1: EDCI (104 mg, 0.54 mmol) was added to a mixture of N-Cbz-O-TBDMS-D-serine (200 mg, 0.45 mmol), 1,1-di(hydroxymethyl)cyclopropane (116 mg, 1.13 mmol) and DMAP (55 mg, 0.45 mmol) in dry DCM (10 mL) and stirred at rt for 6 hours. Evaporated and chromatographed on silica using EtOAc:heptane as eluent. The Cbz-ester was isolated (140 mg, 70%) as a clear oil.

$^1$HNMR (600 MHz, Chloroform-d) δ 7.41-7.30 (m, 6H), 5.63 (d, J=8.5 Hz, 1H), 5.18-5.09 (m, 2H), 4.43 (dt, J=8.6, 2.9 Hz, 1H), 4.19 (d, J=11.6 Hz, 1H), 4.10 (d, J=11.6 Hz, 1H), 3.87 (dd, J=10.2, 3.1 Hz, 1H), 3.47-3.39 (m, 2H), 0.85 (s, 9H), 0.61-0.50 (m, 4H), 0.03 (s, 3H), 0.02 (s, 3H).

Step 2: Cbz-ester (140 mg, 0.32 mmol) was hydrogenated with H$_2$-balloon over 10% Pd/C (20 mg) in EtOAc (10 mL). The mixture was filtered and evaporated. The resulting material (98 mg, 100%) was used directly as is.

Intermediate 25

(2R)-3-Hydroxy-2-[[(8S)-5-(7H-Pyrrolo[2,3-d]Pyrimidin-4-Yl)-5-Azaspiro[2.5]Octane-8-Carbonyl]amino]propanoic acid

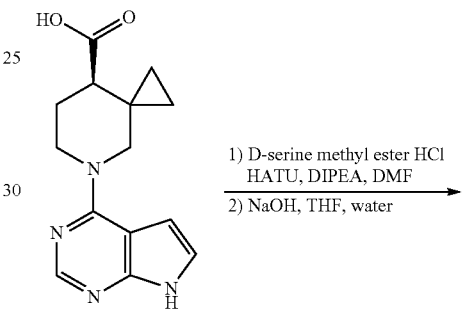

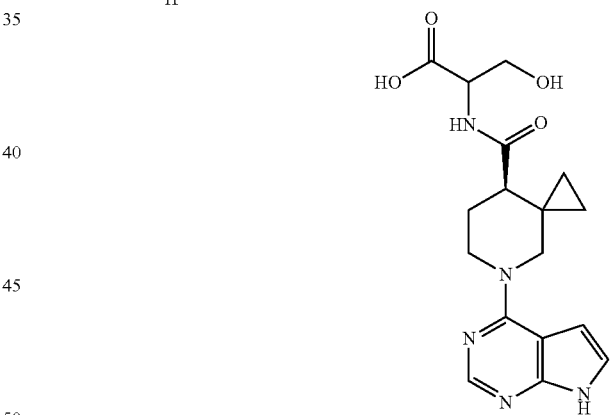

HATU (419 mg, 1.10 mmol) was added to a mixture of Intermediate (S)-acid (250 mg, 0.92 mmol), D-serine methyl ester hydrochloride (171 mg, 1.10 mmol) and DIPEA (0.62 mL, 3.67 mmol) in dry DMF (3 mL) and stirred at rt for 2 hours. HPLC purified. The methyl ester was isolated as a white solid (290 mg, 84%).

UPLC-MS: $t_R$=0.35 (M+H$^+$)=374.3

Ester hydrolysis: The ester (290 mg, 0.777 mmol) was hydrolysed with NaOH (62 mg, 2 eqv) in THF/water (5 mL each). Stirred for 2 hours at rt. All the volatiles were evaporated and the residue was HPLC purified. Intermediate 25 (200 mg, 71%) was isolated as a white solid.

UPLC-MS: $t_R$=0.29 (M+H$^+$)=360.2

$^1$HNMR (300 MHz, DMSO-d$_6$) δ 12.53 (s br, 1H), 11.61 (s, 1H), 8.09 (s, 1H), 7.90 (d, J=7.9 Hz, 1H), 7.14 (dd, J=3.6, 2.1 Hz, 1H), 6.53 (dd, J=3.7, 1.6 Hz, 1H), 4.28 (dt, J=8.1, 4.9

Hz, 1H), 4.14 (ddd, J=11.8, 7.5, 3.6 Hz, 1H), 4.02-3.82 (m, 2H), 3.74-3.53 (m, 3H), 2.50-2.43 (m, 1H), 2.02-1.75 (m, 2H), 0.63-0.52 (m, 1H), 0.49-0.34 (m, 3H).

Intermediate 26

Racemic Trans-2-(Aminomethyl)Cyclopropanecarbonitrile

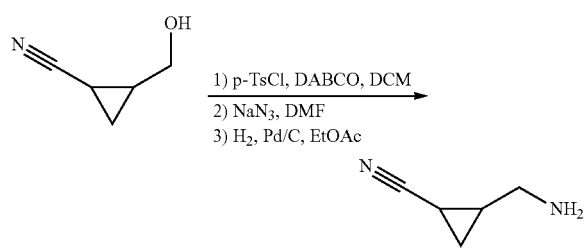

p-TsCl (215 mg, 1.13 mmol) was added to a solution of racemic trans-2-(hydroxymethyl)cyclopropanecarbonitrile (100 mg, 1.03 mmol) and DABCO (144 mg, 1.28 mmol) in DCM (1.25 mL) at 2-6° C. The ice bath was removed and the white suspension was warmed to rt and stirred for another 30 min. Poured into 0.1 M HCl (10 mL) and extracted with MBTE (2×10 mL). Org. layer was dried (Na$_2$SO$_4$) and evaporated. The crude tosylate (206 mg, 78%) was isolated as a pale yellow oil and used directly in the following step.

A mixture of tosylate (202 mg, 0.78 mmol) and sodium azide (77 mg, 1.18 mmol) in dry DMF (1.8 mL) was stirred overnight at rt under argon. Water (16 mL) was added and extracted with Et$_2$O (2×10 mL). Org. layer was dried (Na$_2$SO$_4$) and evaporated. The crude azide was isolated as a colorless liquid (154 mg, 96%) and was used in the following step without further purification.

The crude azide (145 mg, 0.71 mmol) was dissolved in EtOAc (3 mL) and hydrogenated over 10% Pd/C (10 mg) using a H$_2$-balloon. The mixture was filtered and 1 M HCl in MeOH (1 mL) was added and then all the volatiles were evaporated.

Intermediate 26 (98 mg, 98%) was isolated as the HCl salt.

$^1$HNMR (300 MHz, DMSO-d6) δ 8.16 (s br, 3H, —NH$_3$+), 2.90 (dt, J=12.1, 5.8 Hz, 1H), 2.65 (ddd, J=13.3, 8.0, 5.2 Hz, 1H), 1.86-1.58 (m, 2H), 1.31 (dt, J=8.9, 5.2 Hz, 1H), 1.10 (ddd, J=8.8, 6.2, 5.0 Hz, 1H).

Intermediate 27

Cis/Trans-3-(Aminomethyl)Cyclobutanecarbonitrile

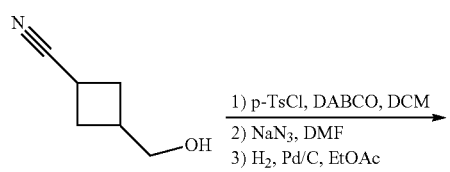

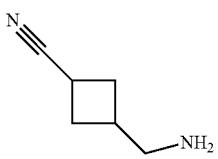

The cyclobutane analogue was prepared using the same method as described for Intermediate 26.

$^1$HNMR (300 MHz, DMSO-d$_6$) δ 7.99 (s, 3H), 3.29-3.17 (m, 1H), 2.86 (d, J=7.1 Hz, 2H), 2.63-2.53 (m, 1H), 2.47-2.34 (m, 2H), 2.19-2.04 (m, 2H).

EXAMPLES

General Procedure for Amide Formation with SEM-Protected Acid:

A mixture of Intermediate (S)-SEM-acid (0.10 mmol, 40.2 mg), amine (0.15 mmol), HOBt (0.10 mmol, 14 mg) and DIPEA (0.20 mmol, 35 µL) in DCM (1 mL) was stirred for 5 minutes. EDCI (0.11 mmol, 21 mg) was added, the mixture was stirred at rt for 18 hour. Diluted with DCM (3 mL), washed with 0.1 M KHSO$_4$ (2 mL), dried (Na$_2$SO$_4$) and evaporated. Chromatographed on silica using EtOAc: heptane as eluent gave the SEM protected amide intermediates.

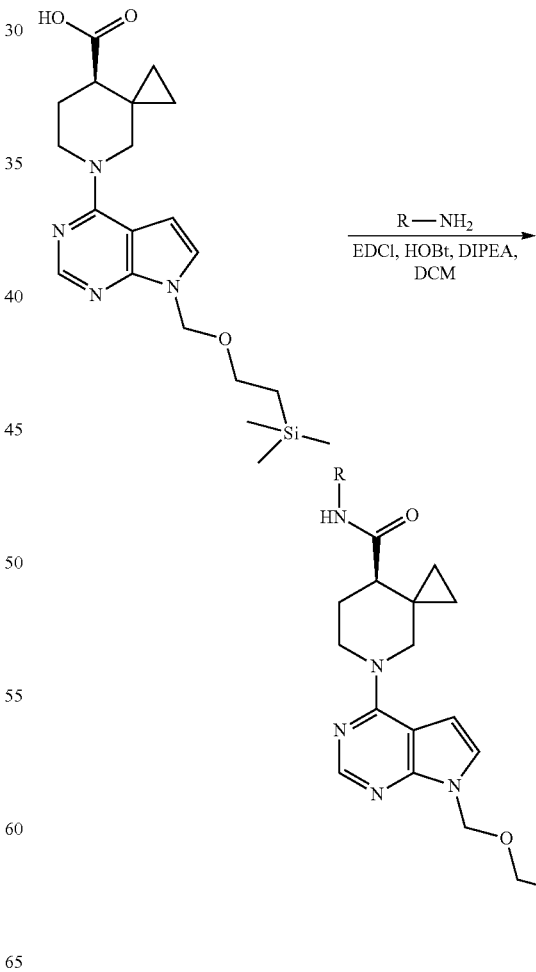

General Procedure for SEM-Deprotection of Amides:

TFA (4 eqv) was added to a solution of SEM protected amide intermediates from above (1.0 eqv) in DCM at rt. Stirred at rt until LCMS showed full conversion (typically 3-6 hours). Evaporated and redissolved in MeCN and 1,2-diaminoethane (6 eqv) was added and stirred at rt for 2 hours, or longer where noted. Evaporated and HPLC purified or triturated with water and filtered off and dried in vacuo.

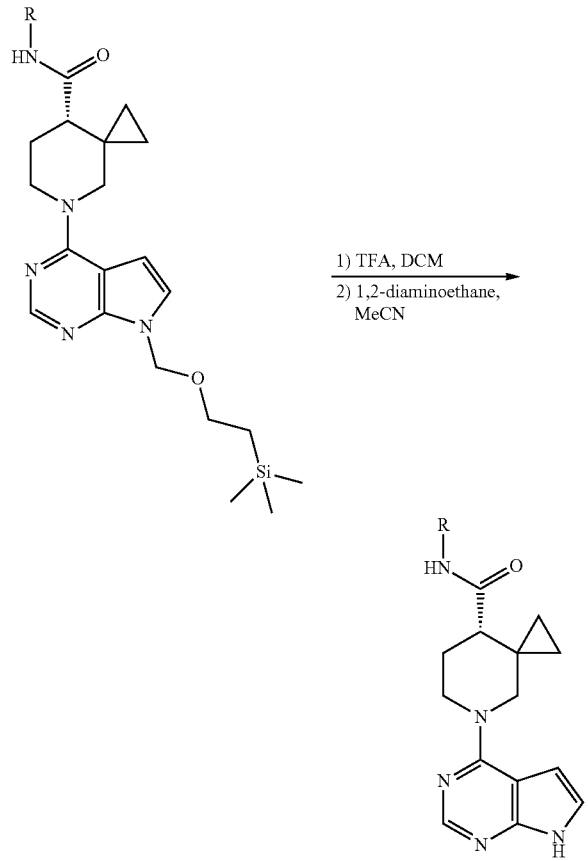

Example 5

(8S)—N-[(1S,2S)-2-Cyclopentyl-2-Hydroxy-1-Methyl-Ethyl]-5-(7H-Pyrrolo[2,3-d]-Pyrimidin-4-Yl)-5-Azaspiro[2.5]Octane-8-Carboxamide

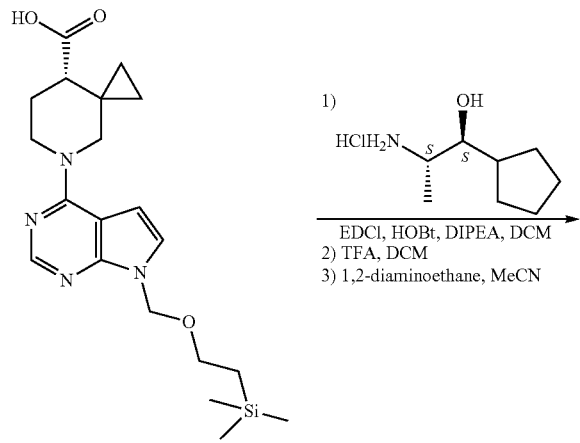

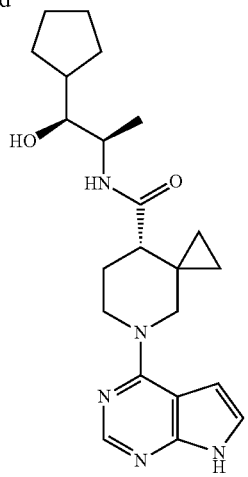

SEM-Amide formation:

EDCI (11 mmol, 2.2 g) was added to a mixture of Intermediate 8 (13.2 mmol, 2.37 g), Intermdiate (S)-SEM-acid (9.0 mmol, 3.6 g), HOBt (9.0 mmol, 1.4 g) and DIPEA (27 mmol, 3.5 g, 4.7 mL) in DCM (30 mL) and stirred at rt for 1 hour and the at 50° C. for 1 hour. LCMS showed full conversion. Diluted with DCM (100 mL), washed with water, 2% citric acid, dried ($Na_2SO_4$) and evaporated. The SEM-protected amide (4.79 g) was isolated as a white solid in 100% yield and used directly in the next step. UPLC-MS: $t_R$=0.88 (M+H$^+$)=528.5

SEM-Deprotection:

TFA (182 mmol, 20.7 g, 13.9 mL) was added slowly to a solution of the above SEM-protected amide (9.08 mmol, 4.79 g) in DCM (35 mL) and stirred at rt for ~3 hours (until LCMS showed full deprotection). Evaporation of volatiles followed by redissolution in MeCN (20 mL), cooling of the of mixture on ice batch, and slow addition of 1,2-diaminoethane (90.8 mmol, 5.45 g, 6.07 mL) gave a yellow solution. LCMS showed after ca. 30 min full deprotection. Evaporation of volatiles gave a white slurry. Diluted with water (40 mL) and pH was adjusted to 5-6 with AcOH. Stirred for 30 min at rt, the precipitate was filtered off, washed with water and dried in vacuo. Recrystallised by dissolving in boiling 96% EtOH (ca. 35-40 mL) and then slowly addition of hot (70° C.) water (35 mL). Left for slow crystallisation. Precipitate was filtered off and dried in vacuo.

(8S)—N-[(1S,2S)-2-cyclopentyl-2-hydroxy-1-methyl-ethyl]-5-(7H-pyrrolo[2,3-d]pyrimidin-4-yl)-5-azaspiro[2.5]octane-8-carboxamide (2.25 g) was isolated as a white solid in 62.4% yield.

UPLC-MS: $t_R$=0.51 (M+H$^+$)=398.4

$^1$HNMR (600 MHz, DMSO-d$_6$): δ 11.63 (s, 1H), 8.08 (s, 1H), 7.29 (d, J=8.8 Hz, 1H), 7.14 (dd, J=3.6, 2.3 Hz, 1H), 6.52 (dd, J=3.7, 1.8 Hz, 1H), 4.64 (d, J=6.1 Hz, 1H), 4.19 (ddd, J=13.0, 7.6, 3.6 Hz, 1H), 3.92 (d, J=13.2 Hz, 1H), 3.90-3.83 (m, 2H), 3.59 (d, J=13.2 Hz, 1H), 3.09 (ddd, J=8.4, 5.5, 2.5 Hz, 1H), 2.37 (dd, J=6.9, 4.8 Hz, 1H), 1.92 (dtd, J=13.1, 7.4, 3.6 Hz, 1H), 1.86-1.76 (m, 2H), 1.75-1.68 (m, 1H), 1.63-1.37 (m, 3H), 1.32 (dq, J=12.3, 8.2 Hz, 1H), 1.12-1.06 (m, 1H), 1.04 (d, J=6.8 Hz, 3H), 0.59 (ddd, J=9.3, 5.3, 3.7 Hz, 1H), 0.44 (dddd, J=26.8, 9.0, 5.4, 3.7 Hz, 2H), 0.37 (ddd, J=8.6, 5.2, 3.9 Hz, 1H).

Example 41

(8S)—N-[(1S,2R)-2-(5-Fluoro-2-Pyridyl)-2-Hydroxy-1-Methyl-Ethyl]-5-(7H-Pyrrolo[2,3-d]Pyrimidin-4-Yl)-5-Azaspiro[2.5]Octane-8-Carboxamide

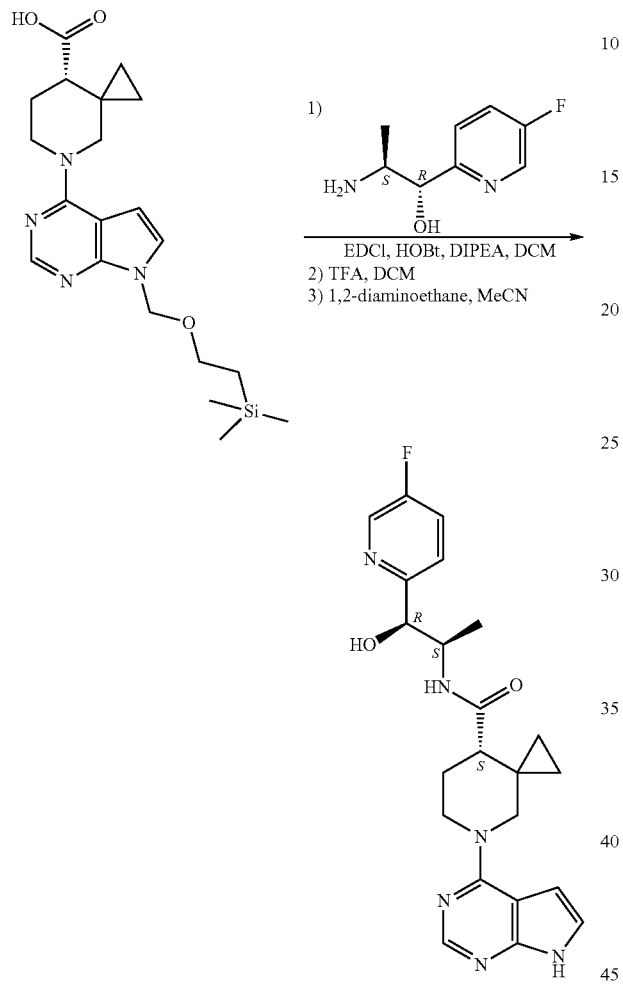

SEM-Amide Formation:

A mixture of Intermediate (S)-SEM-acid (10.00 mmol, 4.026 g), Intermediate 10 (12.7 mmol, 2.16 g), HOBt (11.00 mmol, 1.486 g) and DIPEA (20.00 mmol, 2.585 g, 3.48 mL) in DCM (30 mL) was stirred for 5 minutes, then EDCI (12.50 mmol, 2.396 g) was added. The mixture was stirred at rt for 18 hour. Diluted with DCM (30 mL), washed with 0.5 M $KHSO_4$ (30 mL), dried ($Na_2SO_4$) and evaporated to an orange syrup. Chromatographed on silica using EtOAc: heptane as eluent. SEM amide (5.01 g) was isolated in 90% yield as a clear syrup.

UPLC-MS: $t_R$=0.80 (M+H$^+$)=555.5

SEM-Deprotection:

TFA (261.2 mmol, 20.00 mL) was added to a solution of SEM-protected amide from above (9.03 mmol, 5.01 g) in DCM (25 mL) at rt. Stirred at rt for ca. 3 hours (until LCMS showed full conversion). Evaporated and redissolved in MeCN (25 mL) and 1,2-diaminoethane (150 mmol, 10.0 mL) was added and stirred at rt for 2 hours giving a white suspension. Evaporated and triturated with water (50 mL) and neutralised with AcOH. The resulting solid was filtered off and washed with water. Dried in vacuo.

(8S)—N-[(1S,2R)-2-(5-fluoro-2-pyridyl)-2-hydroxy-1-methyl-ethyl]-5-(7H-pyrrolo[2,3-d]pyrimidin-4-yl)-5-azaspiro[2.5]octane-8-carboxamide (3.20 g) was isolated in 83.5% yield as a white solid.

UPLC-MS: $t_R$=0.43 (M+H$^+$)=425.4

$^1$HNMR (600 MHz, DMSO-$d_6$) δ 11.71 (s, 1H), 8.48 (d, J=2.9 Hz, 1H), 8.09 (s, 1H), 7.71 (td, J=8.8, 2.9 Hz, 1H), 7.56 (dd, J=8.7, 4.6 Hz, 1H), 7.42 (d, J=8.7 Hz, 1H), 7.16 (dd, J=3.7, 2.2 Hz, 1H), 6.52 (dd, J=3.7, 1.6 Hz, 1H), 5.75 (d, J=5.1 Hz, 1H), 4.30-4.19 (m, 1H), 4.02 (ddd, J=13.1, 8.0, 3.6 Hz, 1H), 3.86 (ddd, J=13.0, 7.4, 3.9 Hz, 1H), 3.69 (d, J=13.2 Hz, 1H), 3.51 (d, J=13.2 Hz, 1H), 2.23 (dd, J=6.5, 4.9 Hz, 1H), 1.86 (dtd, J=13.6, 6.9, 3.6 Hz, 1H), 1.74 (ddt, J=12.9, 8.6, 4.3 Hz, 1H), 1.07 (d, J=6.8 Hz, 3H), 0.43-0.27 (m, 3H), 0.19-0.07 (m, 1H).

The following examples were prepared analogously starting from coupling of Intermediate (S)-SEM-acid with the specific amine relevant of the example in question instead of Intermediate 10: Example 40 and Example 152

The following examples were prepared analogously starting from coupling of Intermediate (S)-acid, instead of (S)-SEM-acid hence avoiding the SEM de-protections step, with the specific amine relevant of the example in question instead of Intermediate 10: Example 6, 15, 23, 45, 73, 74 and 107.

The following examples were prepared analogously to Example 154, starting from coupling of Intermediate (S)-SEM-acid with the specific amine relevant of the example in question instead of (3,3-difluorocyclobutyl)methanol: Example 2, 10, 11, and 25

Example 9

(8S)—N-[(1S,2S)-2-(4-Fluorophenyl)-2-Hydroxy-1-(Hydroxymethypethyl]-5-(7H-Pyrrolo[2,3-d]Pyrimidin-4-Yl)-5-Azaspiro[2.5]Octane-8-Carboxamide and

Example 50

(8S)—N-[(1S,2R)-2-(4-Fluorophenyl)-2-Hydroxy-1-(Hydroxymethypethyl]-5-(7H-Pyrrolo[2,3-d]Pyrimidin-4-Yl)-5-Azaspiro[2.5]Octane-8-Carboxamide

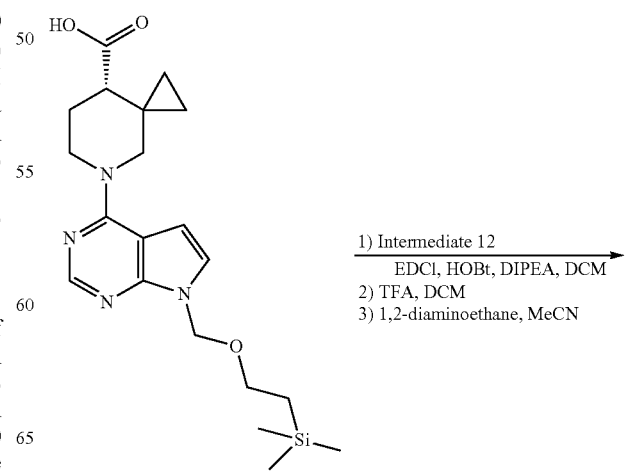

1) Intermediate 12
EDCl, HOBt, DIPEA, DCM
2) TFA, DCM
3) 1,2-diaminoethane, MeCN -continued

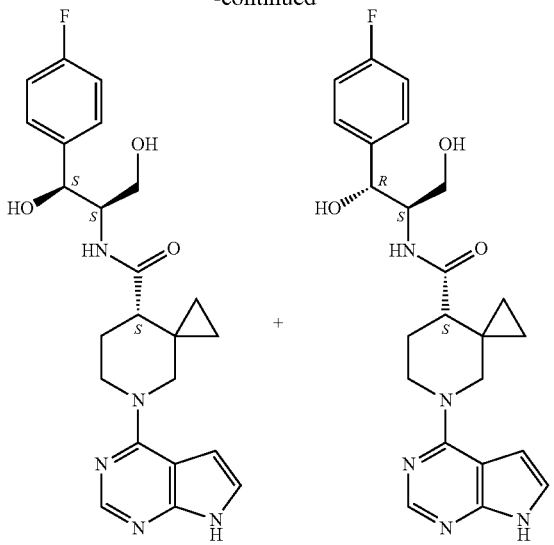

EDCI (3.0 mmol, 570 mg) was added to a mixture of diastereomeric mixture Intermediate 12 (0.90 g, 4.0 mmol), Intermediate (S)-SEM-acid (2.0 mmol, 800 mg), HOBt (2.2 mmol, 330 mg) and DIPEA (7.9 mmol, 1.4 mL) in DCM (25 mL). Stirred overnight at rt. LCMS showed full conversion to diastereomeric amide mixture. Diluted with DCM (100 mL), washed with water, 5% citric acid (20 mL), dried (Na$_2$SO$_4$) and evaporated to a brown syrup (1.20 g, quantitative).

TLC (EtOAc) only one spot is observed (Rf=0.22)

UPLC-MS: $t_R$=0.74 (R,S,S)-isomer (ca. 35%) and $t_R$=0.76 (S,S,S)-isomer (ca. 65%) The crude SEM-protected amide mixture was separated by prep. HPLC. Dissolved in 3 mL MeOH and 10 injections (300 μL, 120 mg pr injection).

(8S)—N-[(1S,2S)-2-(4-fluorophenyl)-2-hydroxy-1-(hydroxymethyl)ethyl]-5-[7-(2-trimethylsilylethoxymethyl)pyrrolo[2,3-d]pyrimidin-4-yl]-5-azaspiro[2.5]octane-8-carboxamide was isolated as a white solid (0.55 g, 49%) of 99% purity.

(8S)—N-[(1S,2R)-2-(4-fluorophenyl)-2-hydroxy-1-(hydroxymethyl)ethyl]-5-[7-(2-trimethylsilylethoxymethyl)pyrrolo[2,3-d]pyrimidin-4-yl]-5-azaspiro[2.5]octane-8-carboxamide was isolated as a white solid (0.235 g, 21%) of 99% purity.

SEM-Deprotection (S,S,S)-Isomer:

TFA (19 mmol, 1.5 mL) was added to a solution of (8S)—N-[(1S,2S)-2-(4-fluorophenyl)-2-hydroxy-1-(hydroxymethyl)ethyl]-5-[7-(2-trimethylsilylethoxymethyl)pyrrolo[2,3-d]pyrimidin-4-yl]-5-azaspiro[2.5]octane-8-carboxamide (0.97 mmol, 0.55 g) in DCM (10 mL) at rt. Stirred at rt for ~3 hours (until LCMS showed full conversion). Evaporated and redissolved in MeCN (10 mL) and 1,2-diaminoethane (14 mmol, 0.97 mL) was added and stirred at rt for 2 hours giving a white suspension. Evaporated and triturated with water (10 mL) and neutralised with AcOH. The resulting solid was filtered off and washed with water. Dried in vacuo.

(8S)—N-[(1S,2S)-2-(4-fluorophenyl)-2-hydroxymethypethyl]-5-(7H-pyrrolo[2,3-d]pyrimidin-4-yl)-5-azaspiro[2.5]octane-8-carboxamide (0.32 g) was isolated as a white solid in 75% yield (99% purity).

UPLC-MS: $t_R$=0.42 (M+H$^+$)=440.4

$^1$HNMR (600 MHz, DMSO-d$_6$) δ 11.73 (s, 1H), 8.09 (s, 1H), 7.37 (dd, J=8.5, 5.6 Hz, 2H), 7.29 (d, J=8.9 Hz, 1H), 7.18-7.07 (m, 3H), 6.53 (dd, J=3.5, 1.7 Hz, 1H), 5.55 (d, J=4.9 Hz, 1H), 4.91 (d, J=3.3 Hz, 1H), 4.77 (s, 1H), 3.97 (dt, J=8.3, 4.1 Hz, 2H), 3.89 (ddd, J=13.2, 7.1, 4.0 Hz, 1H), 3.68 (d, J=13.2 Hz, 1H), 3.55-3.47 (m, 2H), 2.28 (t, J=5.6 Hz, 1H), 1.86 (dtd, J=13.3, 6.7, 3.6 Hz, 1H), 1.75 (ddt, J=13.0, 8.5, 4.3 Hz, 1H), 0.40-0.24 (m, 3H), 0.12-0.04 (m, 1H).

SEM-Deprotection (S,S,R)-Isomer:

TFA (8.25 mmol, 0.62 mL) was added to a solution of (8S)—N-[(1S,2R)-2-(4-fluorophenyl)-2-hydroxy-1-(hydroxymethyl)ethyl]-5-[7-(2-trimethylsilylethoxymethyl)pyrrolo[2,3-d]pyrimidin-4-yl]-5-azaspiro[2.5]octane-8-carboxamide (0.412 mmol, 0.235 g) in DCM (5 mL) at rt. Stirred at rt for ~3 hours (until LCMS showed full conversion). Evaporated and redissolved in MeCN (5 mL) and 1,2-diaminoethane (6.19 mmol, 0.414 mL) was added and stirred at rt for 2 hours giving a white suspension. Evaporated and triturated with water (6 mL) and neutralised with AcOH. The resulting solid was filtered off and washed with water. Dried in vacuo.

(8S)—N-[(1S,2S)-2-(4-fluorophenyl)-2-hydroxy-1-(hydroxymethypethyl]-5-(7H-pyrrolo[2,3-d]pyrimidin-4-yl)-5-azaspiro[2.5]octane-8-carboxamide (0.109 g) was isolated as a white solid in 60% yield (99% purity).

UPLC-MS: $t_R$=0.40 (M+H$^+$)=440.4

$^1$HNMR (600 MHz, DMSO-d$_6$) δ 11.61 (s, 1H), 8.06 (s, 1H), 7.45 (d, J=8.9 Hz, 1H), 7.39-7.31 (m, 2H), 7.16-7.06 (m, 3H), 6.48 (dd, J=3.6, 1.7 Hz, 1H), 5.43 (d, J=4.9 Hz, 1H), 4.60-4.52 (m, 2H), 4.34 (t, J=5.1 Hz, 1H), 4.09-4.00 (m, 1H), 3.95 (tq, J=8.9, 5.6, 4.6 Hz, 1H), 3.86-3.79 (m, 1H), 3.71 (d, J=13.2 Hz, 1H), 3.63 (dt, J=10.9, 5.5 Hz, 1H), 3.52-3.40 (m, 1H), 2.16 (dd, J=6.8, 4.8 Hz, 1H), 1.86 (ddq, J=13.3, 7.1, 3.6 Hz, 1H), 1.74 (ddt, J=12.5, 8.3, 4.2 Hz, 1H), 0.32-0.22 (m, 2H), 0.18 (ddd, J=8.9, 5.6, 3.8 Hz, 1H), −0.05 (dt, J=9.2, 4.4 Hz, 1H).

Example 44

(8S)—N-[(2R)-2-(5-Fluoro-4-Methyl-2-Pyridyl)-2-Hydroxy-Ethyl]-5-(7H-Pyrrolo[2,3-d]Pyrimidin-4-Yl)-5-Azaspiro[2.5]Octane-8-Carboxamide and Example 110

(8S)—N-[(2S)-2-(5-Fluoro-4-Methyl-2-Pyridyl)-2-Hydroxy-Ethyl]-5-(7H-Pyrrolo[2,3-d]Pyrimidin-4-Yl)-5-Azaspiro[2.5]Octane-8-Carboxamide

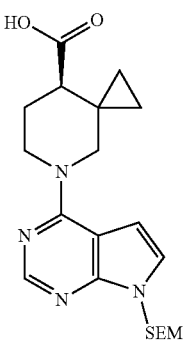

1) Intermediate 22, EDCl, HOBt, DIPEA, DCM
2) Chiral SFC separation
3) SEM deprotection

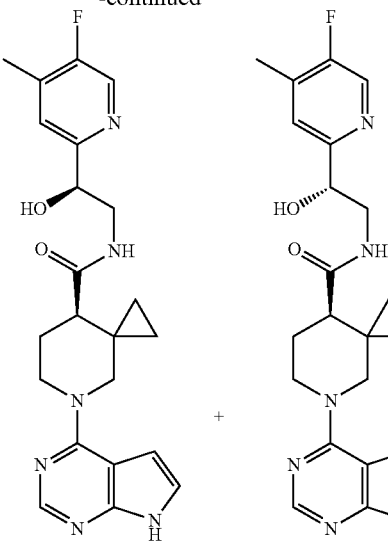

+

3.61-3.51 (m, 2H), 3.17 (ddd, J=13.0, 7.3, 5.3 Hz, 1H), 2.33-2.27 (m, 4H), 1.88 (dtd, J=13.1, 7.4, 3.6 Hz, 1H), 1.82-1.74 (m, 1H), 0.53-0.47 (m, 1H), 0.44-0.37 (m, 2H), 0.33-0.28 (m, 1H).

Examples 12, 38 and 46 were synthesized in a similar manner as described for examples 44 and 110, using racemic 2-amino-1-(5-fluoro-2-pyridyl)ethanol.

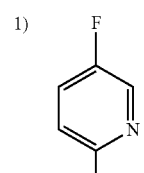

EDCI (360 mg, 1.90 mmol) was added to a solution of Intermediate (S)-SEM-acid (500 mg, 1.20 mmol), Intermediate 22 (360 mg, 1.20 mmol), HOBt (250 mg, 1.90 mmol) and DIPEA (0.43 mL, 2.50 mmol) in DCM (50 mL) and stirred overnight at rt. Washed with water (40 mL), sat. NaHCO$_3$ (40 mL), dried (Na$_2$SO$_4$) and evaporated. The crude product was chromatographed on silica using EtOAc:heptane as eluent. The diastereomeric mixture (380 mg, 55%) was isolated as a white solid. The two diastereomers (380 mg) were separated by means of chiral SFC with a purity greater than 99% de. Both isomers were SEM deprotected as described in the general procedure.

Example 44

First eluting isomer: White solid (63 mg, 22%), UPLC-MS: t$_R$=0.44 (M+H$^+$)=425.4 $^1$HNMR (600 MHz, DMSO-d$_6$) δ 11.63 (s br, 1H), 8.36 (d, J=1.2 Hz, 1H), 8.08 (s, 1H), 7.76 (t, J=5.8 Hz, 1H), 7.43 (d, J=6.3 Hz, 1H), 7.14 (d, J=3.6 Hz, 1H), 6.51 (d, J=3.6 Hz, 1H), 4.63 (dd, J=6.8, 5.0 Hz, 1H), 4.08 (ddd, J=13.1, 7.8, 3.6 Hz, 1H), 3.90-3.82 (m, 2H), 3.56 (d, J=13.2 Hz, 1H), 3.41 (dt, J=13.3, 5.3 Hz, 1H), 3.36-3.28 (m, 1H), 2.28 (s, 4H), 1.93-1.84 (m, 2H), 1.82-1.74 (m, 1H), 0.50-0.43 (m, 1H), 0.42-0.34 (m, 2H), 0.29-0.24 (m, 1H).

Example 110

Second eluting isomer: White solid (70 mg, 24%), UPLC-MS: t$_R$=0.44 (M+H$^+$)=425.4 $^1$HNMR (600 MHz, DMSO-d$_6$) δ 11.64 (s br, 1H), 8.36 (d, J=1.2 Hz, 1H), 8.08 (s, 1H), 7.82 (t, J=5.8 Hz, 1H), 7.43 (d, J=6.4 Hz, 1H), 7.14 (dd, J=3.6, 1.5 Hz, 1H), 6.52 (d, J=3.5 Hz, 1H), 5.68 (s, 1H), 4.61 (dd, J=7.3, 4.8 Hz, 1H), 4.10 (ddd, J=13.1, 7.6, 3.6 Hz, 1H), 3.91 (d, J=13.2 Hz, 1H), 3.85 (ddd, J=13.1, 7.7, 3.6 Hz, 1H),

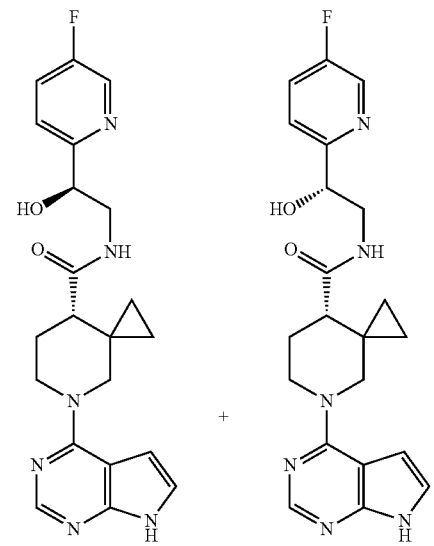

+

Example 38 was isolated omitting the chiral SFC separation step, hence being a 1:1 mixture of examples 12 and 46.

Example 12 was prepared by SEM deproctecion of the first eluting isomer isolated by SFC separation.

Example 46 was prepared by SEM deproctecion of the second eluting isomer isolated by SFC separation.

Example 75

(8S)—N-[(1S,2R)-2-(5-Fluoro-4-Methyl-2-Pyridyl)-2-Hydroxy-1-Methyl-Ethyl]-5-(7H-Pyrrolo[2,3-d]Pyrimidin-4-Yl)-5-Azaspiro[2.5]Octane-8-Carboxamide and

Example 133

(8S)—N-[(1S,2S)-2-(5-Fluoro-4-Methyl-2-Pyridyl)-2-Hydroxy-1-Methyl-Ethyl]-5-(7H-Pyrrolo[2,3-d]Pyrimidin-4-Yl)-5-Azaspiro[2.5]Octane-8-Carboxamide

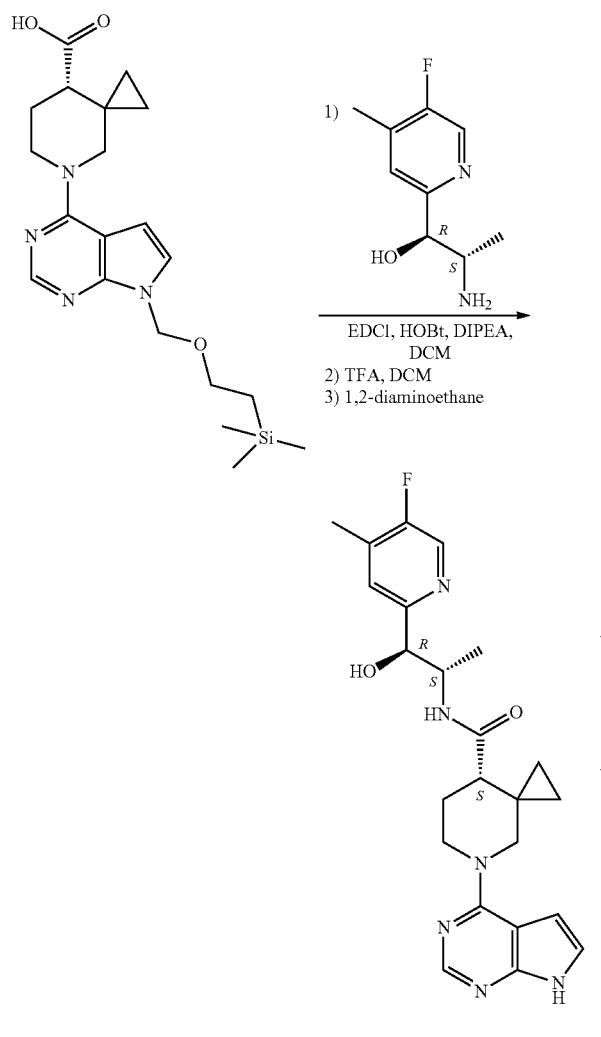

Example 75 and 133 were synthesised in a similar manner as for described for example 5. The aminoalcohol (1R,2S)-2-amino-1-(5-fluoro-4-methyl-2-pyridyl)propan-1-ol was synthesised in a similar manner as described for intermediates 9 and 10.

UPLC-MS: $t_R$=0.47 (M+H$^+$)=439.4

Example 75

$^1$HNMR (600 MHz, DMSO-d$_6$) δ 11.66 (s, 1H), 8.36 (s, 1H), 8.07 (s, 1H), 7.46-7.40 (m, 2H), 7.14 (dd, J=3.6, 2.1 Hz, 1H), 6.49 (dd, J=3.7, 1.6 Hz, 1H), 5.77 (br s, 1H), 4.56 (br s, 1H), 4.26-4.18 (m, 1H), 4.03-3.97 (ddd, J=13.1, 7.7, 3.6 Hz, 1H), 3.84-3.78 (ddd, J=13.0, 7.6, 3.8 Hz, 1H), 3.69 (d, J=13.2 Hz, 1H), 3.51 (d, J=13.2 Hz, 1H), 2.27 (br s, 2H), 1.89-1.82 (m, 1H), 1.75-1.68 (m, 1H), 1.06 (d, J=6.9 Hz, 3H), 0.37-0.26 (m, 3H), 0.18-0.11 (m, 1H).

Example 133

UPLC-MS: $t_R$=0.48 (M+H$^+$)=439.4
$^1$HNMR (600 MHz, DMSO-d$_6$) δ 11.67 (s, 1H), 8.38 (d, J=1.1 Hz, 1H), 8.08 (s, 1H), 7.75 (d, J=8.6 Hz, 1H), 7.40 (d, J=6.4 Hz, 1H), 7.15 (d, J=2.0 Hz, 1H), 6.52 (d, J=3.5 Hz, 1H), 5.68 (d, J=5.3 Hz, 1H), 4.51 (t, J=5.1 Hz, 1H), 4.27-4.16 (m, 2H), 3.88 (d, J=13.2 Hz, 1H), 3.77 (ddd, J=12.6, 8.2, 3.6 Hz, 1H), 3.53 (d, J=13.2 Hz, 1H), 2.32 (dd, J=7.5, 4.7 Hz, 1H), 2.29 (s, 3H), 1.92-1.85 (m, 1H), 1.80-1.73 (m, 1H), 0.90 (d, J=6.8 Hz, 3H), 0.44-0.34 (m, 2H), 0.30 (ddd, J=9.0, 5.6, 3.7 Hz, 1H), 0.19 (dt, J=9.2, 4.1 Hz, 1H).

Example 130

(8S)—N-[(2R)-3-[(3,3-Difluorocyclobutyl)Methyl-amino]-2-Hydroxy-3-Oxo-Propyl]-5-(7H-Pyrrolo[2,3-d]Pyrimidin-4-Yl)-5-Azaspiro[2.5]-Octane-8-Carboxamide

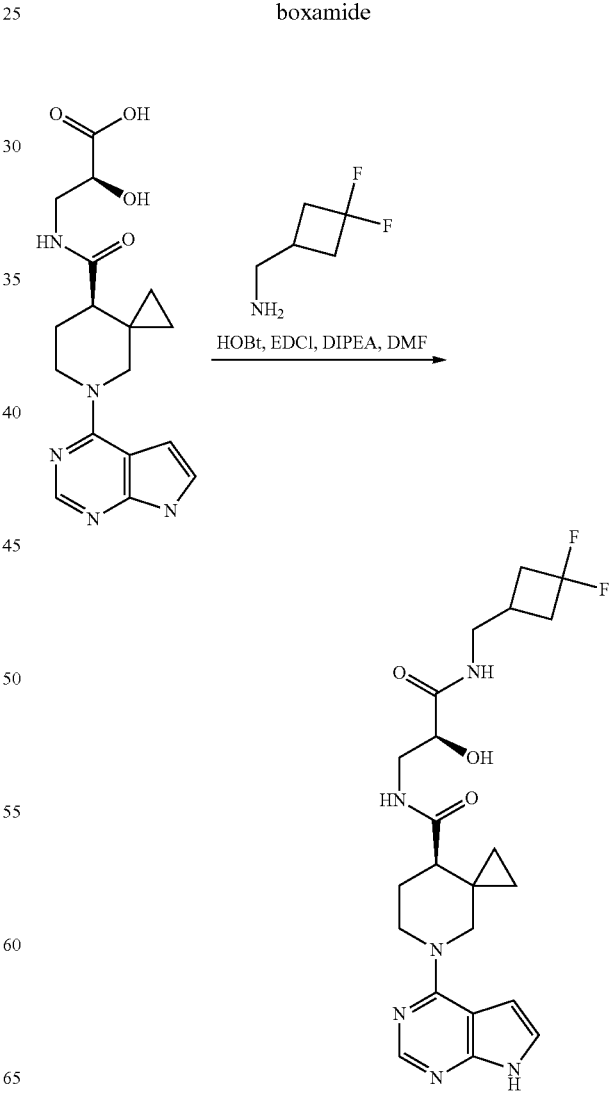

EDCI (6.4 mg, 0.0334 mmol) was added to a mixture of Intermediate 23 (10 mg, 0.0278 mmol), (3,3-difluorocyclobutyl)methanamine hydrochloride (6.6 mg, 0.0417 mmol), HOBt (3.8 mg, 0.0278 mmol) and DIPEA (6 µL, 0.0278 mmol) in dry DMF (600 µL) and stirred at rt for 4 hours. HPLC purified. The compound was isolated as a white solid.

UPLC-MS: $t_R$=0.43 (M+H$^+$)=463.3

$^1$HNMR (600 MHz, DMSO-d$_6$) δ 11.64 (s, 1H), 8.09 (s, 1H), 8.06 (t, J=6.2 Hz, 1H), 7.79 (t, J=5.7 Hz, 1H), 7.14 (d, J=3.6 Hz, 1H), 6.52 (d, J=3.6 Hz, 1H), 5.77 (s, 1H), 4.15 (ddd, J=13.0, 7.6, 3.5 Hz, 1H), 3.97-3.92 (m, 2H), 3.87 (ddd, J=13.1, 7.7, 3.7 Hz, 1H), 3.59 (d, J=13.2 Hz, 1H), 3.38-3.33 (m, 1H), 3.25-3.13 (m, 3H), 2.56 (m, 2H), 2.38-2.21 (m, 4H), 1.97-1.89 (m, 1H), 1.87-1.76 (m, 1H), 0.58-0.53 (m, 1H), 0.47-0.33 (m, 3H).

Example 129

(8S)—N-[(2R)-3-[[3,3-Difluoro-1-(Hydroxymethyl) Cyclobutyl]Methylamino]-2-Hydroxy-3-Oxo-Propyl]-5-(7H-Pyrrolo[2,3-d]Pyrimidin-4-Yl)-5-Azaspiro[2.5]Octane-8-Carboxamide This compound was prepared in a manner similar to example 130 using [1-(aminomethyl)-3,3-difluoro-cyclobutyl]methanol

Example 116

[1-(Hydroxymethyl)Cyclopropyl]Methyl (2R)-3-Hydroxy-2-[[(8S)-5-(7H-Pyrrolo[2,3-d]Pyrimidin-4-Yl)-5-Azaspiro[2.5]Octane-8-Carbonyl]Amino]Propanoate

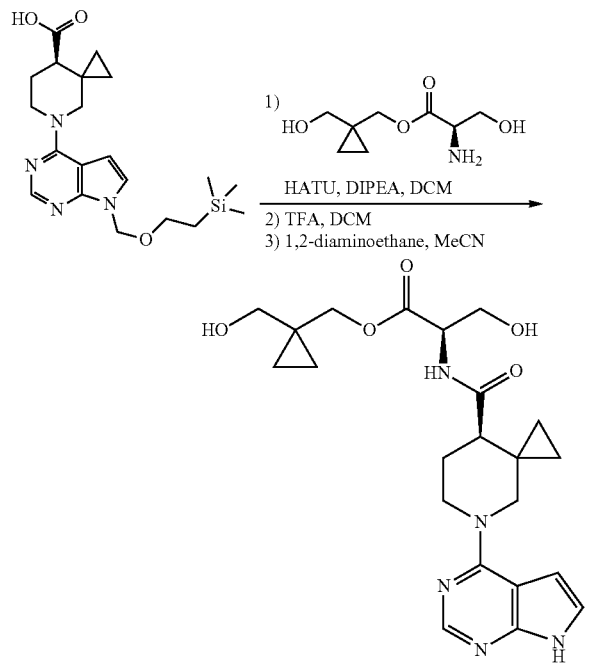

Step 1: HATU (56 mg, 0.15 mmol) was added to a mixture of Intermediate (S)-SEM-acid (50 mg, 0.12 mmol), intermediate 24 (42 mg, 0.14 mmol) and DIPEA (65 µL, 0.37 mmol) in dry DCM (2 mL) and stirred at rt for 4 hours. Evaporated and chromatographed on silica using EtOAc:heptane as eluent. The SEM-protected amide was isolated as a pale yellow oil (64 mg, 75%).

UPLC-MS: $t_R$=1.03 (M+H$^+$)=688.4

Step 2 and 3: The SEM group was removed as described in the general procedure.

UPLC-MS: $t_R$=0.39 (M+H$^+$)=444.3

$^1$HNMR (600 MHz, DMSO-d$_6$) δ 11.67 (s, 1H), 8.13 (d, J=7.7 Hz, 1H), 8.09 (s, 1H), 7.15 (dd, J=3.7, 1.6 Hz, 1H), 6.53 (d, J=3.5 Hz, 1H), 5.07 (s br, 1H), 4.62 (t, J=5.6 Hz, 1H), 4.36-4.31 (m, 1H), 4.13 (ddd, J=13.1, 7.7, 3.5 Hz, 1H), 4.03 (d, J=11.2 Hz, 1H), 3.99-3.88 (m, 3H), 3.73-3.58 (m, 3H), 3.34-3.24 (m, 2H), 2.48-2.42 (m, 1H), 1.97-1.89 (m, 1H), 1.88-1.80 (m, 1H), 0.60-0.51 (m, 1H), 0.49-0.32 (m, 7H).

The following compounds were prepared analogously starting from coupling of Intermediate (S)-SEM-acid with the specific amine relevant of the example in question instead of Intermediate 24 and replacing DCM with DMF in step 1:

Examples 1, 3,4, 7-8, 13-14, 16-18, 20, 22, 24, 27, 29-32, 34, 36-37, 43, 48, 51, 54, 62, 64, 67, 71, 84, 93, 97, 101, 104-105, 122, 126, 132, 135, 146 and 149-151

The following compounds were prepared analogously starting from coupling of Intermediate (S)-SEM-acid with the specific amine relevant of the example in question instead of Intermediate 24, but prepared analogously to Intermediate 24, and replacing DCM with DMF in step 1: 42, 91 and 98.

The following compounds were prepared analogously starting from coupling of Intermediate (R)-SEM-acid with the specific amine relevant of the example in question and replacing DCM with DMF in step 1: Example 142 and Example 145.

Example 80

Benzyl (2R)-3-Hydroxy-2-[[(8S)-5-(7H-Pyrrolo[2,3-d]Pyrimidin-4-Yl)-5-Azaspiro[2.5]Octane-8-Carbonyl]Amino]Propanoate

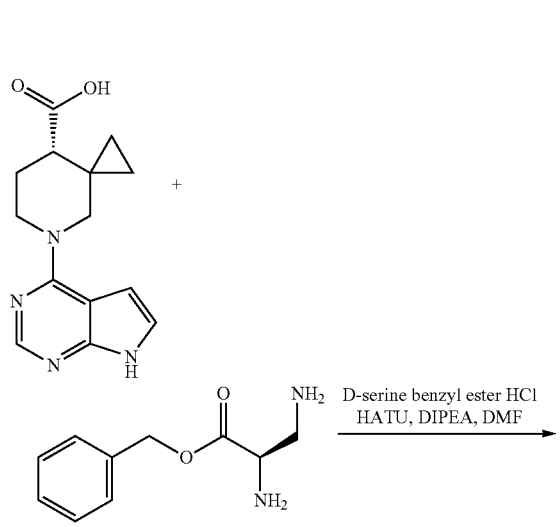

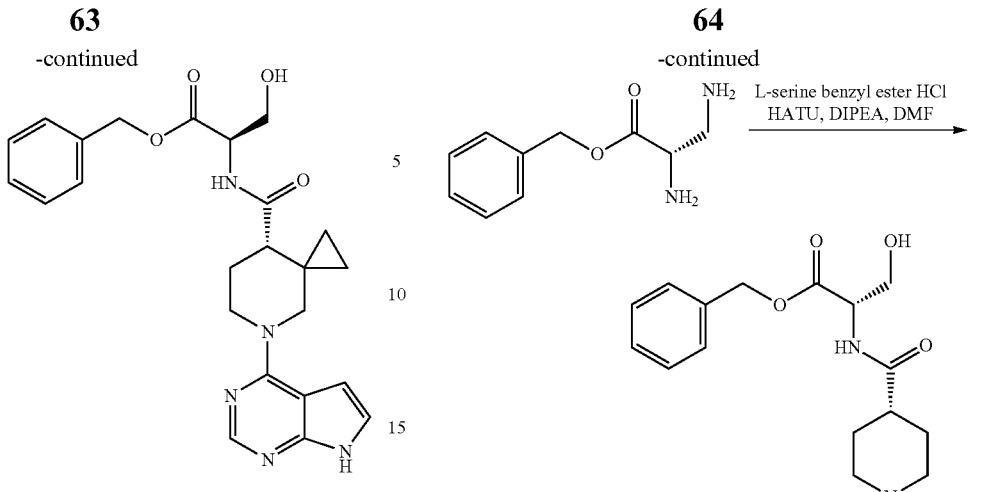

HATU (16.7681 mg, 0.0441 mmol) was added to a mixture of Intermediate (S)-acid (10 mg, 0.0367 mmol) and L-serine benzyl ester HCl (10.2169 mg, 0.0441 mmol) and DIPEA (18.9858 mg, 0.1469 mmol, 0.025 mL) dissolved in dry DMF (0.300 mL) and stirred at rt for 1 hour.

Reaction was purified on HPLC (54% yield).

UPLC-MS: $t_R$=0.505 (M+H$^+$)=450.46

$^1$H NMR (300 MHz, DMSO-d$_6$) δ 11.62 (s, 1H), 8.12 (d, J=7.6 Hz, 1H), 8.09 (s, 1H), 7.52-7.23 (m, 5H), 7.14 (d, J=3.6 Hz, 1H), 6.51 (d, J=3.6 Hz, 1H), 5.22-4.93 (m, 3H), 4.40 (dt, J=5.0, 7.6 Hz, 1H), 4.18-4.02 (m, 1H), 3.95 (d, J=13.2 Hz, 1H), 3.91-3.81 (m, 1H), 3.70 (qd, J=5.1, 11.0 Hz, 2H), 3.60 (d, J=13.2 Hz, 1H), 2.44 (t, J=5.8 Hz, 1H), 2.02-1.70 (m, 2H), 0.69-0.27 (m, 4H).

The following compounds were prepared analogously starting from coupling of Intermediate (S)-acid with the specific amine relevant of the example in question instead of L-serine benzyl ester HCl:

Example 28, 47, 49, 52, 57, 68, 77, 78, 100, 106, 108, 109, 120, 121, 147 and 148

The following compounds were prepared analogously starting from coupling of Intermediate rac-acid with the specific amine relevant of the example in question instead of L-serine benzyl ester HCl:

Example 19, 21, 26, 33, 35, 39, 53, 55, 56, 58, 59, 61, 63, 66, 69, 70, 76, 79, 81, 82, 83, 85, 86, 88, 90, 94, 95, 99, 102, 103, 111, 112, 113, 114, 115, 117, 118, 119, 123, 124, 127, 128, 131, 134, 136, 137, 139, 141, 143 and 144.

Example 138

Benzyl (2S)-3-Hydroxy-2-[[(8S)-5-(7H-Pyrrolo[2,3-d]Pyrimidin-4-Yl)-5-Azaspiro[2.5]Octane-8-Carbonyl]Amino]Propanoate

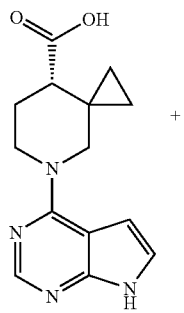

HATU (16.7681 mg, 0.0441 mmol) was added to a mixture of Intermediate (S)-acid (10 mg, 0.0367 mmol) and L-serine benzyl ester HCl (10.2169 mg, 0.0441 mmol) and DIPEA (18.9858 mg, 0.1469 mmol, 0.025 mL) dissolved in dry DMF (0.300 mL) and stirred at rt for 1 hour.

Reaction was purified on HPLC (54% yield).

UPLC-MS: $t_R$=0.49 (M+H$^+$)=450.48

$^1$H NMR (300 MHz, DMSO-d$_6$) δ 11.62 (s, 1H), 8.14 (d, J=7.6 Hz, 1H), 8.09 (s, 1H), 7.48-7.24 (m, 5H), 7.14 (d, J=3.5 Hz, 1H), 6.51 (d, J=3.6 Hz, 1H), 5.13 (s, 2H), 5.07 (s, 1H), 4.40 (dt, J=4.9, 7.7 Hz, 1H), 4.21 (ddd, J=3.7, 6.9, 11.1 Hz, 1H), 3.93 (d, J=13.2 Hz, 1H), 3.87-3.61 (m, 3H), 3.56 (d, J=13.2 Hz, 1H), 2.51 (s, 1H), 2.04-1.71 (m, 2H), 0.65-0.45 (m, 2H), 0.45-0.29 (m, 2H).

Example 87

Cyclopentylmethyl (2R)-3-Hydroxy-2-[[(8S)-5-(7H-Pyrrolo[2,3-d]Pyrimidin-4-Yl)-5-Azaspiro[2.5]Octane-8-Carbonyl]Amino]Propanoate

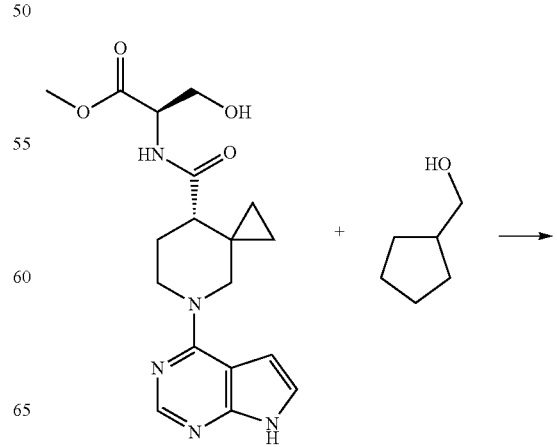

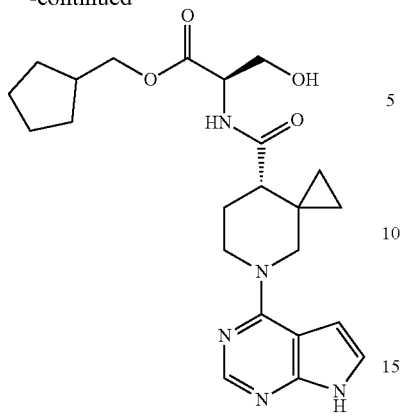

Cyclopentylmethanol (0.3 ml) was added to a mixture of Me-ester of Intermediate 25 (13 mg, 0.0348 mmol) DMSO (0.3 mL) and DBU (0.1 mL). The reaction mixture was stirred at 65° C. for 20 hours. Reaction was cooled to room temperature.
Reaction was purified on HPLC (8.6% yield).
UPLC-MS: $t_R$=0.57 (M+H$^+$)=442.47

Example 96

Cyclopentyl (2R)-3-Hydroxy-2-[[(8S)-5-(7H-Pyrrolo[2,3-d]Pyrimidin-4-Yl)-5-Azaspiro[2.5]Octane-8-Carbonyl]Amino]Propanoate

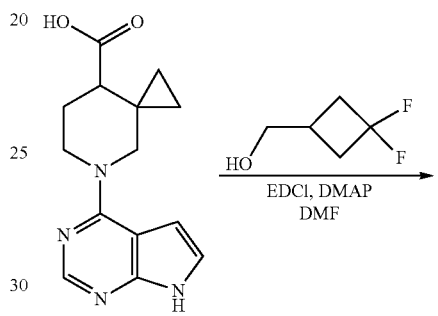

Cyclopentanol (0.5 ml) was added to a mixture of Me-ester of Intermediate 25 (13 mg, 0.0348 mmol) DMSO (0.3 mL) and DBU (0.1 mL). The reaction mixture was stirred at 65° C. for 20 hours. Reaction was cooled to room temperature.
Reaction was purified on prep. HPLC (4.1% yield).
UPLC-MS: $t_R$=0.51 (M+H$^+$)=428.47

Example 153

(3,3-Difluorocyclobutyl)Methyl 5-(7H-Pyrrolo[2,3-d]Pyrimidin-4-Yl)-5-Azaspiro[2.5]Octane-8-Carboxylate

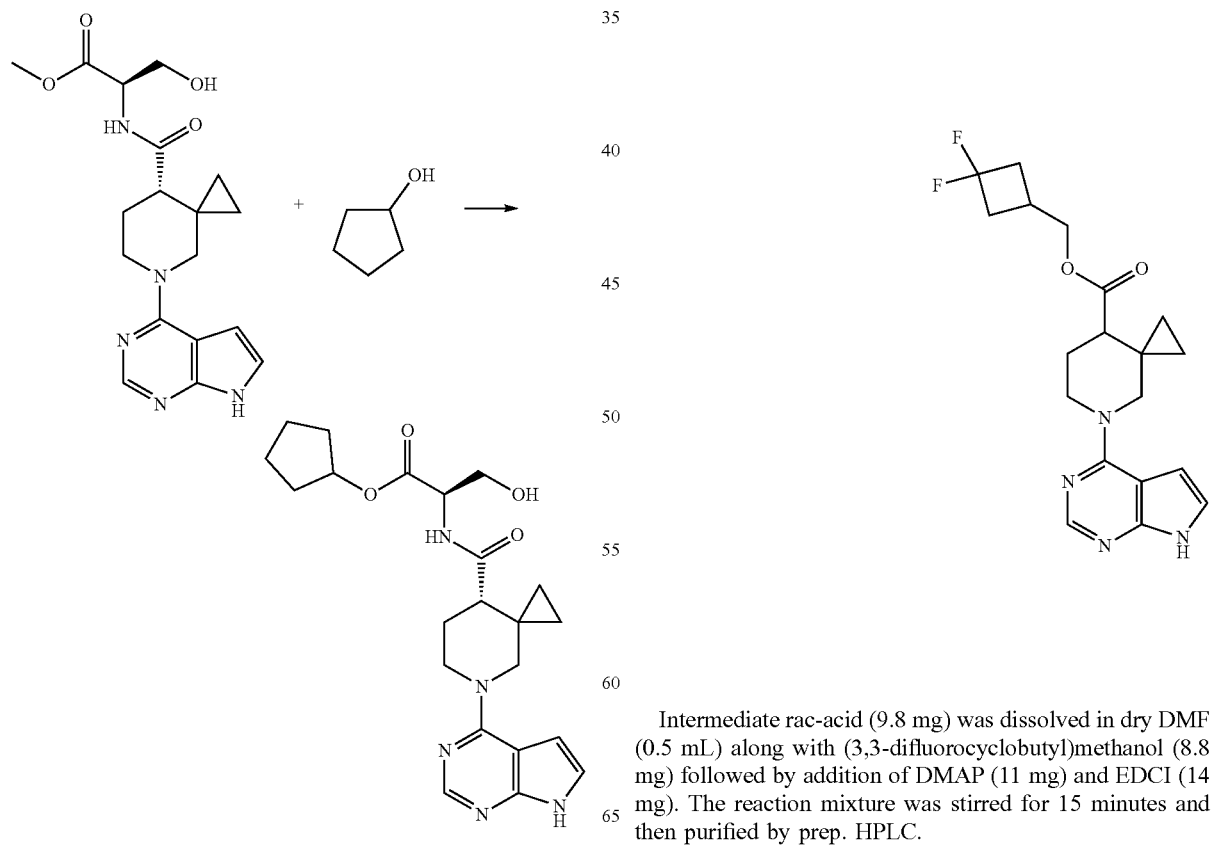

Intermediate rac-acid (9.8 mg) was dissolved in dry DMF (0.5 mL) along with (3,3-difluorocyclobutyl)methanol (8.8 mg) followed by addition of DMAP (11 mg) and EDCI (14 mg). The reaction mixture was stirred for 15 minutes and then purified by prep. HPLC.
UPLC-MS method 7: $t_R$=2.1 (M+H$^+$)=377.17

Example 154

(3,3-Difluorocyclobutyl)Methyl (8S)-5-(7H-Pyrrolo[2,3-d]Pyrimidin-4-Yl)-5-Azaspiro[2.5]Octane-8-Carboxylate

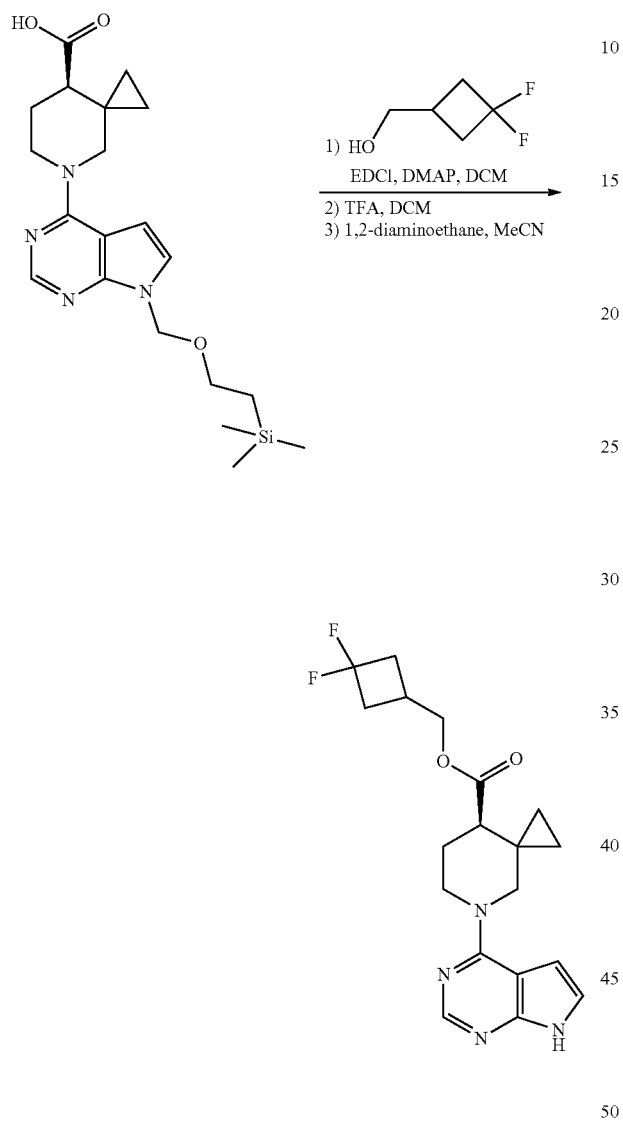

Ester Formation:

Intermediate (S)-SEM-acid (680 mg, 1.7 mmol) was dissolved in dry DCM (35 mL) along with (3,3-difluorocyclobutyl)methanol (410 mg, 3.4 mmol) and DMAP (210 mg, 1.7 mmol). Then was added EDCI (490 mg, 2.5 mmol) and the mixture was stirred at rt for 2 hours. The mixture was washed with 0.1 M KHSO$_4$ (20 mL), dried over Na$_2$SO$_4$ and evaporated to dryness to yield a clear oil which was used directly in the next step.

SEM De-Protection:

The clear oil from above was dissolved in DCM (25 mL) followed by addition of TFA (1.56 mL) and stirred at rt for 4 hours. All volatiles were evaporated and the residue was taken up in MeCN (10 mL) and 1,2-diaminoethane (306 mg, 5.1 mmol) was added. The mixture was stirred at rt overnight. All volatiles were evaporated and the white solid was triturated with 2% AcOH (aq., 20 mL) and the solid was filtered off to give the desired product (540 mg, 85% yield).

UPLC-MS method 7: t$_R$=2.1 (M+H$^+$)=377.17

$^1$H NMR (600 MHz, DMSO-d$_6$) δ 11.66 (s, 1H), 8.09 (s, 1H), 7.16 (m, 1H), 6.54 (m, 1H), 4.28-4.22 (m, 1H), 4.19-4.10 (m, 2H), 3.79-3.66 (m, 3H), 2.71-2.62 (m, 2H), 2.50-2.36 (m, 4H), 2.05-1.90 (m, 2H), 0.63-0.59 (m, 1H), 0.56-0.45 (m, 2H), 0.41-0.36 (m, 1H).

Example 155

(3,3-Difluorocyclobutyl)Methyl (8R)-5-(7H-Pyrrolo[2,3-d]Pyrimidin-4-Yl)-5-Azaspiro[2.5]Octane-8-Carboxylate

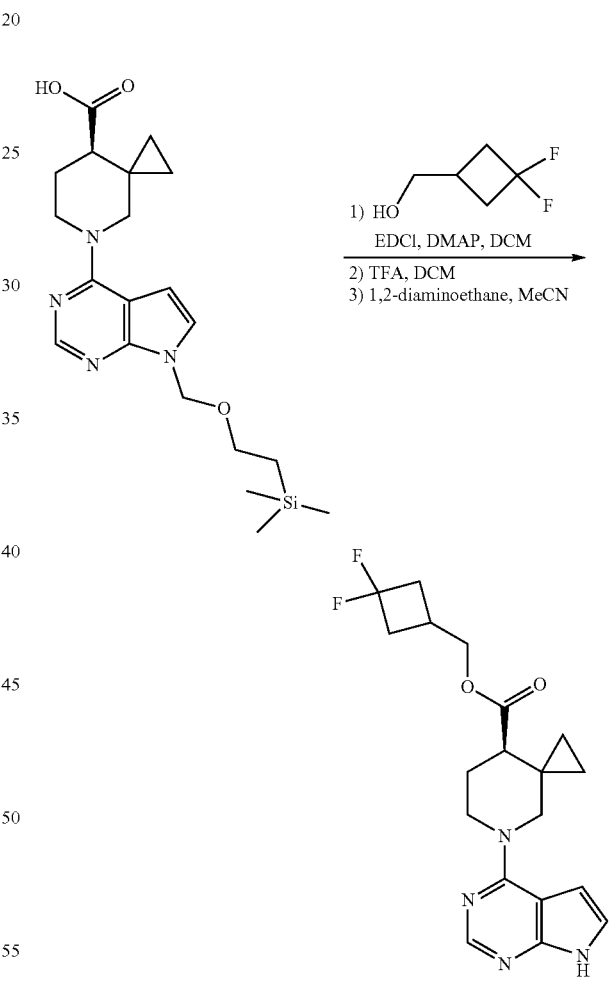

Example 155 was synthesized as described for example 154, except starting from (R)-SEM-acid.

Purified by prep. HPLC.

UPLC-MS method 7: t$_R$=2.1 (M+H$^+$)=377.17

$^1$H NMR (300 MHz, DMSO-d$_6$) δ 11.63 (s, 1H), 8.10 (s, 1H), 7.16 (m, 1H), 6.53 (m, 1H), 4.31-4.06 (m, 3H), 3.80-3.63 (m, 3H), 2.77-2.57 (m, 2H), 2.50-2.29 (m, 4H), 2.09-1.88 (m, 2H), 0.66-0.33 (m, 4H).

Example 156

[1-(Hydroxymethyl)Cyclopropyl]Methyl (8S)-5-(7H-Pyrrolo[2,3-d]Pyrimidin-4-Yl)-5-Azaspiro[2.5]Octane-8-Carboxylate

Example 157

[1-(hydroxymethyl)cyclobutyl]methyl (8S)-5-(7H-pyrrolo[2,3-d]pyrimidin-4-yl)-5-azaspiro[2.5]octane-8-carboxylate

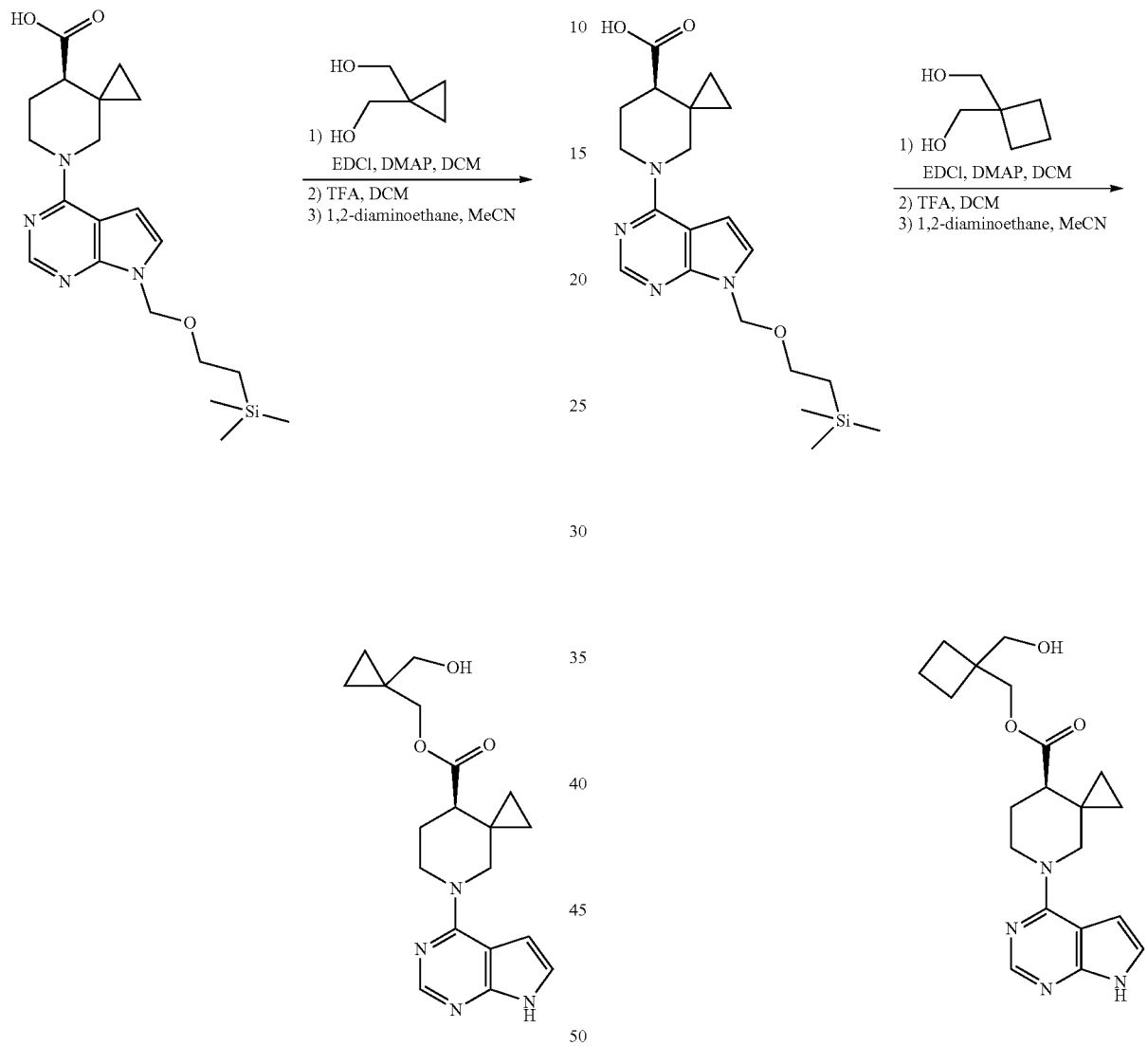

Prepared as described for example 154, starting from Intermediate (S)-SEM-acid (700 mg, 1.74 mmol) and [1-(hydroxymethyl)cyclopropyl]methanol (1.78 g, 17.4 mmol). Purified by prep. HPLC.

UPLC-MS method 7: $t_R$=1.79 (M+H$^+$)=357.18

$^1$H NMR (600 MHz, DMSO-d$_6$) δ 11.66 (s, 1H), 8.09 (s, 1H), 7.16 (m, 1H), 6.54 (m, 1H), 4.62 (t, 1H), 4.22-4.14 (m, 1H), 4.04-3.97 (m, 4H), 3.80-3.71 (m, 3H), 3.31-3.29 (br m, 2H), 2.45-2.40 (m, 1H), 2.05-1.90 (br m, 2H), 0.61-0.38 (br m, 8H).

Prepared as described for example 154, starting from Intermediate (S)-SEM-acid (600 mg, 1.49 mmol) and [1-(hydroxymethyl)cyclobutyl]methanol (519 mg, 4.47 mmol). Purified by prep. HPLC.

UPLC-MS method 7: $t_R$=1.88 (M+H$^+$)=371.20

$^1$H NMR (600 MHz, DMSO-d$_6$) δ 11.66 (s, 1H), 8.08 (s, 1H), 7.16 (m, 1H), 6.54 (m, 1H), 4.70 (t, 1H), 4.09-4.01 (m, 2H), 3.80-3.66 (m, 3H), 3.42 (m, 2H), 3.30 (s, 1H), 2.39 (m, 1H), 2.06-1.91 (br m, 2H), 1.86-1.71 (br m, 6H), 0.63-0.59 (m, 1H), 0.56-0.51 (m, 1H), 0.49-0.45 (m, 1H), 0.41-0.37 (m, 1H).

Example 159

[1-(Hydroxymethyl)Cyclopentyl]Methyl (8S)-5-(7H-Pyrrolo[2,3-d]Pyrimidin-4-Yl)-5-Azaspiro[2.5]Octane-8-Carboxylate

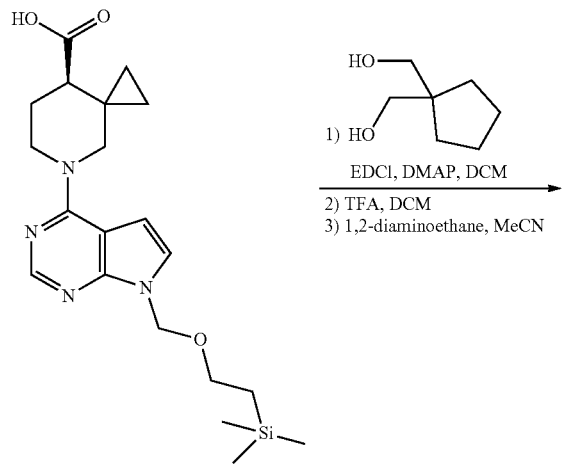

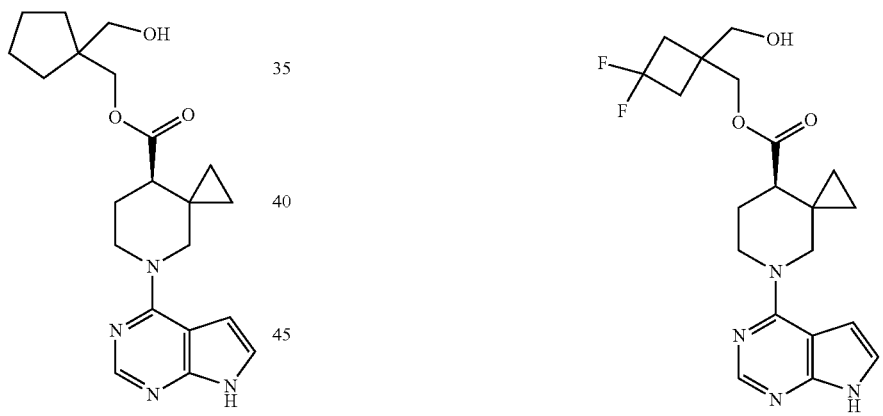

Prepared as described for example 154, starting from Intermediate (S)-SEM-acid (600 mg, 1.49 mmol) and [1-(hydroxymethyl)cyclopentyl]methanol (485 mg, 3.73 mmol). Purified by prep. HPLC.

UPLC-MS method 7: $t_R$=1.96 (M+H$^+$)=385.22

$^1$H NMR (600 MHz, DMSO-d$_6$) δ 11.66 (s, 1H), 8.08 (s, 1H), 7.16 (m, 1H), 6.52 (m, 1H), 4.68 (t, 1H), 4.29-4.23 (br m, 1H), 3.96-3.90 (m, 2H), 3.79-3.63 (br m, 3H), 3.27 (m, 2H), 2.36 (m, 1H), 2.05-1.90 (br m, 2H), 1.586-1.52 (br m, 4H), 1.47-1.41 (br, 2H), 1.37-1.29 (br, 2H), 0.63-0.59 (m, 1H), 0.55-0.50 (m, 1H), 0.49-0.45 (m, 1H), 0.41-0.36 (m, 1H).

Example 160

[3,3-Difluoro-1-(Hydroxymethyl)Cyclobutyl]Methyl (8S)-5-(7H-Pyrrolo[2,3-d]Pyrimidin-4-Yl)-5-Azaspiro[2.5]Octane-8-Carboxylate

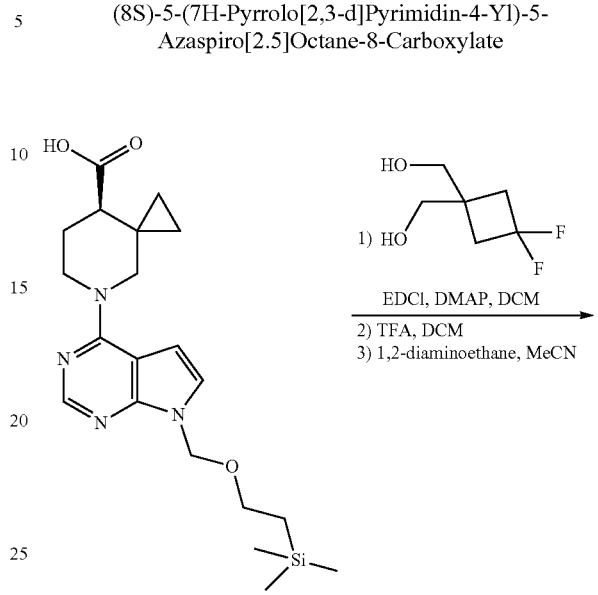

Prepared as described for example 154, starting from Intermediate (S)-SEM-acid (600 mg, 1.49 mmol) and [3,3-difluoro-1-(hydroxymethyl)cyclobutyl]methanol (453 mg, 2.98 mmol). Purified by prep. HPLC.

UPLC-MS method 7: $t_R$=1.92 (M+H$^+$)=407.18

$^1$H NMR (600 MHz, DMSO-d$_6$) δ 11.69 (s, 1H), 8.12 (s, 1H), 7.16 (m, 1H), 6.55 (m, 1H), 5.10 (t, 1H), 4.31 (br m, 1H), 4.12 (m, 2H), 3.79 (m, 1H), 3.70-3.59 (br m, 2H), 3.46 (m, 2H), 2.48-2.36 (br, 4H), 2.06-2.01 (br m, 1H), 1.98-1.91 (br, 1H), 0.65-0.60 (m, 1H), 0.56-0.51 (m, 1H), 0.48-0.44 (m, 1H), 0.40-0.35 (m, 1H).

Example 161

[1-(Hydroxymethyl)Cyclohexyl]Methyl (8S)-5-(7H-Pyrrolo[2,3-d]Pyrimidin-4-Yl)-5-Azaspiro[2.5]Octane-8-Carboxylate

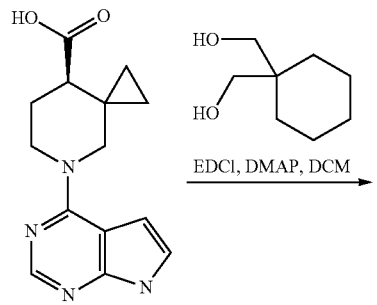
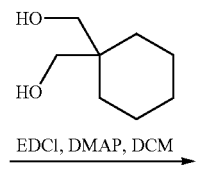

Intermediate (S)-acid (27 mg, 0.099 mmol), [1-(hydroxymethyl)cyclohexyl]methanol (28.6 mg, 0.198 mmol), DMAP (12.1 mg, 0.099 mmol) was dissolved in DMSO (1 mL) and DMF (1 mL) followed by addition of EDCI (19 mg, 0.099 mmol).

The mixture was stirred overnight at rt and then purified by prep. HPLC.

UPLC-MS method 7: $t_R$=2.05 (M+H$^+$)=398.23

$^1$H NMR (300 MHz, DMSO-d$_6$) δ 11.64 (s, 1H), 8.10 (s, 1H), 7.14 (m, 1H), 6.55 (m, 1H), 4.53-4.47 (br, 1H), 4.31-4.21 (br, 1H), 3.96-3.92 (m, 2H), 3.82-3.62 (br m, 3H), 2.37 (m, 1H), 2.06-1.91 (br m, 2H), 1.46-1.31 (br m, 12H), 0.65-0.36 (m, 4H).

Example 162

[3-(Hydroxymethyl)-1,1-Dioxo-Thietan-3-Yl]Methyl (8S)-5-(7H-Pyrrolo[2,3-d]Pyrimidin-4-Yl)-5-Azaspiro[2.5]Octane-8-Carboxylate

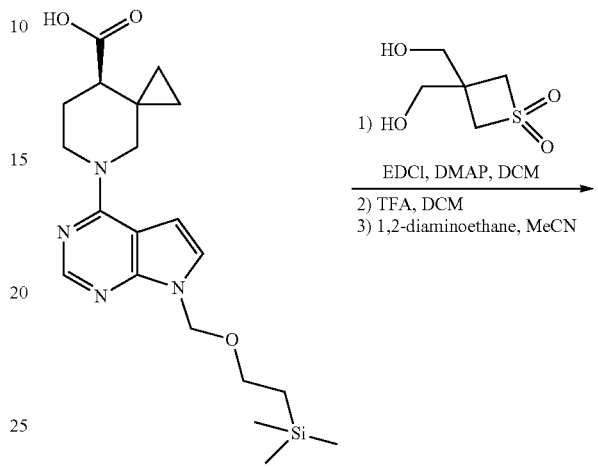
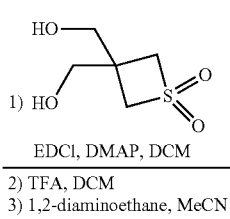
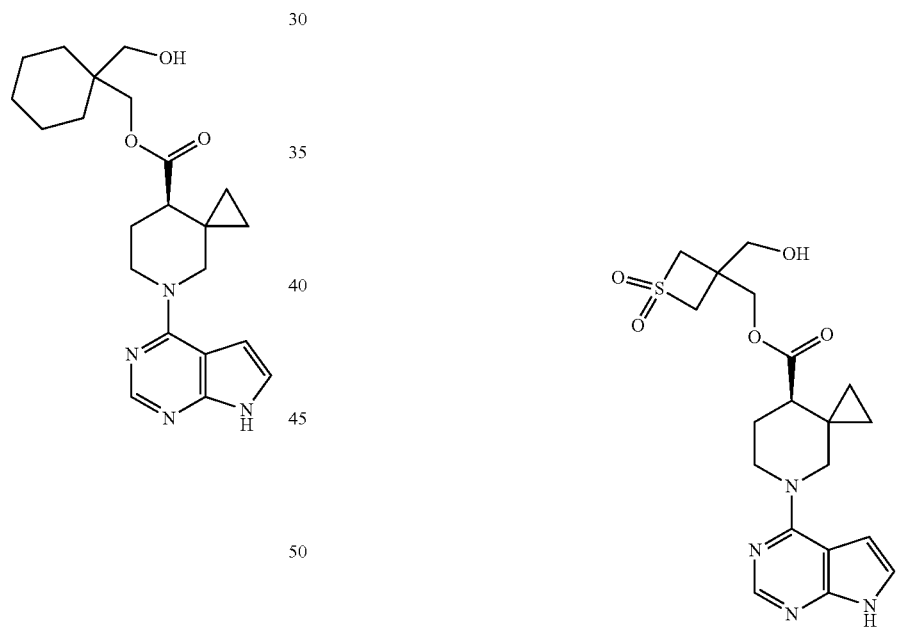

Prepared as described for example 154, starting from Intermediate (S)-SEM-acid (30 mg, 0.075 mmol) and [3-(hydroxymethyl)-1,1-dioxo-thietan-3-yl]methanol (61.9 mg, 0.373 mmol). Purified by prep. HPLC.

UPLC-MS method 7: $t_R$=1.71 (M+H$^+$)=421.15

Examples 163

[1-(Cyanomethyl)Cyclopropyl]Methyl (8S)-5-(7H-Pyrrolo[2,3-d]Pyrimidin-4-Yl)-5-Azaspiro[2.5]Octane-8-Carboxylate

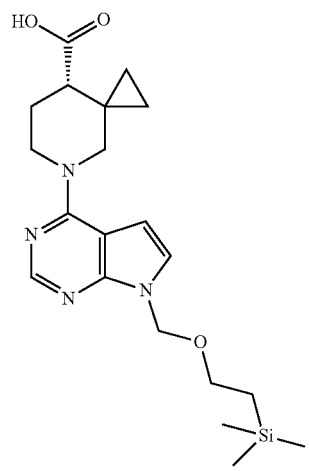

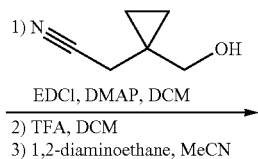

EDCl, DMAP, DCM
2) TFA, DCM
3) 1,2-diaminoethane, MeCN

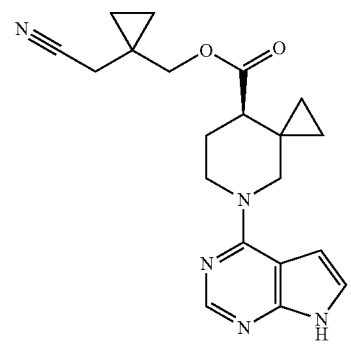 [SMILES: N#CCC1(COC(=O)C2CCN(c3ncnc4[nH]ccc34)CC23CC3)CC1]

Prepared as described for Example 162, using 2-[1-(hydroxymethyl) cyclopropyl]acetonitrile in stead of [3-(hydroxymethyl)-1,1-dioxo-thietan-3-yl]methanol.

UPLC-MS method 7: $t_R$=1.96 (M+H$^+$)=366.19

Example 164

[1-(Cyanomethyl)Cyclopropyl]Methyl 5-(7H-Pyrrolo[2,3-d]Pyrimidin-4-Yl)-5-Azaspiro[2.5]Octane-8-Carboxylate

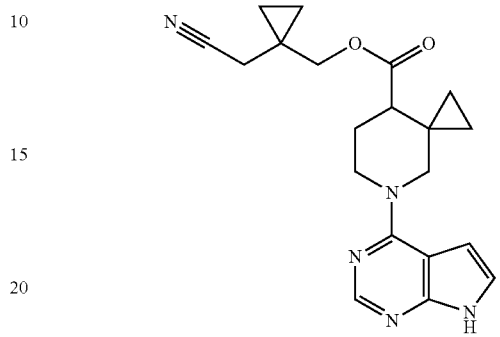

Prepared as described for Example 153, using 2-[1-(hydroxymethyl) cyclopropyl]acetonitrile in stead of (3,3-difluorocyclobutyl)methanol.

UPLC-MS method 7: $t_R$=1.95 (M+H$^+$)=366.19

JAK Kinase Assays:

Human baculovirus-expressed JAK1, 2, 3 and TYK2 were purchased from Carna Biosciences, Inc. All four purified enzymes contain only the catalytic domain. JAK1 (aa 850-1154) and TYK2 (aa 871-1187) are expressed with an N-terminally fused GST-tag, and JAK2 and JAK3 with an N-terminally fused His-tag.

Inhibition of phosphorylation of a synthetic peptide was measured in an HTRF-based assay using the TK substrate-Biotin from the Cisbio HTRFKinEASE TK kit. First, 2 µl of TK solution (TK substrate-biotin in kinase buffer [1× enzymatic buffer from HTRFKinEASE TK kit, 1 mM DTT]) is added to a plate containing 1 µl prediluted compound (final assay concentration DMSO: 0.75%). Then, 5 µl kinase-ATP mix (prepared in kinase buffer) is added to the wells and the plates are incubated at RT for 20-30 min. For all four kinases a concentration of ATP that corresponded to the Km for ATP was used. The final concentrations of buffers, substrate, kinase and ATP were: JAK1: 50 mM Hepes buffer pH 7.0, 0.01% BSA, 10 mM MgCl$_2$, 1 mM DTT, 7 µM ATP, 50 nM SEB, 1 µM TK Substrate-Biotin and 5 ng JAK1; JAK2: 50 mM Hepes buffer pH 7.0, 0.01% BSA, 5 mM MgCl$_2$, 1 mM DTT, 4 µM ATP, 1 µM TK Substrate-Biotin and 0.1 ng JAK2; JAK3: 50 mM Hepes buffer pH 7.0, 0.01% BSA, 5 mM MgCl$_2$, 1 mM DTT, 2 µM ATP, 1 µM TK Substrate-Biotin and 0.3 ng JAK3; TYK2: 50 mM Hepes buffer pH 7.0, 0.01% BSA, 5 mM MgCl$_2$, 1 mM DTT, 13 µM ATP, 50 nM SEB, 1 µM TK Substrate-Biotin and 0.8 ng TYK2. Thereafter, the kinase reaction is stopped by adding 4 µl detection mix (final concentrations: 50 mM Hepes buffer pH 7.0, 0.01% BSA, 0.8 M KF, 20 mM EDTA, 42 nM Streptavidin-XL665 and 1:400 STK Ab Cryptate) and the plates are incubated overnight in the dark. The HTRF signal is read using an Envision plate reader.

In Table 1 selected JAK kinase inhibitory activities are listed along with analytical $t_R$ and observed M+H$^+$ data (UPLC-MS method 7).

TABLE 1

| | | | JAK kinase inhibitory and analytical data | | | | | |
|---|---|---|---|---|---|---|---|---|
| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
| 1 | 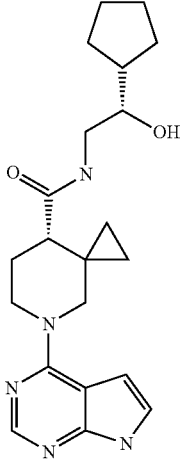 [SMILES: O=C(NC[C@@H](O)C1CCCC1)[C@H]1CCN(c2ncnc3[nH]ccc23)CC12CC2] | (8S)-N-[(2S)-2-cyclopentyl-2-hydroxy-ethyl]-5-(7H-pyrrolo[2,3-d]pyrimidin-4-yl)-5-azaspiro[2.5]octane-8-carboxamide | 0.5 | 1.0 | 3.3 | 3.6 | 1.83 | 384.23 |
| 2 | 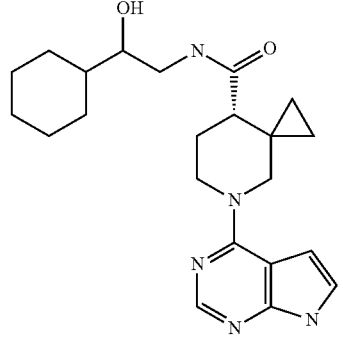 [SMILES: O=C(NCC(O)C1CCCCC1)[C@H]1CCN(c2ncnc3[nH]ccc23)CC12CC2] | (8S)-N-(2-cyclohexyl-2-hydroxy-ethyl)-5-(7H-pyrrolo[2,3-d]pyrimidin-4-yl)-5-azaspiro[2.5]octane-8-carboxamide | 0.5 | 1.3 | 3.7 | 4.6 | 1.89 | 398.25 |
| 3 | 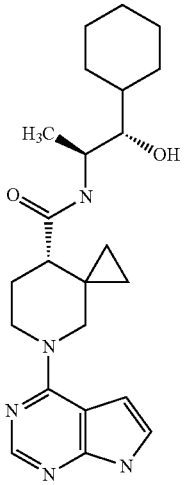 [SMILES: C[C@H](NC(=O)[C@H]1CCN(c2ncnc3[nH]ccc23)CC12CC2)[C@@H](O)C1CCCCC1] | (8S)-N-[(1S,2S)-2-cyclohexyl-2-hydroxy-1-methyl-ethyl]-5-(7H-pyrrolo[2,3-d]pyrimidin-4-yl)-5-azaspiro[2.5]octane-8-carboxamide | 0.5 | 1.1 | 3.4 | 6.2 | 1.92 | 412.26 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 4 | 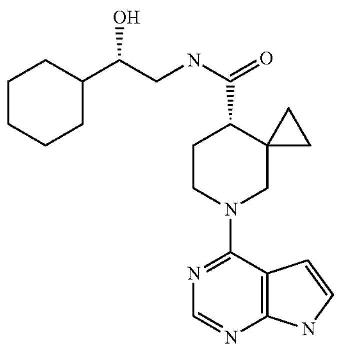 [SMILES: O=C(NC[C@@H](O)C1CCCCC1)[C@H]1CCN(c2ncnc3[nH]ccc23)CC12CC2] | (8S)-N-[(2S)-2-cyclohexyl-2-hydroxy-ethyl]-5-(7H-pyrrolo[2,3-d]pyrimidin-4-yl)-5-azaspiro[2.5]octane-8-carboxamide | 0.5 | 1.2 | 3.4 | 4.0 | 1.89 | 398.25 |
| 5 | 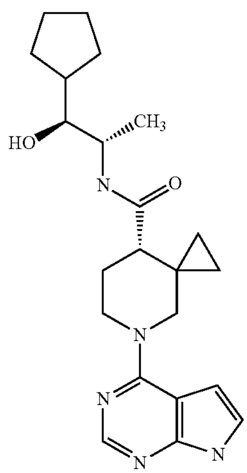 [SMILES: C[C@H](NC(=O)[C@H]1CCN(c2ncnc3[nH]ccc23)CC12CC2)[C@@H](O)C1CCCC1] | (8S)-N-[(1S,2S)-2-cyclopentyl-2-hydroxy-1-methyl-ethyl]-5-(7H-pyrrolo[2,3-d]pyrimidin-4-yl)-5-azaspiro[2.5]octane-8-carboxamide | 0.6 | 1.1 | 2.3 | 6.3 | 1.84 | 398.25 |
| 6 | 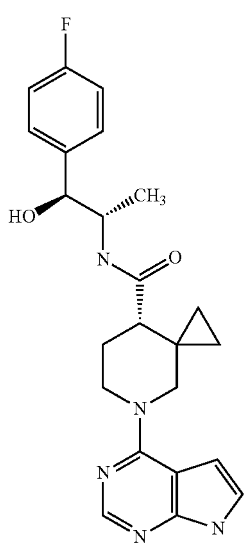 [SMILES: C[C@H](NC(=O)[C@H]1CCN(c2ncnc3[nH]ccc23)CC12CC2)[C@@H](O)c1ccc(F)cc1] | (8S)-N-[(1S,2S)-2-(4-fluorophenyl)-2-hydroxy-1-methyl-ethyl]-5-(7H-pyrrolo[2,3-d]pyrimidin-4-yl)-5-azaspiro[2.5]octane-8-carboxamide | 0.6 | 1.4 | 7.4 | 7.0 | 1.84 | 424.21 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 7 | 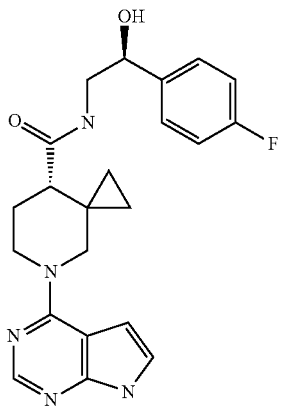 [SMILES: O=C(NC[C@@H](O)c1ccc(F)cc1)[C@H]1CCN(c2ncnc3[nH]ccc23)CC12CC2] | (8S)-N-[(2S)-2-(4-fluorophenyl)-2-hydroxy-ethyl]-5-(7H-pyrrolo[2,3-d]pyrimidin-4-yl)-5-azaspiro[2.5]octane-8-carboxamide | 0.6 | 1.7 | 8.8 | 4.9 | 1.79 | 410.19 |
| 8 | 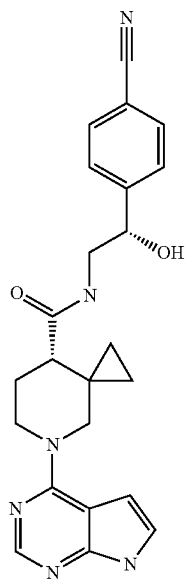 [SMILES: N#Cc1ccc([C@H](O)CNC(=O)[C@H]2CCN(c3ncnc4[nH]ccc34)CC23CC3)cc1] | (8S)-N-[(2S)-2-(4-cyanophenyl)-2-hydroxy-ethyl]-5-(7H-pyrrolo[2,3-d]pyrimidin-4-yl)-5-azaspiro[2.5]octane-8-carboxamide | 0.6 | 2.7 | 4.9 | 17.7 | 1.74 | 417.20 |
| 9 | 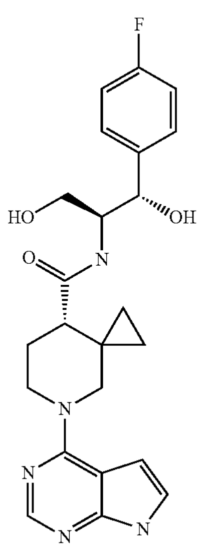 [SMILES: O=C(N[C@@H](CO)[C@@H](O)c1ccc(F)cc1)[C@H]1CCN(c2ncnc3[nH]ccc23)CC12CC2] | (8S)-N-[(1S,2S)-2-(4-fluorophenyl)-2-hydroxy-1-(hydroxymethyl)ethyl]-5-(7H-pyrrolo[2,3-d]pyrimidin-4-yl)-5-azaspiro[2.5]octane-8-carboxamide | 0.7 | 1.6 | 7.0 | 7.7 | 1.73 | 440.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 10 | 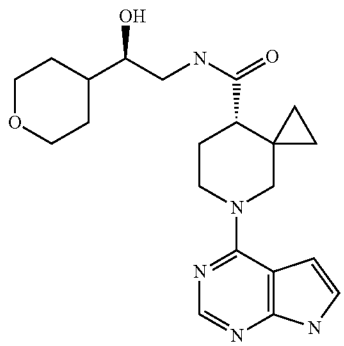 [SMILES: O=C(NC[C@H](O)C1CCOCC1)[C@H]1CCN(c2ncnc3[nH]ccc23)CC12CC2] | (8S)-N-[(2R)-2-hydroxy-2-tetrahydropyran-4-yl-ethyl]-5-(7H-pyrrolo[2,3-d]pyrimidin-4-yl)-5-azaspiro[2.5]octane-8-carboxamide | 0.8 | 2.9 | 11.7 | 10.8 | 1.60 | 400.23 |
| 11 | 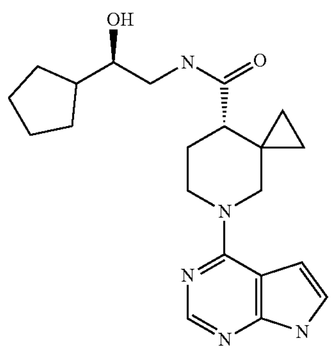 [SMILES: O=C(NC[C@H](O)C1CCCC1)[C@H]1CCN(c2ncnc3[nH]ccc23)CC12CC2] | (8S)-N-[(2R)-2-cyclopentyl-2-hydroxy-ethyl]-5-(7H-pyrrolo[2,3-d]pyrimidin-4-yl)-5-azaspiro[2.5]octane-8-carboxamide | 0.8 | 2.1 | 6.7 | 18.2 | 1.81 | 384.23 |
| 12 | 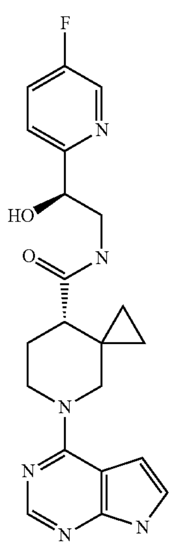 | (8S)-N-[(2R)-2-(5-fluoro-2-pyridyl)-2-hydroxy-ethyl]-5-(7H-pyrrolo[2,3-d]pyrimidin-4-yl)-5-azaspiro[2.5]octane-8-carboxamide | 0.8 | 4.0 | 26.5 | 13.9 | 1.67 | 411.19 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 13 | 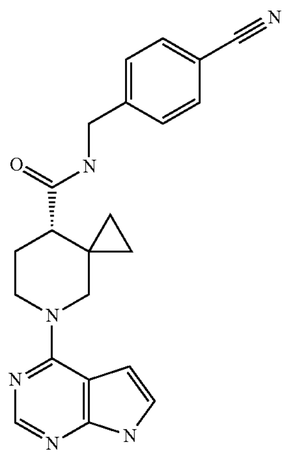 [SMILES: N#Cc1ccc(CNC(=O)[C@H]2CCN(c3ncnc4[nH]ccc34)CC23CC3)cc1] | (8S)-N-[(4-cyanophenyl)methyl]-5-(7H-pyrrolo[2,3-d]pyrimidin-4-yl)-5-azaspiro[2.5]octane-8-carboxamide | 0.9 | 6.1 | 8.9 | 81.1 | 1.84 | 387.19 |
| 14 | 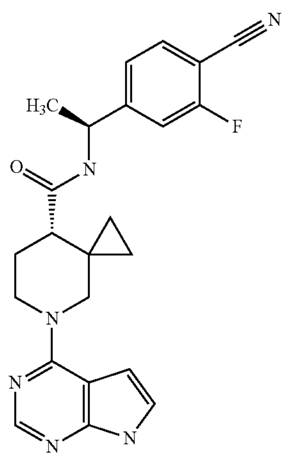 [SMILES: C[C@H](NC(=O)[C@H]1CCN(c2ncnc3[nH]ccc23)CC12CC2)c1ccc(C#N)c(F)c1] | (8S)-N-[(1S)-1-(4-cyano-3-fluoro-phenyl)ethyl]-5-(7H-pyrrolo[2,3-d]pyrimidin-4-yl)-5-azaspiro[2.5]octane-8-carboxamide | 0.9 | 2.2 | 6.5 | 26.8 | 1.94 | 419.19 |
| 15 | 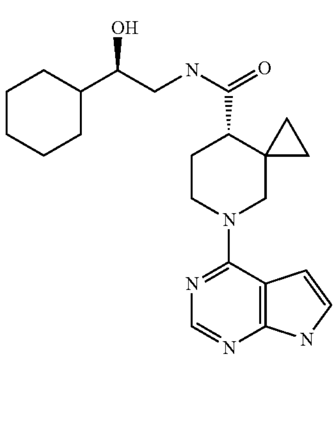 [SMILES: O=C(NC[C@H](O)C1CCCCC1)[C@H]1CCN(c2ncnc3[nH]ccc23)CC12CC2] | (8S)-N-[(2R)-2-cyclohexyl-2-hydroxy-ethyl]-5-(7H-pyrrolo[2,3-d]pyrimidin-4-yl)-5-azaspiro[2.5]octane-8-carboxamide | 0.9 | 1.7 | 3.7 | 7.4 | 1.88 | 398.25 |

TABLE 1-continued

| | | | JAK kinase inhibitory and analytical data | | | | | |
|---|---|---|---|---|---|---|---|---|
| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
| 16 | | (8S)-N-[(4-cyano-3-fluoro-phenyl)methyl]-5-(7H-pyrrolo[2,3-d]pyrimidin-4-yl)-5-azaspiro[2.5]octane-8-carboxamide | 1.0 | 3.6 | 7.1 | 44.3 | 1.89 | 405.18 |
| 17 | | (8S)-N-[(1R)-1-(4-fluorophenyl)-2-hydroxy-ethyl]-5-(7H-pyrrolo[2,3-d]pyrimidin-4-yl)-5-azaspiro[2.5]octane-8-carboxamide | 1.0 | 3.0 | 5.7 | 20.5 | 1.79 | 410.19 |
| 18 | | (8S)-N-[(1R)-1-(4-cyanophenyl)-2-hydroxy-ethyl]-5-(7H-pyrrolo[2,3-d]pyrimidin-4-yl)-5-azaspiro[2.5]octane-8-carboxamide | 1.0 | 3.5 | 7.5 | 45.5 | 1.73 | 417.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 19 | 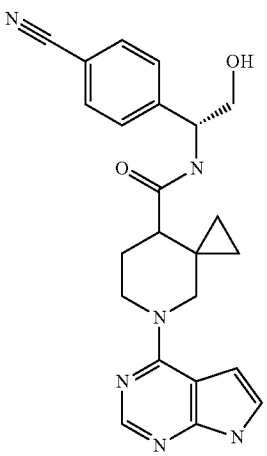 [SMILES: N#Cc1ccc([C@H](CO)NC(=O)C2CCN(c3ncnc4[nH]ccc34)CC23CC3)cc1] | N-[(1R)-1-(4-cyanophenyl)-2-hydroxy-ethyl]-5-(7H-pyrrolo[2,3-d]pyrimidin-4-yl)-5-azaspiro[2.5]octane-8-carboxamide | 1.1 | 4.0 | 8.4 | 109.0 | 1.73 | 417.20 |
| 20 | 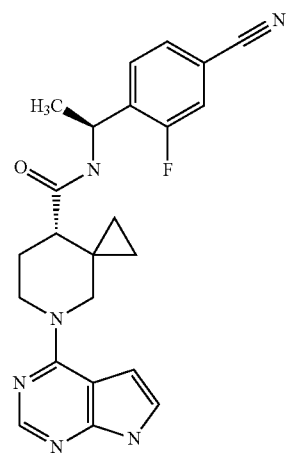 [SMILES: C[C@H](NC(=O)[C@H]1CCN(c2ncnc3[nH]ccc23)CC12CC2)c1ccc(C#N)cc1F] | (8S)-N-[(1S)-1-(4-cyano-2-fluoro-phenyl)ethyl]-5-(7H-pyrrolo[2,3-d]pyrimidin-4-yl)-5-azaspiro[2.5]octane-8-carboxamide | 1.1 | 3.1 | 17.6 | 51.3 | 1.93 | 419.19 |
| 21 | 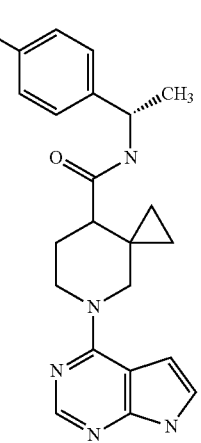 | N-[(1S)-1-(4-cyanophenyl)ethyl]-5-(7H-pyrrolo[2,3-d]pyrimidin-4-yl)-5-azaspiro[2.5]octane-8-carboxamide | 1.1 | 2.5 | 7.7 | 52.1 | 1.89 | 401.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 22 | 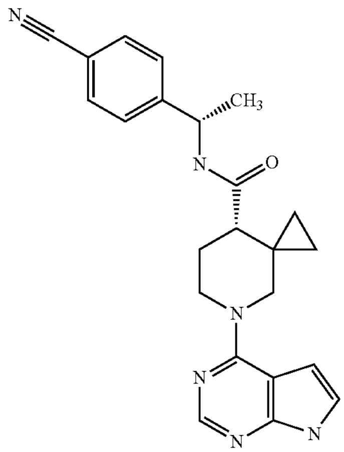 [SMILES: C[C@H](NC(=O)[C@H]1CCN(c2ncnc3[nH]ccc23)CC12CC2)c1ccc(C#N)cc1] | (8S)-N-[(1S)-1-(4-cyanophenyl)ethyl]-5-(7H-pyrrolo[2,3-d]pyrimidin-4-yl)-5-azaspiro[2.5]octane-8-carboxamide | 1.2 | 3.2 | 7.1 | 43.9 | 1.89 | 401.20 |
| 23 | 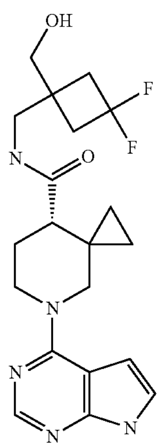 [SMILES: O=C(NCC1(CO)CC(F)(F)C1)[C@H]1CCN(c2ncnc3[nH]ccc23)CC12CC2] | (8S)-N-[[3,3-difluoro-1-(hydroxymethyl)cyclobutyl]methyl]-5-(7H-pyrrolo[2,3-d]pyrimidin-4-yl)-5-azaspiro[2.5]octane-8-carboxamide | 1.3 | 2.7 | 6.7 | 19.8 | 1.76 | 406.20 |
| 24 | 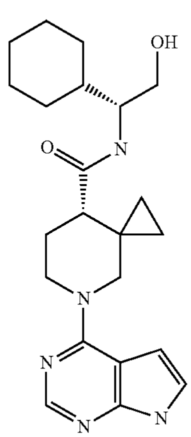 [SMILES: O=C(N[C@@H](CO)C1CCCCC1)[C@H]1CCN(c2ncnc3[nH]ccc23)CC12CC2] | (8S)-N-[(1R)-1-cyclohexyl-2-hydroxy-ethyl]-5-(7H-pyrrolo[2,3-d]pyrimidin-4-yl)-5-azaspiro[2.5]octane-8-carboxamide | 1.3 | 2.7 | 10.9 | 19.9 | 1.86 | 398.25 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 25 | 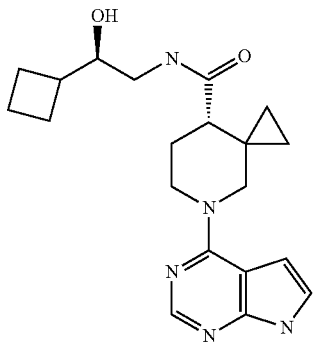 [SMILES: O=C(NC[C@H](O)C1CCC1)[C@H]1CCN(c2ncnc3[nH]ccc23)CC12CC2] | (8S)-N-[(2R)-2-cyclobutyl-2-hydroxy-ethyl]-5-(7H-pyrrolo[2,3-d]pyrimidin-4-yl)-5-azaspiro[2.5]octane-8-carboxamide | 1.3 | 3.4 | 13.6 | 11.1 | 1.73 | 370.22 |
| 26 | 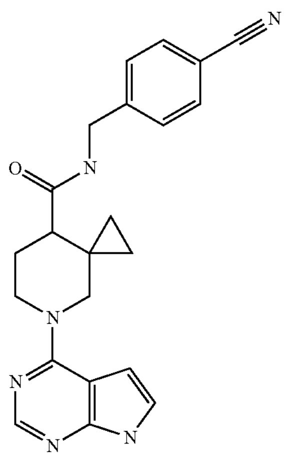 [SMILES: N#Cc1ccc(CNC(=O)C2CCN(c3ncnc4[nH]ccc34)CC23CC3)cc1] | N-[(4-cyanophenyl)methyl]-5-(7H-pyrrolo[2,3-d]pyrimidin-4-yl)-5-azaspiro[2.5]octane-8-carboxamide | 1.4 | 6.4 | 11.2 | 196.0 | 1.84 | 387.19 |
| 27 | 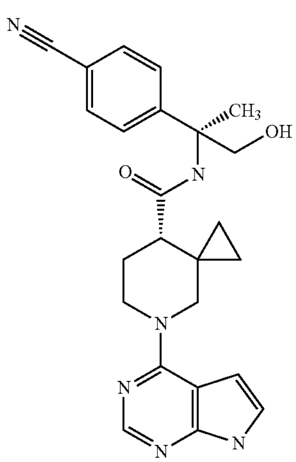 [SMILES: C[C@](CO)(NC(=O)[C@H]1CCN(c2ncnc3[nH]ccc23)CC12CC2)c1ccc(C#N)cc1] | (8S)-N-[(1S)-1-(4-cyanophenyl)-2-hydroxy-1-methyl-ethyl]-5-(7H-pyrrolo[2,3-d]pyrimidin-4-yl)-5-azaspiro[2.5]octane-8-carboxamide | 1.4 | 3.2 | 7.0 | 44.2 | 1.78 | 431.21 |

TABLE 1-continued
JAK kinase inhibitory and analytical data
| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 28 | 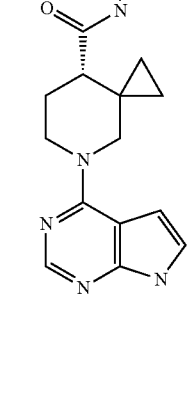 | (8S)-N-[(1R)-1-(4-cyanophenyl)-2-hydroxy-1-methyl-ethyl]-5-(7H-pyrrolo[2,3-d]pyrimidin-4-yl)-5-azaspiro[2.5]octane-8-carboxamide | 1.4 | 5.5 | 9.8 | 55.8 | 1.78 | 431.21 |
| 29 | 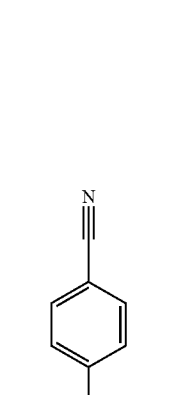 | (8S)-N-[(2R)-2-(4-cyanophenyl)-2-hydroxy-ethyl]-5-(7H-pyrrolo[2,3-d]pyrimidin-4-yl)-5-azaspiro[2.5]octane-8-carboxamide | 1.4 | 2.9 | 6.5 | 40.4 | 1.75 | 417.20 |

TABLE 1-continued

| | | | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| Example | Structure | Iupac Name | | | | | | |
| 30 | | (8S)-N-[(1S,2S)-2-(5-fluoro-2-pyridyl)-2-hydroxy-1-(hydroxymethyl)ethyl]-5-(7H-pyrrolo[2,3-d]pyrimidin-4-yl)-5-azaspiro[2.5]octane-8-carboxamide | 1.4 | 2.4 | 27.1 | 30.5 | 1.64 | 441.20 |
| 31 | | (8S)-N-[(4-cyano-2-fluoro-phenyl)methyl]-5-(7H-pyrrolo[2,3-d]pyrimidin-4-yl)-5-azaspiro[2.5]octane-8-carboxamide | 1.4 | 6.4 | 15.6 | 63.7 | 1.88 | 405.18 |
| 32 | | (8S)-N-[(2S)-2-cyclopentyl-2-hydroxy-ethyl]-5-(7H-pyrrolo[2,3-d]pyrimidin-4-yl)-5-azaspiro[2.5]octane-8-carboxamide | 1.8 | 5.2 | 8.3 | 25.4 | 1.80 | 384.23 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 33 | 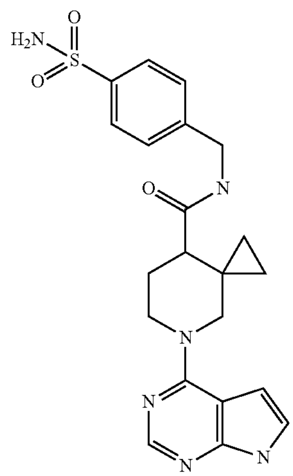 [SMILES: NS(=O)(=O)c1ccc(CNC(=O)C2CCN(c3ncnc4[nH]ccc34)CC23CC3)cc1] | 5-(7H-pyrrolo[2,3-d]pyrimidin-4-yl)-N-[(4-sulfamoylphenyl)methyl]-5-azaspiro[2.5]octane-8-carboxamide | 1.9 | 5.0 | 6.0 | 28.9 | 1.68 | 441.16 |
| 34 | 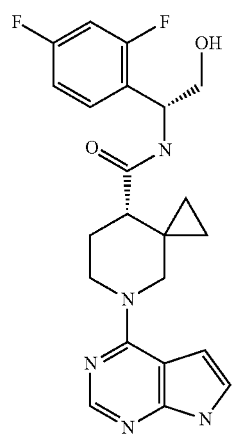 [SMILES: O=C(N[C@@H](CO)c1ccc(F)cc1F)[C@H]1CCN(c2ncnc3[nH]ccc23)CC12CC2] | (8S)-N-[(1R)-1-(2,4-difluorophenyl)-2-hydroxy-ethyl]-5-(7H-pyrrolo[2,3-d]pyrimidin-4-yl)-5-azaspiro[2.5]octane-8-carboxamide | 1.9 | 3.7 | 6.4 | 32.9 | 1.81 | 428.18 |
| 35 | 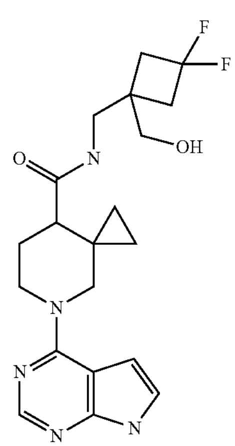 [SMILES: O=C(NCC1(CO)CC(F)(F)C1)C1CCN(c2ncnc3[nH]ccc23)CC12CC2] | N-[[3,3-difluoro-1-(hydroxymethyl)cyclobutyl]methyl]-5-(7H-pyrrolo[2,3-d]pyrimidin-4-yl)-5-azaspiro[2.5]octane-8-carboxamide | 1.9 | 4.8 | 8.6 | 71.8 | 1.76 | 406.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 36 | 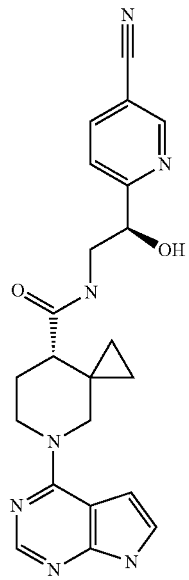 [SMILES: N#Cc1ccc([C@@H](O)CNC(=O)[C@H]2CCN(c3ncnc4[nH]ccc34)CC23CC3)nc1] | (8S)-N-[(2S)-2-(5-cyano-2-pyridyl)-2-hydroxy-ethyl]-5-(7H-pyrrolo[2,3-d]pyrimidin-4-yl)-5-azaspiro[2.5]octane-8-carboxamide | 2.0 | 8.7 | 25.2 | 70.5 | 1.66 | 418.19 |
| 37 | 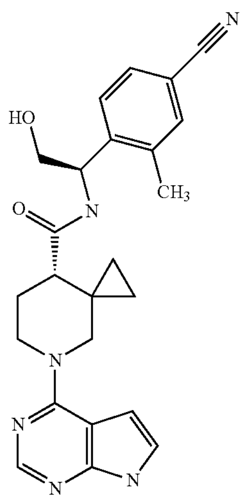 [SMILES: Cc1cc(C#N)ccc1[C@H](CO)NC(=O)[C@H]1CCN(c2ncnc3[nH]ccc23)CC12CC2] | (8S)-N-[(1R)-1-(4-cyano-2-methyl-phenyl)-2-hydroxy-ethyl]-5-(7H-pyrrolo[2,3-d]pyrimidin-4-yl)-5-azaspiro[2.5]octane-8-carboxamide | 2.0 | 10.2 | 36.4 | 102.0 | 1.79 | 431.21 |
| 38 | 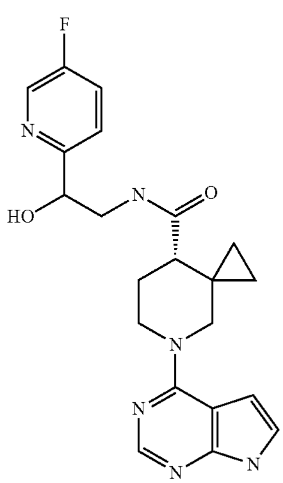 [SMILES: O=C(NCC(O)c1ccc(F)cn1)[C@H]1CCN(c2ncnc3[nH]ccc23)CC12CC2] | (8S)-N-[2-(5-fluoro-2-pyridyl)-2-hydroxy-ethyl]-5-(7H-pyrrolo[2,3-d]pyrimidin-4-yl)-5-azaspiro[2.5]octane-8-carboxamide | 2.2 | 9.0 | 33.6 | 32.1 | 1.67 | 411.19 |

TABLE 1-continued
JAK kinase inhibitory and analytical data
| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 39 | 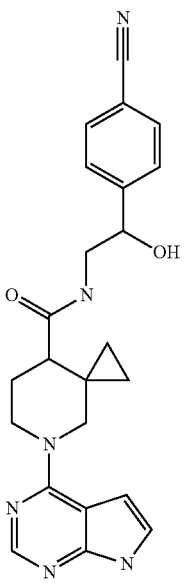 [SMILES: N#Cc1ccc(C(O)CNC(=O)C2CCN(c3ncnc4[nH]ccc34)CC23CC3)cc1] | N-[2-(4-cyanophenyl)-2-hydroxy-ethyl]-5-(7H-pyrrolo[2,3-d]pyrimidin-4-yl)-5-azaspiro[2.5]octane-8-carboxamide | 2.4 | 4.8 | 11.5 | 75.4 | 1.75 | 417.20 |
| 40 | 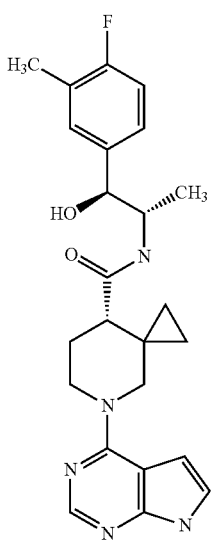 [SMILES: Cc1cc([C@H](O)[C@H](C)NC(=O)[C@H]2CCN(c3ncnc4[nH]ccc34)CC23CC3)ccc1F] | (8S)-N-[(1S,2S)-2-(4-fluoro-3-methyl-phenyl)-2-hydroxy-1-methyl-ethyl]-5-(7H-pyrrolo[2,3-d]pyrimidin-4-yl)-5-azaspiro[2.5]octane-8-carboxamide | 2.4 | 8.3 | 39.5 | 40.6 | 1.91 | 438.22 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 41 | 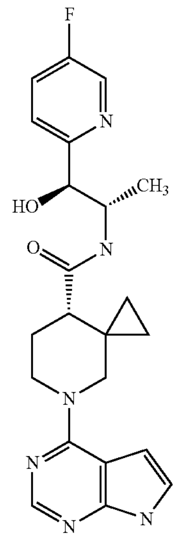 | (8S)-N-[(1S,2R)-2-(5-fluoro-2-pyridyl)-2-hydroxy-1-methyl-ethyl]-5-(7H-pyrrolo[2,3-d]pyrimidin-4-yl)-5-azaspiro[2.5]octane-8-carboxamide | 2.5 | 5.0 | 48.9 | 33.5 | 1.73 | 425.20 |
| 42 | 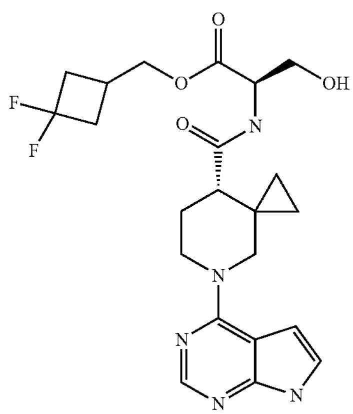 [SMILES: O=C(N[C@H](CO)C(=O)OCC1CC(F)(F)C1)[C@H]1CCN(c2ncnc3[nH]ccc23)CC12CC2] | (3,3-difluorocyclobutyl)methyl (2R)-3-hydroxy-2-[[(8S)-5-(7H-pyrrolo[2,3-d]pyrimidin-4-yl)-5-azaspiro[2.5]octane-8-carbonyl]amino]propanoate | 2.7 | 6.7 | 20.2 | 51.3 | 1.82 | 464.20 |
| 43 | 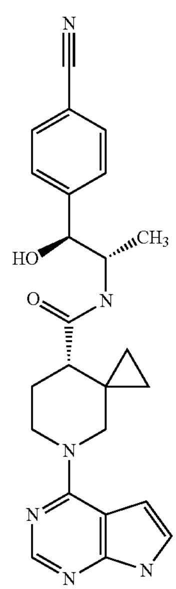 | (8S)-N-[(1S,2S)-2-(4-cyanophenyl)-2-hydroxy-1-methyl-ethyl]-5-(7H-pyrrolo[2,3-d]pyrimidin-4-yl)-5-azaspiro[2.5]octane-8-carboxamide | 2.8 | 5.2 | 8.8 | 131.0 | 1.77 | 431.21 |

TABLE 1-continued

| | | | JAK kinase inhibitory and analytical data | | | | | |
|---|---|---|---|---|---|---|---|---|
| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | $t_R$ (min) | M+H$^+$ |
| 44 | | (8S)-N-[(2R)-2-(5-fluoro-4-methyl-2-pyridyl)-2-hydroxy-ethyl]-5-(7H-pyrrolo[2,3-d]pyrimidin-4-yl)-5-azaspiro[2.5]octane-8-carboxamide | 3.1 | 15.8 | 68.5 | 63.2 | 1.73 | 425.20 |
| 45 | | (8S)-N-[(1S,2R)-2-(4-fluorophenyl)-2-hydroxy-1-methyl-ethyl]-5-(7H-pyrrolo[2,3-d]pyrimidin-4-yl)-5-azaspiro[2.5]octane-8-carboxamide | 3.1 | 4.6 | 15.7 | 37.9 | 1.81 | 424.21 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 46 | 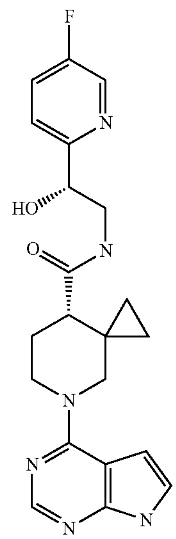 | (8S)-N-[(2S)-2-(5-fluoro-2-pyridyl)-2-hydroxy-ethyl]-5-(7H-pyrrolo[2,3-d]pyrimidin-4-yl)-5-azaspiro[2.5]octane-8-carboxamide | 3.1 | 8.8 | 23.8 | 48.1 | 1.67 | 411.19 |
| 47 | 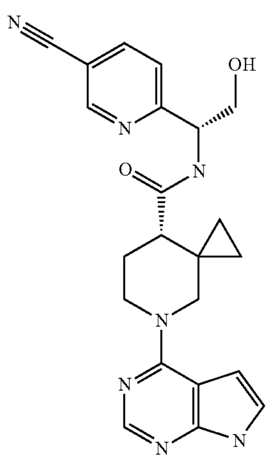 [SMILES: N#Cc1ccc([C@H](CO)NC(=O)[C@H]2CCN(c3ncnc4[nH]ccc34)CC23CC3)nc1] | (8S)-N-[(1R)-1-(5-cyano-2-pyridyl)-2-hydroxy-ethyl]-5-(7H-pyrrolo[2,3-d]pyrimidin-4-yl)-5-azaspiro[2.5]octane-8-carboxamide | 3.1 | 13.7 | 32.4 | 176.0 | 1.66 | 418.19 |
| 48 | 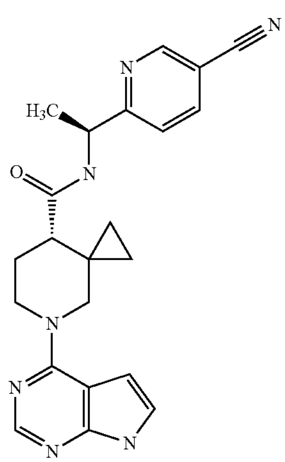 [SMILES: C[C@H](NC(=O)[C@H]1CCN(c2ncnc3[nH]ccc23)CC12CC2)c1ccc(C#N)cn1] | (8S)-N-[(1S)-1-(5-cyano-2-pyridyl)ethyl]-5-(7H-pyrrolo[2,3-d]pyrimidin-4-yl)-5-azaspiro[2.5]octane-8-carboxamide | 3.2 | 10.2 | 40.3 | 128.0 | 1.77 | 402.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 49 | 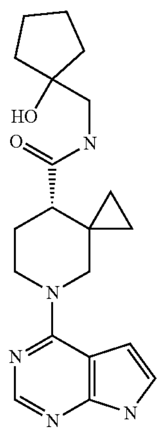 [SMILES: O=C(NCC1(O)CCCC1)[C@H]1CCN(c2ncnc3[nH]ccc23)CC12CC2] | (8S)-N-[(1-hydroxycyclopentyl)methyl]-5-(7H-pyrrolo[2,3-d]pyrimidin-4-yl)-5-azaspiro[2.5]octane-8-carboxamide | 3.4 | 15.1 | 26.1 | 43.4 | 1.70 | 370.22 |
| 50 | 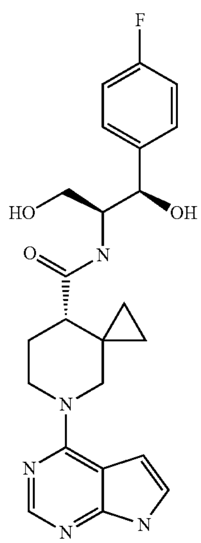 [SMILES: O=C(N[C@@H](CO)[C@H](O)c1ccc(F)cc1)[C@H]1CCN(c2ncnc3[nH]ccc23)CC12CC2] | (8S)-N-[(1S,2R)-2-(4-fluorophenyl)-2-hydroxy-1-(hydroxymethyl)ethyl]-5-(7H-pyrrolo[2,3-d]pyrimidin-4-yl)-5-azaspiro[2.5]octane-8-carboxamide | 3.5 | 7.0 | 22.7 | 53.2 | 1.69 | 440.20 |
| 51 | 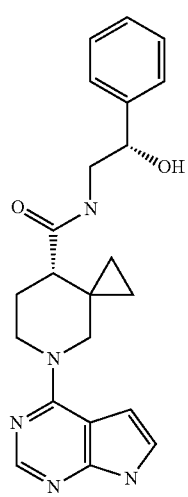 [SMILES: O=C(NC[C@@H](O)c1ccccc1)[C@H]1CCN(c2ncnc3[nH]ccc23)CC12CC2] | (8S)-N-[(2S)-2-hydroxy-2-phenyl-ethyl]-5-(7H-pyrrolo[2,3-d]pyrimidin-4-yl)-5-azaspiro[2.5]octane-8-carboxamide | 3.5 | 11.3 | 49.2 | 40.5 | 1.75 | 392.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 52 | 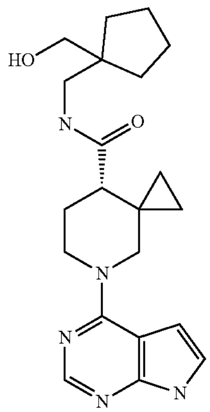 [SMILES: O=C(NCC1(CO)CCCC1)[C@H]1CCN(c2ncnc3[nH]ccc23)CC12CC2] | (8S)-N-[[1-(hydroxymethyl)cyclopentyl]methyl]-5-(7H-pyrrolo[2,3-d]pyrimidin-4-yl)-5-azaspiro[2.5]octane-8-carboxamide | 3.6 | 10.2 | 22.8 | 38.0 | 1.80 | 384.23 |
| 53 | 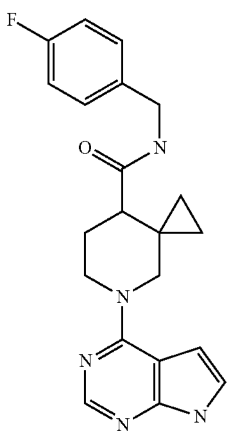 [SMILES: O=C(NCc1ccc(F)cc1)C1CCN(c2ncnc3[nH]ccc23)CC12CC2] | N-[(4-fluorophenyl)methyl]-5-(7H-pyrrolo[2,3-d]pyrimidin-4-yl)-5-azaspiro[2.5]octane-8-carboxamide | 3.6 | 8.9 | 20.8 | 106.0 | 1.92 | 380.18 |
| 54 | 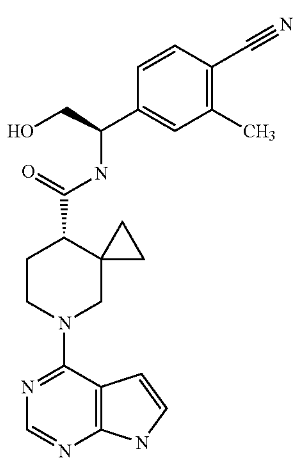 [SMILES: Cc1cc([C@H](CO)NC(=O)[C@H]2CCN(c3ncnc4[nH]ccc34)CC23CC3)ccc1C#N] | (8S)-N-[(1R)-1-(4-cyano-3-methyl-phenyl)-2-hydroxy-ethyl]-5-(7H-pyrrolo[2,3-d]pyrimidin-4-yl)-5-azaspiro[2.5]octane-8-carboxamide | 3.6 | 13.5 | 33.0 | 135.0 | 1.79 | 431.21 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 55 | 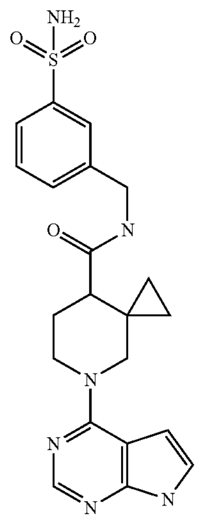 [SMILES: NS(=O)(=O)c1cccc(CNC(=O)C2CCN(c3ncnc4[nH]ccc34)CC23CC3)c1] | 5-(7H-pyrrolo[2,3-d]pyrimidin-4-yl)-N-[(3-sulfamoylphenyl)methyl]-5-azaspiro[2.5]octane-8-carboxamide | 3.7 | 18.5 | 13.4 | 141.0 | 1.69 | 441.16 |
| 56 | 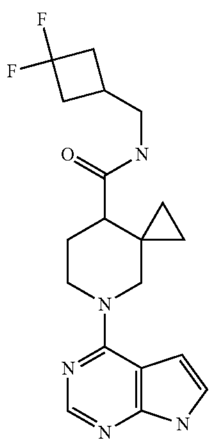 [SMILES: O=C(NCC1CC(F)(F)C1)C1CCN(c2ncnc3[nH]ccc23)CC12CC2] | N-[(3,3-difluorocyclobutyl)methyl]-5-(7H-pyrrolo[2,3-d]pyrimidin-4-yl)-5-azaspiro[2.5]octane-8-carboxamide | 3.9 | 8.3 | 18.1 | 170.0 | 1.85 | 376.19 |
| 57 | 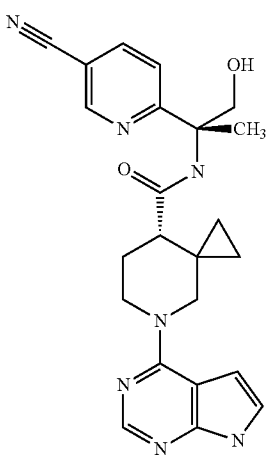 [SMILES: C[C@@](CO)(NC(=O)[C@H]1CCN(c2ncnc3[nH]ccc23)CC12CC2)c1ccc(C#N)cn1] | (8S)-N-[(1R)-1-(5-cyano-2-pyridyl)-2-hydroxy-1-methyl-ethyl]-5-(7H-pyrrolo[2,3-d]pyrimidin-4-yl)-5-azaspiro[2.5]octane-8-carboxamide | 4.1 | 9.0 | 21.3 | 193.0 | 1.72 | 432.21 |

TABLE 1-continued

| | | | JAK kinase inhibitory and analytical data | | | | | |
|---|---|---|---|---|---|---|---|---|
| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
| 58 | 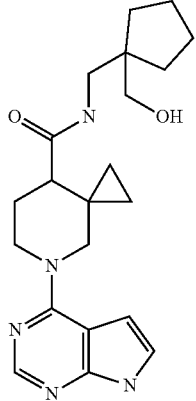 [SMILES: O=C(NCC1(CO)CCCC1)C1CCN(c2ncnc3[nH]ccc23)CC12CC2] | N-[[1-(hydroxymethyl)cyclopentyl]methyl]-5-(7H-pyrrolo[2,3-d]pyrimidin-4-yl)-5-azaspiro[2.5]octane-8-carboxamide | 4.1 | 13.0 | 30.3 | 142.0 | 1.81 | 384.23 |
| 59 | 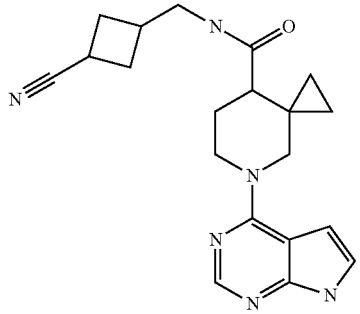 [SMILES: N#CC1CC(CNC(=O)C2CCN(c3ncnc4[nH]ccc34)CC23CC3)C1] | N-[(3-cyanocyclobutyl)methyl]-5-(7H-pyrrolo[2,3-d]pyrimidin-4-yl)-5-azaspiro[2.5]octane-8-carboxamide | 4.2 | 12.1 | 24.5 | 322.0 | 1.71 | 365.20 |
| 61 | 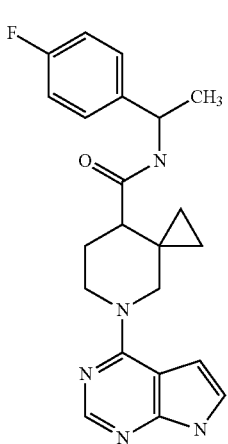 [SMILES: CC(NC(=O)C1CCN(c2ncnc3[nH]ccc23)CC12CC2)c1ccc(F)cc1] | N-[1-(4-fluorophenyl)ethyl]-5-(7H-pyrrolo[2,3-d]pyrimidin-4-yl)-5-azaspiro[2.5]octane-8-carboxamide | 4.3 | 7.2 | 22.1 | | 1.97 | 394.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 62 | 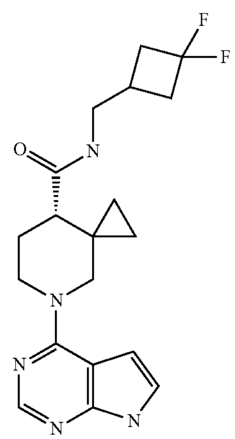 [SMILES: O=C(NCC1CC(F)(F)C1)[C@H]1CCN(c2ncnc3[nH]ccc23)CC12CC2] | (8S)-N-[(3,3-difluorocyclobutyl)methyl]-5-(7H-pyrrolo[2,3-d]pyrimidin-4-yl)-5-azaspiro[2.5]octane-8-carboxamide | 4.5 | 7.0 | 15.7 | 47.5 | 1.83 | 376.19 |
| 63 | 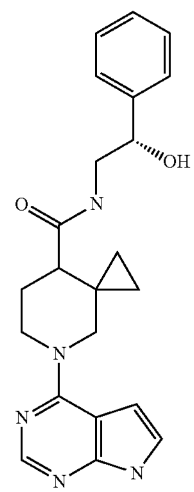 [SMILES: O=C(NC[C@@H](O)c1ccccc1)C1CCN(c2ncnc3[nH]ccc23)CC12CC2] | N-[(2S)-2-hydroxy-2-phenyl-ethyl]-5-(7H-pyrrolo[2,3-d]pyrimidin-4-yl)-5-azaspiro[2.5]octane-8-carboxamide | 4.5 | 15.9 | 58.5 | 147.0 | 1.76 | 392.20 |
| 64 | 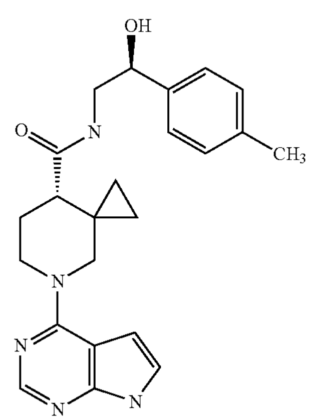 [SMILES: Cc1ccc([C@H](O)CNC(=O)[C@H]2CCN(c3ncnc4[nH]ccc34)CC23CC3)cc1] | (8S)-N-[(2S)-2-hydroxy-2-(p-tolyl)ethyl]-5-(7H-pyrrolo[2,3-d]pyrimidin-4-yl)-5-azaspiro[2.5]octane-8-carboxamide | 4.5 | 6.7 | 28.5 | 90.9 | 1.83 | 406.22 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 66 | 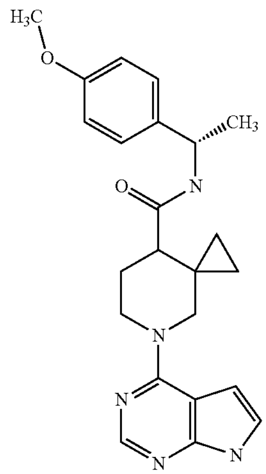 [SMILES: COc1ccc([C@H](C)NC(=O)C2CCN(c3ncnc4[nH]ccc34)CC23CC3)cc1] | N-[(1S)-1-(4-methoxyphenyl)ethyl]-5-(7H-pyrrolo[2,3-d]pyrimidin-4-yl)-5-azaspiro[2.5]octane-8-carboxamide | 4.8 | 8.3 | 40.7 | n/a | 1.95 | 406.22 |
| 67 | 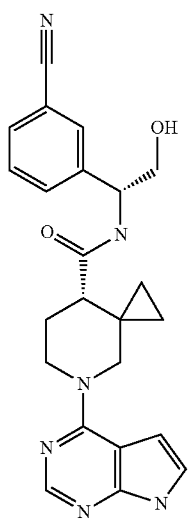 [SMILES: N#Cc1cccc([C@H](CO)NC(=O)[C@H]2CCN(c3ncnc4[nH]ccc34)CC23CC3)c1] | (8S)-N-[(1R)-1-(3-cyanophenyl)-2-hydroxy-ethyl]-5-(7H-pyrrolo[2,3-d]pyrimidin-4-yl)-5-azaspiro[2.5]octane-8-carboxamide | 5.1 | 5.2 | 13.8 | 45.0 | 1.75 | 417.20 |
| 68 | 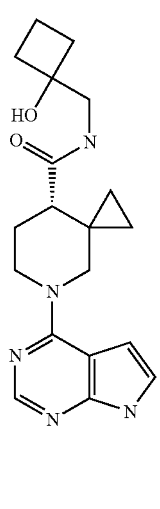 [SMILES: O=C(NCC1(O)CCC1)[C@H]1CCN(c2ncnc3[nH]ccc23)CC12CC2] | (8S)-N-[(1-hydroxycyclobutyl)methyl]-5-(7H-pyrrolo[2,3-d]pyrimidin-4-yl)-5-azaspiro[2.5]octane-8-carboxamide | 5.1 | 11.8 | 29.6 | 78.1 | 1.64 | 356.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 69 | 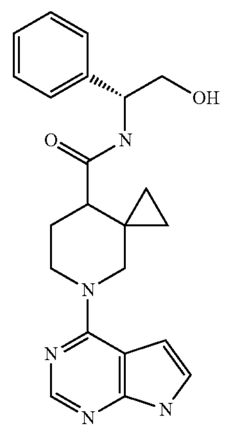 [SMILES: O=C(N[C@@H](CO)c1ccccc1)C1CCN(c2ncnc3[nH]ccc23)CC12CC2] | N-[(1R)-2-hydroxy-1-phenyl-ethyl]-5-(7H-pyrrolo[2,3-d]pyrimidin-4-yl)-5-azaspiro[2.5]octane-8-carboxamide | 5.1 | 12.0 | 29.1 | 298.0 | 1.75 | 392.20 |
| 70 | 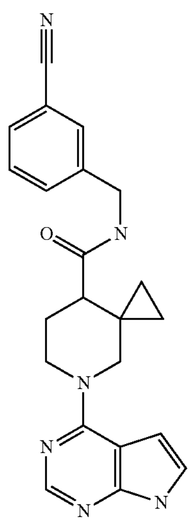 [SMILES: N#Cc1cccc(CNC(=O)C2CCN(c3ncnc4[nH]ccc34)CC23CC3)c1] | N-[(3-cyanophenyl)methyl]-5-(7H-pyrrolo[2,3-d]pyrimidin-4-yl)-5-azaspiro[2.5]octane-8-carboxamide | 5.5 | 8.6 | 32.6 | | 1.85 | 387.19 |
| 71 | 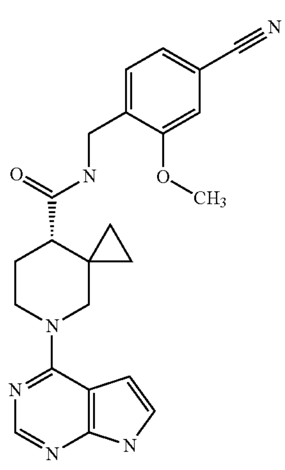 [SMILES: COc1cc(C#N)ccc1CNC(=O)[C@H]1CCN(c2ncnc3[nH]ccc23)CC12CC2] | (8S)-N-[(4-cyano-2-methoxy-phenyl)methyl]-5-(7H-pyrrolo[2,3-d]pyrimidin-4-yl)-5-azaspiro[2.5]octane-8-carboxamide | 5.8 | 14.2 | 63.1 | 121.0 | 1.90 | 417.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 73 | 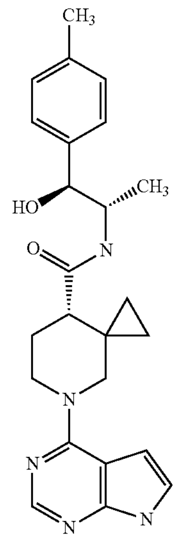 | (8S)-N-[(1S,2S)-2-hydroxy-1-methyl-2-(p-tolyl)ethyl]-5-(7H-pyrrolo[2,3-d]pyrimidin-4-yl)-5-azaspiro[2.5]octane-8-carboxamide | 6.1 | 8.3 | 30.9 | 171.0 | 1.87 | 420.23 |
| 74 | 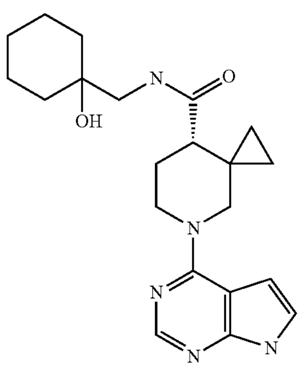 [SMILES: O=C(NCC1(O)CCCCC1)[C@H]1CCN(c2ncnc3[nH]ccc23)CC12CC2] | (8S)-N-[(1-hydroxycyclohexyl)methyl]-5-(7H-pyrrolo[2,3-d]pyrimidin-4-yl)-5-azaspiro[2.5]octane-8-carboxamide | 6.1 | 15.3 | 23.2 | 55.7 | 1.77 | 384.23 |
| 75 | 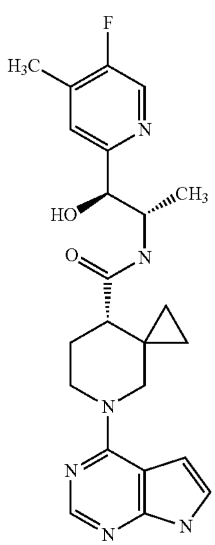 [SMILES: Cc1cc([C@H](O)[C@H](C)NC(=O)[C@H]2CCN(c3ncnc4[nH]ccc34)CC23CC3)ncc1F] | (8S)-N-[(1S,2R)-2-(5-fluoro-4-methyl-2-pyridyl)-2-hydroxy-1-methyl-ethyl]-5-(7H-pyrrolo[2,3-d]pyrimidin-4-yl)-5-azaspiro[2.5]octane-8-carboxamide | 6.1 | 16.3 | 102.0 | 50.2 | 1.75 | 439.22 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 76 | 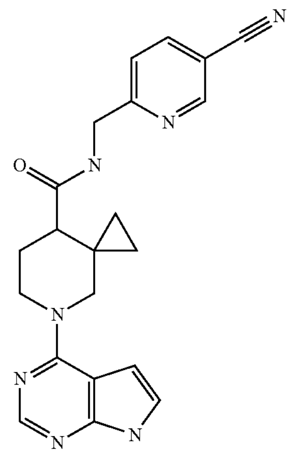 [SMILES: N#Cc1ccc(CNC(=O)C2CCN(c3ncnc4[nH]ccc34)CC23CC3)nc1] | N-[(5-cyano-2-pyridyl)methyl]-5-(7H-pyrrolo[2,3-d]pyrimidin-4-yl)-5-azaspiro[2.5]octane-8-carboxamide | 6.2 | 43.3 | 53.6 | | 1.71 | 388.18 |
| 77 | 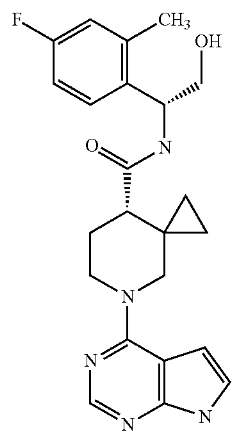 [SMILES: Cc1cc(F)ccc1[C@H](CO)NC(=O)[C@H]1CCN(c2ncnc3[nH]ccc23)CC12CC2] | (8S)-N-[(1R)-1-(4-fluoro-2-methyl-phenyl)-2-hydroxy-ethyl]-5-(7H-pyrrolo[2,3-d]pyrimidin-4-yl)-5-azaspiro[2.5]octane-8-carboxamide | 6.2 | 16.3 | 31.3 | 115.0 | 1.85 | 424.21 |
| 78 | 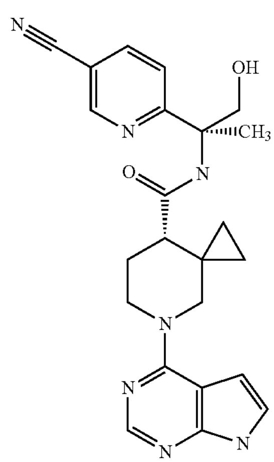 [SMILES: C[C@](CO)(NC(=O)[C@H]1CCN(c2ncnc3[nH]ccc23)CC12CC2)c1ccc(C#N)cn1] | (8S)-N-[(1S)-1-(5-cyano-2-pyridyl)-2-hydroxy-1-methyl-ethyl]-5-(7H-pyrrolo[2,3-d]pyrimidin-4-yl)-5-azaspiro[2.5]octane-8-carboxamide | 6.3 | 17.0 | 39.4 | 231.0 | 1.71 | 432.21 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 80 | 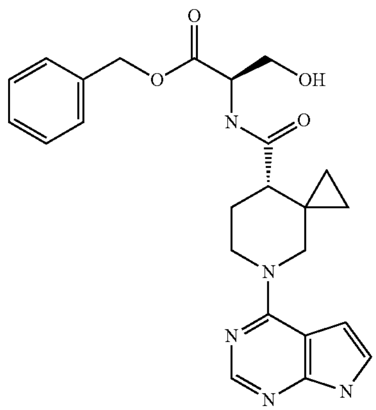 [SMILES: O=C(N[C@H](CO)C(=O)OCc1ccccc1)[C@H]1CCN(c2ncnc3[nH]ccc23)CC12CC2] | benzyl (2R)-3-hydroxy-2-[[(8S)-5-(7H-pyrrolo[2,3-d]pyrimidin-4-yl)-5-azaspiro[2.5]octane-8-carbonyl]amino]propanoate | 6.7 | 21.8 | 24.3 | 119.0 | 1.85 | 450.21 |
| 81 | 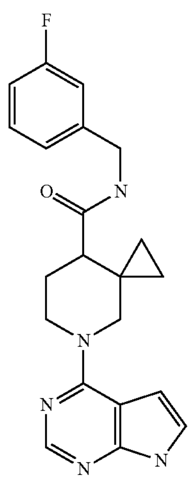 [SMILES: O=C(NCc1cccc(F)c1)C1CCN(c2ncnc3[nH]ccc23)CC12CC2] | N-[(3-fluorophenyl)methyl]-5-(7H-pyrrolo[2,3-d]pyrimidin-4-yl)-5-azaspiro[2.5]octane-8-carboxamide | 6.7 | 14.1 | 37.7 | 117.0 | 1.92 | 380.18 |
| 82 | 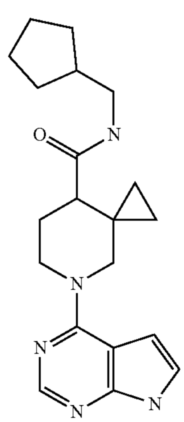 [SMILES: O=C(NCC1CCCC1)C1CCN(c2ncnc3[nH]ccc23)CC12CC2] | N-(cyclopentylmethyl)-5-(7H-pyrrolo[2,3-d]pyrimidin-4-yl)-5-azaspiro[2.5]octane-8-carboxamide | 6.8 | 11.5 | 38.7 | 400.0 | 1.95 | 354.22 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 83 | 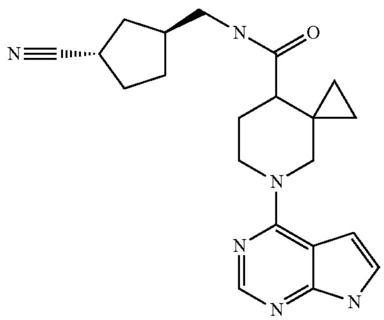 [SMILES: N#C[C@H]1CC[C@H](CNC(=O)C2CCN(c3ncnc4[nH]ccc34)CC23CC3)C1] | N-[[(1S,3S)-3-cyanocyclopentyl]methyl]-5-(7H-pyrrolo[2,3-d]pyrimidin-4-yl)-5-azaspiro[2.5]octane-8-carboxamide | 6.8 | 22.6 | 44.3 | 390.0 | 1.76 | 379.22 |
| 84 | 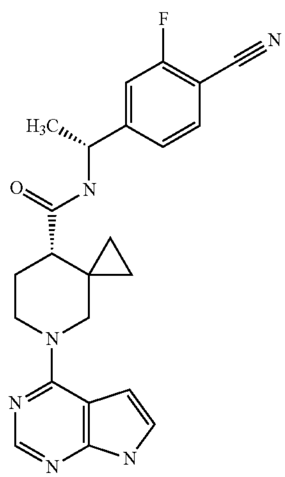 [SMILES: C[C@@H](NC(=O)[C@H]1CCN(c2ncnc3[nH]ccc23)CC12CC2)c1ccc(C#N)c(F)c1] | (8S)-N-[(1R)-1-(4-cyano-3-fluorophenyl)ethyl]-5-(7H-pyrrolo[2,3-d]pyrimidin-4-yl)-5-azaspiro[2.5]octane-8-carboxamide | 7.0 | 24.1 | 55.5 | 249.0 | 1.95 | 419.19 |
| 85 | 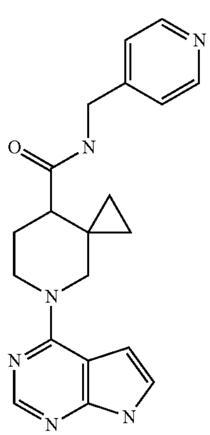 [SMILES: O=C(NCc1ccncc1)C1CCN(c2ncnc3[nH]ccc23)CC12CC2] | N-(4-pyridylmethyl)-5-(7H-pyrrolo[2,3-d]pyrimidin-4-yl)-5-azaspiro[2.5]octane-8-carboxamide | 7.1 | 28.7 | 42.8 | 798.0 | 1.49 | 363.19 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 86 | 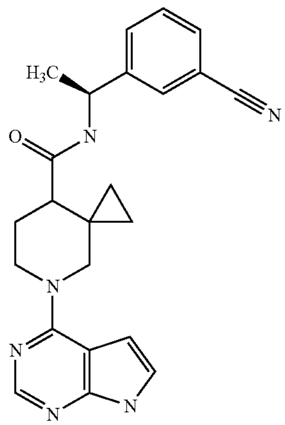 [SMILES: C[C@H](NC(=O)C1CCN(c2ncnc3[nH]ccc23)CC12CC2)c1cccc(C#N)c1] | N-[(1S)-1-(3-cyanophenyl)ethyl]-5-(7H-pyrrolo[2,3-d]pyrimidin-4-yl)-5-azaspiro[2.5]octane-8-carboxamide | 7.1 | 11.3 | 38.0 | 47.7 | 1.91 | 401.20 |
| 87 | 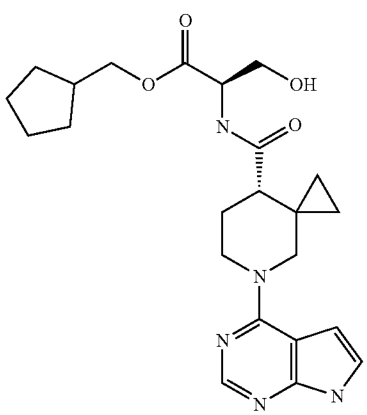 [SMILES: O=C(N[C@H](CO)C(=O)OCC1CCCC1)[C@H]1CCN(c2ncnc3[nH]ccc23)CC12CC2] | cyclopentylmethyl (2R)-3-hydroxy-2-[[(8S)-5-(7H-pyrrolo[2,3-d]pyrimidin-4-yl)-5-azaspiro[2.5]octane-8-carbonyl]amino]propanoate | 7.2 | 25.5 | 43.0 | 124.0 | 1.92 | 442.24 |
| 88 | 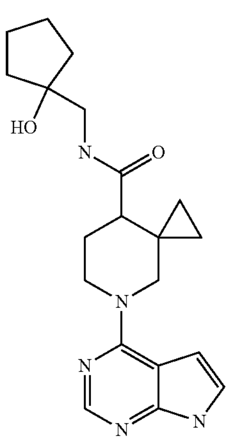 [SMILES: O=C(NCC1(O)CCCC1)C1CCN(c2ncnc3[nH]ccc23)CC12CC2] | N-[(1-hydroxycyclopentyl)methyl]-5-(7H-pyrrolo[2,3-d]pyrimidin-4-yl)-5-azaspiro[2.5]octane-8-carboxamide | 7.2 | 23.7 | 58.6 | 407.0 | 1.70 | 370.22 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 89 | 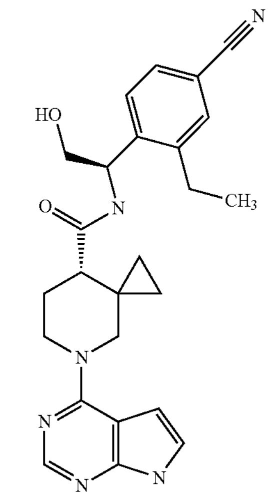 [SMILES: CCc1cc(C#N)ccc1[C@H](CO)NC(=O)[C@H]1CCN(c2ncnc3[nH]ccc23)CC12CC2] | (8S)-N-[(1R)-1-(4-cyano-2-ethyl-phenyl)-2-hydroxy-ethyl]-5-(7H-pyrrolo[2,3-d]pyrimidin-4-yl)-5-azaspiro[2.5]octane-8-carboxamide | 7.5 | 31.0 | 53.7 | 284.0 | 1.86 | 445.23 |
| 90 | 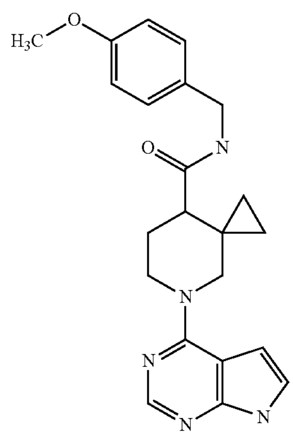 [SMILES: COc1ccc(CNC(=O)C2CCN(c3ncnc4[nH]ccc34)CC23CC3)cc1] | N-[(4-methoxyphenyl)methyl]-5-(7H-pyrrolo[2,3-d]pyrimidin-4-yl)-5-azaspiro[2.5]octane-8-carboxamide | 8.2 | 19.6 | 34.5 | 288.0 | 1.89 | 392.20 |
| 91 | 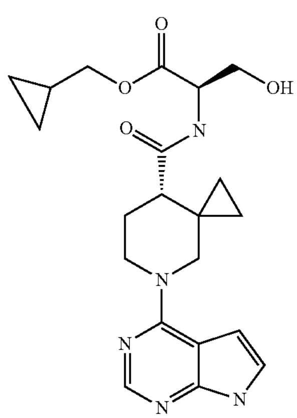 [SMILES: O=C(N[C@H](CO)C(=O)OCC1CC1)[C@H]1CCN(c2ncnc3[nH]ccc23)CC12CC2] | cyclopropylmethyl (2R)-3-hydroxy-2-[[(8S)-5-(7H-pyrrolo[2,3-d]pyrimidin-4-yl)-5-azaspiro[2.5]octane-8-carbonyl]amino]propanoate | 8.2 | 17.7 | 47.3 | 163.0 | 1.75 | 414.21 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 93 | 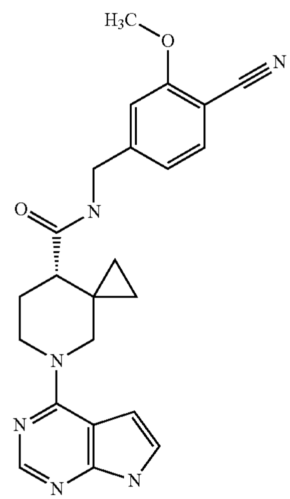 [SMILES: COc1cc(CNC(=O)[C@H]2CCN(c3ncnc4[nH]ccc34)CC23CC3)ccc1C#N] | (8S)-N-[(4-cyano-3-methoxy-phenyl)methyl]-5-(7H-pyrrolo[2,3-d]pyrimidin-4-yl)-5-azaspiro[2.5]octane-8-carboxamide | 8.5 | 29.3 | 74.1 | 118.0 | 1.87 | 417.20 |
| 94 | 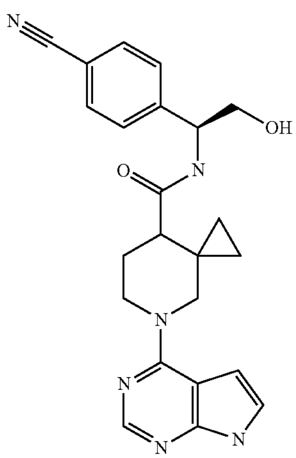 [SMILES: N#Cc1ccc([C@@H](CO)NC(=O)C2CCN(c3ncnc4[nH]ccc34)CC23CC3)cc1] | N-[(1S)-1-(4-cyanophenyl)-2-hydroxy-ethyl]-5-(7H-pyrrolo[2,3-d]pyrimidin-4-yl)-5-azaspiro[2.5]octane-8-carboxamide | 8.6 | 53.7 | 91.1 | 967.0 | 1.74 | 417.20 |
| 95 | 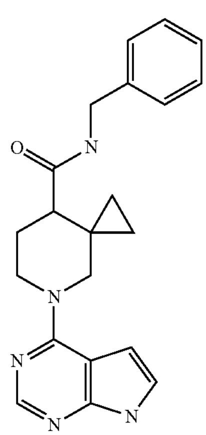 [SMILES: O=C(NCc1ccccc1)C1CCN(c2ncnc3[nH]ccc23)CC12CC2] | N-benzyl-5-(7H-pyrrolo[2,3-d]pyrimidin-4-yl)-5-azaspiro[2.5]octane-8-carboxamide | 8.6 | 17.9 | 31.6 | 502.0 | 1.89 | 362.19 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 96 | 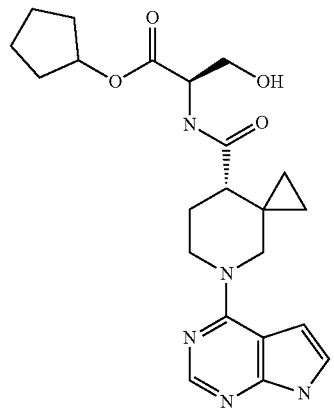 [SMILES: O=C(N[C@H](CO)C(=O)OC1CCCC1)[C@H]1CCN(c2ncnc3[nH]ccc23)CC12CC2] | cyclopentyl (2R)-3-hydroxy-2-[[(8S)-5-(7H-pyrrolo[2,3-d]pyrimidin-4-yl)-5-azaspiro[2.5]octane-8-carbonyl]amino]propanoate | 8.7 | 28.7 | 59.2 | 250.0 | 1.82 | 428.22 |
| 97 | 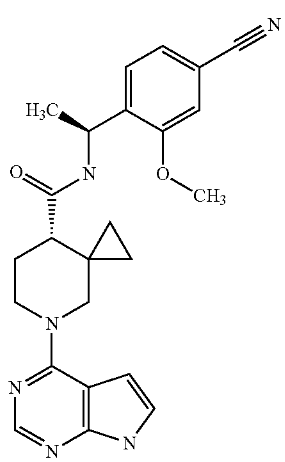 [SMILES: COc1cc(C#N)ccc1[C@H](C)NC(=O)[C@H]1CCN(c2ncnc3[nH]ccc23)CC12CC2] | (8S)-N-[(1S)-1-(4-cyano-2-methoxyphenyl)ethyl]-5-(7H-pyrrolo[2,3-d]pyrimidin-4-yl)-5-azaspiro[2.5]octane-8-carboxamide | 8.7 | 36.0 | 226.0 | 315.0 | 1.95 | 431.21 |
| 98 | 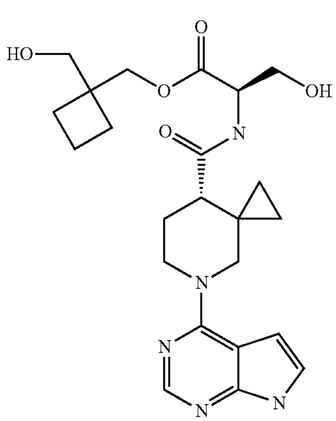 [SMILES: O=C(N[C@H](CO)C(=O)OCC1(CO)CCC1)[C@H]1CCN(c2ncnc3[nH]ccc23)CC12CC2] | [1-(hydroxymethyl)cyclobutyl]methyl (2R)-3-hydroxy-2-[[(8S)-5-(7H-pyrrolo[2,3-d]pyrimidin-4-yl)-5-azaspiro[2.5]octane-8-carbonyl]amino]propanoate | 8.8 | 15.0 | 44.3 | 177.0 | 1.70 | 458.23 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | $t_R$ (min) | M+H$^+$ |
|---|---|---|---|---|---|---|---|---|
| 99 | 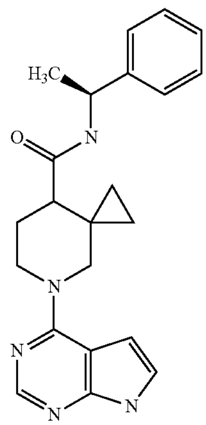 [SMILES: C[C@H](NC(=O)C1CCN(c2ncnc3[nH]ccc23)CC12CC2)c1ccccc1] | N-[(1S)-1-phenylethyl]-5-(7H-pyrrolo[2,3-d]pyrimidin-4-yl)-5-azaspiro[2.5]octane-8-carboxamide | 9.1 | 11.2 | 31.1 | 399.0 | 1.94 | 376.21 |
| 100 | 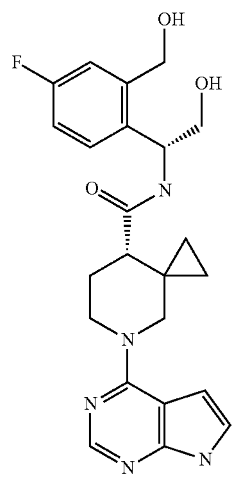 [SMILES: O=C(N[C@@H](CO)c1ccc(F)cc1CO)[C@H]1CCN(c2ncnc3[nH]ccc23)CC12CC2] | (8S)-N-[(1R)-1-[4-fluoro-2-(hydroxymethyl)phenyl]-2-hydroxyethyl]-5-(7H-pyrrolo[2,3-d]pyrimidin-4-yl)-5-azaspiro[2.5]octane-8-carboxamide | 9.1 | 37.3 | 71.9 | 248.0 | 1.72 | 440.20 |
| 101 | 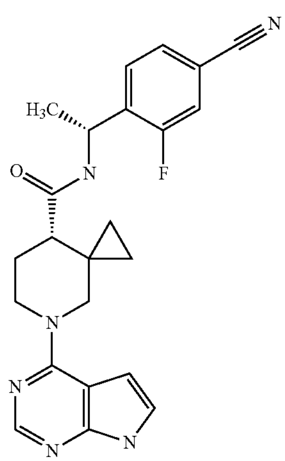 [SMILES: C[C@@H](NC(=O)[C@H]1CCN(c2ncnc3[nH]ccc23)CC12CC2)c1ccc(C#N)cc1F] | (8S)-N-[(1R)-1-(4-cyano-2-fluorophenyl)ethyl]-5-(7H-pyrrolo[2,3-d]pyrimidin-4-yl)-5-azaspiro[2.5]octane-8-carboxamide | 9.3 | 72.8 | 157.0 | 516.0 | 1.94 | 419.19 |

TABLE 1-continued

| | | | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| Example | Structure | Iupac Name | | | | | | |
| 102 | | N-[[(1R,2R)-2-cyanocyclopropyl]methyl]-5-(7H-pyrrolo[2,3-d]pyrimidin-4-yl)-5-azaspiro[2.5]octane-8-carboxamide | 9.5 | 26.2 | 35.0 | 531.0 | 1.67 | 351.19 |
| 103 | | N-[(2R)-2-hydroxy-2-phenyl-ethyl]-5-(7H-pyrrolo[2,3-d]pyrimidin-4-yl)-5-azaspiro[2.5]octane-8-carboxamide | 9.9 | 21.4 | 40.6 | 509.0 | 1.76 | 392.20 |
| 104 | | (8S)-N-[(1S,2R)-2-hydroxy-1-methyl-2-(2-pyridyl)ethyl]-5-(7H-pyrrolo[2,3-d]pyrimidin-4-yl)-5-azaspiro[2.5]octane-8-carboxamide | 10.1 | 30.3 | 163.0 | 149.0 | 1.55 | 407.21 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 105 | 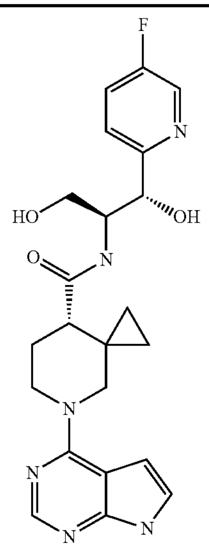 | (8S)-N-[(1S,2R)-2-(5-fluoro-2-pyridyl)-2-hydroxy-1-(hydroxymethyl)ethyl]-5-(7H-pyrrolo[2,3-d]pyrimidin-4-yl)-5-azaspiro[2.5]octane-8-carboxamide | 10.2 | 11.2 | 56.0 | 153.0 | 1.61 | 441.20 |
| 106 | 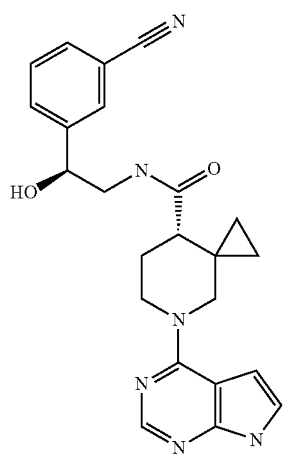 [SMILES: N#Cc1cccc([C@H](O)CNC(=O)[C@H]2CCN(c3ncnc4[nH]ccc34)CC23CC3)c1] | (8S)-N-[(2S)-2-(3-cyanophenyl)-2-hydroxy-ethyl]-5-(7H-pyrrolo[2,3-d]pyrimidin-4-yl)-5-azaspiro[2.5]octane-8-carboxamide | 10.2 | 25.2 | 44.7 | 110.0 | 1.75 | 417.20 |
| 107 | 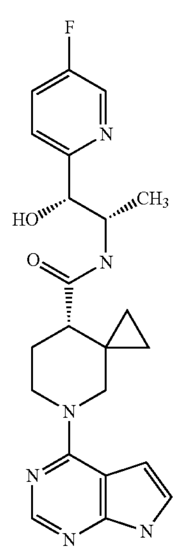 | (8S)-N-[(1S,2S)-2-(5-fluoro-2-pyridyl)-2-hydroxy-1-methyl-ethyl]-5-(7H-pyrrolo[2,3-d]pyrimidin-4-yl)-5-azaspiro[2.5]octane-8-carboxamide | 10.3 | 14.5 | 57.7 | 125.0 | 1.71 | 425.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | $t_R$ (min) | M+H$^+$ |
|---|---|---|---|---|---|---|---|---|
| 108 | 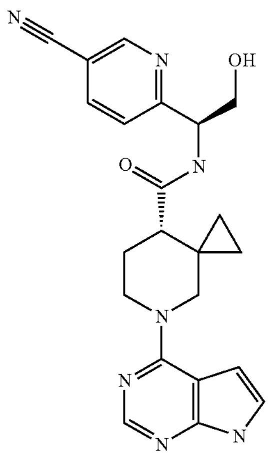 [SMILES: N#Cc1ccc([C@@H](CO)NC(=O)[C@H]2CCN(c3ncnc4[nH]ccc34)CC23CC3)nc1] | (8S)-N-[(1S)-1-(5-cyano-2-pyridyl)-2-hydroxy-ethyl]-5-(7H-pyrrolo[2,3-d]pyrimidin-4-yl)-5-azaspiro[2.5]octane-8-carboxamide | 10.3 | 48.2 | 85.1 | 347.0 | 1.65 | 418.19 |
| 109 | 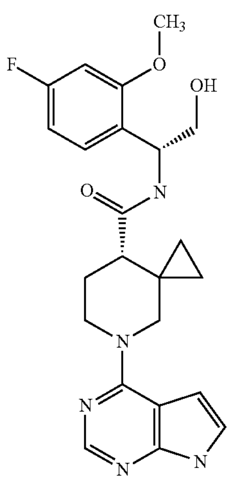 [SMILES: COc1cc(F)ccc1[C@H](CO)NC(=O)[C@H]1CCN(c2ncnc3[nH]ccc23)CC12CC2] | (8S)-N-[(1R)-1-(4-fluoro-2-methoxy-phenyl)-2-hydroxy-ethyl]-5-(7H-pyrrolo[2,3-d]pyrimidin-4-yl)-5-azaspiro[2.5]octane-8-carboxamide | 10.5 | 24.5 | 111.0 | 243.0 | 1.83 | 440.20 |
| 110 | 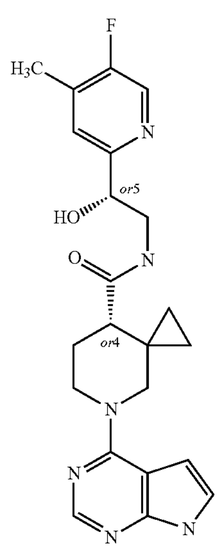 [SMILES: Cc1cc([C@@H](O)CNC(=O)[C@H]2CCN(c3ncnc4[nH]ccc34)CC23CC3)ncc1F] | (8S)-N-[(2S)-2-(5-fluoro-4-methyl-2-pyridyl)-2-hydroxy-ethyl]-5-(7H-pyrrolo[2,3-d]pyrimidin-4-yl)-5-azaspiro[2.5]octane-8-carboxamide | 11.1 | 26.3 | 75.3 | 188.0 | 1.73 | 425.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 111 | 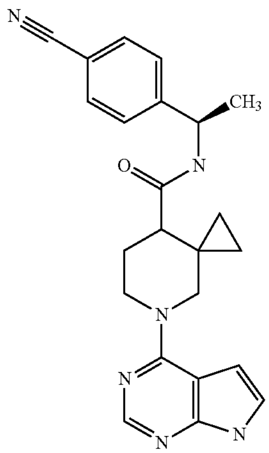 [SMILES: C[C@@H](NC(=O)C1CCN(c2ncnc3[nH]ccc23)CC12CC2)c1ccc(C#N)cc1] | N-[(1R)-1-(4-cyanophenyl)ethyl]-5-(7H-pyrrolo[2,3-d]pyrimidin-4-yl)-5-azaspiro[2.5]octane-8-carboxamide | 11.2 | 52.1 | 123.0 | 930.0 | 1.89 | 401.20 |
| 112 | 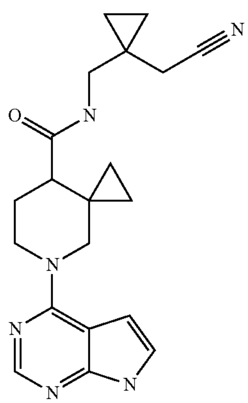 [SMILES: N#CCC1(CNC(=O)C2CCN(c3ncnc4[nH]ccc34)CC23CC3)CC1] | N-[[1-(cyanomethyl)cyclopropyl]methyl]-5-(7H-pyrrolo[2,3-d]pyrimidin-4-yl)-5-azaspiro[2.5]octane-8-carboxamide | 11.3 | 32.7 | 46.0 | 518.0 | 1.74 | 365.20 |
| 113 | 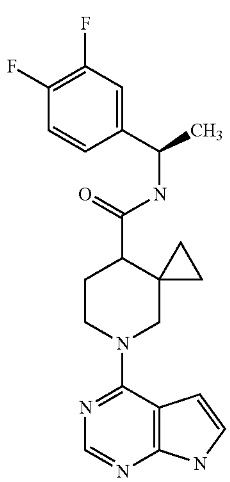 [SMILES: C[C@@H](NC(=O)C1CCN(c2ncnc3[nH]ccc23)CC12CC2)c1ccc(F)c(F)c1] | N-[(1R)-1-(3,4-difluorophenyl)ethyl]-5-(7H-pyrrolo[2,3-d]pyrimidin-4-yl)-5-azaspiro[2.5]octane-8-carboxamide | 11.6 | 19.4 | 51.2 | | 2.00 | 412.19 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 114 | 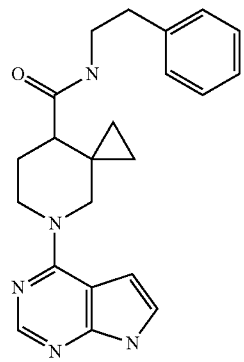 [SMILES: O=C(NCCc1ccccc1)C1CCN(c2ncnc3[nH]ccc23)CC12CC2] | N-phenethyl-5-(7H-pyrrolo[2,3-d]pyrimidin-4-yl)-5-azaspiro[2.5]octane-8-carboxamide | 11.7 | 37.0 | 64.8 | 858.0 | 1.93 | 376.21 |
| 115 | 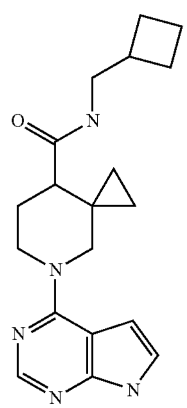 [SMILES: O=C(NCC1CCC1)C1CCN(c2ncnc3[nH]ccc23)CC12CC2] | N-(cyclobutylmethyl)-5-(7H-pyrrolo[2,3-d]pyrimidin-4-yl)-5-azaspiro[2.5]octane-8-carboxamide | 12.2 | 23.6 | 92.4 | 364.0 | 1.87 | 340.21 |
| 116 | 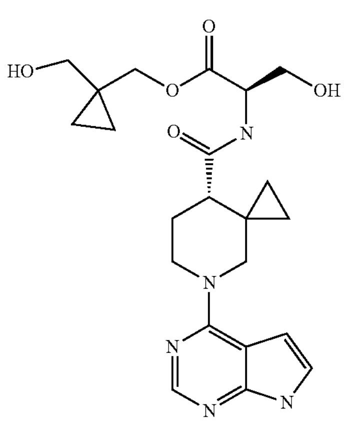 [SMILES: O=C(N[C@H](CO)C(=O)OCC1(CO)CC1)[C@H]1CCN(c2ncnc3[nH]ccc23)CC12CC2] | [1-(hydroxymethyl)cyclopropyl]methyl (2R)-3-hydroxy-2-[[[(8S)-5-(7H-pyrrolo[2,3-d]pyrimidin-4-yl)-5-azaspiro[2.5]octane-8-carbonyl]amino]propanoate | 12.4 | 24.7 | 47.8 | 210.0 | 1.62 | 444.22 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 117 | 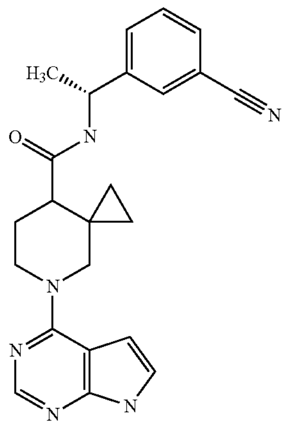 [SMILES: C[C@@H](NC(=O)C1CCN(c2ncnc3[nH]ccc23)CC12CC2)c1cccc(C#N)c1] | N-[(1R)-1-(3-cyanophenyl)ethyl]-5-(7H-pyrrolo[2,3-d]pyrimidin-4-yl)-5-azaspiro[2.5]octane-8-carboxamide | 12.4 | 21.6 | 73.8 | | 1.91 | 401.20 |
| 118 | 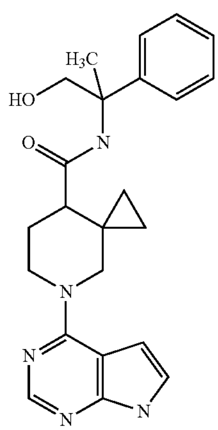 [SMILES: CC(CO)(NC(=O)C1CCN(c2ncnc3[nH]ccc23)CC12CC2)c1ccccc1] | N-(2-hydroxy-1-methyl-1-phenyl-ethyl)-5-(7H-pyrrolo[2,3-d]pyrimidin-4-yl)-5-azaspiro[2.5]octane-8-carboxamide | 13.1 | 24.3 | 77.7 | 832.0 | 1.82 | 406.22 |
| 119 | 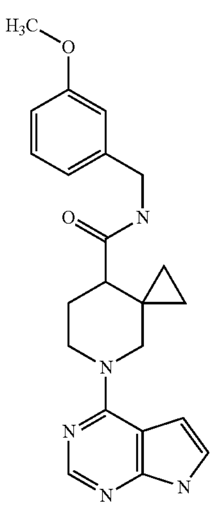 [SMILES: COc1cccc(CNC(=O)C2CCN(c3ncnc4[nH]ccc34)CC23CC3)c1] | N-[(3-methoxyphenyl)methyl]-5-(7H-pyrrolo[2,3-d]pyrimidin-4-yl)-5-azaspiro[2.5]octane-8-carboxamide | 13.4 | 36.8 | 71.1 | 539.0 | 1.90 | 392.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 120 | 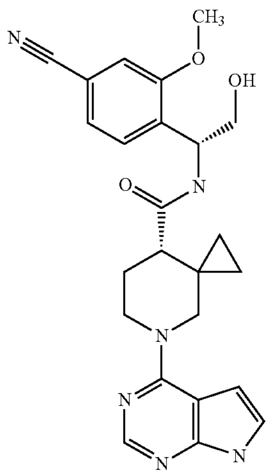 [SMILES: COc1cc(C#N)ccc1[C@H](CO)NC(=O)[C@H]1CCN(c2ncnc3[nH]ccc23)CC12CC2] | (8S)-N-[(1R)-1-(4-cyano-2-methoxy-phenyl)-2-hydroxy-ethyl]-5-(7H-pyrrolo[2,3-d]pyrimidin-4-yl)-5-azaspiro[2.5]octane-8-carboxamide | 13.7 | 40.2 | 154.0 | 392.0 | 1.78 | 447.21 |
| 121 | 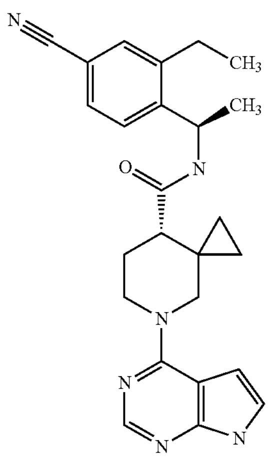 [SMILES: CCc1cc(C#N)ccc1[C@@H](C)NC(=O)[C@H]1CCN(c2ncnc3[nH]ccc23)CC12CC2] | (8S)-N-[(1R)-1-(4-cyano-2-ethyl-phenyl)ethyl]-5-(7H-pyrrolo[2,3-d]pyrimidin-4-yl)-5-azaspiro[2.5]octane-8-carboxamide | 15.3 | 44.7 | 141.0 | 289.0 | 2.04 | 429.23 |
| 122 | 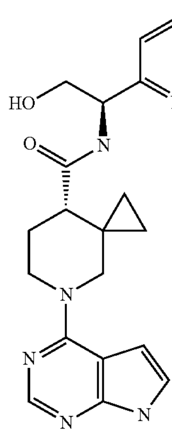 | (8S)-N-[(1R)-2-hydroxy-1-(2-pyridyl)ethyl]-5-(7H-pyrrolo[2,3-d]pyrimidin-4-yl)-5-azaspiro[2.5]octane-8-carboxamide | 16.3 | 37.3 | 153.0 | 203.0 | 1.59 | 393.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 123 | 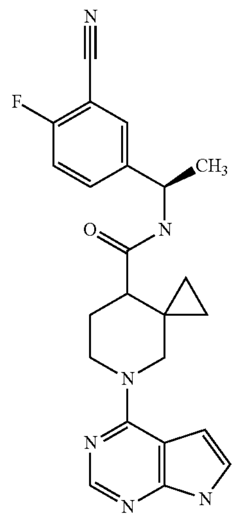 [SMILES: C[C@@H](NC(=O)C1CCN(c2ncnc3[nH]ccc23)CC12CC2)c1ccc(F)c(C#N)c1] | N-[(1R)-1-(3-cyano-4-fluoro-phenyl)ethyl]-5-(7H-pyrrolo[2,3-d]pyrimidin-4-yl)-5-azaspiro[2.5]octane-8-carboxamide | 16.3 | 21.4 | 63.9 | | 1.95 | 419.19 |
| 124 | 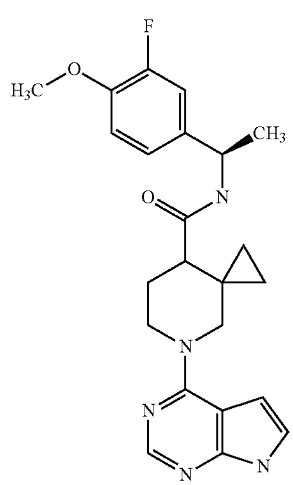 [SMILES: COc1ccc([C@@H](C)NC(=O)C2CCN(c3ncnc4[nH]ccc34)CC23CC3)cc1F] | N-[(1R)-1-(3-fluoro-4-methoxy-phenyl)ethyl]-5-(7H-pyrrolo[2,3-d]pyrimidin-4-yl)-5-azaspiro[2.5]octane-8-carboxamide | 18.6 | 59.7 | 144.0 | | 1.97 | 424.21 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 126 | 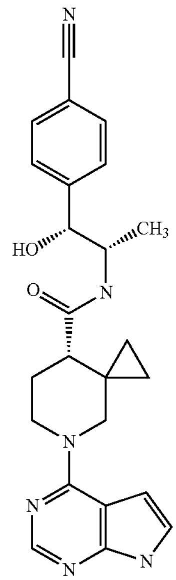 | (8S)-N-[(1S,2R)-2-(4-cyanophenyl)-2-hydroxy-1-methyl-ethyl]-5-(7H-pyrrolo[2,3-d]pyrimidin-4-yl)-5-azaspiro[2.5]octane-8-carboxamide | 19.5 | 25.7 | 29.8 | 987.0 | 1.78 | 431.21 |
| 127 | 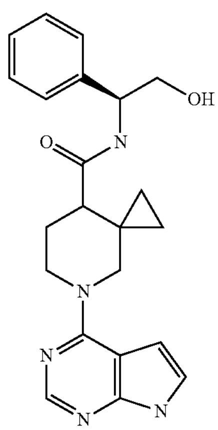 [SMILES: O=C(N[C@H](CO)c1ccccc1)C1CCN(c2ncnc3[nH]ccc23)CC12CC2] | N-[(1S)-2-hydroxy-1-phenyl-ethyl]-5-(7H-pyrrolo[2,3-d]pyrimidin-4-yl)-5-azaspiro[2.5]octane-8-carboxamide | 19.9 | 52.1 | 68.1 | 1100.0 | 1.75 | 392.20 |
| 128 | 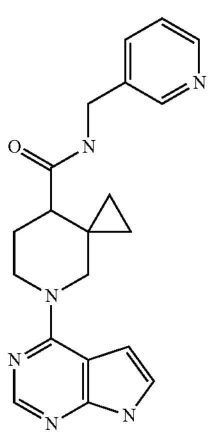 [SMILES: O=C(NCc1cccnc1)C1CCN(c2ncnc3[nH]ccc23)CC12CC2] | N-(3-pyridylmethyl)-5-(7H-pyrrolo[2,3-d]pyrimidin-4-yl)-5-azaspiro[2.5]octane-8-carboxamide | 20.5 | 38.2 | 58.6 | 1410.0 | 1.53 | 363.19 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 129 | 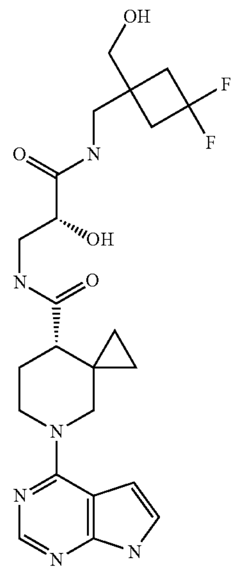 [SMILES: O=C(NCC1(CO)CC(F)(F)C1)[C@H](O)CNC(=O)[C@H]1CCN(c2ncnc3[nH]ccc23)CC12CC2] | (8S)-N-[(2R)-3-[[3,3-difluoro-1-(hydroxymethyl)cyclobutyl]methylamino]-2-hydroxy-3-oxo-propyl]-5-(7H-pyrrolo[2,3-d]pyrimidin-4-yl)-5-azaspiro[2.5]octane-8-carboxamide | 21.2 | 37.6 | 41.1 | 385.0 | 1.67 | 493.23 |
| 130 | 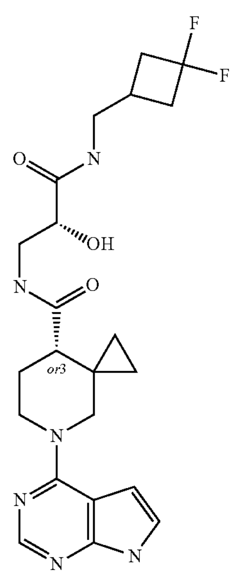 [SMILES: O=C(NCC1CC(F)(F)C1)[C@H](O)CNC(=O)[C@H]1CCN(c2ncnc3[nH]ccc23)CC12CC2] | (8S)-N-[(2R)-3-[(3,3-difluorocyclobutyl)methylamino]-2-hydroxy-3-oxo-propyl]-5-(7H-pyrrolo[2,3-d]pyrimidin-4-yl)-5-azaspiro[2.5]octane-8-carboxamide | 23.2 | 45.9 | 51.0 | 490.0 | 1.74 | 463.22 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 131 | 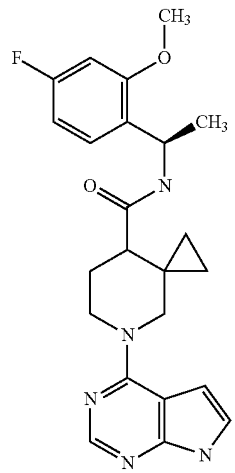 [SMILES: COc1cc(F)ccc1[C@@H](C)NC(=O)C1CCN(c2ncnc3[nH]ccc23)CC12CC2] | N-[(1R)-1-(4-fluoro-2-methoxy-phenyl)ethyl]-5-(7H-pyrrolo[2,3-d]pyrimidin-4-yl)-5-azaspiro[2.5]octane-8-carboxamide | 24.6 | 30.3 | 247.0 | | 2.03 | 424.24 |
| 132 | 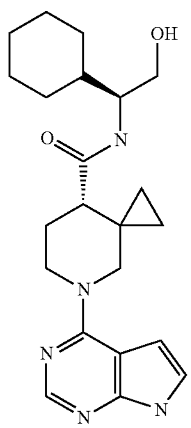 [SMILES: O=C(N[C@H](CO)C1CCCCC1)[C@H]1CCN(c2ncnc3[nH]ccc23)CC12CC2] | (8S)-N-[(1S)-1-cyclohexyl-2-hydroxy-ethyl]-5-(7H-pyrrolo[2,3-d]pyrimidin-4-yl)-5-azaspiro[2.5]octane-8-carboxamide | 25.3 | 94.5 | 162.0 | 665.0 | 1.86 | 398.25 |
| 133 | 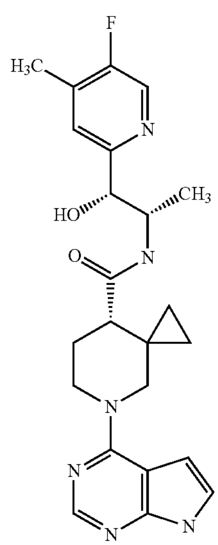 [SMILES: Cc1cc([C@@H](O)[C@H](C)NC(=O)[C@H]2CCN(c3ncnc4[nH]ccc34)CC23CC3)ncc1F] | (8S)-N-[(1S,2S)-2-(5-fluoro-4-methyl-2-pyridyl)-2-hydroxy-1-methyl-ethyl]-5-(7H-pyrrolo[2,3-d]pyrimidin-4-yl)-5-azaspiro[2.5]octane-8-carboxamide | 27.3 | 37.5 | 148.0 | 375.0 | 1.77 | 439.22 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 134 | 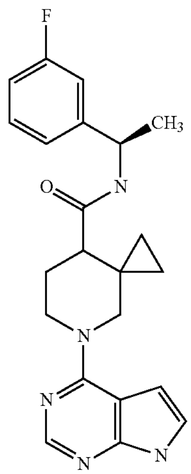 [SMILES: C[C@@H](NC(=O)C1CCN(c2ncnc3[nH]ccc23)CC12CC2)c1cccc(F)c1] | N-[(1R)-1-(3-fluorophenyl)ethyl]-5-(7H-pyrrolo[2,3-d]pyrimidin-4-yl)-5-azaspiro[2.5]octane-8-carboxamide | 32.8 | 80.6 | 171.0 | | 1.98 | 394.20 |
| 135 | 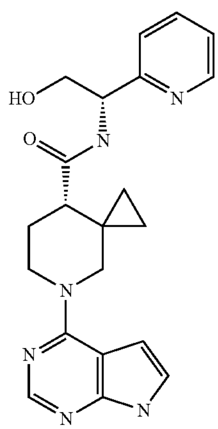 [SMILES: O=C(N[C@H](CO)c1ccccn1)[C@H]1CCN(c2ncnc3[nH]ccc23)CC12CC2] | (8S)-N-[(1S)-2-hydroxy-1-(2-pyridyl)ethyl]-5-(7H-pyrrolo[2,3-d]pyrimidin-4-yl)-5-azaspiro[2.5]octane-8-carboxamide | 33.2 | 83.8 | 148.0 | 466.0 | 1.58 | 393.20 |
| 136 | 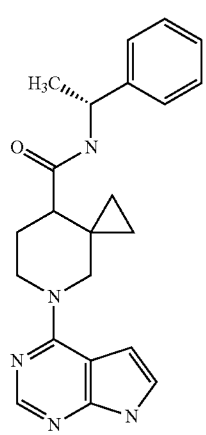 [SMILES: C[C@@H](NC(=O)C1CCN(c2ncnc3[nH]ccc23)CC12CC2)c1ccccc1] | N-[(1R)-1-phenylethyl]-5-(7H-pyrrolo[2,3-d]pyrimidin-4-yl)-5-azaspiro[2.5]octane-8-carboxamide | 33.8 | 55.1 | 111.0 | 1460.0 | 1.95 | 376.21 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 137 | 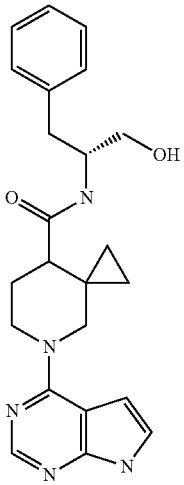 [SMILES: O=C(N[C@@H](CO)Cc1ccccc1)C1CCN(c2ncnc3[nH]ccc23)CC12CC2] | N-[(1R)-1-benzyl-2-hydroxy-ethyl]-5-(7H-pyrrolo[2,3-d]pyrimidin-4-yl)-5-azaspiro[2.5]octane-8-carboxamide | 38.0 | 30.5 | 91.6 | 1380.0 | 1.80 | 406.22 |
| 138 | 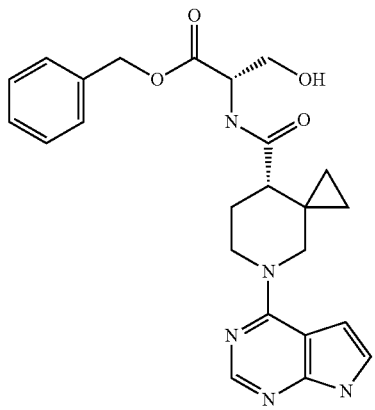 [SMILES: O=C(OCc1ccccc1)[C@H](CO)NC(=O)[C@H]1CCN(c2ncnc3[nH]ccc23)CC12CC2] | Benzyl (2S)-3-hydroxy-2-[[(8S)-5-(7H-pyrrolo[2,3-d]pyrimidin-4-yl)-5-azaspiro[2.5]octane-8-carbonyl]amino]propanoate | 38.2 | 112.0 | 90.9 | 1100.0 | 1.85 | 450.21 |
| 139 | 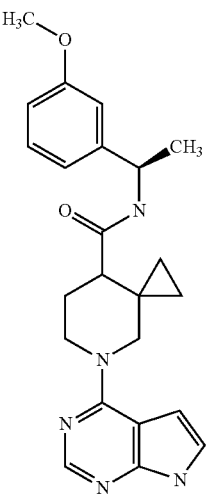 [SMILES: COc1cccc([C@@H](C)NC(=O)C2CCN(c3ncnc4[nH]ccc34)CC23CC3)c1] | N-[(1R)-1-(3-methoxyphenyl)ethyl]-5-(7H-pyrrolo[2,3-d]pyrimidin-4-yl)-5-azaspiro[2.5]octane-8-carboxamide | 39.2 | 61.2 | 99.3 | | 1.96 | 406.22 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 141 | 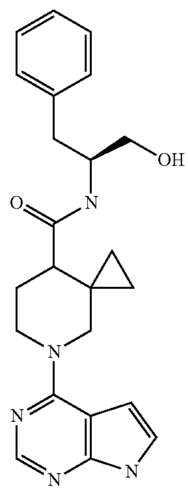 [SMILES: O=C(N[C@H](CO)Cc1ccccc1)C1CCN(c2ncnc3[nH]ccc23)CC12CC2] | N-[(1S)-1-benzyl-2-hydroxy-ethyl]-5-(7H-pyrrolo[2,3-d]pyrimidin-4-yl)-5-azaspiro[2.5]octane-8-carboxamide | 41.2 | 81.6 | 52.0 | 4160.0 | 1.80 | 406.22 |
| 142 | 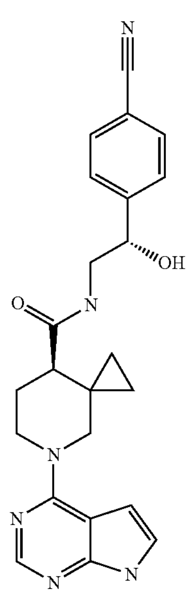 [SMILES: N#Cc1ccc([C@H](O)CNC(=O)[C@@H]2CCN(c3ncnc4[nH]ccc34)CC23CC3)cc1] | (8R)-N-[(2S)-2-(4-cyanophenyl)-2-hydroxy-ethyl]-5-(7H-pyrrolo[2,3-d]pyrimidin-4-yl)-5-azaspiro[2.5]octane-8-carboxamide | 42.7 | 179.0 | 278.0 | | 1.74 | 417.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 143 | 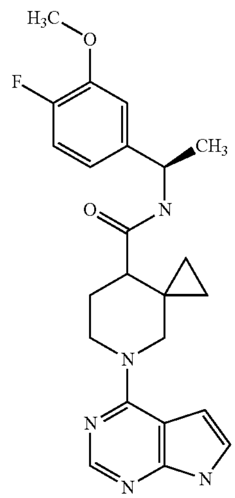 [SMILES: COc1cc([C@@H](C)NC(=O)C2CCN(c3ncnc4[nH]ccc34)CC23CC3)ccc1F] | N-[(1R)-1-(4-fluoro-3-methoxy-phenyl)ethyl]-5-(7H-pyrrolo[2,3-d]pyrimidin-4-yl)-5-azaspiro[2.5]octane-8-carboxamide | 45.1 | 90.4 | 199.0 | | 1.96 | 424.21 |
| 144 | 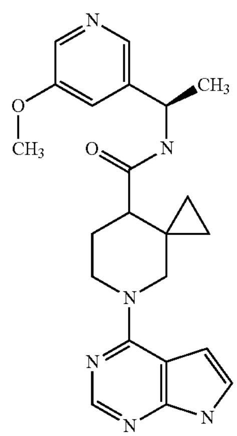 [SMILES: COc1cncc([C@@H](C)NC(=O)C2CCN(c3ncnc4[nH]ccc34)CC23CC3)c1] | N-[(1R)-1-(5-methoxy-3-pyridyl)ethyl]-5-(7H-pyrrolo[2,3-d]pyrimidin-4-yl)-5-azaspiro[2.5]octane-8-carboxamide | 48.5 | 80.6 | 157.0 | | 1.67 | 407.21 |
| 145 | 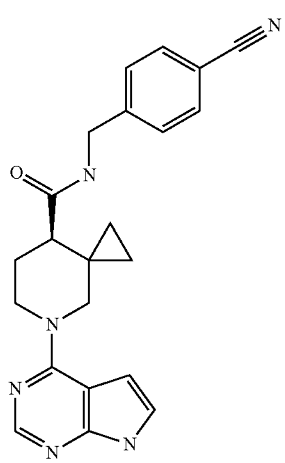 [SMILES: N#Cc1ccc(CNC(=O)[C@@H]2CCN(c3ncnc4[nH]ccc34)CC23CC3)cc1] | (8R)-N-[(4-cyanophenyl)methyl]-5-(7H-pyrrolo[2,3-d]pyrimidin-4-yl)-5-azaspiro[2.5]octane-8-carboxamide | 64.4 | 251.0 | 176.0 | 5740.0 | 1.84 | 387.19 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 146 | 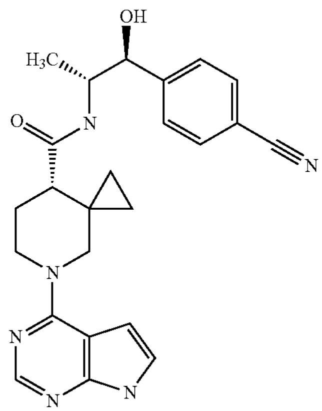 [SMILES: C[C@@H](NC(=O)[C@H]1CCN(c2ncnc3[nH]ccc23)CC12CC2)[C@@H](O)c1ccc(C#N)cc1] | (8S)-N-[(1R,2S)-2-(4-cyanophenyl)-2-hydroxy-1-methyl-ethyl]-5-(7H-pyrrolo[2,3-d]pyrimidin-4-yl)-5-azaspiro[2.5]octane-8-carboxamide | 67.7 | 188.0 | 266.0 | 1840.0 | 1.80 | 431.21 |
| 147 | 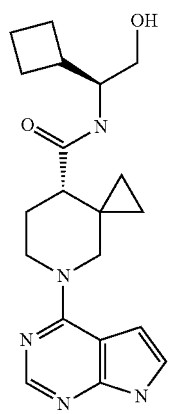 [SMILES: O=C(N[C@H](CO)C1CCC1)[C@H]1CCN(c2ncnc3[nH]ccc23)CC12CC2] | (8S)-N-[(1S)-1-cyclobutyl-2-hydroxy-ethyl]-5-(7H-pyrrolo[2,3-d]pyrimidin-4-yl)-5-azaspiro[2.5]octane-8-carboxamide | 68.1 | 121.0 | 162.0 | 914.0 | 1.72 | 370.22 |
| 148 | 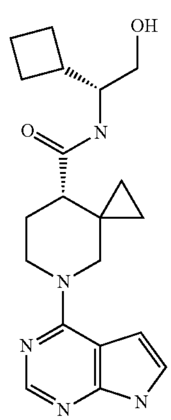 [SMILES: O=C(N[C@@H](CO)C1CCC1)[C@H]1CCN(c2ncnc3[nH]ccc23)CC12CC2] | (8S)-N-[(1R)-1-cyclobutyl-2-hydroxy-ethyl]-5-(7H-pyrrolo[2,3-d]pyrimidin-4-yl)-5-azaspiro[2.5]octane-8-carboxamide | 70.6 | 139.0 | 163.0 | 1080.0 | 1.72 | 370.22 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 149 | 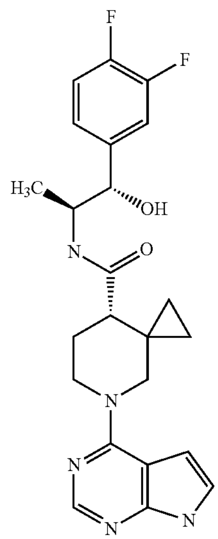 [SMILES: C[C@H](NC(=O)[C@H]1CCN(c2ncnc3[nH]ccc23)CC12CC2)[C@@H](O)c1ccc(F)c(F)c1] | (8S)-N-[(1S,2S)-2-(3,4-difluorophenyl)-2-hydroxy-1-methyl-ethyl]-5-(7H-pyrrolo[2,3-d]pyrimidin-4-yl)-5-azaspiro[2.5]octane-8-carboxamide | 0.4 | 200.0 | 0.6 | 4.2 | 1.88 | 442.20 |
| 150 | 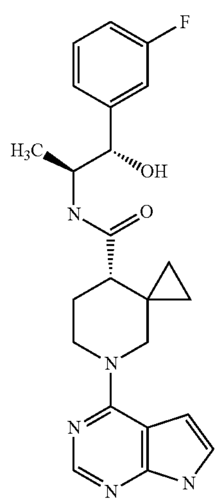 [SMILES: C[C@H](NC(=O)[C@H]1CCN(c2ncnc3[nH]ccc23)CC12CC2)[C@@H](O)c1cccc(F)c1] | (8S)-N-[(1S,2S)-2-(3-fluorophenyl)-2-hydroxy-1-methyl-ethyl]-5-(7H-pyrrolo[2,3-d]pyrimidin-4-yl)-5-azaspiro[2.5]octane-8-carboxamide | 2.7 | n/a | 3.1 | 21.0 | 1.84 | 424.21 |
| 151 | 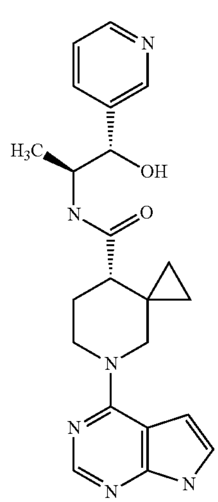 [SMILES: C[C@H](NC(=O)[C@H]1CCN(c2ncnc3[nH]ccc23)CC12CC2)[C@@H](O)c1cccnc1] | (8S)-N-[(1S,2S)-2-hydroxy-1-methyl-2-(3-pyridyl)ethyl]-5-(7H-pyrrolo[2,3-d]pyrimidin-4-yl)-5-azaspiro[2.5]octane-8-carboxamide | 10.9 | n/a | 29.7 | 184.0 | 1.52 | 407.21 |

TABLE 1-continued

| | | | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| Example | Structure | Iupac Name | | | | | | |
| 152 | | (8S)-N-[(1S,2S)-2-hydroxy-1-methyl-2-phenyl-ethyl]-5-(7H-pyrrolo[2,3-d]pyrimidin-4-yl)-5-azaspiro[2.5]octane-8-carboxamide | 2.7 | n/a | 5.8 | 27.7 | 1.81 | 406.22 |
| 153 | | (3,3-difluorocyclobutyl)methyl 5-(7H-pyrrolo[2,3-d]pyrimidin-4-yl)-5-azaspiro[2.5]octane-8-carboxylate | 2.3 | 3.2 | 8.9 | 68.0 | 2.10 | 377.17 |
| 154 | | (3,3-difluorocyclobutyl)methyl (8S)-5-(7H-pyrrolo[2,3-d]pyrimidin-4-yl)-5-azaspiro[2.5]octane-8-carboxylate | 0.9 | 1.7 | 5.1 | 15.7 | 2.10 | 377.17 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 155 | 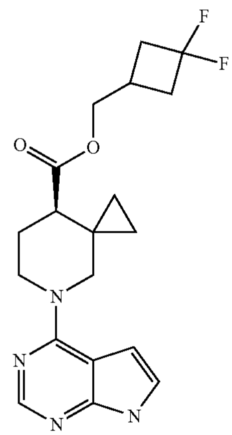 [SMILES: O=C(OCC1CC(F)(F)C1)[C@@H]1CCN(c2ncnc3[nH]ccc23)CC12CC2] | (3,3-difluorocyclobutyl)methyl (8R)-5-(7H-pyrrolo[2,3-d]pyrimidin-4-yl)-5-azaspiro[2.5]octane-8-carboxylate | 30.0 | 58.0 | 144.0 | 1280.0 | 2.10 | 377.17 |
| 156 | 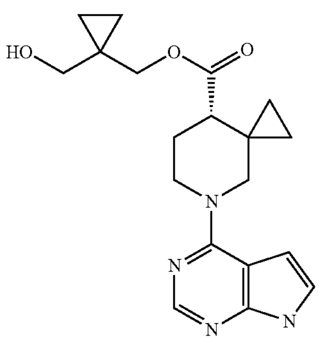 [SMILES: O=C(OCC1(CO)CC1)[C@H]1CCN(c2ncnc3[nH]ccc23)CC12CC2] | [1-(hydroxymethyl)cyclopropyl]methyl (8S)-5-(7H-pyrrolo[2,3-d]pyrimidin-4-yl)-5-azaspiro[2.5]octane-8-carboxylate | 4.0 | 5.4 | 20.4 | 30.0 | 1.79 | 357.18 |
| 157 | 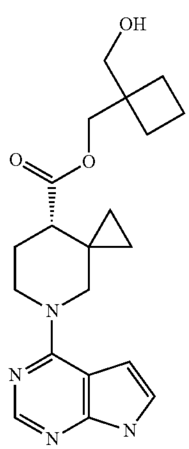 [SMILES: O=C(OCC1(CO)CCC1)[C@H]1CCN(c2ncnc3[nH]ccc23)CC12CC2] | [1-(hydroxymethyl)cyclobutyl]methyl (8S)-5-(7H-pyrrolo[2,3-d]pyrimidin-4-yl)-5-azaspiro[2.5]octane-8-carboxylate | 0.8 | 2.1 | 6.6 | 9.0 | 1.88 | 371.20 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 159 | 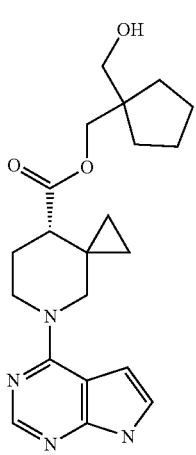 [SMILES: O=C(OCC1(CO)CCCC1)[C@H]1CCN(c2ncnc3[nH]ccc23)CC12CC2] | [1-(hydroxymethyl)cyclopentyl]methyl (8S)-5-(7H-pyrrolo[2,3-d]pyrimidin-4-yl)-5-azaspiro[2.5]octane-8-carboxylate | 0.5 | 1.3 | 3.1 | 5.1 | 1.96 | 385.22 |
| 160 | 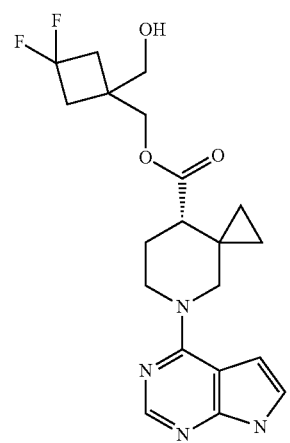 [SMILES: O=C(OCC1(CO)CC(F)(F)C1)[C@H]1CCN(c2ncnc3[nH]ccc23)CC12CC2] | [3,3-difluoro-1-(hydroxymethyl)cyclobutyl]methyl (8S)-5-(7H-pyrrolo[2,3-d]pyrimidin-4-yl)-5-azaspiro[2.5]octane-8-carboxylate | 0.3 | 0.8 | 1.8 | 3.7 | 1.92 | 407.18 |
| 161 | 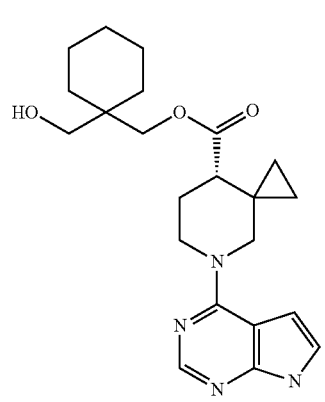 [SMILES: O=C(OCC1(CO)CCCCC1)[C@H]1CCN(c2ncnc3[nH]ccc23)CC12CC2] | [1-(hydroxymethyl)cyclohexyl]methyl (8S)-5-(7H-pyrrolo[2,3-d]pyrimidin-4-yl)-5-azaspiro[2.5]octane-8-carboxylate | 0.5 | 1.7 | 4.7 | 6.4 | 2.05 | 398.23 |

TABLE 1-continued

JAK kinase inhibitory and analytical data

| Example | Structure | Iupac Name | JAK1 EC$_{50}$ (nM) | JAK2 EC$_{50}$ (nM) | JAK3 EC$_{50}$ (nM) | TYK2 EC$_{50}$ (nM) | t$_R$ (min) | M+H$^+$ |
|---|---|---|---|---|---|---|---|---|
| 162 | 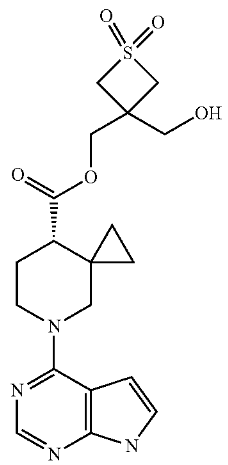 [SMILES: O=C(OCC1(CO)CS(=O)(=O)C1)[C@H]1CCN(c2ncnc3[nH]ccc23)CC12CC2] | [3-(hydroxymethyl)-1,1-dioxo-thietan-3-yl]methyl (8S)-5-(7H-pyrrolo[2,3-d]pyrimidin-4-yl)-5-azaspiro[2.5]octane-8-carboxylate | 0.2 | 0.6 | 1.5 | 3.6 | 1.71 | 421.15 |
| 163 | 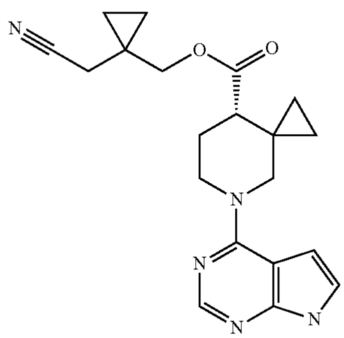 [SMILES: N#CCC1(COC(=O)[C@H]2CCN(c3ncnc4[nH]ccc34)CC23CC3)CC1] | [1-(cyanomethyl)cyclopropyl]methyl (8S)-5-(7H-pyrrolo[2,3-d]pyrimidin-4-yl)-5-azaspiro[2.5]octane-8-carboxylate | 3.1 | 3.8 | 13.0 | 25.0 | 1.96 | 366.19 |
| 164 | 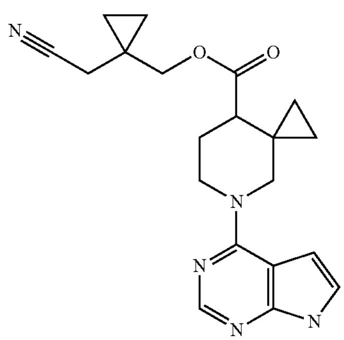 [SMILES: N#CCC1(COC(=O)C2CCN(c3ncnc4[nH]ccc34)CC23CC3)CC1] | [1-(cyanomethyl)cyclopropyl]methyl 5-(7H-pyrrolo[2,3-d]pyrimidin-4-yl)-5-azaspiro[2.5]octane-8-carboxylate | 4.0 | 5.0 | 19.0 | 70.0 | 1.95 | 366.19 |

To assess the in vitro metabolic stability, the compounds (0.5 μM) were incubated in duplicates with human liver microsomes (0.5 mg/mL) in phosphate buffer and NADPH, in 96-well plates for 40 min (37° C.), using a liquid handling robot (Hamilton Microlab Star). Sample aliquots were taken at 0, 5, 10, 20 and 40 min, and dispensed into cold acetonitrile, in order to stop the reactions. The plates were centrifuged for 30 minutes before the samples were analyzed using liquid chromatography coupled to a time-of-flight mass spectrometer (AB Sciex API5600). The compound depletion over time was used to estimate the elimination rate constant, from which the apparent intrinsic clearance, Clapp, was calculated and the values are listed in Table 2.

TABLE 2

Human liver microsome Cl$_{app}$ data

| Example | Clapp (ml/min/kg) |
|---|---|
| 1 | 190 |
| 2 | >200 |
| 3 | >200 |
| 4 | >200 |
| 5 | >200 |
| 6 | >200 |
| 7 | >200 |
| 8 | >200 |

TABLE 2-continued

Human liver microsome Cl_app data

| Example | Clapp (ml/min/kg) |
|---|---|
| 9 | >200 |
| 10 | 28 |
| 11 | 148 |
| 12 | 143 |
| 13 | 82 |
| 14 | >200 |
| 15 | >200 |
| 16 | 180 |
| 17 | 43 |
| 18 | 44 |
| 19 | 88 |
| 20 | 161 |
| 21 | 170 |
| 22 | 123 |
| 23 | 40 |
| 24 | 159 |
| 25 | 46 |
| 26 | 78 |
| 27 | 61 |
| 28 | 132 |
| 29 | 115 |
| 30 | 50 |
| 31 | 166 |
| 32 | 159 |
| 34 | 69 |
| 35 | 41 |
| 36 | 72 |
| 37 | 91 |
| 38 | 73 |
| 39 | 186 |
| 40 | >200 |
| 41 | 166 |
| 42 | >200 |
| 43 | 166 |
| 44 | >200 |
| 45 | >200 |
| 48 | 48 |
| 49 | 35 |
| 50 | 109 |
| 51 | >200 |
| 52 | 118 |
| 54 | 142 |
| 56 | 63 |
| 57 | 39 |
| 58 | 143 |
| 59 | 28 |
| 62 | 48 |
| 63 | >200 |
| 64 | >200 |
| 68 | 23 |
| 69 | 44 |
| 74 | 37 |
| 76 | 139 |
| 82 | 198 |
| 86 | >200 |
| 91 | 17 |
| 94 | 23 |
| 95 | 135 |
| 103 | 128 |
| 105 | 15 |
| 110 | 195 |
| 111 | 111 |
| 127 | 44 |
| 149 | >200 |
| 153 | 160 |
| 154 | 149 |
| 155 | >200 |
| 156 | 94 |
| 157 | >200 |
| 159 | >200 |
| 160 | 121 |
| 161 | >200 |
| 162 | <10 |
| 163 | >200 |
| 164 | >200 |

The invention claimed is:

1. A compound according to general formula I

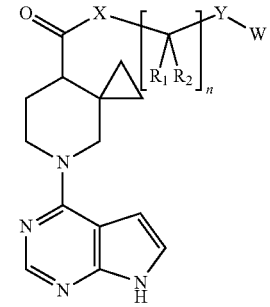

I wherein X represents NH or O;
wherein $R_1$ and $R_2$ each independently are selected from the group consisting of hydrogen, deuterium, hydroxyl, cyano, halogen, $(C_1$-$C_3)$alkyl and hydroxyl$(C_1$-$C_3)$ alkyl;
n is an integer selected from 1-3;
Y represents a bond, —C(O)O—*, —C(O)OR$_3$—*or —C(O)NHR$_3$—* wherein * denotes the point of attachment to W, and wherein R$_3$ represents $(C_1$-$C_4)$ alkylene;
W is selected from the group consisting of phenyl, pyridyl, $(C_3$-$C_7)$cycloalkyl and 4-6 membered heterocycloalkyl comprising one or two heteroatoms selected from O, S or N, wherein said phenyl, pyridyl, $(C_3$-$C_7)$ cycloalkyl and 4-6 membered heterocycloalkyl comprising one or two heteroatoms selected from O, S or N, are optionally substituted with one or more substitutents independently selected from hydroxyl, cyano, halogen, oxo, $(C_1$-$C_4)$alkyl, hydroxyl$(C_1$-$C_4)$alkyl, halo$(C_1$-$C_4)$alkyl, cyano$(C_1$-$C_4)$alkyl, $(C_1$-$C_4)$alkoxy, halo$(C_1$-$C_4)$alkoxy and —SO$_2$NH$_2$;
or a pharmaceutically acceptable salt, hydrate or solvate thereof.

2. The compound according to claim 1, wherein X represents NH.

3. The compound according to claim 1, wherein X represents O.

4. The compound according to claim 1, wherein n is 1.

5. The compound according to claim 1, wherein n is 2.

6. The compound according to claim 1, wherein Y represents a bond.

7. The compound according to claim 1, wherein Y represents a —C(O)O—*, —C(O)OR$_3$—* or —C(O)NHR$_3$— *wherein * denotes the point of attachment to W, and wherein R$_3$ represents methylene.

8. The compound according to claim 1, wherein R$_1$ and R$_2$ each independently are selected from the group consisting of hydrogen, hydroxyl, methyl and hydroxymethyl.

9. The compound according to claim 1, wherein W is selected from the group consisting of $(C_3$-$C_6)$cycloalkyl, phenyl, pyridyl, tetrahydropyranyl and thiethanyl, wherein said $(C_3$-$C_6)$cycloalkyl, phenyl, pyridyl, tetrahydropyranyl and thiethanyl are optionally substituted with one or more substitutents independently selected from fluoro, cyano, —SO$_2$NH$_2$, hydroxyl, oxo, methyl, ethyl, hydroxymethyl, cyanomethy and methoxy.

10. The compound according to claim 1, wherein the compound is selected from the list consisting of (i) (8S)—N-[(2S)-2-cyclopentyl-2-hydroxy-ethyl]-5-(7H-pyrrolo[2,3-d]pyrimidin-4-yl-5-azaspiro[2.5]octane-8-carboxamide, (ii) (8S)—N-(2-cyclohexyl-2-hydroxy-ethyl)-5-(7H-pyrrolo[2,3-d]pyrimidin-4-yl)-5-azaspiro[2.5]octane-8-carboxamide, (iii) (8S)—N-[(1S,2S)-2-cyclohexyl-2-hydroxy-1-methyl-ethyl]-5-(7H-pyrrolo[2,3-d]pyrimidin-4-yl)-5-azaspiro[2.5]octane-8-carboxamide, (iv) (8S)—N-[(2S)-2-cyclohexyl-2-hydroxy-ethyl]-5-(7H-pyrrolo[2,3-d]pyrimidin-4-yl)-5-azaspiro[2.5]octane-8-carboxamide, (v) (8S)—N-[(1S,2S)-2-cyclopentyl-2-hydroxy-1-methyl-ethyl]-5-(7H-pyrrolo[2,3-d]pyrimidin-4-yl)-5-azaspiro[2.5]octane-8-carboxamide, (vi) (8S)—N-[(1S,2S)-2-(4-fluorophenyl)-2-hydroxy-1-methyl-ethyl]-5-(7H-pyrrolo[2,3-d]pyrimidin-4-yl)-5-azaspiro[2.5]octane-8-carboxamide, (vii) (8S)—N-[(2S)-2-(4-fluorophenyl)-2-hydroxy-ethyl]-5-(7H-pyrrolo[2,3-d]pyrimidin-4-yl-5-azaspiro[2.5]octane-8-carboxamide, (viii) (8S)—N-[(2S)-2-(4-cyanophenyl)-2-hydroxy-ethyl]-5-(7H-pyrrolo[2,3-d]pyrimidin-4-yl-5-azaspiro[2.5]octane-8-carboxamide, (ix) (8S)—N-[(1S,2S)-2-(4-fluorophenyl)-2-hydroxy-1-(hydroxymethyl)ethyl]-5-(7H-pyrrolo[2,3-d]pyrimidin-4-yl)-5-azaspiro[2.5]octane-8-carboxamide, (x) (8S)—N-[(2R)-2-hydroxy-2-tetrahydropyran-4-yl-ethyl]-5-(7H-pyrrolo[2,3-d]pyrimidin-4-yl)-5-azaspiro[2.5]octane-8-carboxamide, (xi) (8S)—N-[(2R)-2-cyclopentyl-2-hydroxy-ethyl]-5-(7H-pyrrolo[2,3-d]pyrimidin-4-0)-5-azaspiro[2.5]octane-8-carboxamide, (xii) (8S)—N-[(2R)-2-(5-fluoro-2-pyridyl)-2-hydroxy-ethyl]-5-(7H-pyrrolo[2,3-d]pyrimidin-4-yl)-5-azaspiro[2.5]octane-8-carboxamide (xiii) (8S)—N-[(4-cyanophenyl)methyl]-5-(7H-pyrrolo[2,3-d]pyrimidin-4-yl)-5-azaspiro[2.5]octane-8-carboxamide, (xiv) (8S)—N-[(1 S)-1-(4-cyano-3-fluoro-phenyl)ethyl]-5-(7H-pyrrolo[2,3-d]pyrimidin-4-yl)-5-azaspiro[2.5]octane-8-carboxamide, (xv) (8S)—N-[(2R)-2-cyclohexyl-2-hydroxy-ethyl]-5-(7H-pyrrolo[2,3-d]pyrimidin-4-yl)-5-azaspiro[2.5]octane-8-carboxamide, (xvi) (8S)—N-[(4-cyano-3-fluoro-phenyl)methyl]-5-(7H-pyrrolo[2,3-d]pyrimidin-4-yl)-5-azaspiro[2.5]octane-8-carboxamide, (xvii) (8S)—N-[(1R)-1-(4-fluorophenyl)-2-hydroxy-ethyl]-5-(7H-pyrrolo[2,3-d]pyrimidin-4-yl)-5-azaspiro[2.5]octane-8-carboxamide, (xviii) (8S)—N-[(1R)-1-(4-cyanophenyl)-2-hydroxy-ethyl]-5-(7H-pyrrolo[2,3-d]pyrimidin-4-yl)-5-azaspiro[2.5]octane-8-carboxamide, (xix) N-[(1R)-1-(4-cyanophenyl)-2-hydroxy-ethyl]-5-(7H-pyrrolo[2,3-d]pyrimidin-4-yl)-5-azaspiro[2.5]octane-8-carboxamide, (xx) (8S)—N-[(1 S)-1-(4-cyano-fluoro-phenyl)ethyl]-5-(7H-pyrrolo[2,3-d]pyrimidin-4-yl)-5-azaspiro[2.5]octane-8-carboxamide, (xxi) N-[(1 S)-1-(4-cyanophenyl)ethyl]-5-(7H-pyrrolo[2,3-d]pyrimidin-4-yl)-5-azaspiro[2.5]octane-8-carboxamide, (xxii) (8S)—N-[(1 S)-1-(4-cyanophenyl)ethyl]-5-(7H-pyrrolo[2,3-d]pyrimidin-4-yl)-5-azaspiro[2.5]octane-8-carboxamide, (xxiii) (8S)—N-[[3,3-difluoro-1-(hydroxymethyl)cyclobutyl]methyl]-5-(7H-pyrrolo[2,3-d]pyrimidin-4-yl)-5-azaspiro[2.5]octane-8-carboxamide, (xxiv) (8S)—N-[(1R)-1-cyclohexyl-2-hydroxy-ethyl]-5-(7H-pyrrolo[2,3-d]pyrimidin-4-yl)-5-azaspiro[2.5]octane-8-carboxamide, (xxv) (8S)—N-[(2R)-2-cyclobutyl-2-hydroxy-ethyl]-5-(7H-pyrrolo[2,3-d]pyrimidin-4-yl)-5-azaspiro[2.5]octane-8-carboxamide, (xxvi) N-[(4-cyanophenyl)methyl]-5-(7H-pyrrolo[2,3-d]pyrimidin-4-yl)-5-azaspiro[2.5]octane-8-carboxamide, (xxvii) (8S)—N-[(1 S)-1-(4-cyanophenyl)-2-hydroxy-1-methyl-ethyl]-5-(7H-pyrrolo[2,3-d]pyrimidin-4-yl)-5-azaspiro[2.5]octane-8-carboxamide, (xxviii) (8S)—N-[(1R)-1-(4-cyanophenyl)-2-hydroxy-1-methyl-ethyl]-5-(7H-pyrrolo[2,3-d]pyrimidin-4-yl)-5-azaspiro[2.5]octane-8-carboxamide, (xxix) (8S)—N-[(2R)-2-(4-cyanophenyl)-2-hydroxy-ethyl]-5-(7H-pyrrolo[2,3-d]pyrimidin-4-yl)-5-azaspiro[2.5]octane-8-carboxamide, (xxx) (8S)—N-[(1 S,2S)-2-(5-fluoro-2-pyridyl)-2-hydroxy-1-(hydroxymethyl)ethyl]-5-(7H-pyrrolo[2,3-d]pyrimidin-4-yl)-5-azaspiro[2.5]octane-8-carboxamide, (xxxi) (8S)—N-[(4-cyano-2-fluoro-phenyl)methyl]-5-(7H-pyrrolo[2,3-d]pyrimidin-4-yl)-5-azaspiro[2.5]octane-8-carboxamide, (xxxii) (8S)—N-[(2S)-2-cyclopentyl-2-hydroxy-ethyl]-5-(7H-pyrrolo[2,3-d]pyrimidin-4-yl)-5-azaspiro[2.5]octane-8-carboxamide, (xxxiii) 5-(7H-pyrrolo[2,3-d]pyrimidin-4-yl)-N-[(4-sulfamoylphenyl)methyl]-5-azaspiro[2.5]octane-8-carboxamide, (xxxiv) (8S)—N-[(1R)-1-(2,4-difluorophenyl)-2-hydroxy-ethyl]-5-(7H-pyrrolo[2,3-d]pyrimidin-4-yl)-5-azaspiro[2.5]octane-8-carboxamide, (xxxv) N-[[3,3-difluoro-1-(hydroxymethyl)cyclobutyl]methyl]-5-(7H-pyrrolo[2,3-d]pyrimidin-4-yl)-5-azaspiro[2.5]octane-8-carboxamide, (xxxvi) (8S)—N-[(2S)-2-(5-cyano-2-pyridyl)-2-hydroxy-ethyl]-5-(7H-pyrrolo[2,3-d]pyrimidin-4-yl)-5-azaspiro[2.5]octane-8-carboxamide, (xxxvii) (8S)—N-[(1R)-1-(4-cyano-2-methyl-phenyl)-2-hydroxy-ethyl]-5-(7H-pyrrolo[2,3-d]pyrimidin-4-yl)-5-azaspiro[2.5]octane-8-carboxamide, (xxxviii) (8S)—N-[2-(5-fluoro-2-pyridyl)-2-hydroxy-ethyl]-5-(7H-pyrrolo[2,3-d]pyrimidin-4-yl)-5-azaspiro[2.5]octane-8-carboxamide, (xxxix) N-[2-(4-cyanophenyl)-2-hydroxy-ethyl]-5-(7H-pyrrolo[2,3-d]pyrimidin-4-yl)-5-azaspiro[2.5]octane-8-carboxamide, (xl) (8S)—N-[(1 S,2S)-2-(4-fluoro-3-methyl-phenyl)-2-hydroxy-1-methyl-ethyl]-5-(7H-pyrrolo[2,3-d]pyrimidin-4-yl)-5-azaspiro[2.5]octane-8-carboxamide, (xli) (8S)—N-[(1 S,2R)-2-(5-fluoro-2-pyridyl)-2-hydroxy-1-methyl-ethyl]-5-(7H-pyrrolo[2,3-d]pyrimidin-4-yl)-5-azaspiro[2.5]octane-8-carboxamide, (xlii) (3,3-difluorocyclobutyl)methyl (2R)-3-hydroxy-2-[[(8S)-5-(7H-pyrrolo[2,3-d]pyrimidin-4-yl)-5-azaspiro[2.5]octane-8-carbonyl]amino]propanoate, (xliii) (8S)—N-[(1S,2S)-2-(4-cyanophenyl)-2-hydroxy-1-methyl-ethyl]-5-(7H-pyrrolo[2,3-d]pyrimidin-4-yl)-5-azaspiro[2.5]octane-8-carboxamide, (xliv) (8S)—N-[(2R)-2-(5-fluoro-4-methyl-2-pyridyl)-2-hydroxy-ethyl]-5-(7H-pyrrolo[2,3-d]pyrimidin-4-yl)-5-azaspiro[2.5]octane-8-carboxamide, (xlv) (8S)—N-[(1S,2R)-2-(4-fluorophenyl)-2-hydroxy-1-methyl-ethyl]-5-(7H-pyrrolo[2,3-d]pyrimidin-4-yl)-5-azaspiro[2.5]octane-8-carboxamide, (xlvi) (8S)—N-[(2S)-2-(5-fluoro-2-pyridyl)-2-hydroxy-ethyl]-5-(7H-pyrrolo[2,3-d]pyrimidin-4-yl-5-azaspiro[2.5]octane-8-carboxamide, (xlvii) (8S)—N-[(1R)-1-(5-cyano-2-pyridyl)-2-hydroxy-ethyl]-5-(7H-pyrrolo[2,3-d]pyrimidin-4-yl)-5-azaspiro[2.5]octane-8-carboxamide, (xlviii) (8S)—N-[(1S)-1-(5-cyano-2-pyridyl)ethyl]-5-(7H-pyrrolo[2,3-d]pyrimidin-4-yl)-5-azaspiro[2.5]octane-8-carboxamide, (xlix) (8S)—N-[(1-hydroxycyclopentyl)methyl]-5-(7H-pyrrolo[2,3-d]pyrimidin-4-yl)-5-azaspiro[2.5]octane-8-carboxamide, (l) (8S)—N-[(1S,2R)-2-(4-fluorophenyl)-2-hydroxy-1-(hydroxymethyl)ethyl]-5-(7H-pyrrolo[2,3-d]pyrimidin-4-yl)-5-azaspiro[2.5]octane-8-carboxamide, (li) (8S)—N-[(2S)-2-hydroxy-2-phenyl-ethyl]-5-(7H-pyrrolo[2,3-d]pyrimidin-4-yl)-5-azaspiro[2.5]octane-8-carboxamide, (lii) (8S)—N-[[1-(hydroxymethyl)cyclopentyl]methyl]-5-(7H-pyrrolo[2,3-d]pyrimidin-4-yl)-5-azaspiro[2.5]octane-8-carboxamide, (liii) N-[(4-fluorophenyl)methyl]-5-(7H-pyrrolo[2,3-d]pyrimidin-4-yl)-5-azaspiro[2.5]octane-8-carboxamide, (liv) (8S)—N-[(1R)-1-(4-cyano-3-methyl-phenyl)-2-hydroxy-ethyl]-5-(7H-pyrrolo[2,3-d]pyrimidin-4-yl)-5-azaspiro[2.5]octane-8-carboxamide, (lv) 5-(7H-pyrrolo[2,3-d]pyrimidin-4-yl)-N-[(3-sulfamoylphenyl)methyl]-5-azaspiro[2.5]octane-8-carboxamide, (lvi) N-[(3,3-difluorocyclobutyl)methyl]-5-(7H-pyrrolo[2,3-d]pyrimidin-4-yl)-5-azaspiro[2.5]octane-8-carboxamide, (lvii) (8S)—N-[(1R)-1-(5-cyano-2-pyridyl)-2-hydroxy-1-methyl-ethyl]-5-(7H-pyrrolo[2,3-d]pyrimidin-4-yl)-5-azaspiro[2.5]octane-8-carboxamide, (lviii) N-[[1-(hydroxymethyl)cyclopentyl]methyl]-5-(7H-pyrrolo[2,3-d]pyrimidin-4-yl)-5-azaspiro[2.5]octane-8-carboxamide, (lix) N-[(3-cyanocyclobutyl)methyl]-5-(7H-pyrrolo[2,3-d]pyrimidin-4-yl)-5-azaspiro[2.5]octane-8-carboxamide, (lx) N-[1-(4-fluorophenyl)ethyl]-5-(7H-pyrrolo[2,3-d]pyrimidin-4-yl)-5-azaspiro[2.5]octane-8-carboxamide, (lxi) (8S)—N-[(3,3-difluorocyclobutyl)methyl]-5-(7H-pyrrolo[2,3-d]pyrimidin-4-yl)-5-azaspiro[2.5]octane-8-carboxamide, (lxii) N-[(2S)-2-hydroxy-2-phenyl-ethyl]-5-(7H-pyrrolo[2,3-d]pyrimidin-4-yl-5-azaspiro[2.5]octane-8-carboxamide, (lxiii) (8S)—N-[(2S)-2-hydroxy-2-(p-tolyl)ethyl]-5-(7H-pyrrolo[2,3-d]pyrimidin-4-yl)-5-azaspiro[2.5]octane-8-carboxamide, (lxiv) N-[(1S)-1-(4-methoxyphenyl)ethyl]-5-(7H-pyrrolo[2,3-d]pyrimidin-4-yl)-5-azaspiro[2.5]octane-8-carboxamide, (lxv) (8S)—N-[(1R)-1-(3-cyanophenyl)-2-hydroxy-ethyl]-5-(7H-pyrrolo[2,3-d]pyrimidin-4-yl)-5-azaspiro[2.5]octane-8-carboxamide, (lxvi) (8S)—N-[(1-hydroxycyclobutyl)methyl]-5-(7H-pyrrolo[2,3-d]pyrimidin-4-yl)-5-azaspiro[2.5]octane-8-carboxamide, (lxvii) N-[(1R)-2-hydroxy-1-phenyl-ethyl]-5-(7H-pyrrolo[2,3-d]pyrimidin-4-yl)-5-azaspiro[2.5]octane-8-carboxamide, (lxviii) N-[(3-cyanophenyl)methyl]-5-(7H-pyrrolo[2,3-d]pyrimidin-4-yl)-5-azaspiro[2.5]octane-8-carboxamide, (lxix) (8S)—N-[(4-cyano-2-methoxy-phenyl)methyl]-5-(7H-pyrrolo[2,3-d]pyrimidin-4-yl)-5-azaspiro[2.5]octane-8-carboxamide, (lxx) (8S)—N-[(1S,2S)-2-hydroxy-1-methyl-2-(p-tolyl)ethyl]-5-(7H-pyrrolo[2,3-d]pyrimidin-4-yl)-5-azaspiro[2.5]octane-8-carboxamide, (lxxi) (8S)—N-[(1-hydroxycyclohexyl)methyl]-5-(7H-pyrrolo[2,3-d]pyrimidin-4-yl)-5-azaspiro[2.5]octane-8-carboxamide, (lxxii) (8S)—N-[(1S,2R)-2-(5-fluoro-4-methyl-2-pyridyl)-2-hydroxy-1-methyl-ethyl]-5-(7H-pyrrolo[2,3-d]pyrimidin-4-yl)-5-azaspiro[2.5]octane-8-carboxamide, (lxxiii) N-[(5-cyano-2-pyridyl)methyl]-5-(7H-pyrrolo[2,3-d]pyrimidin-4-yl)-5-azaspiro[2.5]octane-8-carboxamide, (lxxiv) (8S)—N-[(1R)-1-(4-fluoro-2-methyl-phenyl)-2-hydroxy-ethyl]-5-(7H-pyrrolo[2,3-d]pyrimidin-4-yl)-5-azaspiro[2.5]octane-8-carboxamide, (lxxv) (8S)—N-[(1S)-1-(5-cyano-2-pyridyl)-2-hydroxy-1-methyl-ethyl]-5-(7H-pyrrolo[2,3-d]pyrimidin-4-yl)-5-azaspiro[2.5]octane-8-carboxamide, (lxxvi) benzyl (2R)-3-hydroxy-2-[[(8S)-5-(7H-pyrrolo[2,3-d]pyrimidin-4-yl)-5-azaspiro[2.5]octane-8-carbonyl]amino]propanoate, (lxxvii) N-[(3-fluorophenyl)methyl]-5-(7H-pyrrolo[2,3-d]pyrimidin-4-yl)-5-azaspiro[2.5]octane-8-carboxamide, (lxxviii) N-(cyclopentylmethyl)-5-(7H-pyrrolo[2,3-d]pyrimidin-4-yl)-5-azaspiro[2.5]octane-8-carboxamide, (lxxix) N-[[(1S,3S)-3-cyanocyclopentyl]methyl]-5-(7H-pyrrolo[2,3-d]pyrimidin-4-yl)-5-azaspiro[2.5]octane-8-carboxamide, (lxxx) (8S)—N-[(1R)-1-(4-cyano-3-fluoro-phenyl)ethyl]-5-(7H-pyrrolo[2,3-d]pyrimidin-4-yl)-5-azaspiro[2.5]octane-8-carboxamide, (lxxxi) N-(4-pyridylmethyl)-5-(7H-pyrrolo[2,3-d]pyrimidin-4-yl)-5-azaspiro[2.5]octane-8-carboxamide, (lxxxii) N-[(1S)-1-(3-cyanophenyl)ethyl]-5-(7H-pyrrolo[2,3-d]pyrimidin-4-yl)-5-azaspiro[2.5]octane-8-carboxamide, (lxxxiii) cyclopentylmethyl (2R)-3-hydroxy-2-[[(8S)-5-(7H-pyrrolo[2,3-d]pyrimidin-4-yl)-5-azaspiro[2.5]octane-8-carbonyl]amino]propanoate, (lxxxiv) N-[(1-hydroxycyclopentyl)methyl]-5-(7H-pyrrolo[2,3-d]pyrimidin-4-yl)-5-azaspiro[2.5]octane-8-carboxamide, (lxxxv) (8S)—N-[(1R)-1-(4-cyano-2-ethyl-phenyl)-2-hydroxy-ethyl]-5-(7H-pyrrolo[2,3-d]pyrimidin-4-yl)-5-azaspiro[2.5]octane-8-carboxamide, (lxxxvi) N-[(4-methoxyphenyl)methyl]-5-(7H-pyrrolo[2,3-d]pyrimidin-4-yl)-5-azaspiro[2.5]octane-8-carboxamide, (lxxxvii) cyclopropylmethyl (2R)-3-hydroxy-2-[[(8S)-5-(7H-pyrrolo[2,3-d]pyrimidin-4-yl)-5-azaspiro[2.5]octane-8-carbonyl]amino]propanoate, (lxxxviii) (8S)—N-[(4-cyano-3-methoxy-phenyl)methyl]-5-(7H-pyrrolo[2,3-d]pyrimidin-4-yl)-5-azaspiro[2.5]octane-8-carboxamide, (lxxxix) N-[(1S)-1-(4-cyanophenyl)-2-hydroxy-ethyl]-5-(7H-pyrrolo[2,3-d]pyrimidin-4-yl)-5-azaspiro[2.5]octane-8-carboxamide, (xc) N-benzyl-5-(7H-pyrrolo[2,3-d]pyrimidin-4-yl)-5-azaspiro[2.5]octane-8-carboxamide (xci) cyclopentyl (2R)-3-hydroxy-2-[[(8S)-5-(7H-pyrrolo[2,3-d]pyrimidin-4-yl)-5-azaspiro[2.5]octane-8-carbonyl]amino]propanoate, (xcii) (8S)—N-[(1S)-1-(4-cyano-2-methoxy-phenyl)ethyl]-5-(7H-pyrrolo[2,3-d]pyrimidin-4-yl)-5-azaspiro[2.5]octane-8-carboxamide, (xciii) [1-(hydroxymethyl)cyclobutyl]methyl (2R)-3-hydroxy-2-[[(8S)-5-(7H-pyrrolo[2,3-d]pyrimidin-4-yl)-5-azaspiro[2.5]octane-8-carbonyl]amino]propanoate, (xciv) N-[(1S)-1-phenylethyl]-5-(7H-pyrrolo[2,3-d]pyrimidin-4-yl)-5-azaspiro[2.5]octane-8-carboxamide, (xcv) (8S)—N-[(1R)-1-[4-fluoro-2-(hydroxymethyl)phenyl]-2-hydroxy-ethyl]-5-(7H-pyrrolo[2,3-d]pyrimidin-4-yl)-5-azaspiro[2.5]octane-8-carboxamide, (xcvi) (8S)—N-[(1R)-1-(4-cyano-2-fluoro-phenyl)ethyl]-5-(7H-pyrrolo[2,3-d]pyrimidin-4-yl)-5-azaspiro[2.5]octane-8-carboxamide, (xcvii) N—[[(1R,2R)-2-cyanocyclopropyl]methyl]-5-(7H-pyrrolo[2,3-d]pyrimidin-4-yl)-5-azaspiro[2.5]octane-8-carboxamide, (xcviii) N-[(2R)-2-hydroxy-2-phenyl-ethyl]-5-(7H-pyrrolo[2,3-d]pyrimidin-4-yl)-5-azaspiro[2.5]octane-8-carboxamide, (xcix) (8S)—N-[(1 S,2R)-2-hydroxy-1-methyl-2-(2-pyridyl)ethyl]-5-(7H-pyrrolo[2,3-d]pyrimidin-4-yl)-5-azaspiro[2.5]octane-8-carboxamide, (c) (8S)—N-[(1 S,2R)-2-(5-fluoro-2-pyridyl)-2-hydroxy-1-(hydroxymethyl)ethyl]-5-(7H-pyrrolo[2,3-d]pyrimidin-4-yl)-5-azaspiro[2.5]octane-8-carboxamide, (ci) (8S)—N-[(2S)-2-(3-cyanophenyl)-2-hydroxy-ethyl]-5-(7H-pyrrolo[2,3-d]pyrimidin-4-yl)-5-azaspiro[2.5]octane-8-carboxamide, (cii) (8S)—N-[(1 S,2S)-2-(5-fluoro-2-pyridyl)-2-hydroxy-1-methyl-ethyl]-5-(7H-pyrrolo[2,3-d]pyrimidin-4-yl)-5-azaspiro[2.5]octane-8-carboxamide, (ciii) (8S)—N-[(1 S)-1-(5-cyano-2-pyridyl)-2-hydroxy-ethyl]-5-(7H-pyrrolo[2,3-d]pyrimidin-4-yl)-5-azaspiro[2.5]octane-8-carboxamide, (civ) (8S)—N-[(1R)-1-(4-fluoro-2-methoxy-phenyl)-2-hydroxy-ethyl]-5-(7H-pyrrolo[2,3-d]pyrimidin-4-yl)-5-azaspiro[2.5]octane-8-carboxamide, (cv) (8S)—N-[(2S)-2-(5-fluoro-4-methyl-2-pyridyl)-2-hydroxy-ethyl]-5-(7H-pyrrolo[2,3-d]pyrimidin-4-yl)-5-azaspiro[2.5]octane-8-carboxamide, (cvi) N-[(1R)-1-(4-cyanophenyl)ethyl]-5-(7H-pyrrolo[2,3-d]pyrimidin-4-yl)-5-azaspiro[2.5]octane-8-carboxamide, (cvii) N-[[1-(cyanomethyl)cyclopropyl]methyl]-5-(7H-pyrrolo[2,3-d]pyrimidin-4-yl)-5-azaspiro[2.5]octane-8-carboxamide, (cviii) N-[(1R)-1-(3,4-difluorophenyl)ethyl]-5-(7H-pyrrolo[2,3-d]pyrimidin-4-yl)-5-azaspiro[2.5]octane-8-carboxamide, (cix) N-phenethyl-5-(7H-pyrrolo[2,3-d]pyrimidin-4-yl)-5-azaspiro[2.5]octane-8-carboxamide (cx) N-(cyclobutylmethyl)-5-(7H-pyrrolo[2,3-d]pyrimidin-4-yl)-5-azaspiro[2.5]octane-8-carboxamide, (cxi) [1-(hydroxymethyl)cyclopropyl]methyl (2R)-3-hydroxy-2-[[(8S)-5-(7H-pyrrolo[2,3-d]pyrimidin-4-yl)-5-azaspiro[2.5]octane-8-carbonyl]amino]propanoate, (cxii) N-[(1R)-1-(3-cyanophenyl)ethyl]-5-(7H-pyrrolo[2,3-d]pyrimidin-4-yl)-5-azaspiro[2.5]octane-8-carboxamide, (cxiii) N-(2-hydroxy-1-methyl-1-phenyl-ethyl)-5-(7H-pyrrolo[2,3-d]pyrimidin-4-yl)-5-azaspiro[2.5]octane-8-carboxamide, (cxiv) N-[(3-methoxyphenyl)methyl]-5-(7H-pyrrolo[2,3-d]pyrimidin-4-yl)-5-azaspiro[2.5]octane-8-carboxamide, (cxv) (8S)—N-[(1R)-1-(4-cyano-2-methoxy-phenyl)-2-hydroxy-ethyl]-5-(7H-pyrrolo[2,3-d]pyrimidin-4-yl)-5-azaspiro[2.5]octane-8-carboxamide, (cxvi) (8S)—N-[(1R)-1-(4-cyano-2-ethyl-phenyl)ethyl]-5-(7H-pyrrolo[2,3-d]pyrimidin-4-yl)-5-azaspiro[2.5]octane-8-carboxamide, (cxvii) (8S)—N-[(1R)-2-hydroxy-1-(2-pyridyl)ethyl]-5-(7H-pyrrolo[2,3-d]pyrimidin-4-yl)-5-azaspiro[2.5]octane-8-carboxamide, (cxviii) N-[(1R)-1-(3-cyano-4-fluoro-phenyl)ethyl]-5-(7H-pyrrolo[2,3-d]pyrimidin-4-yl)-5-azaspiro[2.5]octane-8-carboxamide, (cxix) N-[(1R)-1-(3-fluoro-4-methoxy-phenyl)ethyl]-5-(7H-pyrrolo[2,3-d]pyrimidin-4-yl)-5-azaspiro[2.5]octane-8-carboxamide, (cxx) (8S)—N-[(1 S,2R)-2-(4-cyanophenyl)-2-hydroxy-1-methyl-ethyl]-5-(7H-pyrrolo[2,3-d]pyrimidin-4-yl)-5-azaspiro[2.5]octane-8-carboxamide, (cxxi) N-[(1 S)-2-hydroxy-1-phenyl-ethyl]-5-(7H-pyrrolo[2,3-d]pyrimidin-4-yl)-5-azaspiro[2.5]octane-8-carboxamide, (cxxii) N-(3-pyridylmethyl)-5-(7H-pyrrolo[2,3-d]pyrimidin-4-yl)-5-azaspiro[2.5]octane-8-carboxamide, (cxxiii) (8S)—N-[(2R)-3-[[3,3-difluoro-1-(hydroxymethyl)cyclobutyl]methylamino]-2-hydroxy-3-oxo-propyl]-5-(7H-pyrrolo[2,3-d]pyrimidin-4-yl)-5-azaspiro[2.5]octane-8-carboxamide, (cxxiv) (8S)—N-[(2R)-3-[(3,3-difluorocyclobutyl)methylamino]-2-hydroxy-3-oxo-propyl]-5-(7H-pyrrolo[2,3-d]pyrim id in-4-yl)-5-azaspiro[2.5]octane-8-carboxamide, (cxxv) N-[(1R)-1-(4-fluoro-2-methoxy-phenyl)ethyl]-5-(7H-pyrrolo[2,3-d]pyrimidin-4-yl)-5-azaspiro[2.5]octane-8-carboxamide, (cxxvi) (8S)—N-[(1 S)-1-cyclohexyl-2-hydroxy-ethyl]-5-(7H-pyrrolo[2,3-d]pyrimidin-4-yl)-5-azaspiro[2.5]octane-8-carboxamide, (cxxvii) (8S)—N-[(1 S,2S)-2-(5-fluoro-4-methyl-2-pyridyl)-2-hydroxy-1-methyl-ethyl]-5-(7H-pyrrolo[2,3-d]pyrimidin-4-yl)-5-azaspiro[2.5]octane-8-carboxamide, (cxxviii) N-[(1R)-1-(3-fluorophenyl)ethyl]-5-(7H-pyrrolo[2,3-d]pyrimidin-4-yl)-5-azaspiro[2.5]octane-8-carboxamide, (cxxix) (8S)—N-[(1 S)-2-hydroxy-1-(2-pyridyl)ethyl]-5-(7H-pyrrolo[2,3-d]pyrimidin-4-yl)-5-azaspiro[2.5]octane-8-carboxamide, (cxxx) N-[(1R)-1-phenylethyl]-5-(7H-pyrrolo[2,3-d]pyrimidin-4-yl)-5-azaspiro[2.5]octane-8-carboxamide, (cxxxi) N-[(1R)-1-benzyl-2-hydroxy-ethyl]-5-(7H-pyrrolo[2,3-d]pyrimidin-4-yl)-5-azaspiro[2.5]octane-8-carboxamide, (cxxxii) Benzyl (2S)-3-hydroxy-2-[[(8S)-5-(7H-pyrrolo[2,3-d]pyrimidin-4-yl)-5-azaspiro[2.5]octane-8-carbonyl]amino]propanoate, (cxxxiii) N-[(1R)-1-(3-methoxyphenyl)ethyl]-5-(7H-pyrrolo[2,3-d]pyrimidin-4-yl)-5-azaspiro[2.5]octane-8-carboxamide, (cxxxiv) N-[(1 S)-1-benzyl-2-hydroxy-ethyl]-5-(7H-pyrrolo[2,3-d]pyrimidin-4-yl)-5-azaspiro[2.5]octane-8-carboxamide, (cxxxv) (8R)—N-[(2S)-2-(4-cyanophenyl)-2-hydroxy-ethyl]-5-(7H-pyrrolo[2,3-d]pyrimidin-4-yl)-5-azaspiro[2.5]octane-8-carboxamide, (cxxxvi) N-[(1R)-1-(4-fluoro-3-methoxy-phenyl)ethyl]-5-(7H-pyrrolo[2,3-d]pyrimidin-4-yl)-5-azaspiro[2.5]octane-8-carboxamide, (cxxxvii) N-[(1R)-1-(5-methoxy-3-pyridyl)ethyl]-5-(7H-pyrrolo[2,3-d]pyrimidin-4-yl)-5-azaspiro[2.5]octane-8-carboxamide, (cxxxviii) (8R)—N-[(4-cyanophenyl)methyl]-5-(7H-pyrrolo[2,3-d]pyrimidin-4-yl)-5-azaspiro[2.5]octane-8-carboxamide, (cxxxix) (8S)—N-[(1R,2S)-2-(4-cyanophenyl)-2-hydroxy-1-methyl-ethyl]-5-(7H-pyrrolo[2,3-d]pyrimidin-4-yl)-5-azaspiro[2.5]octane-8-carboxamide, (cxl) (8S)—N-[(1S)-1-cyclobutyl-2-hydroxy-ethyl]-5-(7H-pyrrolo[2,3-d]pyrimidin-4-yl)-5-azaspiro[2.5]octane-8-carboxamide, (cxli) (8S)—N-[(1R)-1-cyclobutyl-2-hydroxy-ethyl]-5-(7H-pyrrolo[2,3-d]pyrimidin-4-yl)-5-azaspiro[2.5]octane-8-carboxamide, (cxlii) (8S)—N-[(1S,2S)-2-(3,4-difluorophenyl)-2-hydroxy-1-methyl-ethyl]-5-(7H-pyrrolo[2,3-d]pyrimidin-4-yl)-5-azaspiro[2.5]octane-8-carboxamide, (cxliii) (8S)—N-[(1S,2S)-2-(3-fluorophenyl)-2-hydroxy-1-methyl-ethyl]-5-(7H-pyrrolo[2,3-d]pyrimidin-4-yl)-5-azaspiro[2.5]octane-8-carboxamide, (cxliv)(8S)—N-[(1S,2S)-2-hydroxy-1-methyl-2-(3-pyridyl)ethyl]-5-(7H-pyrrolo[2,3-d]pyrimidin-4-yl)-5-azaspiro[2.5]octane-8-carboxamide, (cxlv) (8S)—N-[(1S,2S)-2-hydroxy-1-methyl-2-phenyl-ethyl]-5-(7H-pyrrolo[2,3-d]pyrimidin-4-yl)-5-azaspiro[2.5]octane-8-carboxamide, (cxlvi) (3,3-difluorocyclobutyl)methyl 5-(7H-pyrrolo[2,3-d]pyrimidin-4-yl)-5-azaspiro[2.5]octane-8-carboxylate, (cxlvii) (3,3-difluorocyclobutyl)methyl (8S)-5-(7H-pyrrolo[2,3-d]pyrimidin-4-yl)-5-azaspiro[2.5]octane-8-carboxylate, (cxlviii) (3,3-difluorocyclobutyl)methyl (8R)-5-(7H-pyrrolo[2,3-d]pyrimidin-4-yl)-5-azaspiro[2.5]octane-8-carboxylate, (cxlix) [1-(hydroxymethyl)cyclopropyl]methyl (8S)-5-(7H-pyrrolo[2,3-d]pyrimidin-4-yl)-5-azaspiro[2.5]octane-8-carboxylate, (cl) [1-(hydroxymethyl)cyclobutyl]methyl (8S)-5-(7H-pyrrolo[2,3-d]pyrimidin-4-yl)-5-azaspiro[2.5]octane-8-carboxylate, (cli) [1-(hydroxymethyl)cyclopentyl]methyl (8S)-5-(7H-pyrrolo[2,3-d]pyrimidin-4-yl)-5-azaspiro[2.5]octane-8-carboxylate, (clii) [3,3-difluoro-1-(hydroxymethyl)cyclobutyl]methyl (8S)-5-(7H-pyrrolo[2,3-d]pyrimidin-4-yl)-5-azaspiro[2.5]octane-8-carboxylate, (cliii) [1-(hydroxymethyl)cyclohexyl]methyl (8S)-5-(7H-pyrrolo[2,3-d]pyrimidin-4-yl)-5-azaspiro[2.5]octane-8-carboxylate, (cliv) [3-(hydroxymethyl)-1,1-dioxo-thietan-3-yl]methyl (8S)-5-(7H-pyrrolo[2,3-d]pyrimidin-4-yl)-5-azaspiro[2.5]octane-8-carboxylate, (clv) [1-(cyanomethyl)cyclopropyl]methyl (8S)-5-(7H-pyrrolo[2,3-d]pyrimidin-4-yl)-5-azaspiro[2.5]octane-8-carboxylate, and (clvi) [1-(cyanomethyl)cyclopropyl]methyl 5-(7H-pyrrolo[2,3-d]pyrimidin-4-yl)-5-azaspiro[2.5]octane-8-carboxylate, or a pharmaceutically acceptable salt, hydrate or solvate thereof.

11. The compound according to claim 1, wherein the compound is selected from (8S)—N-[(1S,2R)-2-(5-fluoro-2-pyridyl)-2-hydroxy-1-methyl-ethyl]-5-(7H-pyrrolo[2,3-d]pyrimidin-4-yl)-5-azaspiro[2.5]octane-8-carboxamide or a pharmaceutically acceptable salt, hydrate or solvate thereof.

12. A pharmaceutical composition comprising a compound according to claim 1 and one or more pharmaceutically acceptable vehicles and/or excipients or pharmaceutically acceptable carriers.

13. The pharmaceutical composition according to claim 12 further comprising one or more other therapeutically active compounds.

14. A method of treatment of one or more skin diseases, comprising administering to a person suffering from at least one of said skin diseases an effective amount of one or more compounds according to according to claim 1.

15. The method of claim 14, wherein the skin disease is a proliferative and inflammatory skin disorder, psoriasis, atopic dermatitis, scleroderma, rosacea, skin cancer, dermatitis, dermatitis herpetiformis, dermatomyositis, vitiligo, alopecia areata, contact dermatitis, eczema, xerosis, urticaria, or chronic idiopathic pruritus.

16. The method of claim 14, wherein the disease is psoriasis or atopic dermatitis.

17. The method of claim 14, wherein the disease of the immune system is responsive to the inhibition of protein tyrosine kinases of the JAK family of protein tyrosine kinases or TYK2 protein tyrosine kinases.

18. The method of claim 17, wherein the protein tyrosine kinases of the JAK family of protein tyrosine kinases are JAK1, JAK2, and/or JAK3.

19. A method of treatment of one or more skin diseases, comprising administering to a person suffering from at least one of said diseases an effective amount of the pharmaceutical composition according to claim 12.

20. The method of claim 19, wherein the skin disease is a proliferative and inflammatory skin disorder, psoriasis, atopic dermatitis, scleroderma, rosacea, skin cancer, dermatitis, dermatitis herpetiformis, dermatomyositis, vitiligo, alopecia areata, contact dermatitis, eczema, xerosis, urticaria, or chronic idiopathic pruritus.

* * * * *

UNITED STATES PATENT AND TRADEMARK OFFICE
CERTIFICATE OF CORRECTION

PATENT NO. : 10,799,507 B2
APPLICATION NO. : 16/483079
DATED : October 13, 2020
INVENTOR(S) : Mogens Larsen et al.

It is certified that error appears in the above-identified patent and that said Letters Patent is hereby corrected as shown below:

In the Claims

In Claim 1, Column 186, Line 26, "—C(O)OR3—*or" should read -- —C(O)OR3—* or--.

In Claim 7, Column 186, Lines 53-54, "—C(O)NHR3—*wherein" should read -- —C(O)NHR3—* wherein--.

In Claim 9, Column 186, Line 67, "cyanomethy" should read --cyanomethyl--.

In Claim 10, Column 187, Lines 3-5, "(i) (8S)-N-[(2S)-2-cyclopentyl-2-hydroxy-ethyl]-5-(7H-pyrrolo[2,3-d]pyrimidin-4-yl-5-azaspiro[2.5]octane-8-carboxamide," should read --(i) (8S)-N-[(2S)-2-cyclopentyl-2-hydroxy-ethyl]-5-(7H-pyrrolo[2,3-d]pyrimidin-4-yl)-5-azaspiro[2.5]octane-8-carboxamide,--.

In Claim 10, Column 187, Lines 22-24, "(vii) (8S)-N-[(2S)-2-(4-fluorophenyl)-2-hydroxy-ethyl]-5-(7H-pyrrolo[2,3-d]pyrimidin-4-yl-5-azaspiro[2.5]octane-8-carboxamide," should read --(vii) (8S)-N-[(2S)-2-(4-fluorophenyl)-2-hydroxy-ethyl]-5-(7H-pyrrolo[2,3-d]pyrimidin-4-yl)-5-azaspiro[2.5]octane-8-carboxamide,--.

In Claim 10, Column 187, Lines 25-27, "(viii) (8S)-N-[(2S)-2-(4-cyanophenyl)-2-hydroxy-ethyl]-5-(7H-pyrrolo[2,3-d]pyrimidin-4-yl-5-azaspiro[2.5]octane-8-carboxamide," should read --(viii) (8S)-N-[(2S)-2-(4-cyanophenyl)-2-hydroxy-ethyl]-5-(7H-pyrrolo[2,3-d]pyrimidin-4-yl)-5-azaspiro[2.5]octane-8-carboxamide,--.

In Claim 10, Column 187, Lines 35-37, "(xi) (8S)-N-[(2R)-2-cyclopentyl-2-hydroxy-ethyl]-5-(7H-pyrrolo[2,3-d]pyrimidin-4-0)-5-azaspiro[2.5]octane-8-carboxamide," should read --(xi) (8S)-N-[(2R)-2-cyclopentyl-2-hydroxy-ethyl]-5-(7H-pyrrolo[2,3-d]pyrimidin-4-yl)-5-azaspiro[2.5]octane-8-carboxamide,--.

Signed and Sealed this
Sixteenth Day of July, 2024

Katherine Kelly Vidal
*Director of the United States Patent and Trademark Office*

CERTIFICATE OF CORRECTION (continued)
U.S. Pat. No. 10,799,507 B2

In Claim 10, Column 189, Lines 7-9, "(xlvi) (8S)-N-[(2S)-2-(5-fluoro-2-pyridyl)-2-hydroxy-ethyl]-5-(7H-pyrrolo[2,3-d]pyrimidin-4-yl-5-azaspiro[2.5]octane-8-carboxamide," should read --(xlvi) (8S)-N-[(2S)-2-(5-fluoro-2-pyridyl)-2-hydroxy-ethyl]-5-(7H-pyrrolo[2,3-d]pyrimidin-4-yl)-5-azaspiro[2.5]octane-8-carboxamide,--.

In Claim 10, Column 189, Lines 53-55, "(lxii) N-[(2S)-2-hydroxy-2-phenyl-ethyl]-5-(7H-pyrrolo[2,3-d]pyrimidin-4-yl-5-azaspiro[2.5]octane-8-carboxamide," should read --(lxii) N-[(2S)-2-hydroxy-2-phenyl-ethyl]-5-(7H-pyrrolo[2,3-d]pyrimidin-4-yl)-5-azaspiro[2.5]octane-8-carboxamide,--.

In Claim 10, Column 192, Lines 34-37, "(cxxiv) (8S)-N-[(2R)-3-[(3,3-difluorocyclobutyl)methylamino]-2-hydroxy-3-oxo-propyl]-5-(7H-pyrrolo[2,3-d]pyrim id in-4-yl)-5-azaspiro[2.5]octane-8-carboxamide," should read --(cxxiv) (8S)-N-[(2R)-3-[(3,3-difluorocyclobutyl)methylamino]-2-hydroxy-3-oxo-propyl]-5-(7H-pyrrolo[2,3-d]pyrimidin-4-yl)-5-azaspiro[2.5]octane-8-carboxamide,--.

In Claim 14, Column 194, Line 29, "compounds according to according to claim 1." should read --compounds according to claim 1.--.